United States Patent
Fu et al.

(10) Patent No.: US 11,518,772 B2
(45) Date of Patent: Dec. 6, 2022

(54) FUSED TRICYCLIC RING DERIVATIVES AS SRC HOMOLOGY-2 PHOSPHATE INHIBITORS

(71) Applicant: NiKang Therapeutics, Inc., Wilmington, DE (US)

(72) Inventors: Jiping Fu, Danville, CA (US); Yan Lou, Pleasanton, CA (US); Yigang He, Newark, DE (US)

(73) Assignee: NIKANG THERAPEUTICS, INC., Wilmington, DE (US)

( * ) Notice: Subject to any disclaimer, the term of this patent is extended or adjusted under 35 U.S.C. 154(b) by 0 days.

(21) Appl. No.: 17/025,790

(22) Filed: Sep. 18, 2020

(65) Prior Publication Data

US 2021/0188876 A1 Jun. 24, 2021

Related U.S. Application Data

(63) Continuation of application No. 15/930,309, filed on May 12, 2020, now Pat. No. 10,894,797, which is a continuation of application No. 16/573,900, filed on Sep. 17, 2019, now abandoned.

(60) Provisional application No. 62/883,121, filed on Aug. 6, 2019, provisional application No. 62/883,120, filed on Aug. 6, 2019, provisional application No. 62/810,911, filed on Feb. 26, 2019, provisional application No. 62/749,655, filed on Oct. 23, 2018, provisional application No. 62/733,061, filed on Sep. 18, 2018.

(51) Int. Cl.
| | |
|---|---|
| C07D 519/00 | (2006.01) |
| A61P 35/00 | (2006.01) |
| A61K 31/5383 | (2006.01) |
| C07D 401/14 | (2006.01) |
| C07D 471/10 | (2006.01) |
| C07D 491/107 | (2006.01) |

(52) U.S. Cl.
CPC ........ C07D 519/00 (2013.01); A61K 31/5383 (2013.01); A61P 35/00 (2018.01); C07D 401/14 (2013.01); C07D 471/10 (2013.01); C07D 491/107 (2013.01)

(58) Field of Classification Search
CPC . C07D 471/10; C07D 491/107; C07D 519/00
USPC ............................................. 544/101; 546/84
See application file for complete search history.

(56) References Cited

U.S. PATENT DOCUMENTS

| | | | |
|---|---|---|---|
| 4,169,846 A | 10/1979 | Inagaki et al. | |
| 4,261,989 A | 4/1981 | Sasaki et al. | |
| 4,775,612 A | 10/1988 | Abe et al. | |
| 4,828,973 A | 5/1989 | Hirano et al. | |
| 4,931,434 A | 6/1990 | Broom et al. | |
| 5,266,573 A | 11/1993 | Croci et al. | |
| 5,360,459 A | 11/1994 | Kolp et al. | |
| 5,621,002 A | 4/1997 | Bosslet et al. | |
| 5,977,134 A | 11/1999 | Ciccarone et al. | |
| 6,225,052 B1 | 5/2001 | Batz et al. | |
| 6,465,467 B1 | 10/2002 | Nilsson et al. | |
| 6,514,964 B1 | 2/2003 | Chen et al. | |
| 6,528,460 B2 | 3/2003 | Kawata et al. | |
| 6,544,725 B2 | 4/2003 | Morimoto | |
| 6,599,917 B1 | 7/2003 | Okada et al. | |
| 6,620,946 B2 | 9/2003 | Dershem et al. | |
| 6,670,377 B1 | 12/2003 | Mekouar et al. | |
| 6,699,873 B1 | 3/2004 | Maguire et al. | |
| 6,699,994 B1 | 3/2004 | Babu et al. | |
| 6,780,996 B2 | 8/2004 | Boschelli et al. | |
| 6,812,225 B2 | 11/2004 | Pierson et al. | |
| 6,831,175 B2 | 12/2004 | Li et al. | |
| 6,953,857 B2 | 10/2005 | Nazaré et al. | |
| 6,963,001 B2 | 11/2005 | Dershem et al. | |
| 7,026,314 B2 | 4/2006 | Chapdelaine et al. | |
| 7,071,355 B2 | 7/2006 | Leban et al. | |
| 7,125,879 B2 | 10/2006 | Arts et al. | |
| 7,148,237 B2 | 12/2006 | Fuji et al. | |
| 7,183,313 B2 | 2/2007 | Makriyannis et al. | |
| 7,229,943 B2 | 6/2007 | Gibson et al. | |
| 7,244,739 B2 | 7/2007 | Cheng et al. | |
| 7,342,004 B2 | 3/2008 | Potter et al. | |
| 7,442,842 B2 | 10/2008 | Jaekel et al. | |
| 7,632,865 B2 | 12/2009 | Kato et al. | |
| 7,700,620 B2 | 4/2010 | Sutton et al. | |
| 7,728,008 B2 | 6/2010 | Qiao et al. | |
| 7,763,739 B2 | 7/2010 | Kadyrov et al. | |
| 7,842,638 B2 | 11/2010 | Gibson et al. | |
| 7,897,607 B2 | 3/2011 | Gyorkos et al. | |
| 7,910,741 B2 | 3/2011 | Nishizawa et al. | |

(Continued)

FOREIGN PATENT DOCUMENTS

| | | |
|---|---|---|
| CN | 108794485 A | 11/2018 |
| CN | 108863982 A | 11/2018 |

(Continued)

OTHER PUBLICATIONS

CAS No. 1029872-29-4, 5 pages, (updated CAS Registry No. 934660-93-2), retrieved from web on May 18, 2020, 5 pages.

(Continued)

*Primary Examiner* — Deepak R Rao
(74) *Attorney, Agent, or Firm* — Wilson Sonsini Goodrich & Rosati

(57) ABSTRACT

The present disclosure provides certain fused tricyclic ring derivatives that are Src Homology-2 phosphatase (SHP2) inhibitors and are therefore useful for the treatment of diseases treatable by inhibition of SHP2. Also provided are pharmaceutical compositions containing such compounds and processes for preparing such compounds.

10 Claims, No Drawings

(56) References Cited

U.S. PATENT DOCUMENTS

| | | |
|---|---|---|
| 7,919,046 B2 | 4/2011 | Delapierre et al. |
| 7,956,020 B2 | 6/2011 | Negoro et al. |
| 7,989,565 B2 | 8/2011 | Gibson et al. |
| 8,039,674 B2 | 10/2011 | Habashita et al. |
| 8,067,328 B2 | 11/2011 | Gibson et al. |
| 8,143,276 B2 | 3/2012 | Yang et al. |
| 8,288,425 B2 | 10/2012 | Edwards et al. |
| 8,304,553 B2 | 11/2012 | Liu et al. |
| 8,362,181 B2 | 1/2013 | Hogan et al. |
| 8,414,983 B2 | 4/2013 | Parri et al. |
| 8,501,955 B2 | 8/2013 | Bhuniya et al. |
| 8,545,720 B2 | 10/2013 | Goetz et al. |
| 8,575,283 B1 | 11/2013 | Fang et al. |
| 8,585,925 B2 | 11/2013 | Czanta et al. |
| 8,598,164 B2 | 12/2013 | Hadida-ruah et al. |
| 8,642,278 B2 | 2/2014 | Sebti et al. |
| 8,673,911 B2 | 3/2014 | Mallais et al. |
| 8,686,009 B2 | 4/2014 | Blumberg et al. |
| 8,710,233 B2 | 4/2014 | Lee et al. |
| 8,791,136 B2 | 7/2014 | Goff et al. |
| 8,796,280 B2 | 8/2014 | Page et al. |
| 8,815,918 B2 | 8/2014 | Pastor Fernandez et al. |
| 8,822,513 B2 | 9/2014 | Lu et al. |
| 8,859,581 B2 | 10/2014 | Heinrich et al. |
| 8,877,930 B2 | 11/2014 | Bedore et al. |
| 8,883,793 B2 | 11/2014 | Chen et al. |
| 8,907,091 B2 | 12/2014 | Raeppel et al. |
| 8,951,890 B2 | 2/2015 | Yamamoto et al. |
| 8,969,349 B2 | 3/2015 | Campbell et al. |
| 8,987,271 B2 | 3/2015 | Cardone et al. |
| 8,999,459 B2 | 4/2015 | Bernatz et al. |
| 9,005,720 B2 | 4/2015 | Goetz et al. |
| 9,012,498 B2 | 4/2015 | Manoharan et al. |
| 9,073,801 B2 | 7/2015 | Hoveyda et al. |
| 9,090,633 B2 | 7/2015 | Kasina et al. |
| 9,212,311 B2 | 12/2015 | Lee et al. |
| 9,217,050 B2 | 12/2015 | Fornof et al. |
| 9,234,136 B2 | 1/2016 | Archetti et al. |
| 9,290,528 B1 | 3/2016 | Glazer et al. |
| 9,295,754 B2 | 3/2016 | Boden et al. |
| 9,326,926 B2 | 5/2016 | Pressly et al. |
| 9,334,242 B2 | 5/2016 | Lu et al. |
| 9,340,506 B2 | 5/2016 | Bhuniya et al. |
| 9,340,528 B2 | 5/2016 | Bader et al. |
| 9,347,002 B2 | 5/2016 | Klasen-memmer et al. |
| 9,376,425 B2 | 6/2016 | Bartberger et al. |
| 9,394,290 B2 | 7/2016 | Hartmann et al. |
| 9,399,623 B2 | 7/2016 | Karra et al. |
| 9,410,105 B2 | 8/2016 | Desantis et al. |
| 9,421,274 B2 | 8/2016 | Robillard et al. |
| 9,427,482 B2 | 8/2016 | Rossin et al. |
| 9,458,308 B1 | 10/2016 | Park et al. |
| 9,463,256 B2 | 10/2016 | Lub et al. |
| 9,464,065 B2 | 10/2016 | Schultz et al. |
| 9,487,472 B2 | 11/2016 | Betley et al. |
| 9,520,565 B2 | 12/2016 | Wang et al. |
| 9,550,000 B2 | 1/2017 | Robinson et al. |
| 9,556,166 B2 | 1/2017 | Foley et al. |
| 9,580,400 B2 | 2/2017 | Makriyannis et al. |
| 9,580,653 B2 | 2/2017 | Archetti et al. |
| 9,586,947 B2 | 3/2017 | Lu et al. |
| 9,593,115 B2 | 3/2017 | Barawkar et al. |
| 9,617,291 B2 | 4/2017 | Li et al. |
| 9,676,757 B2 | 6/2017 | Sherer et al. |
| 9,714,381 B2 | 7/2017 | Archetti et al. |
| 9,725,479 B2 | 8/2017 | Manoharan et al. |
| 9,802,965 B2 | 10/2017 | Fürstner et al. |
| 9,815,859 B2 | 11/2017 | Duan et al. |
| 9,818,959 B2 | 11/2017 | Li et al. |
| 9,862,789 B2 | 1/2018 | Asandei |
| 9,908,884 B2 | 3/2018 | Gray et al. |
| 9,913,921 B2 | 3/2018 | Robillard et al. |
| 9,932,305 B2 | 4/2018 | List et al. |
| 9,938,234 B2 | 4/2018 | Evans et al. |
| 9,947,876 B2 | 4/2018 | Kawamura et al. |
| 9,963,452 B2 | 5/2018 | Grueneberg et al. |
| 9,963,637 B2 | 5/2018 | Lee et al. |
| 10,017,520 B2 | 7/2018 | Koehler et al. |
| 10,023,800 B2 | 7/2018 | Kim et al. |
| 10,069,079 B2 | 9/2018 | Stoessel et al. |
| 10,072,017 B2 | 9/2018 | Zawistoski et al. |
| 10,076,581 B2 | 9/2018 | Marik et al. |
| 10,087,151 B2 | 10/2018 | Tsvetkov et al. |
| 10,120,281 B2 | 11/2018 | Takahashi et al. |
| 10,125,126 B2 | 11/2018 | Braun et al. |
| 10,131,841 B2 | 11/2018 | Archetti et al. |
| 10,164,200 B2 | 12/2018 | Hwang et al. |
| 10,180,626 B2 | 1/2019 | Fujiwara et al. |
| 10,199,583 B1 | 2/2019 | Hang et al. |
| 10,201,531 B2 | 2/2019 | Saitoh et al. |
| 10,205,190 B2 | 2/2019 | Lee et al. |
| 10,240,085 B2 | 3/2019 | Ihn et al. |
| 10,243,149 B2 | 3/2019 | Kang et al. |
| 10,280,171 B2 | 5/2019 | Jones et al. |
| 10,329,270 B2 | 6/2019 | Qiu et al. |
| 10,336,772 B2 | 7/2019 | Ishii et al. |
| 10,376,594 B2 | 8/2019 | Robillard et al. |
| 10,435,369 B2 | 10/2019 | Marcoux et al. |
| 10,463,661 B2 | 11/2019 | Long et al. |
| 10,478,445 B2 | 11/2019 | Bae et al. |
| 10,894,797 B2 | 1/2021 | Fu et al. |
| 11,034,705 B2 | 6/2021 | Fu et al. |
| 2002/0012960 A1 | 1/2002 | Schallner et al. |
| 2002/0173524 A1 | 11/2002 | Collins et al. |
| 2003/0187026 A1 | 10/2003 | Li et al. |
| 2004/0110745 A1 | 6/2004 | Chapdelaine et al. |
| 2005/0009894 A1 | 1/2005 | Babin et al. |
| 2005/0107268 A1 | 5/2005 | Negoro et al. |
| 2005/0247001 A1 | 11/2005 | Gouliaev et al. |
| 2006/0156481 A1 | 7/2006 | Lim |
| 2007/0010529 A1 | 1/2007 | Takahashi et al. |
| 2007/0088040 A1 | 4/2007 | Hinman et al. |
| 2007/0135437 A1 | 6/2007 | Benjamin et al. |
| 2007/0244133 A1 | 10/2007 | Bower et al. |
| 2007/0260062 A1 | 11/2007 | Goetz |
| 2008/0134938 A1 | 6/2008 | Negoro et al. |
| 2008/0194821 A1 | 8/2008 | Johannes et al. |
| 2008/0255183 A1 | 10/2008 | Arnould et al. |
| 2009/0118146 A1 | 5/2009 | Negoro et al. |
| 2010/0004284 A1 | 1/2010 | Farina et al. |
| 2010/0190766 A1 | 7/2010 | Moser et al. |
| 2010/0197687 A1 | 8/2010 | Pelcman et al. |
| 2012/0040977 A1 | 2/2012 | Li et al. |
| 2012/0046301 A1 | 2/2012 | Frank et al. |
| 2012/0059179 A1 | 3/2012 | Yu |
| 2012/0077959 A1 | 3/2012 | Zhang et al. |
| 2012/0108819 A1 | 5/2012 | Hashmi et al. |
| 2012/0149663 A1 | 6/2012 | Brown et al. |
| 2012/0232108 A1 | 9/2012 | Huang et al. |
| 2012/0238546 A1 | 9/2012 | Zhu et al. |
| 2012/0245158 A1 | 9/2012 | Huang et al. |
| 2012/0283175 A1 | 11/2012 | Patten et al. |
| 2013/0183252 A1 | 7/2013 | Li et al. |
| 2013/0202652 A1 | 8/2013 | Manoharan et al. |
| 2014/0031547 A1 | 1/2014 | Sheridan et al. |
| 2014/0131628 A1 | 5/2014 | D'lavari et al. |
| 2014/0163229 A1 | 6/2014 | Barany et al. |
| 2015/0036095 A1 | 2/2015 | Jeong et al. |
| 2015/0087673 A1 | 3/2015 | Hitoshi et al. |
| 2015/0221878 A1 | 8/2015 | Rai et al. |
| 2015/0297741 A1 | 10/2015 | Robillard |
| 2015/0340627 A1 | 11/2015 | Jatsch et al. |
| 2015/0344514 A1 | 12/2015 | Robillard et al. |
| 2015/0376198 A1 | 12/2015 | Roberts et al. |
| 2016/0093812 A1 | 3/2016 | Stoessel et al. |
| 2016/0151505 A1 | 6/2016 | Robillard et al. |
| 2016/0190482 A1 | 6/2016 | Jeon et al. |
| 2016/0197289 A1 | 7/2016 | Sado et al. |
| 2016/0211466 A1 | 7/2016 | Ogiwara et al. |
| 2016/0229866 A1 | 8/2016 | Dousson et al. |
| 2016/0257657 A1 | 9/2016 | Wipf et al. |
| 2016/0268519 A1 | 9/2016 | Choi et al. |
| 2017/0029366 A1 | 2/2017 | Cole et al. |
| 2017/0054083 A1 | 2/2017 | Lee |

(56) References Cited

U.S. PATENT DOCUMENTS

| | | |
|---|---|---|
| 2017/0054095 A1 | 2/2017 | Choi et al. |
| 2017/0121606 A1 | 5/2017 | Tong et al. |
| 2017/0170405 A1 | 6/2017 | Cho et al. |
| 2017/0174826 A1 | 6/2017 | Ye et al. |
| 2017/0179395 A1 | 6/2017 | Kim et al. |
| 2017/0179401 A1 | 6/2017 | Kim et al. |
| 2017/0186964 A1 | 6/2017 | Cho et al. |
| 2017/0186975 A1 | 6/2017 | Kim et al. |
| 2017/0213987 A1 | 7/2017 | Kim et al. |
| 2017/0256721 A1 | 9/2017 | Kim et al. |
| 2017/0294613 A1 | 10/2017 | Cho et al. |
| 2018/0002604 A1 | 1/2018 | Yoon et al. |
| 2018/0044591 A1 | 2/2018 | Jeong et al. |
| 2018/0053898 A1 | 2/2018 | Kim et al. |
| 2018/0119010 A1 | 5/2018 | Klasen-memmer et al. |
| 2018/0273562 A1 | 9/2018 | Choi et al. |
| 2018/0305334 A1 | 10/2018 | Larsen et al. |
| 2018/0312511 A1 | 11/2018 | Liu et al. |
| 2018/0340002 A1 | 11/2018 | Park et al. |
| 2018/0362567 A1 | 12/2018 | Hwang et al. |
| 2019/0013485 A1 | 1/2019 | Li et al. |
| 2019/0036042 A1 | 1/2019 | Kim et al. |
| 2019/0040028 A1 | 2/2019 | Diness et al. |
| 2019/0077792 A1 | 3/2019 | Volkmann et al. |
| 2019/0079095 A1 | 3/2019 | Gee et al. |
| 2019/0092784 A1 | 3/2019 | Wu et al. |
| 2019/0099748 A1 | 4/2019 | Ritter et al. |
| 2019/0100546 A1 | 4/2019 | Baik et al. |
| 2019/0152943 A1 | 5/2019 | Lain et al. |
| 2019/0157579 A1 | 5/2019 | Jeon et al. |
| 2019/0192517 A1 | 6/2019 | Burrows et al. |
| 2019/0218240 A1 | 7/2019 | Yoo et al. |
| 2019/0218459 A1 | 7/2019 | Song et al. |
| 2019/0259952 A1 | 8/2019 | Sasada et al. |
| 2019/0280064 A1 | 9/2019 | Kim et al. |
| 2019/0280215 A1 | 9/2019 | Kim et al. |
| 2019/0290649 A1 | 9/2019 | Xie et al. |
| 2019/0300523 A1 | 10/2019 | Liu et al. |
| 2019/0343836 A1 | 11/2019 | Alghalandis et al. |
| 2020/0002330 A1 | 1/2020 | Chen et al. |
| 2020/0115389 A1 | 4/2020 | Fu et al. |
| 2020/0277308 A1 | 9/2020 | Fu et al. |

FOREIGN PATENT DOCUMENTS

| | | |
|---|---|---|
| EP | 2098226 A1 | 9/2009 |
| EP | 2524918 A1 | 11/2012 |
| EP | 3229290 A1 | 10/2017 |
| EP | 3525253 A1 | 8/2019 |
| JP | S62135830 A | 6/1987 |
| JP | S62135834 A | 6/1987 |
| JP | S62135835 A | 6/1987 |
| JP | S62136650 A | 6/1987 |
| JP | S62136651 A | 6/1987 |
| JP | S62136654 A | 6/1987 |
| JP | H05181221 A | 7/1993 |
| JP | H05196976 A | 8/1993 |
| JP | 2000072695 A | 3/2000 |
| JP | 2005170939 A | 6/2005 |
| JP | 2008007634 A | 1/2008 |
| JP | 2009013314 A | 1/2009 |
| JP | 2010217692 A | 9/2010 |
| JP | 4749000 B2 | 5/2011 |
| JP | 2014232188 A | 12/2014 |
| JP | 5782836 B2 | 7/2015 |
| JP | 2015163671 A | 9/2015 |
| JP | 5814141 B2 | 10/2015 |
| JP | 6215674 B2 | 10/2017 |
| JP | 6309834 B2 | 3/2018 |
| JP | 2019050369 A | 3/2019 |
| JP | 6522313 B2 | 5/2019 |
| KR | 20120045905 A | 5/2012 |
| KR | 20150016140 A | 2/2015 |
| KR | 101537860 B1 | 7/2015 |
| KR | 20170138614 A | 12/2017 |
| WO | 93/15047 A1 | 8/1993 |
| WO | 93/16684 A1 | 9/1993 |
| WO | 98/02438 A1 | 1/1998 |
| WO | 98/06709 A1 | 2/1998 |
| WO | 00/76984 A2 | 12/2000 |
| WO | 01/02369 A2 | 1/2001 |
| WO | 01/10842 A2 | 2/2001 |
| WO | 02/00651 A2 | 1/2002 |
| WO | 02/10192 A2 | 2/2002 |
| WO | 02/066470 A1 | 8/2002 |
| WO | 03/003008 A1 | 1/2003 |
| WO | 03/003009 A1 | 1/2003 |
| WO | 03/064383 A2 | 8/2003 |
| WO | 03/075836 A2 | 9/2003 |
| WO | 2004/017922 A2 | 3/2004 |
| WO | 2005/028443 A2 | 3/2005 |
| WO | 2006/028958 A2 | 3/2006 |
| WO | 2006/038594 A1 | 4/2006 |
| WO | 2006/061094 A1 | 6/2006 |
| WO | 2006/122806 A2 | 11/2006 |
| WO | 2007/011721 A1 | 1/2007 |
| WO | 2007/011759 A2 | 1/2007 |
| WO | 2007/064869 A2 | 6/2007 |
| WO | 2008/024423 A2 | 2/2008 |
| WO | 2008/118626 A2 | 10/2008 |
| WO | 2008/118626 A9 | 12/2008 |
| WO | 2009/036082 A2 | 3/2009 |
| WO | 2009/055730 A1 | 4/2009 |
| WO | 2009/155386 A1 | 12/2009 |
| WO | 2010/011666 A2 | 1/2010 |
| WO | 2010/012363 A1 | 2/2010 |
| WO | 2010/048149 A2 | 4/2010 |
| WO | 2010/075273 A1 | 7/2010 |
| WO | 2010/148422 A1 | 12/2010 |
| WO | 2011/093603 A1 | 8/2011 |
| WO | 2011/101644 A1 | 8/2011 |
| WO | 2011/109059 A1 | 9/2011 |
| WO | 2011/111930 A1 | 9/2011 |
| WO | 2011/115378 A1 | 9/2011 |
| WO | 2012/016133 A2 | 2/2012 |
| WO | 2012/020215 A1 | 2/2012 |
| WO | 2012/020357 A1 | 2/2012 |
| WO | 2012/056419 A1 | 5/2012 |
| WO | 2013/190212 A1 | 12/2013 |
| WO | 2014/031872 A2 | 2/2014 |
| WO | 2014/068893 A1 | 5/2014 |
| WO | 2014/081299 A1 | 5/2014 |
| WO | 2014/081300 A1 | 5/2014 |
| WO | 2014/122933 A1 | 8/2014 |
| WO | 2014/157267 A1 | 10/2014 |
| WO | 2014/176488 A1 | 10/2014 |
| WO | 2015/003094 A2 | 1/2015 |
| WO | 2015/008097 A1 | 1/2015 |
| WO | 2015/107493 A1 | 7/2015 |
| WO | 2015/107494 A1 | 7/2015 |
| WO | 2015/107495 A1 | 7/2015 |
| WO | 2016/022645 A1 | 2/2016 |
| WO | 2016/049565 A1 | 3/2016 |
| WO | 2016/145383 A1 | 9/2016 |
| WO | 2016/164675 A1 | 10/2016 |
| WO | 2016/168540 A1 | 10/2016 |
| WO | 2016/203404 A1 | 12/2016 |
| WO | 2016/203405 A1 | 12/2016 |
| WO | 2016/203406 A1 | 12/2016 |
| WO | 2016/207261 A1 | 12/2016 |
| WO | 2017/015562 A1 | 1/2017 |
| WO | 2017/027357 A1 | 2/2017 |
| WO | 2017/027358 A1 | 2/2017 |
| WO | 2017/058092 A1 | 4/2017 |
| WO | 2017/058728 A1 | 4/2017 |
| WO | 2017/058768 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |
| WO | 2017/087528 A1 | 5/2017 |
| WO | 2017/100546 A1 | 6/2017 |
| WO | 2017/170263 A1 | 10/2017 |

(56) References Cited

FOREIGN PATENT DOCUMENTS

| | | | |
|---|---|---|---|
| WO | 2017/172979 A1 | 10/2017 | |
| WO | 2017/201161 A1 | 11/2017 | |
| WO | 2017/210134 A1 | 12/2017 | |
| WO | 2017/211303 A1 | 12/2017 | |
| WO | 2017/216706 A1 | 12/2017 | |
| WO | 2018/013597 A1 | 1/2018 | |
| WO | 2018/057884 A1 | 3/2018 | |
| WO | 2018/064510 A1 | 4/2018 | |
| WO | 2018/068017 A1 | 4/2018 | |
| WO | 2018/081091 A1 | 5/2018 | |
| WO | 2018/119183 A2 | 6/2018 | |
| WO | 2018/119263 A1 | 6/2018 | |
| WO | 2018/136264 A1 | 7/2018 | |
| WO | 2018/136265 A1 | 7/2018 | |
| WO | 2018/146469 A1 | 8/2018 | |
| WO | 2018/146471 A1 | 8/2018 | |
| WO | 2018/161033 A1 | 9/2018 | |
| WO | 2018/172984 A1 | 9/2018 | |
| WO | 2018/218133 A1 | 11/2018 | |
| WO | 2018/230595 A1 | 12/2018 | |
| WO | 2019/002173 A1 | 1/2019 | |
| WO | 2019/018119 A1 | 1/2019 | |
| WO | 2019/020828 A1 | 1/2019 | |
| WO | 2019/051084 A1 | 3/2019 | |
| WO | 2019/051469 A1 | 3/2019 | |
| WO | 2019/020828 A9 | 4/2019 | |
| WO | 2019/063585 A1 | 4/2019 | |
| WO | 2019/067843 A1 | 4/2019 | |
| WO | 2019/075265 A1 | 4/2019 | |
| WO | 2019/118909 A1 | 6/2019 | |
| WO | 2019/126730 A1 | 6/2019 | |
| WO | 2019/136442 A1 | 7/2019 | |
| WO | 2019/144764 A1 | 8/2019 | |
| WO | 2019/144765 A1 | 8/2019 | |
| WO | 2019/158019 A1 | 8/2019 | |
| WO | 2019/165073 A1 | 8/2019 | |
| WO | 2019/167000 A1 | 9/2019 | |
| WO | 2019/182960 A1 | 9/2019 | |
| WO | 2019/183364 A1 | 9/2019 | |
| WO | 2019/183367 A1 | 9/2019 | |
| WO | 2019/213318 A1 | 11/2019 | |
| WO | 2019/218968 A1 | 11/2019 | |
| WO | 2020/022323 A1 | 1/2020 | |
| WO | 2020/033286 A1 | 2/2020 | |
| WO | 2020/033828 A1 | 2/2020 | |
| WO | 2020/061101 A1 | 3/2020 | |
| WO | 2020/061103 A1 | 3/2020 | |
| WO | 2020/065452 A1 | 4/2020 | |
| WO | 2020/065453 A1 | 4/2020 | |
| WO | 2020/076723 A1 | 4/2020 | |

OTHER PUBLICATIONS

CAS No. 1133385-83-7, 4 pages, (updated CAS Registry No. 896466-04-9), retrieved from web on May 18, 2020, 4 pages.
CAS No. 915296-00-3, retrieved from web on May 18, 2020, 6 pages.
CAS No. 934235-44-6, retrieved from web on May 18, 2020, 5 pages.
CAS No. 942487-16-3, retrieved from web on May 18, 2020, 3 pages.
International Search Report and Written Opinion received for PCT Patent International Application No. PCT/US2019/051590, dated Nov. 4, 2019, 11 pages.
International Search Report and Written Opinion received for PCT Patent International Application No. PCT/US2019/051592, dated May 11, 2019, 8 pages.
Bagdanoff et al. (Jan. 28, 2019) "Optimization of Fused Bicyclic Allosteric SHP2 Inhibitors", Journal of Medicinal Chemistry, 62(4);1781-1792.
Chen et al. (Jul. 7, 2016) "Allosteric Inhibition of SHP2 Phosphatase Inhibits Cancers Driven by Receptor Tyrosine Kinases", Nature, 535(7610):148-152.
Dardaei et al. (Mar. 5, 2018) "SHP2 Inhibition Restores Sensitivity in ALK-rearranged Non-Small-Cell Lung Cancer Resistant to ALK Inhibitors", Nature Medicine, 24(4):8 pages.
Fedele et al. (Jul. 25, 2018) "SHP2 Inhibition Prevents Adaptive Resistance to MEK Inhibitors in Multiple Cancer Models", Cancer discovery, 8(10):1237-1249.
Grossmann et al. (2010) "The Tyrosine Phosphatase Shp2 in Development and Cancer", Advances in Cancer Research, 106:53-89.
Gura Trisha (Nov. 7, 1997) "Cancer Models: Systems for Identifying New Drugs are Often Faulty", Science, 278(5340):5 pages.
Hinman et al. (Jul. 11, 2006) "Novel Antibacterial Class: A Series of Tetracyclic Derivatives", Journal of Medicinal Chemistry, 49(16):4842-4856.
Johnson et al. (2001) "Relationships Between Drug Activity in NCI Preclinical in Vitro and in Vivo Models and Early Clinical Trials", British Journal of Cancer, 84(10):1424-1431.
Li et al. (2014) "Discovery of AMG 925, a FLT3 and CDK4 Dual Kinase Inhibitor with Preferential Affinity for the Activated State of FLT3", Journal of Medicinal Chemistry, 57(8):3430-3449.
Maeshima et al. (2016) "Abnormal PTPN11 Enhancer Methylation Promotes Rheumatoid Arthritis Fibroblast-like Synoviocyte Aggressiveness and Joint Inflammation", JCI Insight, 1(7):14 pages.
Mainardi et al. (May 28, 2018) "SHP2 Is Required for Growth of KRAS-Mutant Non-Small-Cell Lung Cancer in Vivo", Nature Medicine, 24:961-967.
Massari et al. (Sep. 8, 2016) "Polymerase Acidic Protein-Basic Protein 1 (PA-PB1) Protein-Protein Interaction as a Target for Next-Generation Anti-influenza Therapeutics", Journal of Medicinal Chemistry, 59(17):7699-7718.
Nichols et al. (Sep. 2018) "RAS nucleotide cycling underlies the SHP2 phosphatase dependence of mutant BRAF-, NF1- and RAS-driven cancers", Nature Cell Biology, 20(9):1064-1073.
Pearce et al. (2008) "Failure Modes in Anticancer Drug Discovery and Development", Cancer Drug Design and Discovery, 18:424-435.
Prahallad et al. (2015) "PTPN11 Is a Central Node in Intrinsic and Acquired Resistance to Targeted Cancer Drugs", Cell Reports, 12:1978-1985.
Ruess et al. (2018) "Mutant KRAS-Driven Cancers Depend on PTPN11/SHP2 Phosphatase", Nature Medicine, 24(7):13 pages.
Sarver et al. (Jan. 28, 2019) "6-Amino-3-methylpyrimidinones as Potent, Selective, and Orally Efficacious SHP2 Inhibitors", Journal of Medicinal Chemistry, 62(4);1793-1802.
Simone Josephv (1996) "Oncology: Introduction", Cecil Textbook of Medicine, 20th Edition, 1996, 1:1004-1010.
Stanford et al. (May 2013) "PTPome Profile of Rheumatoid Arthritis Fibroblast-like Synoviocytes: A Novel Role for SHP-2 as a Modulator of Invasion and Survival", Arthritis & Rheumatology, 65(5):1171-1180.
Tajan et al. (2015) "SHP2 Sails from Physiology to Pathology", European Journal of Medical Genetics, 58(10):509-525.
The Merck Manual (2013) "Acute Leukemia", Merck Manual (Online Edition), 6 Pages.
Wang et al. (May 16, 2016) "Inhibition of SHP2 Ameliorates the Pathogenesis of Systemic Lupus Erythematosus", The Journal of Clinical Investigation, 126(6):2077-2092.
Wong et al. (May 28, 2018) "Targeting wild-type KRAS-amplified gastroesophageal cancer through combined MEK and SHP2 inhibition", Nature Medicine, 24:968-977.
Zehender et al. (Aug. 14, 2018) "The tyrosine phosphatase SHP2 controls TGFβ-induced STAT3 signaling to regulate fibroblast activation and fibrosis", Nature Communications, 9(1):3259:17 pages.
U.S. Appl. No. 15/930,309 Office Action dated Aug. 4, 2020.
U.S. Appl. No. 15/930,309 Office Action dated Jul. 17, 2020.
U.S. Appl. No. 17/074,337 Office Action dated Dec. 14, 2020.

FUSED TRICYCLIC RING DERIVATIVES AS SRC HOMOLOGY-2 PHOSPHATE INHIBITORS

CROSS REFERENCE TO RELATED APPLICATIONS

This application is a continuation of U.S. application Ser. No. 15/930,309, filed May 12, 2020, which is a continuation of U.S. application Ser. No. 16/573,900, filed Sep. 17, 2019, which in turn claims the benefit of U.S. Provisional Application No. 62/733,061 filed Sep. 18, 2018, U.S. Provisional Application No. 62/749,655 filed Oct. 23, 2018, U.S. Provisional Application No. 62/810,911 filed Feb. 26, 2019, U.S. Provisional Application No. 62/883,120 filed Aug. 6, 2019, and U.S. Provisional Application No. 62/883,121 filed Aug. 6, 2019; the entireties of which are herein incorporated by reference.

FIELD OF THE DISCLOSURE

The present disclosure provides certain fused tricyclic ring derivatives that are Src Homology-2 phosphatase (SHP2) inhibitors and are therefore useful for the treatment of diseases treatable by inhibition of SHP2. Also provided are pharmaceutical compositions containing such compounds and processes for preparing such compounds.

BACKGROUND

SHP2 is a non-receptor protein phosphatase ubiquitously expressed in various tissues and cell types (see reviews: Tajan M et al., Eur J Med Genet 2016 58(10):509-25; Grossmann K S et al., Adv Cancer Res 2010 106:53-89). SHP2 is composed of two Src homology 2 (N-SH2 and C-SH2) domains in its NH2-terminus, a catalytic PTP (protein-tyrosine phosphatase) domain, and a C-terminal tail with regulatory properties. At the basal state, the intermolecular interactions between the SH2 domains and the PTP domain prevent the access of substrates to the catalytic pocket, keeping SHP2 into a closed, auto-inhibited conformation. In response to stimulation, SHP2 activating proteins bearing phosphor-tyrosine motifs bind to the SH2 domains, leading to exposure of active site and enzymatic activation of SHP2.

SHP2 plays important roles in fundamental cellular functions including proliferation, differentiation, cell cycle maintenance and motility. By dephosphorylating its associated signaling molecules, SHP2 regulates multiple intracellular signaling pathways in response to a wide range of growth factors, cytokines, and hormones. Cell signaling processes in which SHP2 participates include the RAS-MAPK (mitogen-activated protein kinase), the PI3K (phosphoinositol 3-kinase)-AKT, and the JAK-STAT pathways.

The RAS-MAPK signaling pathway is crucial for tumor formation and maintenance. Genes encoding various components of this pathway, including RTKs (receptor tyrosine kinases), SHP2, NF1, RAS, or RAF are mutated in cancers, leading to upregulation of MAPK signaling. SHP2 also plays a signal-enhancing role on this pathway, acting downstream of RTKs and upstream of RAS. RTK-driven cancer cells were demonstrated to depend on SHP2 for survival. Thus, SHP2 inhibitor has been proposed as a valid treatment for RTK-driven cancers (see Prahallad, A. et al. Cell Reports 12, 1978-1985 (2015); Chen Y N, Nature 535, 148-152 (2016)).

A lot of efforts have been made to develop pharmacological agents targeting various nodes along the RAS-MAPK pathway, such as RTK inhibitors, BRAF inhibitors, and MEK inhibitors for the treatment of cancer. Although these agents demonstrate good initial efficacy, resistance occurs frequently to these agents. One common mechanism of resistance involves activation of RTKs that fuel reactivation of the MAPK signaling. Since SHP2 is required downstream of multiple RTKs for signal transduction, SHP2 inhibition may provide a general strategy for preventing resistance to MAPK pathway targeted cancer drugs. Recent studies in preclinical models have shown that SHP2 inhibition overcomes resistance and offers synergistic therapeutic effects when combined with an ALK inhibitor (see Dardaei L et al. Nat Med. 24, 512-17 (2018)), MEK inhibitor (see Mainardi, S. et al. Nat. Med. https://doi.org/10.1038/s41591-018-0023-9 (2018); Ruess, D. A. et al. Nat. Med. https://doi.org/10.1038/s41591-018-0024-8 (2018); Wong, G. S. et al. Nat. Med. https://doi.org/0.1038/s41591-018-0022-x (2018); Fedele C et al. Cancer Discov pii: CD-18-0444. doi: 10.1158/2159-8290.CD-18-0444 (2018)), or BRAF inhibitor (see Prahallad, A. et al. Cell Reports 12, 1978-1985 (2015)). Especially, the combined inhibition of MEK/SHP2 has been identified to have potential to treat cancers driven by KRAS, the most frequently mutated oncogene. Despite years of efforts, inhibitors directly targeting KRAS has not yet been successfully developed for clinical use. Inhibiting MEK, the downstream effector of KRAS, only transiently suppressed MAPK signaling. The discovery of MEK/SHP2 dual inhibition makes important strides in the long-time effort to better understand and to therapeutically target KRAS-driven cancers.

Given the essential physiological functions SHP2 plays, targeting deregulation of SHP2 is expected to have broad therapeutic applications. Gain of function mutations in PTPN11, the gene that encodes SHP2, have been causally linked to several human diseases, including Noonan Syndrome, juvenile myelomonocytic leukemias, acute myeloid leukemia, myelodysplastic syndrome, and acute B lymphoblastic lymphoblastic leukemia. SHP2 functions as an oncogene, and its overexpression and/or activating mutations are reported in various solid tumors, such as neuroblastoma, breast cancer, colon cancer, lung cancer, melanoma, and hepatocellular carcinoma.

Furthermore, SHP-2 is believed to mediate inhibitory immune checkpoint signaling of multiple receptors (e.g. PD-1) by dephosphorylating CD28. To support this notion, a dominant negative SHP-2 abrogates PD-1 signaling pathways and restores function of cytotoxic CAR T cells. Therefore, SHP-2 inhibitors have potential for use in combination therapy with existing targeted and Immune-Oncolocy (IO) agents.

In addition to human tumors, increases in expression or activity of SHP2 have been implicated in the pathogenesis of autoimmune diseases such as systemic lupus erythematosus (Wang J et al. J Clin Invest. 2016 Jun. 1; 126(6):2077-92) and rheumatoid arthritis (see Stanford S. M et al. Arthritis Rheum. 2013 May; 65(5):1171-80; Maeshima K et al. JCI Insight. 2016 May 19; 1(7)). Recently, SHP2 has also been characterized as a molecular checkpoint for TGFβ-induced JAK2/STAT3 signaling, suggesting that SHP2 inhibition may offer therapeutic benefit for the treatment of fibrosis (see Zehender A et al. Nat Commun. 2018 Aug. 14; 9(1): 3259). Accordingly, SHP2 represents a highly attractive target for the development of novel therapies to treat various diseases.

SUMMARY

In a first aspect, provided is a compound of Formula (I):

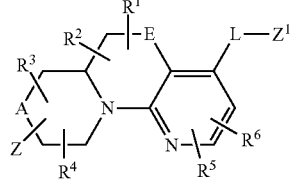

(I)

wherein:

A and E are independently selected from a bond, $CH_2$, O, NH, S, and $S(O)_2$;

Z is hydrogen, alkyl, halo, haloalkyl, haloalkoxy, cyano, cycloalkyl, heterocyclyl, heteroaryl (wherein cycloalkyl, heterocyclyl, and heteroaryl are optionally substituted with one to three halo), —O(alk)$_y$R$^a$, —O(alk)OR$^b$, —S(O)R$^c$, —S(O)$_2$R$^d$, —NR$^e$C(O)R$^f$, —NR$^g$SO$_2$R$^h$, —OC(O)NR$^i$R$^j$, —C(O)NR$^k$R$^m$, —S(O)$_2$NR$^n$R$^o$, —NR$^p$R$^q$, —NR$^r$C(O)C(O)R$^s$ or —Y-M (wherein Y is bond, O, or SO$_2$ and M is alkyl, haloalkyl, cycloalkyl, heterocyclyl, or heteroaryl wherein alkyl, haloalkyl, cycloalkyl, heterocyclyl and heteroaryl are substituted with —O(alk)$_y$R$^a$, —O(alk)OR$^b$, —S(O)R$^c$, —S(O)$_2$R$^d$, —NR$^e$C(O)R$^f$, —NR$^g$SO$_2$R$^h$, —OC(O)NR$^i$R$^j$, —C(O)NR$^k$R$^m$, —S(O)$_2$NR$^n$R$^o$, —NR$^p$R$^q$, or —NR$^r$C(O)C(O)R$^s$ and cycloalkyl, heterocyclyl, and heteroaryl are optionally further substituted with 1 to 3 halo); wherein each y is 0 or 1, each alk is alkylene, and each R$^c$, R$^d$, R$^f$, R$^h$, and R$^s$ are independently alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; and each R$^a$, R$^b$, R$^e$, R$^g$, R$^i$, R$^j$, R$^k$, R$^m$, R$^n$, R$^o$, R$^p$, R$^q$, R$^r$, and R$^s$ are independently hydrogen, alkyl, cycloalkyl, cycloalkylalkyl, hydroxyalkyl, alkoxyalkyl, aminoalkyl, optionally substituted heterocyclyl, optionally substituted heterocyclylalkyl, optionally substituted aryl, optionally substituted aralkyl, optionally substituted heteroaryl, or optionally substituted heteroaralkyl; or, independently of each other, each R$^i$ and R$^j$, R$^k$ and R$^m$, R$^n$ and R$^o$, and R$^p$ and R$^q$, together with the nitrogen atom to which they are attached form optionally substituted heterocyclyl;

R$^1$, R$^2$, R$^3$, and R$^4$ are independently selected from hydrogen, alkyl, cycloalkyl, halo, haloalkyl, haloalkoxy, alkoxy, cyano, hydroxy, hydroxylalkyl, amino, and aminoalkyl;

or one of R$^1$ and R$^2$, and R$^3$ and R$^4$, when attached to the same carbon, combine to form oxo, alkyldienyl, 3 to 6 membered cycloalkylene, or 4 to 6 membered optionally substituted heterocyclylene;

R$^5$ and R$^6$ are independently selected from hydrogen, alkyl, cycloalkyl, halo, haloalkyl, haloalkoxy, alkoxy, hydroxy, cyano, hydroxylalkyl, amino, and aminoalkyl, or one of R$^5$ and R$^6$ is optionally substituted heterocyclyl and the other of R$^5$ and R$^6$ is selected from hydrogen, alkyl, cycloalkyl, halo, haloalkyl, haloalkoxy, alkoxy, hydroxy, cyano, hydroxylalkyl, amino, and aminoalkyl;

L is bond, O, S, S(O), S(O)$_2$, or CR$^7$R$^8$ where R$^7$ and R$^8$ are independently hydrogen or alkyl;

Z$^1$ is a group of formula (a) or (b):

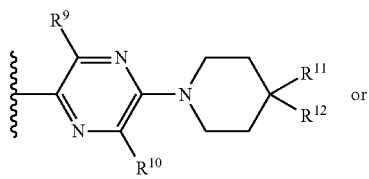

(a)

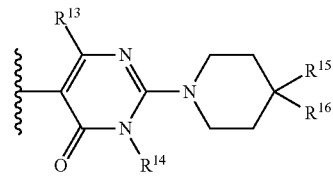

(b)

wherein:

R$^9$ is hydrogen, alkyl, halo, hydroxy, amino, or haloalkyl;

R$^{10}$ is hydrogen, alkyl, halo, hydroxy, hydroxyalkyl, —CD$_2$OH, alkylsulfoxide, alkylsulfonyl, amino, aminoalkyl, aminosulfonyl, aminocarbonyl, carboxy, cyano, or alkoxycarbonyl;

R$^{13}$ is hydrogen, alkyl, halo, hydroxy, amino, or haloalkyl;

R$^{14}$ is hydrogen, alkyl, or haloalkyl;

R$^{11}$ and R$^{15}$ are selected from amino and aminoalkyl;

R$^{12}$ and R$^{16}$ are selected from hydrogen, cyano, halo, alkyl, haloalkyl, alkoxy, haloalkoxy, cycloalkyl, aryl, heterocyclyl, and heteroaryl, where alkyl, cycloalkyl, aryl, heterocyclyl and heteroaryl are optionally substituted with one to three substituents independently selected from alkyl, halo, haloalkyl, haloalkoxy, alkoxy, and cyano;

or R$^{11}$ and R$^{12}$, and R$^{15}$ and R$^{16}$ together with the carbon atom to which they are attached form a ring of formula (c):

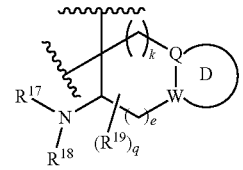

(c)

wherein:

e is 0, 1, or 2;

k is 0, 1, or 2 provided e+k is 1, 2, or 3;

q is 0, 1, or 2, or 3;

R$^{17}$ and R$^{18}$ are independently selected from hydrogen, alkyl, cycloalkyl, and haloalkyl;

each R$^{19}$ is independently selected from hydrogen, alkyl, halo, haloalkyl, haloalkoxy, alkoxy, hydroxy, cyano, alkylsulfoxide, alkylsulfonyl, oxo, cycloalkyl, optionally substituted heterocyclyl, and optionally substituted heteroaryl; or when two R$^{19}$ groups are attached to the same carbon atom, the two R$^{19}$ groups together with the carbon atom to which they are attached form cycloalkylene or heterocyclylene.

ring D is absent or present; wherein:
  (i) when ring D is absent, then one of Q and W is $CH_2$, O, S, S(O), S(O)$_2$, or NH; and the other of Q and W is $CH_2$; and
  (ii) when ring D is present, then Q and W are independently N or C provided only one of Q and W is N; and ring D is phenyl or a 5 or 6 membered heteroaryl ring which, including Q and W, contains one to three heteroatoms independently selected from N, O, and S and ring D is optionally substituted with one or two substituents independently selected from alkyl, cycloalkyl, halo, haloalkyl, alkoxy, haloalkoxy, hydroxy, hydroxyalkyl, cyano, amino, aminoalkyl, carboxy, and optionally substituted heterocyclyl; or a pharmaceutically acceptable salt thereof.

In a second aspect, provided is a compound of Formula (IA):

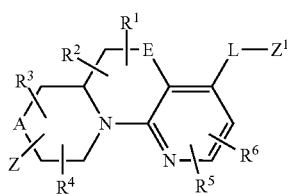

(IA)

wherein:

A and E are independently selected from a bond, CH$_2$, O, NH, S, and S(O)$_2$;

Z is hydrogen, alkyl, halo, haloalkyl, haloalkoxy, cyano, cycloalkyl, heterocyclyl, heteroaryl (wherein cycloalkyl, heterocyclyl, and heteroaryl are optionally substituted with one to three halo), —O(alk)$_y$R$^a$, —O(alk)OR$^b$, —S(O)R$^c$, —S(O)$_2$R$^d$, —NR$^e$C(O)R$^f$, —NR$^g$SO$_2$R$^h$, —OC(O)NR$^i$R$^j$, —C(O)NR$^k$R$^m$, —S(O)$_2$NR$^n$R$^o$, —NR$^p$R$^q$, —NR$^r$C(O)C(O)R$^s$ or —Y-M (wherein Y is bond, O, or SO$_2$ and M is alkyl, haloalkyl, cycloalkyl, heterocyclyl, or heteroaryl wherein alkyl, haloalkyl, cycloalkyl, heterocyclyl and heteroaryl are substituted with —O(alk)$_y$R$^a$, —O(alk)OR$^b$, —S(O)R$^c$, —S(O)$_2$R$^d$, —NR$^e$C(O)R$^f$, —NR$^g$SO$_2$R$^h$, —OC(O)NR$^i$R$^j$, —C(O)NR$^k$R$^m$, —S(O)$_2$NR$^n$R$^o$, —NR$^p$R$^q$, or —NR$^r$C(O)C(O)R$^s$ and cycloalkyl, heterocyclyl, and heteroaryl are optionally further substituted with 1 to 3 halo); wherein each y is 0 or 1, each alk is alkylene, and each R$^c$, R$^d$, R$^f$, R$^h$, and R$^s$ are independently alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; and each R$^a$, R$^b$, R$^e$, R$^g$, R$^i$, R$^j$, R$^k$, R$^m$, R$^n$, R$^o$, R$^p$, R$^q$, R$^r$, and R$^s$ are independently hydrogen, alkyl, cycloalkyl, cycloalkylalkyl, hydroxyalkyl, alkoxyalkyl, aminoalkyl, optionally substituted heterocyclyl, optionally substituted heterocyclylalkyl, optionally substituted aryl, optionally substituted aralkyl, optionally substituted heteroaryl, or optionally substituted heteroaralkyl; or, independently of each other, each R$^i$ and R$^j$, R$^k$ and R$^m$, R$^n$ and R$^o$, and R$^p$ and R$^q$, together with the nitrogen atom to which they are attached form optionally substituted heterocyclyl;

R$^1$, R$^2$, R$^3$, and R$^4$ are independently selected from hydrogen, alkyl, cycloalkyl, halo, haloalkyl, haloalkoxy, alkoxy, cyano, hydroxy, hydroxyalkyl, amino, and aminoalkyl;

or one of R$^1$ and R$^2$, and R$^3$ and R$^4$, when attached to the same carbon, combine to form oxo, alkyldienyl, 3 to 6 membered cycloalkylene, or 4 to 6 membered optionally substituted heterocyclylene;

R$^5$ and R$^6$ are independently selected from hydrogen, alkyl, cycloalkyl, halo, haloalkyl, haloalkoxy, alkoxy, hydroxy, cyano, hydroxyalkyl, amino, and aminoalkyl, or wherein one of R$^5$ and R$^6$ is optionally substituted heterocyclyl and the other of R$^5$ and R$^6$ is selected from hydrogen, alkyl, cycloalkyl, halo, haloalkyl, haloalkoxy, alkoxy, hydroxy, cyano, hydroxyalkyl, amino, and aminoalkyl;

L is bond, O, S, S(O), S(O)$_2$, or CR$^7$R$^8$ where R$^7$ and R$^8$ are independently hydrogen or alkyl;

Z$^1$ is a group of formula (a) or (b):

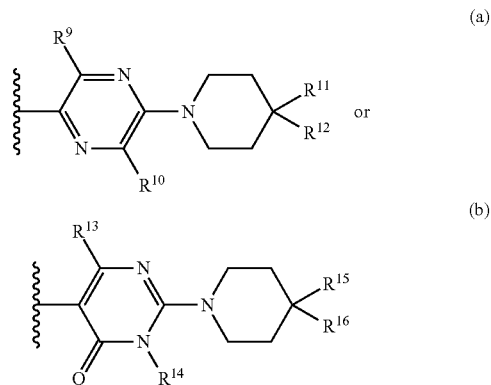

wherein:

R$^9$ is hydrogen, alkyl, halo, hydroxy, amino, or haloalkyl;

R$^{10}$ is hydrogen, alkyl, halo, hydroxy, hydroxyalkyl, —CD$_2$OH, alkylsulfoxide, alkylsulfonyl, amino, aminoalkyl, aminosulfonyl, aminocarbonyl, carboxy, cyano, or alkoxycarbonyl;

R$^{13}$ is hydrogen, alkyl, halo, hydroxy, amino, or haloalkyl;

R$^{14}$ is hydrogen, alkyl, or haloalkyl;

R$^{11}$ and R$^{15}$ are selected from amino and aminoalkyl;

R$^{12}$ and R$^{16}$ are selected from hydrogen, cyano, halo, alkyl, haloalkyl, alkoxy, haloalkoxy, cycloalkyl, aryl, heterocyclyl, and heteroaryl, where alkyl, cycloalkyl, aryl, heterocyclyl and heteroaryl are optionally substituted with one to three substituents independently selected from alkyl, halo, haloalkyl, haloalkoxy, alkoxy, and cyano;

or R$^{11}$ and R$^{12}$, and R$^{15}$ and R$^{16}$ together with the carbon atom to which they are attached form a ring of formula (c):

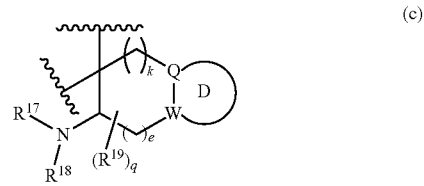

wherein:

e is 0, 1, or 2;

k is 0, 1, or 2 provided e+k is 1, 2, or 3;

q is 0, 1, or 2, or 3;

R$^{17}$ and R$^{18}$ are independently selected from hydrogen, alkyl, cycloalkyl and haloalkyl, each R$^{19}$ is independently selected from hydrogen, alkyl, halo, haloalkyl, haloalkoxy, alkoxy, hydroxy, cyano, alkylsulfoxide, alkylsulfonyl, oxo, cycloalkyl, optionally substituted heterocyclyl, and optionally substituted heteroaryl; or when two R$^{19}$ groups are attached to the same carbon atom, the two R$^{19}$ groups together with the carbon atom to which they are attached form cycloalkylene or heterocyclylene.

ring D is absent or present; wherein:
(i) when ring D is absent, then one of Q and W is $CH_2$, O, S, S(O), $S(O)_2$, or NH; and the other of Q and W is $CH_2$; and
(ii) when ring D is present, then Q and W are independently N or C provided only one of Q and W is N; and ring D is phenyl or a 5 or 6 membered heteroaryl ring which, including Q and W, contains one to three heteroatoms independently selected from N, O, and S and ring D is optionally substituted with one or two substituents independently selected from alkyl, cycloalkyl, halo, haloalkyl, alkoxy, haloalkoxy, hydroxy, hydroxyalkyl, cyano, amino, aminoalkyl, carboxy, and optionally substituted heterocyclyl;

or a pharmaceutically acceptable salt thereof; provided that when the compound of Formula (I), or a pharmaceutically acceptable salt thereof, is a compound of formula

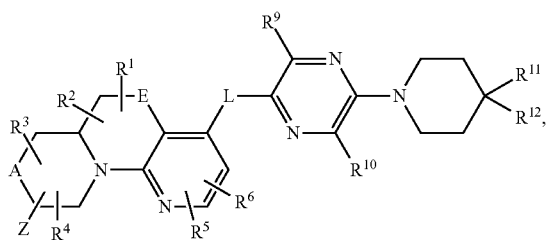

or a pharmaceutically acceptable salt thereof, where $R^9$ is hydrogen, $R^{10}$ is other than hydrogen, amino, and aminoalkyl, and L, $R^{11}$ and $R^{12}$ are as defined in Formula (I); then:

(i) when four of $R^1$, $R^2$, $R^3$, $R^4$, $R^5$, and $R^6$ are hydrogen and remaining two of $R^1$, $R^2$, $R^3$, $R^4$, $R^5$, and $R^6$, are independently selected from hydrogen, alkyl, cycloalkyl, amino, halo, haloalkyl, alkoxy, haloalkoxy, hydroxy, hydroxyalkyl, cyano, and aminoalkyl; then Z is other than hydrogen, alkyl, halo, haloalkyl, haloalkoxy, cyano, —$OR^a$ (where $R^a$ is hydrogen or alkyl), —$OC(O)NH_2$, —O-tetrahydrofuran-3-yl, —O-oxetan-3-yl, cyano, pyrazol-1-yl, —$CH_2OCH_3$, —$OCH_2OCH_3$, —$OCH_2$cyclopropyl, —O—$CH_2CH_2OCH_3$, and —$SO_2CH_3$, (ii) when R and $R^6$ are hydrogen and two of $R^1$, $R^2$, $R^3$, and $R^4$ are hydrogen, and one of a) $R^1$ and $R^2$ and b) $R^3$ and $R^4$, are hydrogen and the other of a) $R^1$ and $R^2$, and b) $R^3$ and $R^4$ are attached to the same carbon and are combined together to form alkylidene, 3 to 6 membered cycloalkylene or 4 to 6 membered heterocyclylene, then Z is other than hydrogen, alkyl, halo, haloalkyl, haloalkoxy, cyano, cycloalkyl, —$OR^a$ (where $R^a$ is hydrogen or alkyl), —$NH_2$, and —Y-M (wherein Y is bond and M is alkyl substituted with —$OR^a$ or —$NR^pR^q$ wherein each $R^a$ is hydrogen or alkyl and $R^p$ and $R^q$ are independently hydrogen, alkyl, hydroxyalkyl or alkoxyalkyl or $R^p$ and $R^q$ together with the nitrogen atom to which they are attached form optionally substituted heterocyclyl); and (iii) when Z is hydrogen, one of a) $R^1$ and $R^2$, and b) $R^3$ and $R^4$ are attached to the same carbon and are combined together to form 3 to 6 membered cycloalkylene or 4 to 6 membered heterocyclylene, and three of the remaining $R^1$, $R^2$, $R^3$, $R^4$, $R^5$, and $R^6$ are hydrogen, then the remaining one of $R^1$, $R^2$, $R^3$, $R^4$, $R^5$, and $R^6$ is not hydrogen, alkyl, cycloalkyl, halo, haloalkyl, cyano, hydroxy, alkoxy, haloalkoxy, hydroxyalkyl, aminoalkyl, or amino.

In a third aspect provided is a compound of Formula (IB):

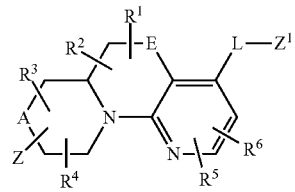

(IB)

wherein:

A and E are independently selected from a bond, $CH_2$, O, NH, S, and $S(O)_2$;

Z is hydrogen, alkyl, haloalkyl, cyano, cycloalkyl, heterocyclyl, heteroaryl (wherein cycloalkyl, heterocyclyl, and heteroaryl are optionally substituted with one to three halo), —$O(alk)_yR^a$, —$O(alk)OR^b$, —$S(O)R^c$, —$S(O)_2R^d$, —$NR^eC(O)R^f$, —$NR^gSO_2R^h$, —$OC(O)NR^iR^j$, —$C(O)NR^kR^m$, —$S(O)_2NR^nR^o$, —$NR^pR^q$, —$NR^rC(O)C(O)R^s$ or —Y-M (wherein Y is bond, O, or $SO_2$ and M is alkyl, haloalkyl, cycloalkyl, heterocyclyl, or heteroaryl wherein alkyl, haloalkyl, cycloalkyl, heterocyclyl and heteroaryl are substituted with —$O(alk)_yR^a$, —$O(alk)OR^b$, —$S(O)R^c$, —$S(O)_2R^d$, —$NR^eC(O)R^f$, —$NR^gSO_2R^h$, —$OC(O)NR^iR^j$, —$C(O)NR^kR^m$, —$S(O)_2NR^nR^o$, —$NR^pR^q$, or —$NR^rC(O)C(O)R^s$ and cycloalkyl, heterocyclyl, and heteroaryl are optionally further substituted with 1 to 3 halo); wherein each y is 0 or 1, each alk is alkylene, and each $R^c$, $R^d$, $R^f$, $R^h$, and $R^s$ are independently alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; and each $R^a$, $R^b$, $R^e$, $R^g$, $R^i$, $R^j$, $R^k$, $R^m$, $R^n$, $R^o$, $R^p$, $R^q$, $R^r$, and $R^s$ are independently hydrogen, alkyl, cycloalkyl, cycloalkylalkyl, hydroxyalkyl, alkoxyalkyl, aminoalkyl, optionally substituted heterocyclyl, optionally substituted heterocyclylalkyl, optionally substituted aryl, optionally substituted aralkyl, optionally substituted heteroaryl, or optionally substituted heteroaralkyl; or, independently of each other, each $R^i$ and $R^j$, $R^k$ and $R^m$, $R^n$ and $R^o$, and $R^p$ and $R^q$, together with the nitrogen atom to which they are attached form optionally substituted heterocyclyl;

$R^1$, $R^2$, $R^3$, and $R^4$ are independently selected from hydrogen, alkyl, cycloalkyl, halo, haloalkyl, haloalkoxy, alkoxy, cyano, hydroxy, hydroxylalkyl, amino, and aminoalkyl;

or one of $R^1$ and $R^2$ and $R^3$ and $R^4$, when attached to the same carbon, combine to form oxo, alkyldienyl, 3 to 6 membered cycloalkylene, or 4 to 6 membered optionally substituted heterocyclylene;

$R^5$ and $R^6$ are independently selected from hydrogen, alkyl, cycloalkyl, halo, haloalkyl, haloalkoxy, alkoxy, hydroxy, cyano, hydroxylalkyl, amino, and aminoalkyl, or wherein one of $R^5$ and $R^6$ is optionally substituted heterocyclyl and the other of $R^5$ and $R^6$ is selected from hydrogen, alkyl, cycloalkyl, halo, haloalkyl, haloalkoxy, alkoxy, hydroxy, cyano, hydroxylalkyl, amino, and aminoalkyl;

L is bond, O, S, S(O), $S(O)_2$, or $CR^7R^8$ where $R^7$ and $R^8$ are independently hydrogen or alkyl;

$Z^1$ is a group of formula (a) or (b):

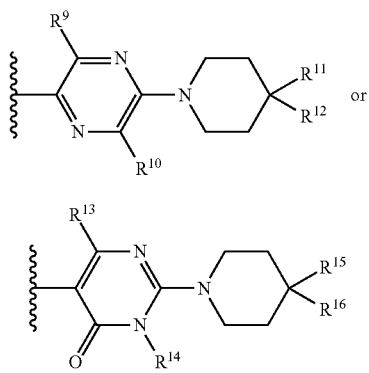

wherein:
$R^9$ is hydrogen, alkyl, halo, hydroxy, amino, or haloalkyl;
$R^{10}$ is hydrogen, alkyl, halo, hydroxy, hydroxyalkyl, —CD$_2$OH, alkylsulfoxide, alkylsulfonyl, amino, aminoalkyl, aminosulfonyl, aminocarbonyl, carboxy, cyano, or alkoxycarbonyl;
$R^{13}$ is hydrogen, alkyl, halo, hydroxy, amino, or haloalkyl;
$R^{14}$ is hydrogen, alkyl, or haloalkyl;
$R^{11}$ and $R^{15}$ are selected from amino and aminoalkyl;
$R^{12}$ and $R^{16}$ are selected from hydrogen, cyano, halo, alkyl, haloalkyl, alkoxy, haloalkoxy, cycloalkyl, aryl, heterocyclyl, and heteroaryl, where alkyl, cycloalkyl, aryl, heterocyclyl and heteroaryl are optionally substituted with one to three substituents independently selected from alkyl, halo, haloalkyl, haloalkoxy, alkoxy, and cyano;
or $R^{11}$ and $R^{12}$, and $R^{15}$ and $R^{16}$ together with the carbon atom to which they are attached form a ring of formula (c):

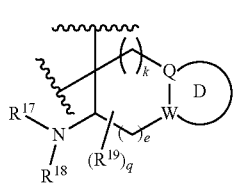

wherein:
e is 0, 1, or 2;
k is 0, 1, or 2 provided e+k is 1, 2, or 3;
q is 0, 1, 2, or 3;
$R^{17}$ and $R^{18}$ are independently selected from hydrogen, alkyl, cycloalkyl and haloalkyl,
each $R^{19}$ is independently selected from hydrogen, alkyl, halo, haloalkyl, haloalkoxy, alkoxy, hydroxy, cyano, alkylsulfoxide, alkylsulfonyl, oxo, cycloalkyl, optionally substituted heterocyclyl, and optionally substituted heteroaryl; or
when two $R^{19}$ groups are attached to the same carbon atom, the two $R^{19}$ groups together with the carbon atom to which they are attached form cycloalkylene or heterocyclylene.
ring D is absent or present; wherein:
(i) when ring D is absent, then one of Q and W is CH$_2$, O, S, S(O), S(O)$_2$, or NH; and the other of Q and W is CH$_2$; and (ii) when ring D is present, then Q and W are independently N or C provided only one of Q and W is N; and ring D is phenyl or a 5 or 6 membered heteroaryl ring which, including Q and W, contains one to three heteroatoms independently selected from N, O, and S and ring D is optionally be substituted with one or two substituents independently selected from alkyl, cycloalkyl, halo, haloalkyl, alkoxy, haloalkoxy, hydroxy, hydroxyalkyl, cyano, amino, aminoalkyl, carboxy, and optionally substituted heterocyclyl;
or a pharmaceutically acceptable salt thereof; provided that when the compound of Formula (I), or a pharmaceutically acceptable salt thereof, is a compound of formula

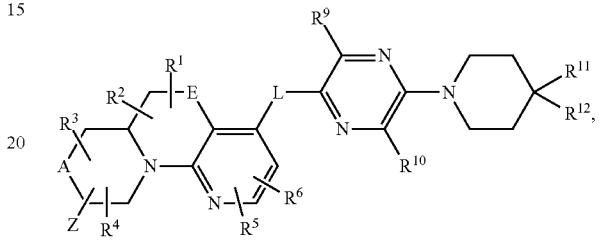

or a pharmaceutically acceptable salt thereof, where $R^9$ is hydrogen, $R^{10}$ is other than hydrogen, amino, and aminoalkyl, and L, $R^{11}$ and $R^{12}$ are as defined in Formula (IB); then
(i) when four of $R^1$, $R^2$, $R^3$, $R^4$, $R^5$, and $R^6$ are hydrogen and remaining two of $R^1$, $R^2$, $R^3$, $R^4$, $R^5$, and $R^6$ are independently selected from hydrogen, alkyl, cycloalkyl, halo, haloalkyl, alkoxy, haloalkoxy, hydroxy, hydroxyalkyl, cyano, amino, and aminoalkyl; then Z is other than hydrogen, halo, alkyl, haloalkyl, cyano, cycloalkyl, heterocyclyl, heteroaryl (wherein cycloalkyl, heterocyclyl, and heteroaryl are optionally substituted with one to three halo), —OR$^a$, —S(O)R$^c$, —S(O)$_2$R$^d$, —NR$^e$C(O)R$^f$, —NR$^g$SO$_2$R$^h$, —OC(O)NR$^i$R$^j$, —C(O)NR$^k$R$^m$, —S(O)$_2$NR$^n$R$^o$, —NR$^p$R$^q$, —NR$^r$C(O)C(O)R$^s$ (wherein R$^c$, R$^d$, R$^f$, R$^h$, and R$^s$ are independently alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; and R$^a$, R$^e$, R$^g$, R$^i$, Rj, R$^k$, R$^m$, R$^n$, R$^o$, R$^p$, R$^q$, and Rare independently hydrogen, alkyl, cycloalkylalkyl, hydroxyalkyl, alkoxyalkyl, aminoalkyl, optionally substituted heterocyclyl, optionally substituted heterocyclylalkyl, optionally substituted aryl, optionally substituted aralkyl, optionally substituted heteroaryl, or optionally substituted heteroaralkyl; or, independently of each other, each R$^i$ and R$^j$, R$^k$ and R$^m$, R$^n$ and R$^o$, and R$^p$ and R$^q$, together with the nitrogen atom to which they are attached form optionally substituted heterocyclyl) and Y-M (wherein (a) Y is bond or O and M is alkyl substituted with —OR$^a$ or —NR$^p$R$^q$ wherein R$^a$ is hydrogen or alkyl and R$^p$ and R$^q$ are independently hydrogen, alkyl, hydroxyalkyl or alkoxyalkyl or R$^p$ and R$^q$ together with the nitrogen atom to which they are attached form optionally substituted heterocyclyl and (b) Y is SO$_2$ and M is cycloalkyl (substituted with —OR$^a$), heteroaryl or heterocyclyl wherein heteroaryl or heterocyclyl are independently substituted with —OR$^a$, —S(O)$_2$R$^d$, or —NR$^p$R$^q$; where R$^a$ is hydrogen or alkyl, R$^d$ is alkyl, and R$^p$ and R$^q$ are independently hydrogen or alkyl and cycloalkyl is optionally further substituted with one halo and heterocyclyl, and heteroaryl are optionally further substituted with 1 or 2 halo);
(ii) when $R^5$ and $R^6$ are each hydrogen and two of $R^1$, $R^2$, $R^3$, and $R^4$ are each hydrogen, and one of a) $R^1$ and $R^2$, and b) R³ and R⁴ are hydrogen and the other of a) R¹ and R², and b) R³ and R⁴ are attached to the same carbon and are combined together to form alkylidene, 3 to 6 membered cycloalkylene or 4 to 6 membered heterocyclylene, then Z is other than hydrogen, alkyl, halo, haloalkyl, cyano, cycloalkyl, —OR$^a$ (wherein R$^a$ is hydrogen or alkyl), —NH$_2$, and —Y-M (wherein Y is bond and M is alkyl substituted with —OR$^a$ or —NR$^p$R$^q$ wherein each R$^a$ is hydrogen or alkyl and R$^p$ and R$^q$ are independently hydrogen, alkyl, hydroxyalkyl or alkoxyalkyl or R$^p$ and R$^q$ together with the nitrogen atom to which they are attached form optionally substituted heterocyclyl); and (iii) when Z is hydrogen, one of a) R¹ and R², and b) R³ and R⁴ are attached to the same carbon and are combined together to form 3 to 6 membered cycloalkylene or 4 to 6 membered heterocyclylene and three of the remaining R¹, R², R³, R⁴, R⁵, and R⁶ are hydrogen, then the remaining one of R¹, R², R³, R⁴, R⁵, and R⁶ is not hydrogen, alkyl, halo, haloalkyl, cyano, cycloalkyl, hydroxy, alkoxy, haloalkoxy, hydroxyalkyl, aminoalkyl, or amino.

In a fourth aspect, provided is a compound of Formula (IC):

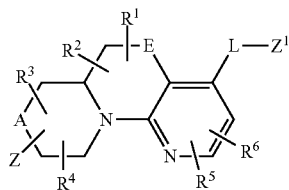

(IC)

wherein:

A and E are independently selected from a bond, CH$_2$, O, NH, S, and S(O)$_2$;

Z is hydrogen, alkyl, halo, haloalkyl, haloalkoxy, cyano, cycloalkyl, heterocyclyl, heteroaryl (wherein cycloalkyl, heterocyclyl, and heteroaryl are optionally substituted with one to three halo), —O(alk)$_y$R$^a$, —O(alk)OR$^b$, —S(O)R$^c$, —S(O)$_2$R$^d$, —NR$^e$C(O)R$^f$, —NR$^g$SO$_2$R$^h$, —OC(O)NR$^i$R$^j$, —C(O)NR$^k$R$^m$, —S(O)$_2$NR$^n$R$^o$, —NR$^p$R$^q$, —NR$^r$C(O)C(O)R$^s$ or —Y-M (wherein Y is bond, O, or SO$_2$ and M is alkyl, haloalkyl, cycloalkyl, heterocyclyl, or heteroaryl wherein alkyl, haloalkyl, cycloalkyl, heterocyclyl and heteroaryl are substituted with —O(alk)$_y$R$^a$, —O(alk)OR$^b$, —S(O)R$^c$, —S(O)$_2$R$^d$, —NR$^e$C(O)R$^f$, —NR$^g$SO$_2$R$^h$, —OC(O)NR$^i$R$^j$, —C(O)NR$^k$R$^m$, —S(O)$_2$NR$^n$R$^o$, —NR$^p$R$^q$, or —NR$^r$C(O)C(O)R$^s$ and cycloalkyl, heterocyclyl, and heteroaryl are optionally further substituted with 1 to 3 halo); wherein each y is 0 or 1, each alk is alkylene, and each R$^e$, R$^d$, R$^f$, R$^h$, and R$^s$ are independently alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; and each R$^a$, R$^b$, R$^e$, R$^g$, R$^i$, R$^j$, R$^k$, R$^m$, R$^n$, R$^o$, R$^p$, R$^q$, R$^r$, and R$^s$ are independently hydrogen, alkyl, cycloalkyl, cycloalkylalkyl, hydroxyalkyl, alkoxyalkyl, aminoalkyl, optionally substituted heterocyclyl, optionally substituted heterocyclylalkyl, optionally substituted aryl, optionally substituted aralkyl, optionally substituted heteroaryl, or optionally substituted heteroaralkyl; or, independently of each other, each R$^i$ and R$^j$, R$^k$ and R$^m$, R$^n$ and R$^o$, and R$^p$ and R$^q$, together with the nitrogen atom to which they are attached form optionally substituted heterocyclyl;

R¹, R², R³, and R⁴ are independently selected from hydrogen, alkyl, cycloalkyl, halo, haloalkyl, haloalkoxy, alkoxy, cyano, hydroxy, hydroxylalkyl, amino, and aminoalkyl;

or one of R¹ and R², and R³ and R⁴, when attached to the same carbon, combine to form oxo, alkyldienyl, 3 to 6 membered cycloalkylene, or 4 to 6 membered optionally substituted heterocyclylene;

R⁵ and R⁶ are independently selected from hydrogen, alkyl, cycloalkyl, halo, haloalkyl, haloalkoxy, alkoxy, hydroxy, cyano, hydroxylalkyl, amino, and aminoalkyl, or wherein one of R⁵ and R⁶ is optionally substituted heterocyclyl and the other is selected from hydrogen, alkyl, cycloalkyl, halo, haloalkyl, haloalkoxy, alkoxy, hydroxy, cyano, hydroxylalkyl, amino, and aminoalkyl;

L is bond, O, S, S(O), S(O)$_2$, or CR⁷R⁸ where R⁷ and R⁸ are independently hydrogen or alkyl;

Z¹ is a group of formula (a) or (b):

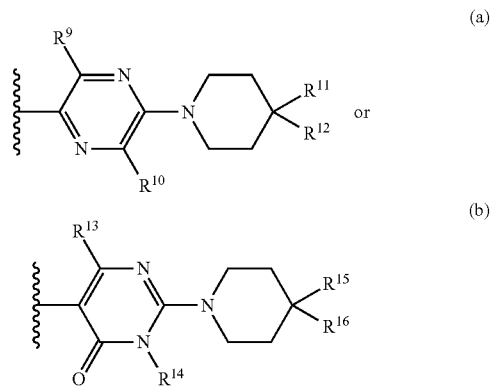

wherein:

R⁹ is hydrogen, alkyl, halo, hydroxy, amino, or haloalkyl;

R¹⁰ is hydrogen, alkyl, halo, hydroxy, hydroxyalkyl, —CD$_2$OH, alkylsulfoxide, alkylsulfonyl, amino, aminoalkyl, aminosulfonyl, aminocarbonyl, carboxy, cyano, or alkoxycarbonyl;

R¹³ is hydrogen, alkyl, halo, hydroxy, amino, or haloalkyl;

R¹⁴ is hydrogen, alkyl, or haloalkyl;

R¹¹ and R¹⁵ are selected from amino and aminoalkyl;

R¹² and R¹⁶ are selected from hydrogen, cyano, halo, alkyl, haloalkyl, alkoxy, haloalkoxy, cycloalkyl, aryl, heterocyclyl, and heteroaryl, where alkyl, cycloalkyl, aryl, heterocyclyl and heteroaryl are optionally substituted with one to three substituents independently selected from alkyl, halo, haloalkyl, haloalkoxy, alkoxy, and cyano;

or R¹¹ and R¹², and R¹⁵ and R¹⁶ together with the carbon atom to which they are attached form a ring of formula (c):

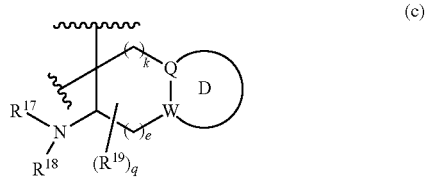

wherein:
e is 0, 1, or 2;
k is 0, 1, or 2 provided e+k is 1, 2, or 3;
q is 0, 1, or 2, or 3;
$R^{17}$ and $R^{18}$ are independently selected from hydrogen, alkyl, cycloalkyl, and haloalkyl;
each $R^{19}$ is independently selected from hydrogen, alkyl, halo, haloalkyl, haloalkoxy, alkoxy, hydroxy, cyano, alkylsulfoxide, alkylsulfonyl, oxo, cycloalkyl, optionally substituted heterocyclyl, and optionally substituted heteroaryl; or
when two $R^{19}$ groups are attached to the same carbon atom, the two $R^{19}$ groups together with the carbon atom to which they are attached form cycloalkylene or heterocyclylene.
ring D is absent or present; wherein:
(i) when ring D is absent, then one of Q and W is $CH_2$, O, S, S(O), $S(O)_2$, or NH; and the other of Q and W is $CH_2$; and
(ii) when ring D is present, then Q and W are independently N or C provided only one of Q and W is N; and ring D is phenyl or a 5 or 6 membered heteroaryl ring which, including Q and W, contains one to three heteroatoms independently selected from N, O, and S and ring D is optionally substituted with one or two substituents independently selected from alkyl, cycloalkyl, halo, haloalkyl, alkoxy, haloalkoxy, hydroxy, hydroxyalkyl, cyano, amino, aminoalkyl, carboxy, and optionally substituted heterocyclyl; or a pharmaceutically acceptable salt thereof; provided that the compound of Formula (IC) is not a compound of any one of embodiments 37 to 42 and 45 to 63 disclosed herein below and embodiments contained therein, or a pharmaceutically acceptable salt thereof.

In a fifth aspect, provided a pharmaceutical composition comprising a compound of Formula (I), (IA), (IB), or (IC) (or any of the embodiments thereof described herein), or a pharmaceutically acceptable salt thereof; and a pharmaceutically acceptable excipient.

In a sixth aspect, provided is a method of treating a disease treatable by inhibition of SHP2 in a patient which method comprises administering to the patient, preferably a patient in need of such treatment, a therapeutically effective amount thereof a compound of Formula (I), (IA), (IB), or (IC) (or any of the embodiments thereof described herein), or comprises administering to the patient, preferably a patient in of such treatment, a pharmaceutical composition comprising a compound of Formula (I), (IA), (IB), or (IC) (or any of the embodiments thereof described herein) and a pharmaceutically acceptable excipient. In one embodiment, the disease is cancer. In another embodiment, the disease is cancer selected from lung, stomach, liver, colon, kidney, breast, pancreatitis, juvenile myelomonocytic leukemias, neurolastoma, melanoma, and acute myeloid leukemia. In one embodiment, the disease is selected from Noonan syndrome and Leopard syndrome.

In a seventh aspect, provided is a compound of Formula (I), (IA), (IB), or (IC) (or any embodiments thereof described herein) or a pharmaceutically acceptable salt thereof for use as a medicament.

In a eighth aspect provided is the use of a compound of Formula (I), (IA), (IB), or (IC) or a pharmaceutically acceptable salt thereof (and any embodiments thereof disclosed herein) in the manufacture of a medicament for treating a disease in a patient in need of such treatment in which the activity of SHP2 contributes to the pathology and/or symptoms of the disease.

In a ninth aspect provided is a method of inhibiting SHP2 which method comprises contacting SHP2 with a compound of Formula (I), (IA), (IB), or (IC) (or any of the embodiments thereof described herein) or a pharmaceutically acceptable salt thereof; or contacting SHP2 with a pharmaceutical composition comprising a compound of the present disclosure (or any of the embodiments thereof described herein) or a pharmaceutically acceptable salt thereof, and a pharmaceutically acceptable excipient.

In a tenth aspect, provided is an intermediate of Formula (V):

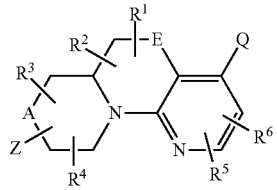

wherein:
Q is halo or SH;
A and E are independently selected from a bond, $CH_2$, O, NH, S, and $S(O)_2$;
Z is hydrogen, alkyl, halo, haloalkyl, haloalkoxy, cyano, cycloalkyl, heterocyclyl, heteroaryl (wherein cycloalkyl, heterocyclyl, and heteroaryl are optionally substituted with one to three halo), $-O(alk)_yR^a$, $-O(alk)OR^b$, $-S(O)R^c$, $-S(O)_2R^d$, $-NR^eC(O)R^f$, $-NR^gSO_2R^h$, $-OC(O)NR^iR^j$, $-C(O)NR^kR^m$, $-S(O)_2NR^nR^o$, $-NR^pR^q$, $-NR^rC(O)C(O)R^s$ or $-Y-M$ (wherein Y is bond, O, or $SO_2$ and M is alkyl, haloalkyl, cycloalkyl, heterocyclyl, or heteroaryl wherein alkyl, haloalkyl, cycloalkyl, heterocyclyl and heteroaryl are substituted with $-O(alk)_yR^a$, $-O(alk)_yOR^b$, $-S(O)R^c$, $-S(O)_2R^d$, $-NR^eC(O)R^f$, $-NR^gSO_2R^h$, $-OC(O)NR^iR^j$, $-C(O)NR^kR^m$, $-S(O)_2NR^nR^o$, $-NR^pR^q$, or $-NR^rC(O)C(O)R^s$ and cycloalkyl, heterocyclyl, and heteroaryl are optionally further substituted with 1 to 3 halo); wherein each y is 0 or 1, each alk is alkylene, and each $R^c$, $R^d$, $R^f$, $R^h$, and $R^s$ are independently alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; and each $R^a$, $R^b$, $R^e$, $R^g$, $R^i$, $R^j$, $R^k$, $R^m$, $R^n$, $R^o$, $R^p$, $R^q$, $R^r$, and $R^s$ are independently hydrogen, alkyl, cycloalkyl, cycloalkylalkyl, hydroxyalkyl, alkoxyalkyl, aminoalkyl, optionally substituted heterocyclyl, optionally substituted heterocyclylalkyl, optionally substituted aryl, optionally substituted aralkyl, optionally substituted heteroaryl, or optionally substituted heteroaralkyl; or, independently of each other, each $R^i$ and $R^j$, $R^k$ and $R^m$, $R^n$ and $R^o$, and $R^p$ and $R^q$, together with the nitrogen atom to which they are attached form optionally substituted heterocyclyl;

$R^1$, $R^2$, $R^3$, and $R^4$ are independently selected from hydrogen, alkyl, cycloalkyl, halo, haloalkyl, haloalkoxy, alkoxy, cyano, hydroxy, hydroxyalkyl, amino, and aminoalkyl;
or one of $R^1$ and $R^2$, and $R^3$ and $R^4$, when attached to the same carbon, combine to form oxo, alkyldienyl, 3 to 6 membered cycloalkylene, or 4 to 6 membered optionally substituted heterocyclylene;
$R^5$ and $R^6$ are independently selected from hydrogen, alkyl, cycloalkyl, halo, haloalkyl, haloalkoxy, alkoxy, hydroxy, cyano, hydroxylalkyl, amino, and aminoalkyl, or wherein one of $R^5$ and $R^6$ is optionally substituted heterocyclyl and the other of $R^5$ and $R^6$ is selected from hydrogen, alkyl, cycloalkyl, halo, haloalkyl, haloalkoxy, alkoxy, hydroxy, cyano, hydroxylalkyl, amino, and aminoalkyl;

or an acceptable salt thereof.

In a first embodiment of the tenth aspect, Q is halo. In a subembodiment of the first embodiment, Q is chloro, bromo, or iodo.

In a second embodiment of the tenth aspect, Q is —S⁻M⁺ where M⁺ metal ion. In a subembodiment of the second embodiment, M⁺ is sodium or potassium.

In a third embodiment of any one of tenth aspect, first and second embodiments and subembodiments contained therein,

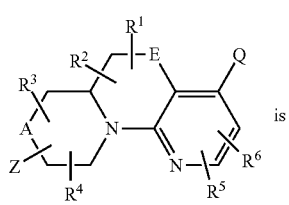

is

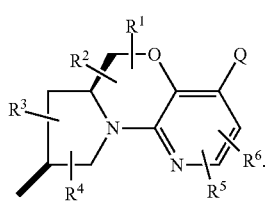

In a fourth embodiment of any one of tenth aspect, first, second, and third embodiments and subembodiments contained therein, A, E, Z, R, $R^2$, $R^3$, $R^4$ $R^5$, and $R^6$ are as defined in the embodiment section herein below.

DETAILED DESCRIPTION

Certain structures provided herein are drawn with one or more floating substituents. Unless provided otherwise or otherwise clear from the context, the substituent(s) may be present on any atom of the ring to which it is attached, where chemically feasible and valency rules permitting. For example, in the structure:

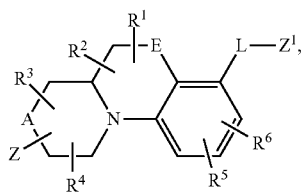

the $R^3$, $R^4$, and Z substituents can replace any hydrogen on the 6-membered ring which comprises group A, including one or both of the hydrogens of the $CH_2$ group when A is $CH_2$, and including the hydrogen of NH when A is NH. In another example, in the ring of formula (c):

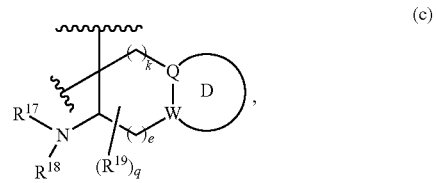

when ring D is absent and Q and/or W is $CH_2$, one or both of the hydrogens are optionally replaced by one or two $R^{19}$ groups.

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like. It will be recognized by a person skilled in the art that the term "alkyl" may include "alkylene" groups.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkenyl" means a linear monovalent hydrocarbon radical of two to six carbon atoms or a branched monovalent hydrocarbon radical of three to six carbon atoms containing a double bond, e.g., propenyl, butenyl, and the like.

"Alkyldienyl" is alkenyl as defined above that is attached via the terminal divalent carbon. For example, in the compound below:

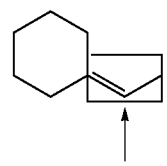

the alkyldienyl group is enclosed by the box which is indicated by the arrow.

"Alkylthio" means a —SR radical where R is alkyl as defined above, e.g., methylthio, ethylthio, and the like.

"Alkylsulfonyl" means a —$SO_2R$ radical where R is alkyl as defined above, e.g., methylsulfonyl, ethylsulfonyl, and the like.

"Alkylsulfoxide" means a —SOR radical where R is alkyl as defined above, e.g., methylsulfoxide, ethylsulfoxide, and the like.

"Amino" means a —$NH_2$.

"Alkylamino" means a —NHR radical where R is alkyl as defined above, e.g., methylamino, ethylamino, propylamino, or 2-propylamino, and the like.

"Acylamino" means a —NHC(O)R radical where R is alkyl as defined above, e.g., acetylamino, propionoylamino, and the like.

"Aminoalkyl" means a linear monovalent hydrocarbon radical of one to six carbon atoms or a branched monovalent hydrocarbon radical of three to six carbons substituted with —NR'R" where R' and R" are independently hydrogen, alkyl, haloalkyl, hydroxyalkyl, or alkoxyalkyl, or R' and R" together with the nitrogen atom to which they are attached form optionally substituted heterocyclyl, each as defined herein, e.g., aminomethyl, aminoethyl, methylaminomethyl, morpholinylethyl, piperazin-1-ylethyl, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, such as one or two alkoxy groups, as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Aryl" means a monovalent monocyclic or bicyclic aromatic hydrocarbon radical of 6 to 10 ring atoms e.g., phenyl or naphthyl.

"Aralkyl" means -(alkylene)-R where R is aryl as defined above e.g., benzyl or phenethyl.

"Cycloalkyl" means a monocyclic saturated monovalent hydrocarbon radical of three to ten carbon atoms optionally substituted with one or two substituents independently selected from alkyl, halo, alkoxy, hydroxy, and cyano, unless stated otherwise. Examples include, but are not limited to, cyclopropyl, cyclobutyl, cyclopentyl, or cyclohexyl, and the like.

"Cycloalkylalkyl" means a -(alkylene)-R radical where R is cycloalkyl as defined above, e.g., cyclopropylmethyl, cyclohexylmethyl, and the like.

"Cycloalkylene" means, unless stated otherwise, a monocyclic saturated divalent hydrocarbon radical of three to six carbon atoms optionally substituted with one or two substituents independently selected from alkyl, halo, alkoxy, hydroxy, and cyano, each as defined herein. Examples include, but are not limited to, cyclopropylene, cyclobutylene, cyclopentylene, or cyclohexylene, and the like.

"Carboxy" means —C(O)OH.

"Dialkylamino" means a —NRR' radical where R and R' are alkyl as defined above, e.g., dimethylamino, methylethylamino, and the like.

"Aminosulfonyl" means a —SO$_2$NRR' radical where R and R' are independently hydrogen, alkyl, haloalkyl, hydroxyalkyl, or alkoxyalkyl, each as defined herein, e.g., aminosulfonyl, methylaminosulfonyl, dimethylaminosulfonyl, and the like.

"Aminocarbonyl" means a —CONRR' radical where R and R' are independently hydrogen, alkyl, haloalkyl, hydroxyalkyl, or alkoxyalkyl, each as defined herein, e.g., aminocarbonyl, methylaminocarbonyl, dimethylaminocarbonyl, ethylmethylaminocarbonyl, and the like.

"Aminocarboxy" means a —C(O)ONRR' radical where R and R' are independently hydrogen, alkyl, haloalkyl, hydroxyalkyl, or alkoxyalkyl, each as defined herein, e.g., aminocarbonyloxy, methylaminocarbonyloxy, dimethylaminocarbonyloxy, and the like.

"Halo" means fluoro, chloro, bromo, or iodo, preferably fluoro or chloro.

"Haloalkyl" means alkyl radical as defined above, which is substituted with one or more halogen atoms, e.g., one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" means a saturated or unsaturated monovalent monocyclic or bicyclic ring of 4 to 10 ring atoms in which one, two, or three ring atoms are heteroatom selected from N, O, and S(O), where n is an integer from 0 to 2, the remaining ring atoms being C. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydro-pyranyl, thiomorpholino, 6,7,8,9-tetrahydro-4H-pyrido[1,2-a]pyrimidin-4-one, 6,7-dihydropyrimido[2,1-c][1,4]oxazin-4(9H)-one, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

"Heterocyclylene" means, unless stated otherwise, a saturated or unsaturated divalent monocyclic or bicyclic ring of 4 to 6 ring atoms in which one, two, or three ring atoms are heteroatom selected from N, O, and S(O), where n is an integer from 0 to 2, the remaining ring atoms being C. Heterocyclylene can be optionally substituted with one or two substituents independently selected from alkyl, halo, haloalkyl, haloalkoxy, cyano, or hydroxy, each as defined herein.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. When the heteroaryl ring contains 5- or 6 ring atoms it is also referred to herein as 5- or 6-membered heteroaryl.

"Heteroaralkyl" means -(alkylene)-R where R is heteroaryl as defined above e.g., benzyl or phenethyl.

The term "oxo," as used herein, alone or in combination, refers to =(O).

When needed, any definition herein may be used in combination with any other definition to describe a composite structural group. By convention, the trailing element of any such definition is that which attaches to the parent moiety. For example, the composite group alkoxyalkyl means that an alkoxy group attached to the parent molecule through an alkyl group.

The present disclosure also includes protected derivatives of compounds of Formula (I), (IA), (IB), or (IC) or embodiments thereof. For example, when compounds of Formula (I), (IA), (IB), or (IC) contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, $5^{th}$ Ed., John Wiley & Sons, Inc. (2014), the disclosure of which is incorporated herein by reference in its entirety. The protected derivatives of compounds of Formula (I), (IA), (IB), or (IC) can be prepared by methods well known in the art.

The present disclosure also includes polymorphic forms and deuterated forms of the compounds of Formula (I), (IA), (IB), or (IC). The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the active compound. Prodrugs are often useful because, in some situations, they may be easier to administer than the compound, or parent drug. They may, for instance, be bioavailable by oral administration whereas the parent drug is not. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

A "pharmaceutically acceptable salt" of a compound of Formula (I), (IA), (IB), or (IC) means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference in its entirety.

The compounds of Formula (I), (IA), (IB), or (IC) may have asymmetric centers. Compounds of Formula (I), (IA), (IB), or (IC) containing an asymmetrically substituted atom may be isolated in optically active or racemic forms. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. All chiral, diastereomeric, all mixtures of chiral or diasteromeric forms, and racemic forms are within the scope of this disclosure, unless the specific stereochemistry or isomeric form is specifically indicated. It will also be understood by a person of ordinary skill in the art that when a compound is denoted as (R) stereoisomer, it may contain the corresponding (S) stereoisomer as an impurity and vice versa.

Certain compounds of Formula (I), (IA), (IB), or (IC) can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all hydrates of a compound of Formula (I), (IA), (IB), or (IC) are within the scope of this disclosure.

The compounds of Formula (I), (IA), (IB), or (IC) may also contain unnatural amounts of isotopes at one or more of the atoms that constitute such compounds. Unnatural amounts of an isotope may be defined as ranging from the amount found in nature to an amount 100% of the atom in question. that differ only in the presence of one or more isotopically enriched atoms. Exemplary isotopes that can be incorporated into compounds of the present invention, such as a compound of Formula (I), (IA), (IB), or (IC) (and any embodiment thereof disclosed herein including specific compounds) include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds disclosed herein, including in Table 1 below one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{15}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

"Optionally substituted aryl" means aryl that is optionally substituted with one, two, or three substituents independently selected from alkyl, hydroxyl, cycloalkyl, carboxy, alkoxycarbonyl, hydroxy, alkoxy, alkylthio, alkylsulfonyl, amino, alkylamino, dialkylamino, halo, haloalkyl, haloalkoxy, and cyano.

"Optionally substituted aralkyl" means -(alkylene)-R where R is optionally substituted aryl as defined above.

"Optionally substituted heteroaryl" means heteroaryl as defined above that is optionally substituted with one, two, or three substituents independently selected from alkyl, alkylthio, alkylsulfonyl, hydroxyl, cycloalkyl, carboxy, alkoxycarbonyl, hydroxy, alkoxy, halo, haloalkyl, haloalkoxy, amino, alkylamino, dialkylamino, and cyano.

"Optionally substituted heteroaralkyl" means -(alkylene)-R where R is optionally substituted heteroaryl as defined above.

"Optionally substituted heterocyclyl" means heterocyclyl as defined above that is optionally substituted with one, two, or three substituents independently selected from alkyl, alkylthio, alkylsulfonyl, hydroxyl, cycloalkyl, carboxy, alkoxycarbonyl, hydroxy, hydroxyalkyl, alkoxy, alkoxyalkyl, aminoalkyl, halo, haloalkyl, haloalkoxy, and cyano.

"Optionally substituted heterocyclylalkyl" means -(alkylene)-R where R is optionally substituted heterocyclyl as defined above.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass ±10%, preferably ±5%, the recited value and the range is included.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a disease or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms. In one embodiment, treating or treatment means (2) or (3) above.

A "therapeutically effective amount" means the amount of a compound of Formula (I), (IA), (IB), or (IC) or a pharmaceutically acceptable salt thereof that, when administered to a patient for treating a disease, is sufficient to affect such treatment for the disease. The "therapeutically effective amount" will vary depending on the compound, the disease and its severity and the age, weight, etc., of the mammal to be treated.

The terms "inhibiting" and "reducing," or any variation of these terms in relation of SHP2, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of SHP2 activity compared to normal.

Representative compounds of Formula (I) are disclosed in Table (I) below

TABLE 1

| Compound # | Structure | Name |
|---|---|---|
| 1 | 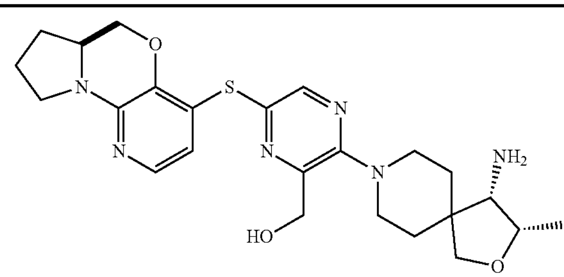 | (3-((3S,4S)-4-amino-3-methyl-2-oxa-8-azaspiro[4.5]decan-8-yl)-6-(((S)-6a,7,8,9-tetrahydro-6H-pyrido[3,2-b]pyrrolo[1,2-d][1,4]oxazin-4-yl)thio)pyrazin-2-yl)methanol |

TABLE 1-continued

| Compound # | Structure | Name |
|---|---|---|
| 2 | 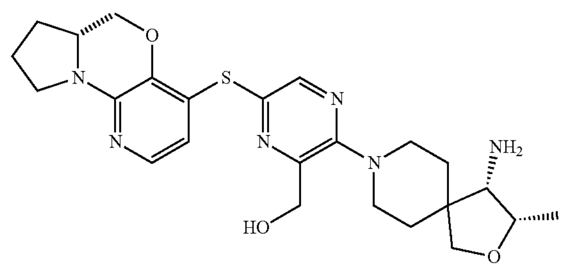 | (3-((3S,4S)-4-amino-3-methyl-2-oxa-8-azaspiro[4.5]decan-8-yl)-6-(((R)-6a,7,8,9-tetrahydro-6H-pyrido[3,2-b]pyrrolo[1,2-d][1,4]oxazin-4-yl)thio)pyrazin-2-yl)methanol |
| 3 | 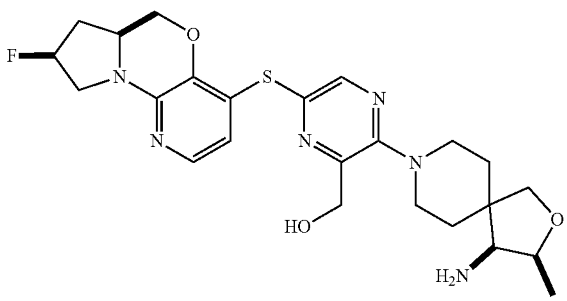 | (3-((3S,4S)-4-amino-3-methyl-2-oxa-8-azaspiro[4.5]decan-8-yl)-6-(((6aS,8S)-8-fluoro-6a,7,8,9-tetrahydro-6H-pyrido[3,2-b]pyrrolo[1,2-d][1,4]oxazin-4-yl)thio)pyrazin-2-yl)methanol |
| 4 | 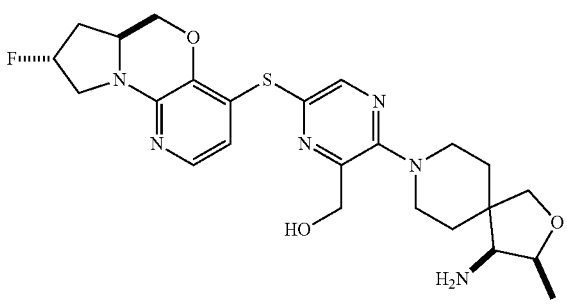 | (3-((3S,4S)-4-amino-3-methyl-2-oxa-8-azaspiro[4.5]decan-8-yl)-6-(((6aS,8R)-8-fluoro-6a,7,8,9-tetrahydro-6H-pyrido[3,2-b]pyrrolo[1,2-d][1,4]oxazin-4-yl)thio)pyrazin-2-yl)methanol |
| 5 | 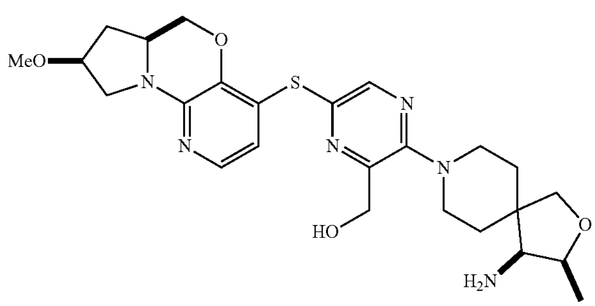 | (3-((3S,4S)-4-amino-3-methyl-2-oxa-8-azaspiro[4.5]decan-8-yl)-6-(((6aS,8S)-8-methoxy-6a,7,8,9-tetrahydro-6H-pyrido[3,2-b]pyrrolo[1,2-d][1,4]oxazin-4-yl)thio)pyrazin-2-yl)methanol |
| 6 | 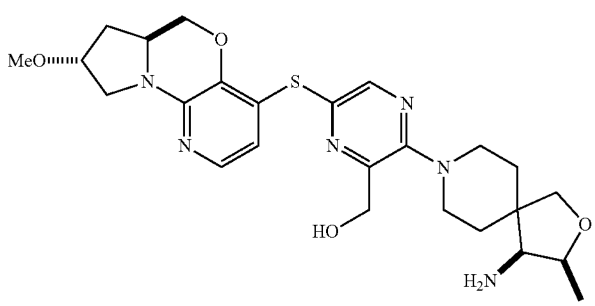 | (3-((3S,4S)-4-amino-3-methyl-2-oxa-8-azaspiro[4.5]decan-8-yl)-6-(((6aS,8R)-8-methoxy-6a,7,8,9-tetrahydro-6H-pyrido[3,2-b]pyrrolo[1,2-d][1,4]oxazin-4-yl)thio)pyrazin-2-yl)methanol |

TABLE 1-continued

| Compound # | Structure | Name |
|---|---|---|
| 7 | 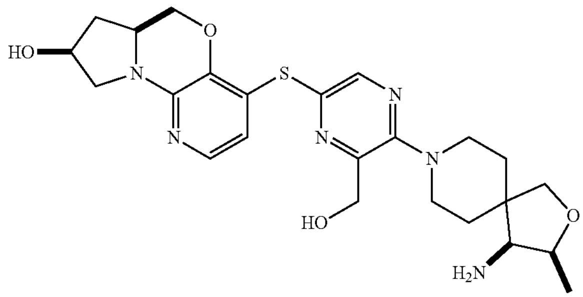 | (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrrolo[3,2-b]pyrrolo[1,2-d][1,4]oxazin-8-ol |
| 8 | 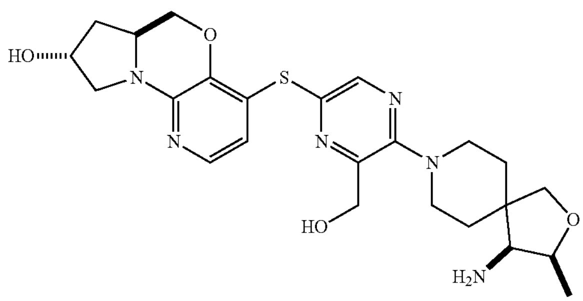 | (6aS,8R)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrrolo[3,2-b]pyrrolo[1,2-d][1,4]oxazin-8-ol |
| 9 | 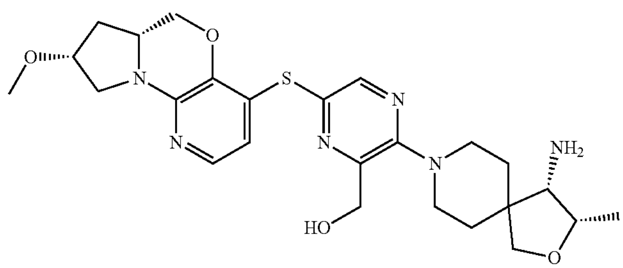 | (3-((3S,4S)-4-amino-3-methyl-2-oxa-8-azaspiro[4.5]decan-8-yl)-6-((((6aR,8R)-8-methoxy-6a,7,8,9-tetrahydro-6H-pyrido[3,2-b]pyrrolo[1,2-d][1,4]oxazin-4-yl)thio)pyrazin-2-yl)methanol |
| 10 | 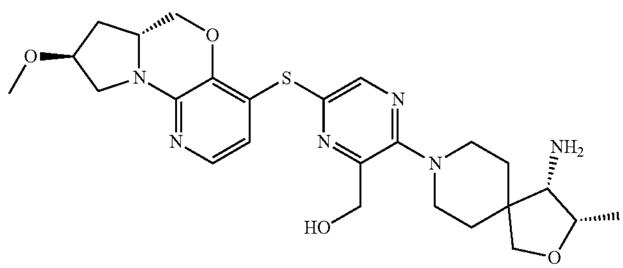 | (3-((3S,4S)-4-amino-3-methyl-2-oxa-8-azaspiro[4.5]decan-8-yl)-6-((((6aR,8S)-8-methoxy-6a,7,8,9-tetrahydro-6H-pyrido[3,2-b]pyrrolo[1,2-d][1,4]oxazin-4-yl)thio)pyrazin-2-yl)methanol |
| 11 | 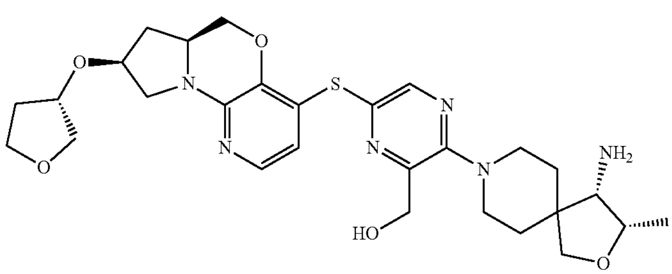 [SMILES: C[C@@H]1OCC2(CCN(c3ncc(Sc4ccnc5c4OC[C@@H]4C[C@H](O[C@H]6CCOC6)CN54)nc3CO)CC2)[C@@H]1N] | (3-((3S,4S)-4-amino-3-methyl-2-oxa-8-azaspiro[4.5]decan-8-yl)-6-((((6aS,8S)-8-(((S)-tetrahydrofuran-3-yl)oxy)-6a,7,8,9-tetrahydro-6H-pyrido[3,2-b]pyrrolo[1,2-d][1,4]oxazin-4-yl)thio)pyrazin-2-yl)methanol |

TABLE 1-continued

| Compound # | Structure | Name |
|---|---|---|
| 12 | 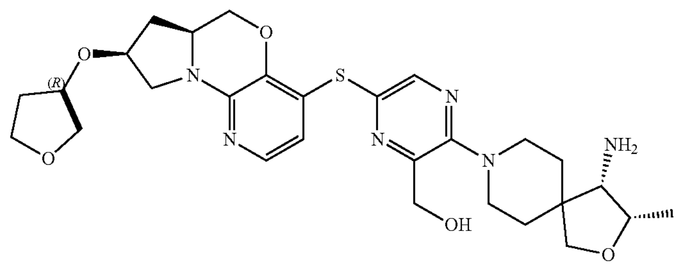 | (3-((3S,4S)-4-amino-3-methyl-2-oxa-8-azaspiro[4.5]decan-8-yl)-6-(((6aS,8S)-8-(((R)-tetrahydrofuran-3-yl)oxy)-6a,7,8,9-tetrahydro-6H-pyrido[3,2-b]pyrrolo[1,2-d][1,4]oxazin-4-yl)thio)pyrazin-2-yl)methanol |
| 13 | 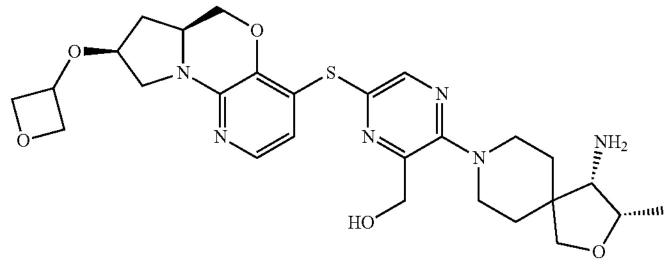 [SMILES: C[C@@H]1OCC2(CCN(c3ncc(Sc4ccnc5c4OC[C@@H]4C[C@H](OC6COC6)CN54)nc3CO)CC2)[C@@H]1N] | (3-((3S,4S)-4-amino-3-methyl-2-oxa-8-azaspiro[4.5]decan-8-yl)-6-(((6aS,8S)-8-(oxetan-3-yloxy)-6a,7,8,9-tetrahydro-6H-pyrido[3,2-b]pyrrolo[1,2-d][1,4]oxazin-4-yl)thio)pyrazin-2-yl)methanol |
| 14 | 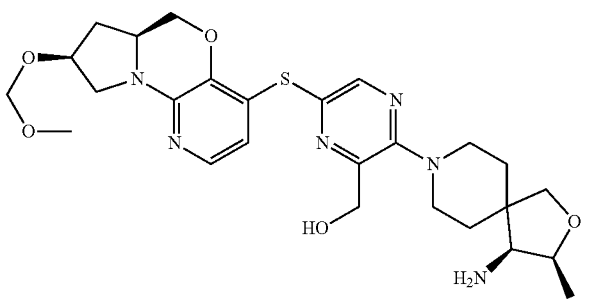 [SMILES: COCO[C@H]1C[C@H]2COc3c(Sc4cnc(N5CCC6(CC5)CO[C@@H](C)[C@H]6N)c(CO)n4)ccnc3N2C1] | (3-((3S,4S)-4-amino-3-methyl-2-oxa-8-azaspiro[4.5]decan-8-yl)-6-(((6aS,8S)-8-(methoxymethoxy)-6a,7,8,9-tetrahydro-6H-pyrido[3,2-b]pyrrolo[1,2-d][1,4]oxazin-4-yl)thio)pyrazin-2-yl)methanol |
| 15 | 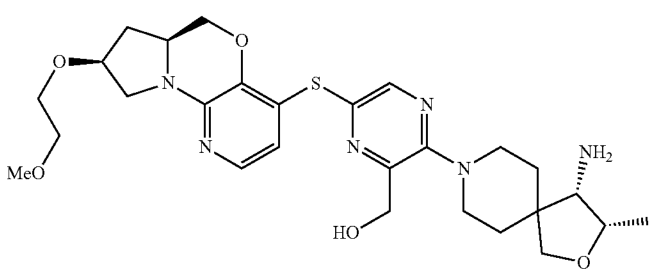 [SMILES: COCCO[C@H]1C[C@H]2COc3c(Sc4cnc(N5CCC6(CC5)CO[C@@H](C)[C@H]6N)c(CO)n4)ccnc3N2C1] | (3-((3S,4S)-4-amino-3-methyl-2-oxa-8-azaspiro[4.5]decan-8-yl)-6-(((6aS,8S)-8-(2-methoxyethoxy)-6a,7,8,9-tetrahydro-6H-pyrido[3,2-b]pyrrolo[1,2-d][1,4]oxazin-4-yl)thio)pyrazin-2-yl)methanol |
| 16 | 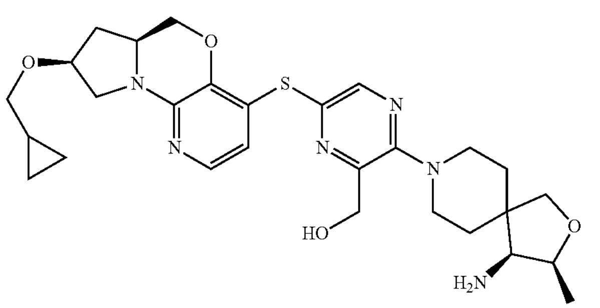 [SMILES: C[C@@H]1OCC2(CCN(c3ncc(Sc4ccnc5c4OC[C@@H]4C[C@H](OCC6CC6)CN54)nc3CO)CC2)[C@@H]1N] | (3-((3S,4S)-4-amino-3-methyl-2-oxa-8-azaspiro[4.5]decan-8-yl)-6-(((6aS,8S)-8-(cyclopropylmethoxy)-6a,7,8,9-tetrahydro-6H-pyrido[3,2-b]pyrrolo[1,2-d][1,4]oxazin-4-yl)thio)pyrazin-2-yl)methanol |

TABLE 1-continued

| Compound # | Structure | Name |
|---|---|---|
| 17 | 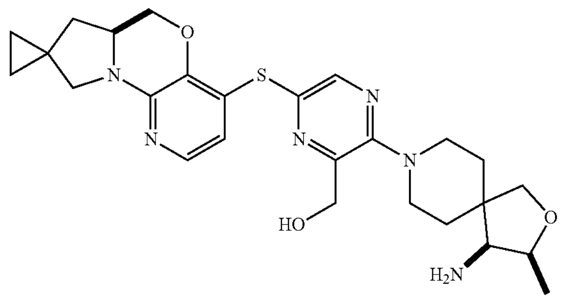 | (3-((3S,4S)-4-amino-3-methyl-2-oxa-8-azaspiro[4.5]decan-8-yl)-6-(((S)-6a',7'-dihydro-6'H,9'H-spiro[cyclopropane-1,8'-pyrido[3,2-b]pyrrolo[1,2-d][1,4]oxazin]-4'-yl)thio)pyrazin-2-yl)methanol |
| 18 | 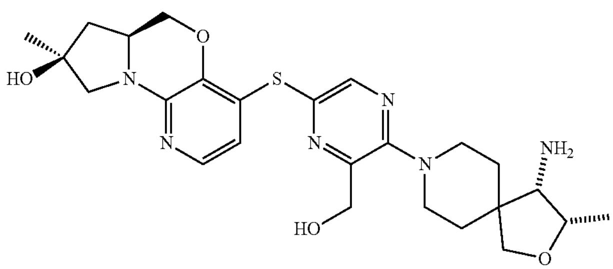 [SMILES: C[C@@H]1OCC2(CCN(c3ncc(Sc4ccnc5c4OC[C@@H]4C[C@](C)(O)CN54)nc3CO)CC2)[C@@H]1N] | (6aS,8S)-4-((5-((3S,4S)-4-amino-3-methyl-2-oxa-8-azaspiro[4.5]decan-8-yl)-6-(hydroxymethyl)pyrazin-2-yl)thio)-8-methyl-6a,7,8,9-tetrahydro-6H-pyrido[3,2-b]pyrrolo[1,2-d][1,4]oxazin-8-ol |
| 19 | 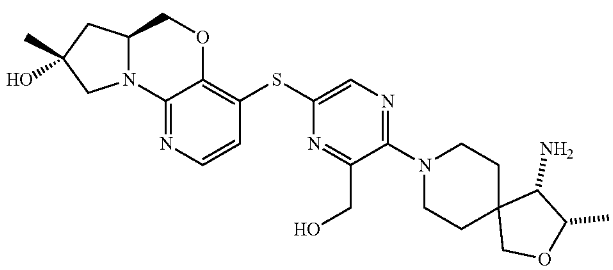 | (6aS,8R)-4-((5-((3S,4S)-4-amino-3-methyl-2-oxa-8-azaspiro[4.5]decan-8-yl)-6-(hydroxymethyl)pyrazin-2-yl)thio)-8-methyl-6a,7,8,9-tetrahydro-6H-pyrido[3,2-b]pyrrolo[1,2-d][1,4]oxazin-8-ol |
| 20 | 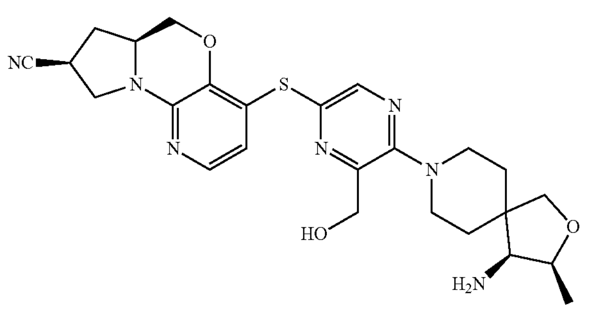 [SMILES: C[C@@H]1OCC2(CCN(c3ncc(Sc4ccnc5c4OC[C@@H]4C[C@H](C#N)CN54)nc3CO)CC2)[C@@H]1N] | (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazine-8-carbonitrile |
| 21 | 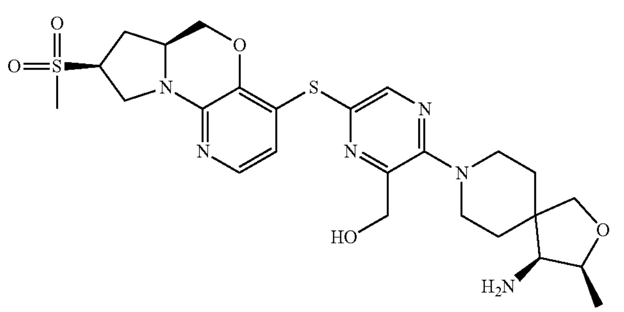 [SMILES: C[C@@H]1OCC2(CCN(c3ncc(Sc4ccnc5c4OC[C@@H]4C[C@H](S(C)(=O)=O)CN54)nc3CO)CC2)[C@@H]1N] | (3-((3S,4S)-4-amino-3-methyl-2-oxa-8-azaspiro[4.5]decan-8-yl)-6-(((6aS,8S)-8-(methylsulfonyl)-6a,7,8,9-tetrahydro-6H-pyrido[3,2-b]pyrrolo[1,2-d][1,4]oxazin-4-yl)thio)pyrazin-2-yl)methanol |

TABLE 1-continued

| Compound # | Structure | Name |
|---|---|---|
| 22 | 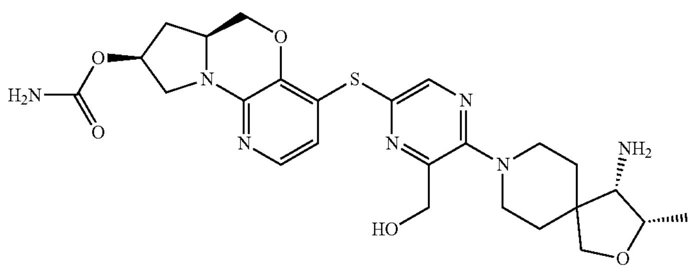 [SMILES: C[C@@H]1OCC2(CCN(c3ncc(Sc4ccnc5c4OC[C@@H]4C[C@H](OC(N)=O)CN54)nc3CO)CC2)[C@@H]1N] | (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-yl carbamate |
| 23 | 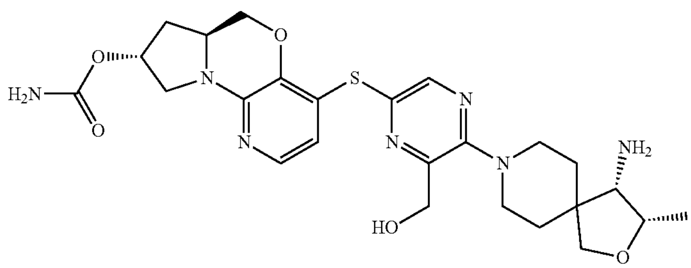 [SMILES: C[C@@H]1OCC2(CCN(c3ncc(Sc4ccnc5c4OC[C@@H]4C[C@@H](OC(N)=O)CN54)nc3CO)CC2)[C@@H]1N] | (6aS,8R)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-yl carbamate |
| 24 | 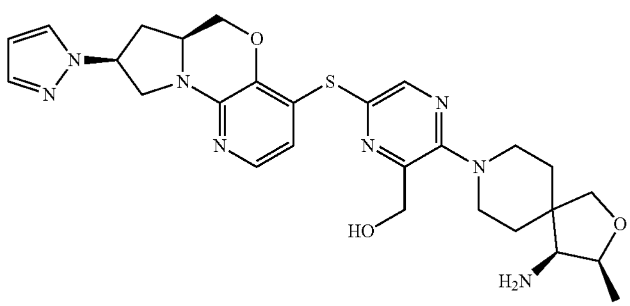 [SMILES: C[C@@H]1OCC2(CCN(c3ncc(Sc4ccnc5c4OC[C@@H]4C[C@H](n6cccn6)CN54)nc3CO)CC2)[C@@H]1N] | (6-(((6aS,8S)-8-(1H-pyrazol-1-yl)-6a,7,8,9-tetrahydro-6H-pyrido[3,2-b]pyrrolo[1,2-d][1,4]oxazin-4-yl)thio)-3-((3S,4S)-4-amino-3-methyl-2-oxa-8-azaspiro[4.5]decan-8-yl)pyrazin-2-yl)methanol |
| 25 | 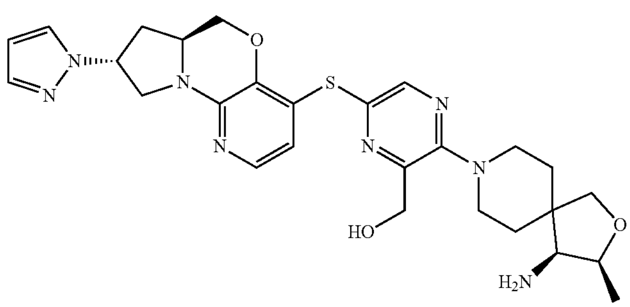 [SMILES: C[C@@H]1OCC2(CCN(c3ncc(Sc4ccnc5c4OC[C@@H]4C[C@@H](n6cccn6)CN54)nc3CO)CC2)[C@@H]1N] | (6-(((6aS,8R)-8-(1H-pyrazol-1-yl)-6a,7,8,9-tetrahydro-6H-pyrido[3,2-b]pyrrolo[1,2-d][1,4]oxazin-4-yl)thio)-3-((3S,4S)-4-amino-3-methyl-2-oxa-8-azaspiro[4.5]decan-8-yl)pyrazin-2-yl)methanol |
| 26 | 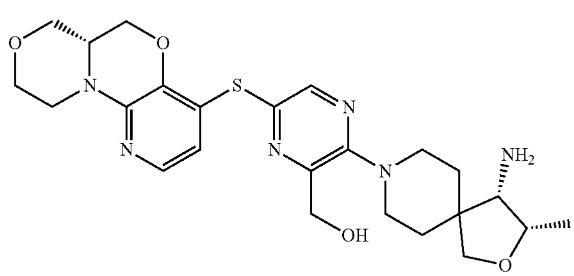 [SMILES: C[C@@H]1OCC2(CCN(c3ncc(Sc4ccnc5c4OC[C@H]4COCCN54)nc3CO)CC2)[C@@H]1N] | (3-((3S,4S)-4-amino-3-methyl-2-oxa-8-azaspiro[4.5]decan-8-yl)-6-(((R)-6a,7,9,10-tetrahydro-6H-[1,4]oxazino[4,3-d]pyrido[3,2-b][1,4]oxazin-4-yl)thio)pyrazin-2-yl)methanol |

TABLE 1-continued

| Compound # | Structure | Name |
|---|---|---|
| 27 | 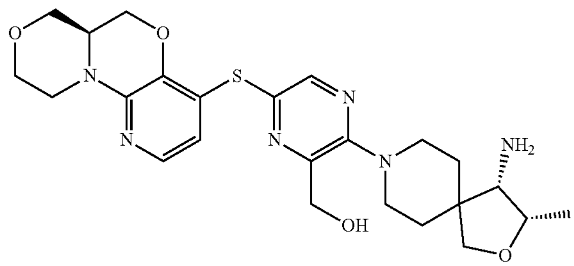 [SMILES: C[C@@H]1OCC2(CCN(c3ncc(Sc4ccnc5c4OC[C@@H]4COCCN54)nc3CO)CC2)[C@@H]1N] | (3-((3S,4S)-4-amino-3-methyl-2-oxa-8-azaspiro[4.5]decan-8-yl)-6-(((S)-6a,7,9,10-tetrahydro-6H-[1,4]oxazino[4,3-d]pyrido[3,2-b][1,4]oxazin-4-yl)thio)pyrazin-2-yl)methanol |
| 28 | 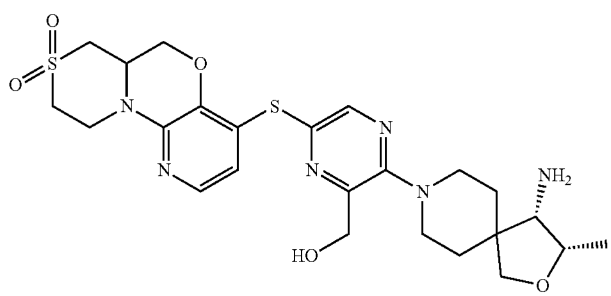 [SMILES: C[C@@H]1OCC2(CCN(c3ncc(Sc4ccnc5c4OCC4CS(=O)(=O)CCN54)nc3CO)CC2)[C@@H]1N] | 4-((5-((3S,4S)-4-amino-3-methyl-2-oxa-8-azaspiro[4.5]decan-8-yl)-6-(hydroxymethyl)pyrazin-2-yl)thio)-6a,7,9,10-tetrahydro-6H-pyrido[3,2-b][1,4]thiazino[4,3-d][1,4]oxazine 8,8-dioxide |
| 29 | 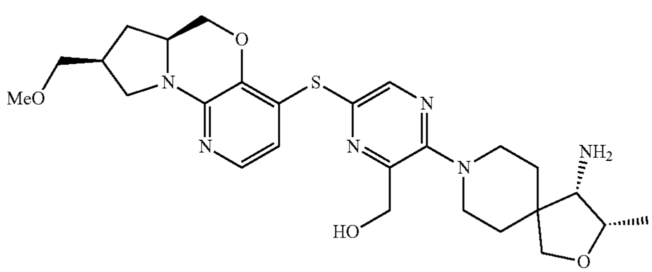 [SMILES: COC[C@H]1C[C@H]2COc3c(Sc4cnc(N5CCC6(CC5)CO[C@@H](C)[C@H]6N)c(CO)n4)ccnc3N2C1] | (3-((3S,4S)-4-amino-3-methyl-2-oxa-8-azaspiro[4.5]decan-8-yl)-6-((((6aS,8S)-8-(methoxymethyl)-6a,7,8,9-tetrahydro-6H-pyrido[3,2-b]pyrrolo[1,2-d][1,4]oxazin-4-yl)thio)pyrazin-2-yl)methanol |
| 30 | 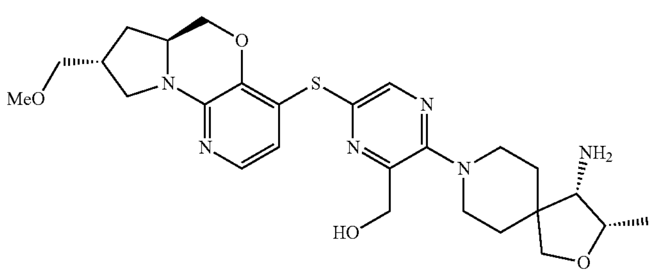 [SMILES: COC[C@@H]1C[C@H]2COc3c(Sc4cnc(N5CCC6(CC5)CO[C@@H](C)[C@H]6N)c(CO)n4)ccnc3N2C1] | (3-((3S,4S)-4-amino-3-methyl-2-oxa-8-azaspiro[4.5]decan-8-yl)-6-((((6aS,8R)-8-(methoxymethyl)-6a,7,8,9-tetrahydro-6H-pyrido[3,2-b]pyrrolo[1,2-d][1,4]oxazin-4-yl)thio)pyrazin-2-yl)methanol |
| 31 | 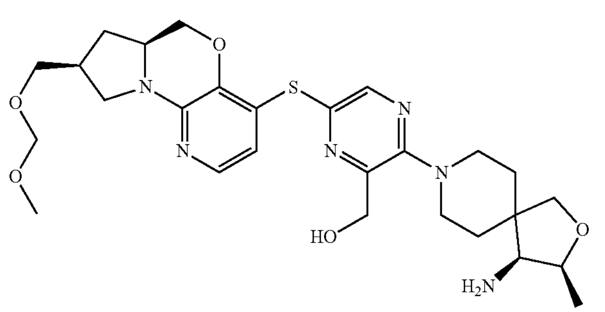 [SMILES: COCOC[C@H]1C[C@H]2COc3c(Sc4cnc(N5CCC6(CC5)CO[C@@H](C)[C@H]6N)c(CO)n4)ccnc3N2C1] | (3-((3S,4S)-4-amino-3-methyl-2-oxa-8-azaspiro[4.5]decan-8-yl)-6-((((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol |

TABLE 1-continued

| Compound # | Structure | Name |
|---|---|---|
| 32 | 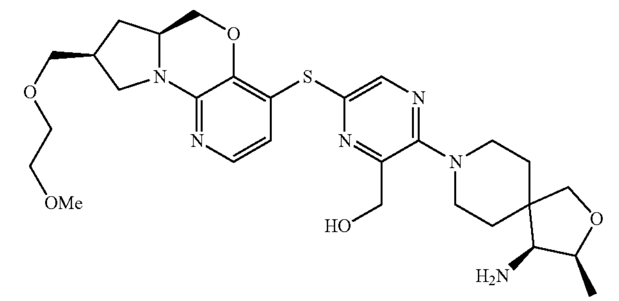 [SMILES: COCCOC[C@H]1C[C@H]2COc3c(Sc4cnc(N5CCC6(CC5)CO[C@@H](C)[C@H]6N)c(CO)n4)ccnc3N2C1] | (3-((3S,4S)-4-amino-3-methyl-2-oxa-8-azaspiro[4.5]decan-8-yl)-6-((((6aS,8S)-8-((2-methoxyethoxy)methyl)-6a,7,8,9-tetrahydro-6H-pyrido[3,2-b]pyrrolo[1,2-d][1,4]oxazin-4-yl)thio)pyrazin-2-yl)methanol |
| 33 | 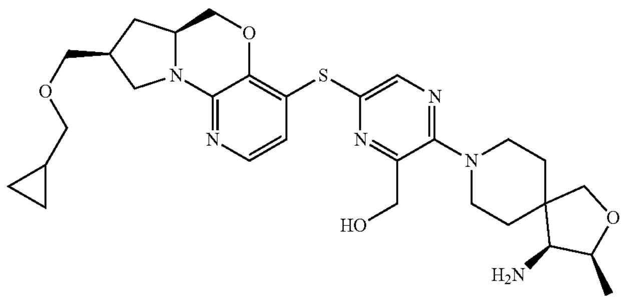 [SMILES: C[C@@H]1OCC2(CCN(c3ncc(Sc4ccnc5c4OC[C@@H]4C[C@H](COCC6CC6)CN54)nc3CO)CC2)[C@@H]1N] | (3-((3S,4S)-4-amino-3-methyl-2-oxa-8-azaspiro[4.5]decan-8-yl)-6-((((6aS,8S)-8-((cyclopropylmethoxy)methyl)-6a,7,8,9-tetrahydro-6H-pyrido[3,2-b]pyrrolo[1,2-d][1,4]oxazin-4-yl)thio)pyrazin-2-yl)methanol |
| 34 | 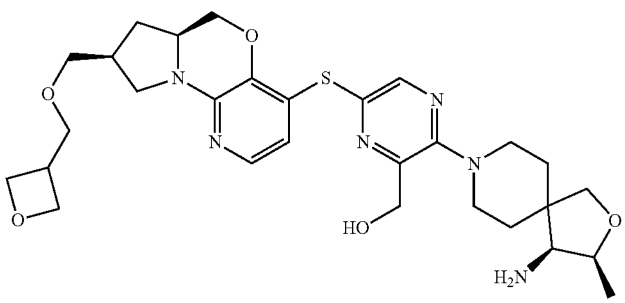 [SMILES: C[C@@H]1OCC2(CCN(c3ncc(Sc4ccnc5c4OC[C@@H]4C[C@H](COCC6COC6)CN54)nc3CO)CC2)[C@@H]1N] | (3-((3S,4S)-4-amino-3-methyl-2-oxa-8-azaspiro[4.5]decan-8-yl)-6-((((6aS,8S)-8-((oxetan-3-ylmethoxy)methyl)-6a,7,8,9-tetrahydro-6H-pyrido[3,2-b]pyrrolo[1,2-d][1,4]oxazin-4-yl)thio)pyrazin-2-yl)methanol |
| 35 | 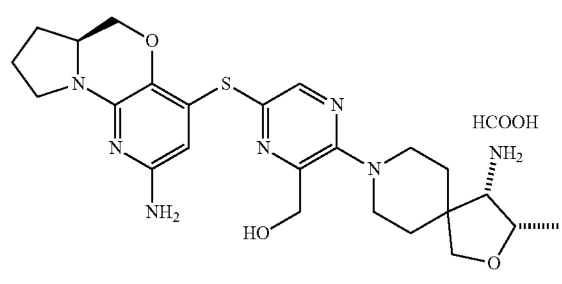 [SMILES: C[C@@H]1OCC2(CCN(c3ncc(Sc4cc(N)nc5c4OC[C@@H]4CCCN54)nc3CO)CC2)[C@@H]1N ; "HCOOH"] | (3-((3S,4S)-4-amino-3-methyl-2-oxa-8-azaspiro[4.5]decan-8-yl)-6-(((S)-2-amino-6a,7,8,9-tetrahydro-6H-pyrido[3,2-b]pyrrolo[1,2-d][1,4]oxazin-4-yl)thio)pyrazin-2-yl)methanol formate |
| 36 | 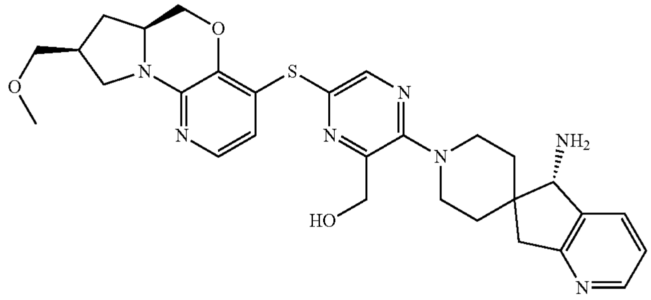 [SMILES: COC[C@H]1C[C@H]2COc3c(Sc4cnc(N5CCC6(CC5)Cc5ncccc5[C@H]6N)c(CO)n4)ccnc3N2C1] | (3-((S)-5-amino-5,7-dihydrospiro[cyclopenta[b]pyridine-6,4'-piperidin]-1'-yl)-6-((((6aS,8S)-8-(methoxymethyl)-6a,7,8,9-tetrahydro-6H-pyrido[3,2-b]pyrrolo[1,2-d][1,4]oxazin-4-yl)thio)pyrazin-2-yl)methanol |

TABLE 1-continued

| Compound # | Structure | Name |
|---|---|---|
| 37 | 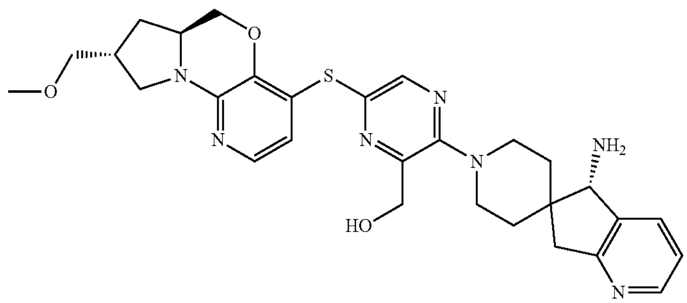 [SMILES: COC[C@@H]1C[C@H]2COc3c(Sc4cnc(N5CCC6(CC5)Cc5ncccc5[C@H]6N)c(CO)n4)ccnc3N2C1] | (3-((S)-5-amino-5,7-dihydrospiro[cyclopenta[b]pyridine-6,4'-piperidin]-1'-yl)-6-((((6aS,8R)-8-(methoxymethyl)-6a,7,8,9-tetrahydro-6H-pyrido[3,2-b]pyrrolo[1,2-d][1,4]oxazin-4-yl)thio)pyrazin-2-yl)methanol |
| 38 | 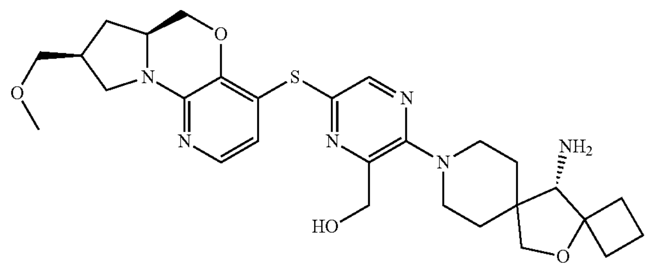 [SMILES: COC[C@H]1C[C@H]2COc3c(Sc4cnc(N5CCC6(CC5)COC5(CCC5)[C@H]6N)c(CO)n4)ccnc3N2C1] | (3-((S)-5-amino-13-oxa-9-azadispiro[3.1.56.24]tridecan-9-yl)-6-((((6aS,8S)-8-(methoxymethyl)-6a,7,8,9-tetrahydro-6H-pyrido[3,2-b]pyrrolo[1,2-d][1,4]oxazin-4-yl)thio)pyrazin-2-yl)methanol |
| 39 | 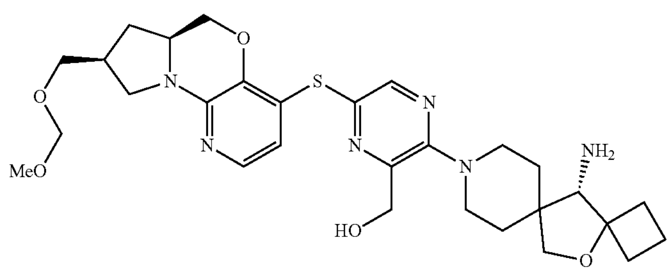 [SMILES: COCOC[C@H]1C[C@H]2COc3c(Sc4cnc(N5CCC6(CC5)COC5(CCC5)[C@H]6N)c(CO)n4)ccnc3N2C1] | (3-((S)-5-amino-13-oxa-9-azadispiro[3.1.56.24]tridecan-9-yl)-6-((((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol |
| 40 | 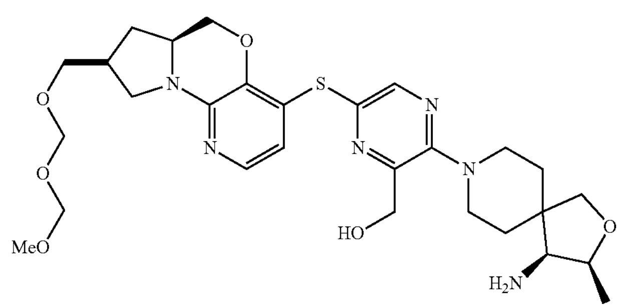 [SMILES: COCOCOC[C@H]1C[C@H]2COc3c(Sc4cnc(N5CCC6(CC5)CO[C@@H](C)[C@H]6N)c(CO)n4)ccnc3N2C1] | (3-((3S,4S)-4-amino-3-methyl-2-oxa-8-azaspiro[4.5]decan-8-yl)-6-((((6aS,8S)-8-(((methoxymethoxy)methoxy)methyl)-6a,7,8,9-tetrahydro-6H-pyrido[3,2-b]pyrrolo[1,2-d][1,4]oxazin-4-yl)thio)pyrazin-2-yl)methanol |
| 41 | 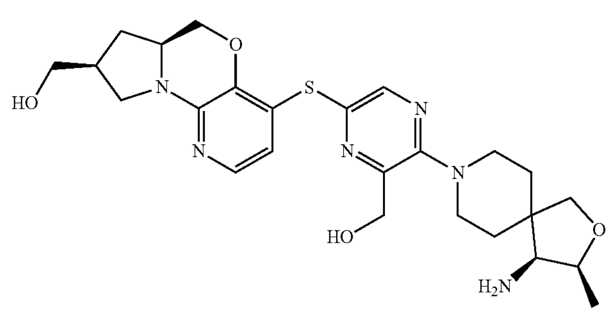 [SMILES: C[C@@H]1OCC2(CCN(c3ncc(Sc4ccnc5c4OC[C@@H]4C[C@H](CO)CN54)nc3CO)CC2)[C@@H]1N] | (3-((3S,4S)-4-amino-3-methyl-2-oxa-8-azaspiro[4.5]decan-8-yl)-6-((((6aS,8S)-8-(hydroxymethyl)-6a,7,8,9-tetrahydro-6H-pyrido[3,2-b]pyrrolo[1,2-d][1,4]oxazin-4-yl)thio)pyrazin-2-yl)methanol |

TABLE 1-continued

| Compound # | Structure | Name |
|---|---|---|
| 42 | 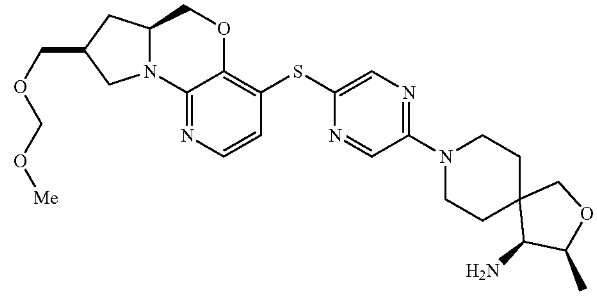 [SMILES: COCOC[C@H]1C[C@H]2COc3c(Sc4cnc(N5CCC6(CC5)CO[C@@H](C)[C@H]6N)cn4)ccnc3N2C1] | (3S,4S)-8-(5-((((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-amine |
| 43 | 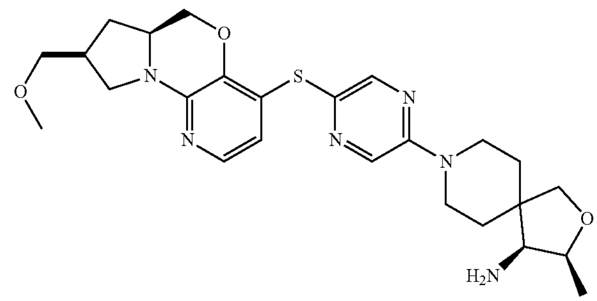 [SMILES: COC[C@H]1C[C@H]2COc3c(Sc4cnc(N5CCC6(CC5)CO[C@@H](C)[C@H]6N)cn4)ccnc3N2C1] | (3S,4S)-8-(5-(((6aS,8S)-8-(methoxymethyl)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-amine |
| 44 | 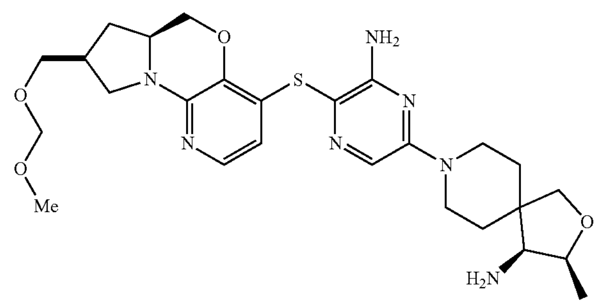 [SMILES: COCOC[C@H]1C[C@H]2COc3c(Sc4ncc(N5CCC6(CC5)CO[C@@H](C)[C@H]6N)nc4N)ccnc3N2C1] | (3S,4S)-8-(6-amino-5-(((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-amine |
| 45 | 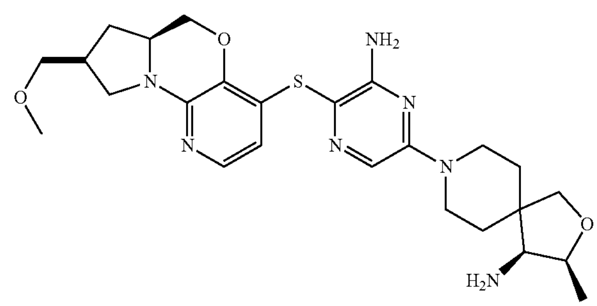 [SMILES: COC[C@H]1C[C@H]2COc3c(Sc4ncc(N5CCC6(CC5)CO[C@@H](C)[C@H]6N)nc4N)ccnc3N2C1] | (3S,4S)-8-(6-amino-5-(((6aS,8S)-8-(methoxymethyl)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-amine |
| 46 | 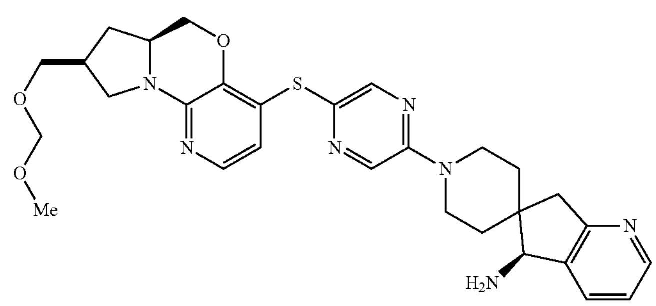 [SMILES: COCOC[C@H]1C[C@H]2COc3c(Sc4cnc(N5CCC6(CC5)Cc5ncccc5[C@H]6N)cn4)ccnc3N2C1] | (S)-1'-(5-(((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-5,7-dihydrospiro[cyclopenta[b]pyridine-6,4'-piperidin]-5-amine |

TABLE 1-continued

| Compound # | Structure | Name |
|---|---|---|
| 47 | 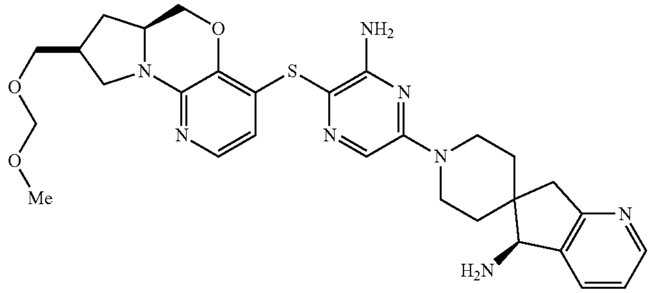 [SMILES: COCOC[C@H]1C[C@H]2COc3c(Sc4ncc(N5CCC6(CC5)Cc5ncccc5[C@H]6N)nc4N)ccnc3N2C1] | (S)-1'-(6-amino-5-((((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-5,7-dihydrospiro[cyclopenta[b]pyridine-6,4'-piperidin]-5-amine |
| 48 | 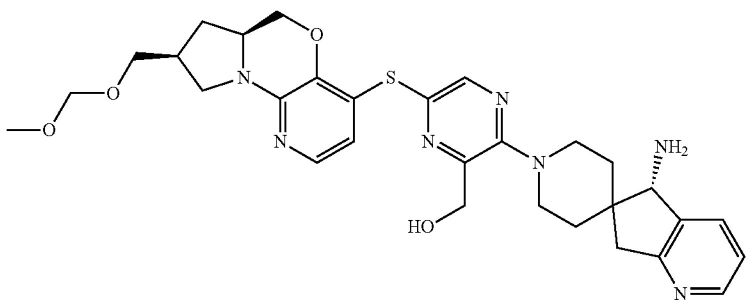 [SMILES: COCOC[C@H]1C[C@H]2COc3c(Sc4cnc(N5CCC6(CC5)Cc5ncccc5[C@H]6N)c(CO)n4)ccnc3N2C1] | (3-((S)-5-amino-5,7-dihydrospiro[cyclopenta[b]pyridine-6,4'-piperidin]-1'-yl)-6-((((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol |
| 49 | 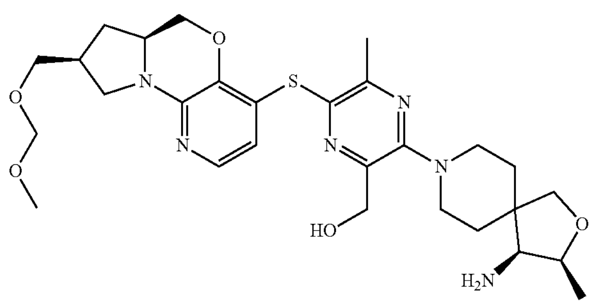 [SMILES: COCOC[C@H]1C[C@H]2COc3c(Sc4nc(CO)c(N5CCC6(CC5)CO[C@@H](C)[C@H]6N)nc4C)ccnc3N2C1] | (3-((3S,4S)-4-amino-3-methyl-2-oxa-8-azaspiro[4.5]decan-8-yl)-6-((((6aS,8S)-8-((methoxymethoxy)methyl)-6a,7,8,9-tetrahydro-6H-pyrido[3,2-b]pyrrolo[1,2-d][1,4]oxazin-4-yl)thio)-5-methylpyrazin-2-yl)methanol |
| 50 | 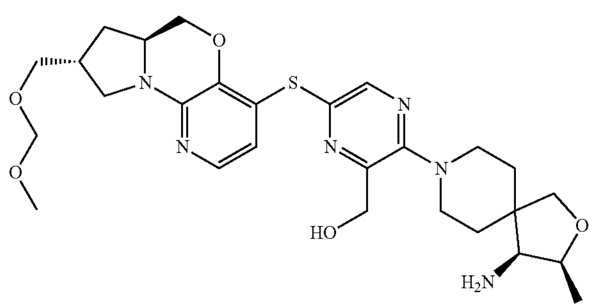 [SMILES: COCOC[C@@H]1C[C@H]2COc3c(Sc4cnc(N5CCC6(CC5)CO[C@@H](C)[C@H]6N)c(CO)n4)ccnc3N2C1] | (3-((3S,4S)-4-amino-3-methyl-2-oxa-8-azaspiro[4.5]decan-8-yl)-6-((((6aS,8R)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol |
| 51 | 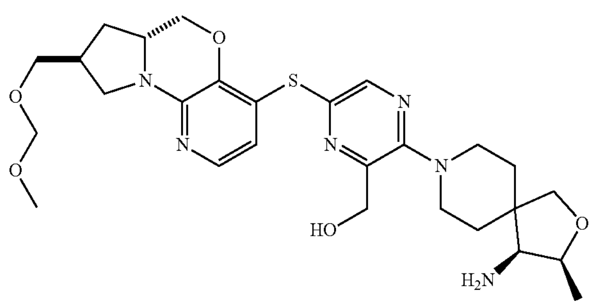 | (3-((3S,4S)-4-amino-3-methyl-2-oxa-8-azaspiro[4.5]decan-8-yl)-6-((((6aR,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol |

TABLE 1-continued

| Compound # | Structure | Name |
|---|---|---|
| 52 | 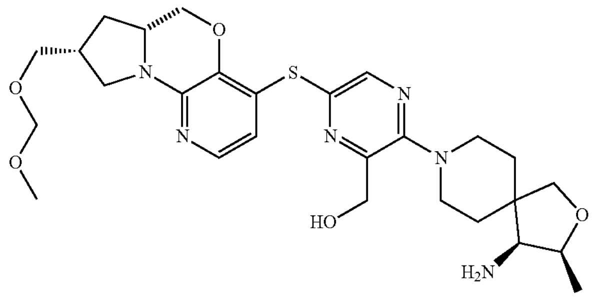 | (3-((3S,4S)-4-amino-3-methyl-2-oxa-8-azaspiro[4.5]decan-8-yl)-6-((((6aR,8R)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol |
| 53 | 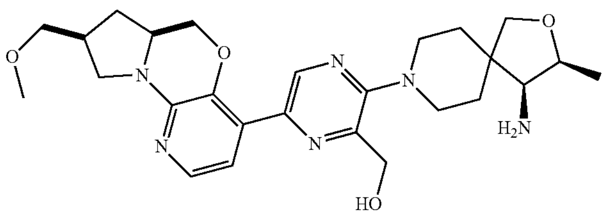 | (3-((3S,4S)-4-amino-3-methyl-2-oxa-8-azaspiro[4.5]decan-8-yl)-6-((6aS,8S)-8-(methoxymethyl)-6a,7,8,9-tetrahydro-6H-pyrido[3,2-b]pyrrolo[1,2-d][1,4]oxazin-4-yl)pyrazin-2-yl)methanol |
| 54 | 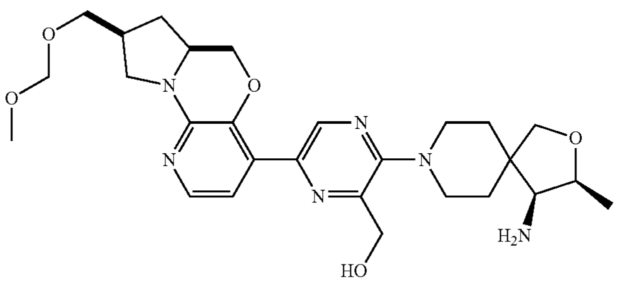 | (3-((3S,4S)-4-amino-3-methyl-2-oxa-8-azaspiro[4.5]decan-8-yl)-6-((6aS,8S)-8-((methoxymethoxy)methyl)-6a,7,8,9-tetrahydro-6H-pyrido[3,2-b]pyrrolo[1,2-d][1,4]oxazin-4-yl)pyrazin-2-yl)methanol |

Contemplated compounds of Formula (I) are disclosed in Table 2 below

| | | |
|---|---|---|
| II-1 | | 6-amino-2-((3S,4S)-4-amino-3-methyl-2-oxa-8-azaspiro[4.5]decan-8-yl)-5-((((6aS,8S)-8-((methoxymethoxy)methyl)-6a,7,8,9-tetrahydro-6H-pyrido[3,2-b]pyrrolo[1,2-d][1,4]oxazin-4-yl)thio)-3-methylpyrimidin-4(3H)-one |
| II-2 | | 2-((3S,4S)-4-amino-3-methyl-2-oxa-8-azaspiro[4.5]decan-8-yl)-5-((((6aS,8S)-8-((methoxymethoxy)methyl)-6a,7,8,9-tetrahydro-6H-pyrido[3,2-b]pyrrolo[1,2-d][1,4]oxazin-4-yl)thio)-3-methylpyrimidin-4(3H)-one |

-continued

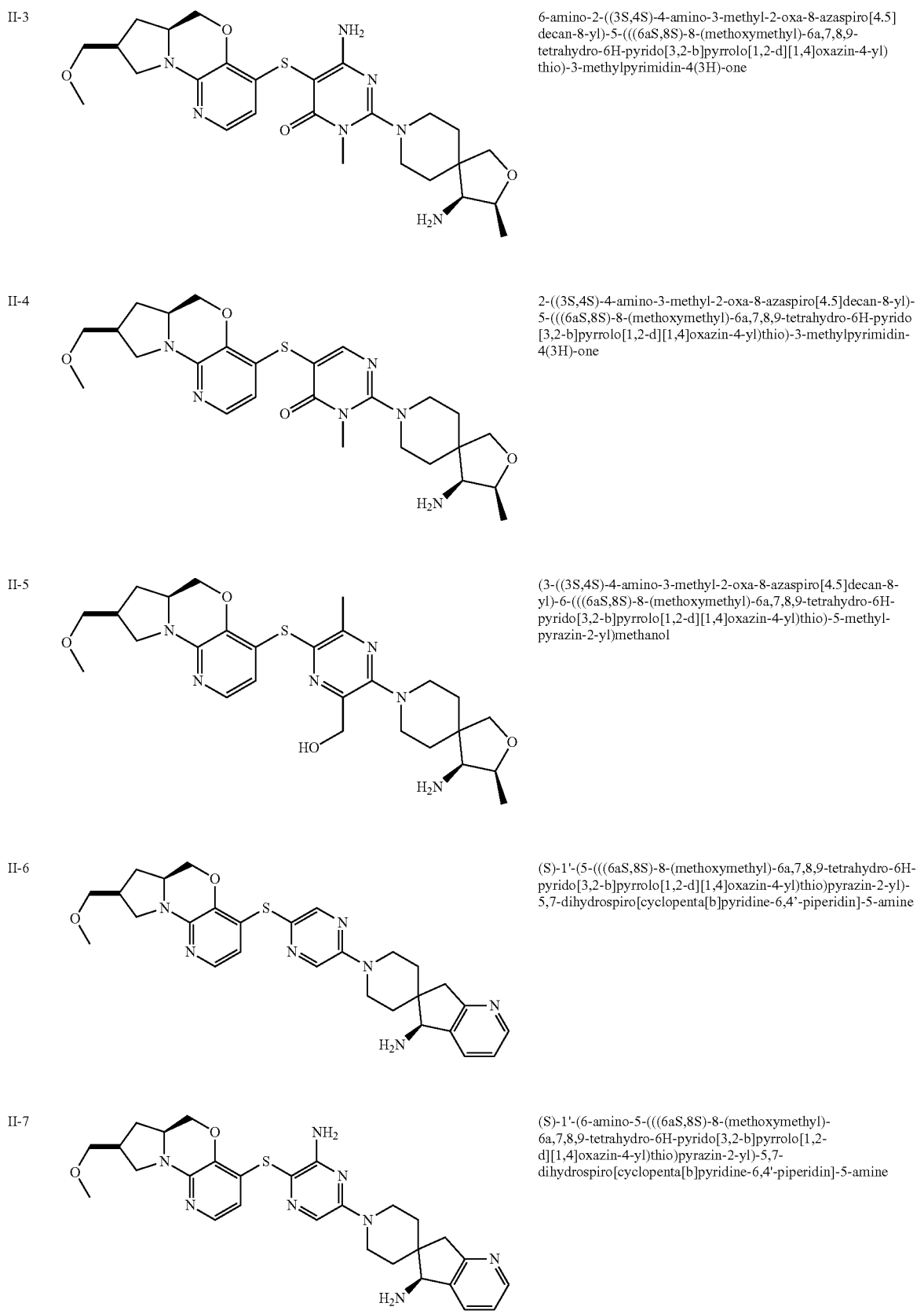

II-3 6-amino-2-((3S,4S)-4-amino-3-methyl-2-oxa-8-azaspiro[4.5]decan-8-yl)-5-(((6aS,8S)-8-(methoxymethyl)-6a,7,8,9-tetrahydro-6H-pyrido[3,2-b]pyrrolo[1,2-d][1,4]oxazin-4-yl)thio)-3-methylpyrimidin-4(3H)-one II-4 2-((3S,4S)-4-amino-3-methyl-2-oxa-8-azaspiro[4.5]decan-8-yl)-5-((((6aS,8S)-8-(methoxymethyl)-6a,7,8,9-tetrahydro-6H-pyrido[3,2-b]pyrrolo[1,2-d][1,4]oxazin-4-yl)thio)-3-methylpyrimidin-4(3H)-one II-5 (3-((3S,4S)-4-amino-3-methyl-2-oxa-8-azaspiro[4.5]decan-8-yl)-6-((((6aS,8S)-8-(methoxymethyl)-6a,7,8,9-tetrahydro-6H-pyrido[3,2-b]pyrrolo[1,2-d][1,4]oxazin-4-yl)thio)-5-methyl-pyrazin-2-yl)methanol II-6 (S)-1'-(5-((((6aS,8S)-8-(methoxymethyl)-6a,7,8,9-tetrahydro-6H-pyrido[3,2-b]pyrrolo[1,2-d][1,4]oxazin-4-yl)thio)pyrazin-2-yl)-5,7-dihydrospiro[cyclopenta[b]pyridine-6,4'-piperidin]-5-amine II-7 (S)-1'-(6-amino-5-((((6aS,8S)-8-(methoxymethyl)-6a,7,8,9-tetrahydro-6H-pyrido[3,2-b]pyrrolo[1,2-d][1,4]oxazin-4-yl)thio)pyrazin-2-yl)-5,7-dihydrospiro[cyclopenta[b]pyridine-6,4'-piperidin]-5-amine

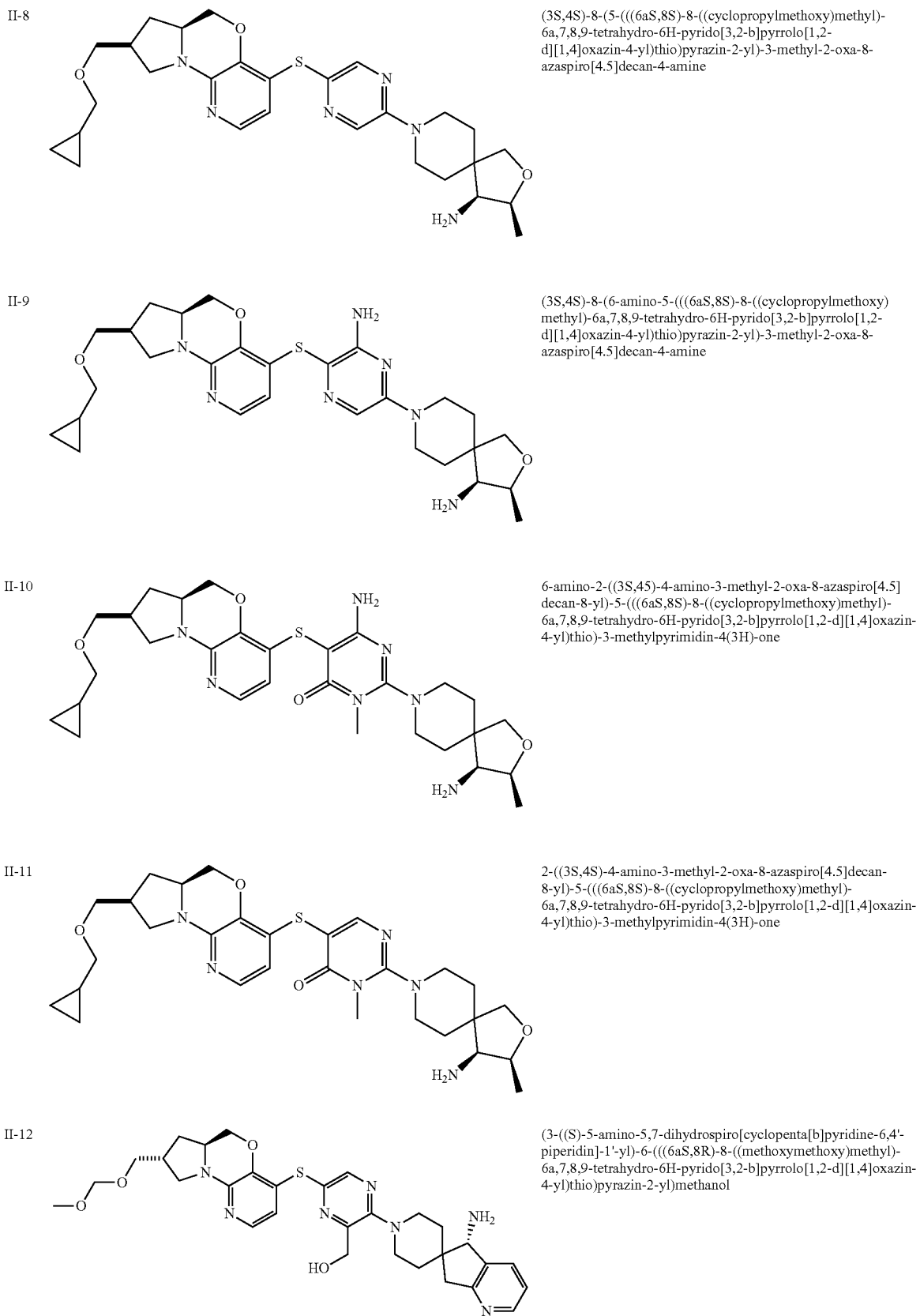

| | |
|---|---|
| II-8 | (3S,4S)-8-(5-((((6aS,8S)-8-((cyclopropylmethoxy)methyl)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-amine |
| II-9 | (3S,4S)-8-(6-amino-5-((((6aS,8S)-8-((cyclopropylmethoxy)methyl)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-amine |
| II-10 | 6-amino-2-((3S,4S)-4-amino-3-methyl-2-oxa-8-azaspiro[4.5]decan-8-yl)-5-((((6aS,8S)-8-((cyclopropylmethoxy)methyl)-6a,7,8,9-tetrahydro-6H-pyrido[3,2-b]pyrrolo[1,2-d][1,4]oxazin-4-yl)thio)-3-methylpyrimidin-4(3H)-one |
| II-11 | 2-((3S,4S)-4-amino-3-methyl-2-oxa-8-azaspiro[4.5]decan-8-yl)-5-((((6aS,8S)-8-((cyclopropylmethoxy)methyl)-6a,7,8,9-tetrahydro-6H-pyrido[3,2-b]pyrrolo[1,2-d][1,4]oxazin-4-yl)thio)-3-methylpyrimidin-4(3H)-one |
| II-12 | (3-((S)-5-amino-5,7-dihydrospiro[cyclopenta[b]pyridine-6,4'-piperidin]-1'-yl)-6-((((6aS,8R)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol |

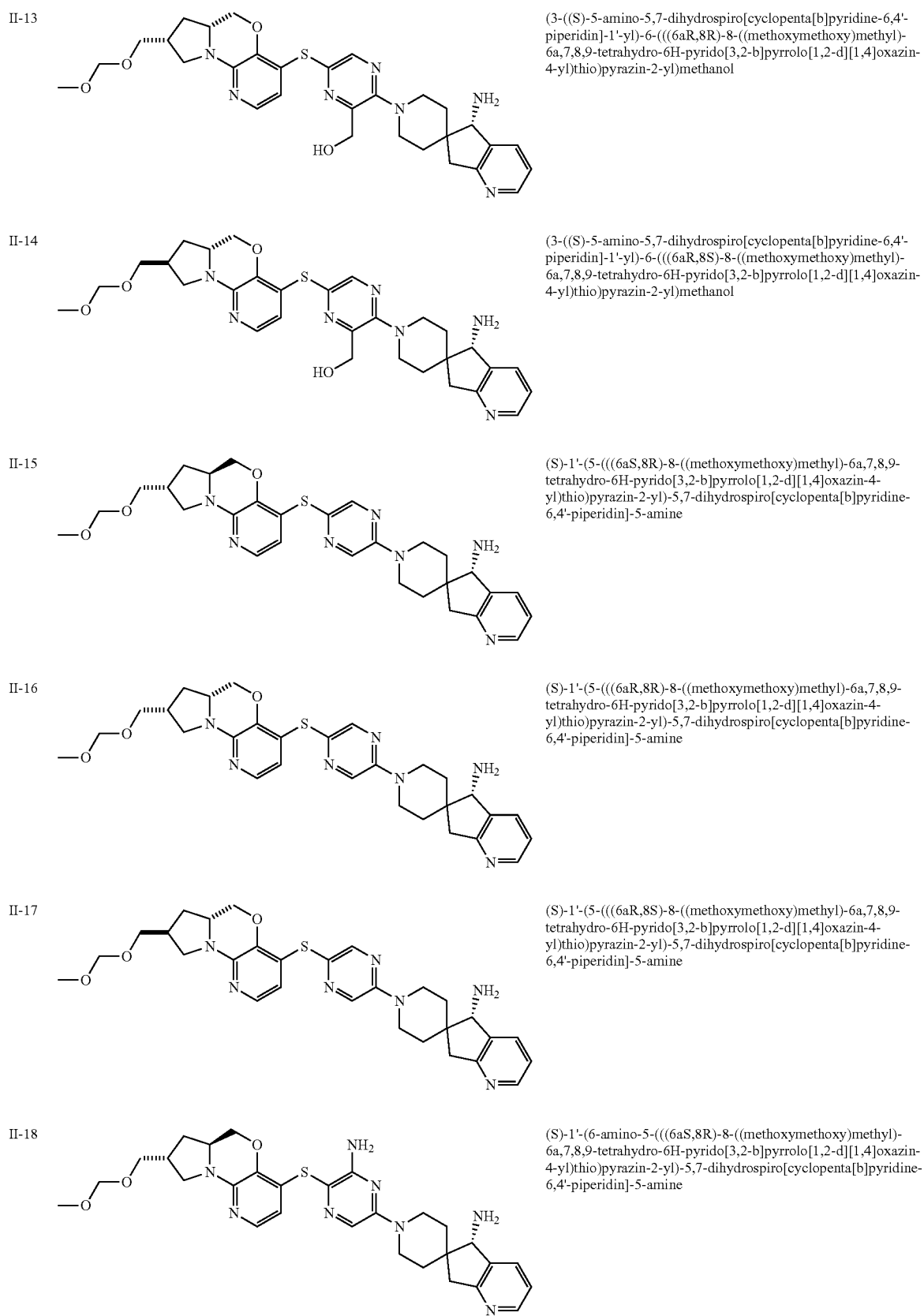

| | |
|---|---|
| II-13 | (3-((S)-5-amino-5,7-dihydrospiro[cyclopenta[b]pyridine-6,4'-piperidin]-1'-yl)-6-((((6aR,8R)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol |
| II-14 | (3-((S)-5-amino-5,7-dihydrospiro[cyclopenta[b]pyridine-6,4'-piperidin]-1'-yl)-6-((((6aR,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol |
| II-15 | (S)-1'-(5-((((6aS,8R)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-5,7-dihydrospiro[cyclopenta[b]pyridine-6,4'-piperidin]-5-amine |
| II-16 | (S)-1'-(5-((((6aR,8R)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-5,7-dihydrospiro[cyclopenta[b]pyridine-6,4'-piperidin]-5-amine |
| II-17 | (S)-1'-(5-((((6aR,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-5,7-dihydrospiro[cyclopenta[b]pyridine-6,4'-piperidin]-5-amine |
| II-18 | (S)-1'-(6-amino-5-((((6aS,8R)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-5,7-dihydrospiro[cyclopenta[b]pyridine-6,4'-piperidin]-5-amine |

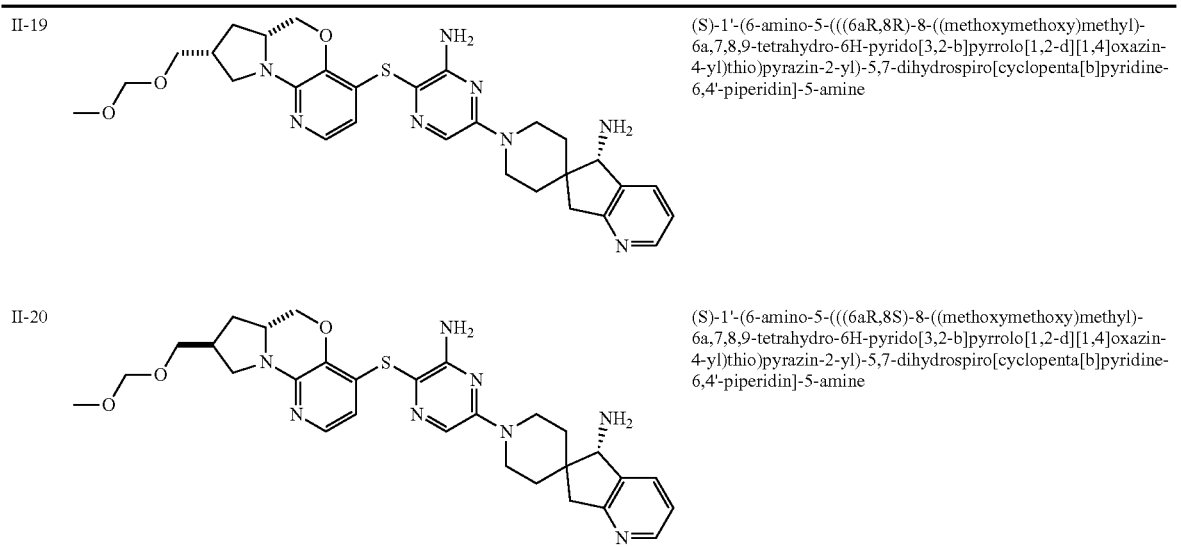

| | | |
|---|---|---|
| II-19 | | (S)-1'-(6-amino-5-((((6aR,8R)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-5,7-dihydrospiro[cyclopenta[b]pyridine-6,4'-piperidin]-5-amine |
| II-20 | | (S)-1'-(6-amino-5-((((6aR,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-5,7-dihydrospiro[cyclopenta[b]pyridine-6,4'-piperidin]-5-amine |

EMBODIMENTS

In further embodiments 1-36 below, the present disclosure includes:

1. In embodiment 1, provided is a compound of Formula (I), (IA), (IB), or (IC) as described in the Summary above, or a pharmaceutically acceptable salt thereof.

In a first subembodiment of embodiment 1, the compound is a compound of Formula (I), or a pharmaceutically acceptable salt thereof. In a second subembodiment of embodiment 1, the compound is a compound of Formula (IA), or a pharmaceutically acceptable salt thereof. In a third subembodiment of embodiment 1, the compound is a compound of Formula (IB), or a pharmaceutically acceptable salt thereof. In a fourth subembodiment of embodiment 1, the compound is a compound of Formula (IC), or a pharmaceutically acceptable salt thereof.

2. In embodiment 2, the compound of any one of embodiment 1 and subembodiments contained within embodiment 1, or a pharmaceutically acceptable salt thereof is wherein the has a structure of formula (II): (i.e., $Z^1$ is a group of formula (a))

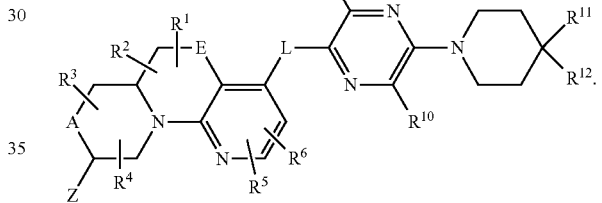

(II)

3. In embodiment 3, the compound of any one of embodiments 1 and 2 and subembodiment contained therein, and or a pharmaceutically acceptable salt thereof is wherein the compound has a structure of Formula (IIA):

(IIA)

4. In embodiment 5, the compound of any one of embodiment 1 and subembodiment contained within embodiment 1, or a pharmaceutically acceptable salt thereof is wherein the compound has a structure of formula (III): (i.e., $Z^1$ is a group of formula (b))

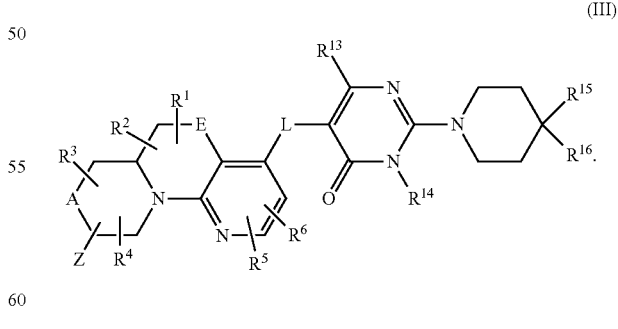

(III)

5. In embodiment 5, the compound of any one of embodiment 1 and 4 and subembodiments contained therein, or a pharmaceutically acceptable salt thereof is wherein the compound has a structure of Formula (IIIA):

(IIIA)

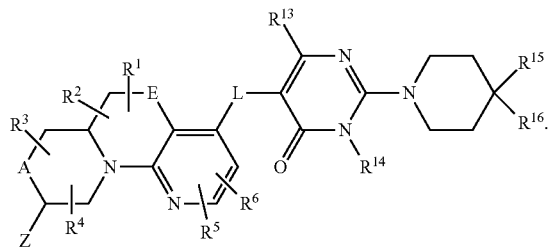

6. In embodiment 6, the compound of any one of embodiments 1 to 5 and subembodiment contained therein, or a pharmaceutically acceptable salt thereof is wherein E is O and A is CH$_2$ or bond.

7. In embodiment 7, the compound of any one of embodiments 1 to 5 and subembodiment contained therein, or a pharmaceutically acceptable salt thereof is wherein E is O and A is bond.

8. In embodiment 8, the compound of embodiment 3 and subembodiment contained therein, or a pharmaceutically acceptable salt thereof has a structure of formula (IIB):

(IIB)

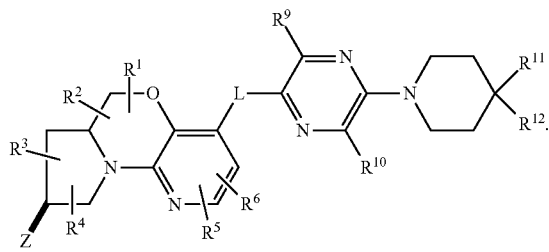

9. In embodiment 9, the compound of embodiment 5 and subembodiment contained therein, or a pharmaceutically acceptable salt thereof has the structure of formula (IIIB):

(IIIB)

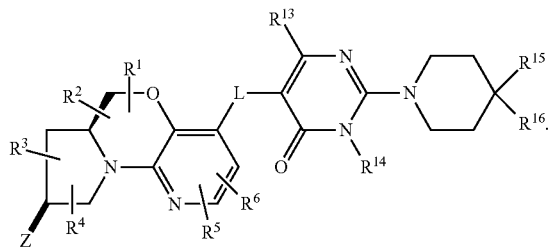

10. In embodiment 10, the compound of any one of embodiments 1 to 9 and subembodiment contained therein, or a pharmaceutically acceptable salt thereof is wherein Z is hydrogen, alkyl, halo, haloalkyl, haloalkoxy, cyano, cycloalkyl, heterocyclyl, heteroaryl (wherein cycloalkyl, heterocyclyl, and heteroaryl are optionally substituted with one to three halo), —O(alk)$_y$R$^a$, —O(alk)OR$^b$, —S(O)$_2$R$^d$, —OC(O)NR$^i$R$^j$, —S(O)$_2$NR$^n$R$^o$, —NR$^p$R$^q$, or —Y-M (wherein Y is bond, O, or SO$_2$ and M is alkyl, haloalkyl, cycloalkyl, heterocyclyl, or heteroaryl wherein alkyl, haloalkyl, cycloalkyl, heterocyclyl and heteroaryl are substituted with —O(alk)$_y$R$^a$, —O(alk)OR$^b$, —S(O)$_2$R$^a$, or —NR$^p$R$^q$ and cycloalkyl, heterocyclyl, and heteroaryl are optionally further substituted with 1 to 3 halo).

11. In embodiment 11, the compound of any one of embodiments 1 to 9 and subembodiment contained therein, or a pharmaceutically acceptable salt thereof is wherein Z is —Y-M (wherein Y is bond or O and M is alkyl, haloalkyl, cycloalkyl, heterocyclyl, or heteroaryl wherein alkyl, haloalkyl, cycloalkyl, heterocyclyl and heteroaryl are substituted with —O(alk)OR$^b$, —S(O)$_2$R$^d$, —NR$^e$C(O)R$^f$, —NR$^g$SO$_2$R$^h$, —OC(O)NR$^i$R$^j$, —C(O)NR$^k$R$^m$, or —S(O)$_2$NR$^n$R$^o$.

12. In embodiment 12, the compound of any one of embodiments 1 to 9 and subembodiment contained therein, or a pharmaceutically acceptable salt thereof is wherein Z is —Y-M (wherein Y is bond and M is alkyl, haloalkyl, cycloalkyl, heterocyclyl, or heteroaryl wherein alkyl, haloalkyl, cycloalkyl, heterocyclyl and heteroaryl are substituted with —O—R$^a$ where R$^a$ is alkyl, cycloalkyl, cycloalkylalkyl, aminoalkyl, optionally substituted heterocyclyl, optionally substituted heterocyclylalkyl, optionally substituted aryl, or optionally substituted heteroaryl.

13. In embodiment 13, the compound of any one of embodiments 1 to 9 and subembodiment contained therein, or a pharmaceutically acceptable salt thereof is wherein Z is —Y-M (wherein Y is bond and M is alkyl, haloalkyl, cycloalkyl, heterocyclyl, or heteroaryl wherein alkyl, haloalkyl, cycloalkyl, heterocyclyl and heteroaryl are substituted with —O(alk)OR$^a$ where R$^a$ is alkyl, cycloalkyl, cycloalkylalkyl, aminoalkyl, optionally substituted heterocyclyl, optionally substituted heterocyclylalkyl, optionally substituted aryl, or optionally substituted heteroaryl.

14. In embodiment 14, the compound of any one of embodiments 1 to 9 and subembodiment contained therein, or a pharmaceutically acceptable salt thereof is wherein Z is —OR$^a$ where R$^a$ is alkyl, cycloalkyl, cycloalkylalkyl, aminoalkyl, optionally substituted heterocyclyl, optionally substituted heterocyclylalkyl, optionally substituted aryl, or optionally substituted heteroaryl.

15. In embodiment 15, the compound of any one of embodiments 1 to 9 and subembodiment contained therein, or a pharmaceutically acceptable salt thereof is wherein Z is —O(alk)OR$^b$ where R$^b$ is alkyl, cycloalkyl, cycloalkylalkyl, aminoalkyl, optionally substituted heterocyclyl, optionally substituted heterocyclylalkyl, optionally substituted aryl, or optionally substituted heteroaryl.

16. In embodiment 16, the compound of any one of embodiments 1 to 9 and subembodiment contained therein, or a pharmaceutically acceptable salt thereof is wherein Z is hydrogen, fluoro, cyano, methoxy, hydroxy, cyclopentyloxy, tetrahydrofuran-3-yloxy, oxetan-3-yloxy, methoxymethyloxy, methoxyethyloxy, methylsulfonyl, aminocarbonyloxy, pyrazol-1-yl, hydroxymethyl, methoxymethyl, ethoxymethyl, methoxymethyloxymethyl, ethoxymethyloxymethyl, methoxyethyloxymethyl, cyclopropylmethyloxy, or oxetan-3-ylmethyloxymethyl.

17. In embodiment 17, the compound of any one of embodiments 1 to 9 and subembodiment contained therein, or a pharmaceutically acceptable salt thereof is wherein Z is methoxymethyloxy, methoxyethyloxy, methoxymethyl, methoxymethyloxymethyl, ethoxymethyloxymethyl, methoxyethyloxymethyl, cyclopropylmethyloxy, or oxetan-3-ylmethyloxymethyl.

18. In embodiment 18, the compound of any one of embodiments 1 to 9 and subembodiment contained therein, or a pharmaceutically acceptable salt thereof is wherein Z is methoxymethyl, methoxymethyloxymethyl, ethoxymethyloxymethyl, methoxyethyloxymethyl, cyclopropylmethyloxymethyl, or oxetan-3-ylmethyloxymethyl.

19. In embodiment 18, the compound of any one of embodiments 1 to 9 and subembodiment contained therein, or a pharmaceutically acceptable salt thereof is wherein Z is fluoro.

20. In embodiment 20, the compound of any one of embodiments 1 to 19 and sub-embodiments contained therein, or a pharmaceutically acceptable salt thereof is wherein $R^9$ and $R^{13}$ are hydrogen.

21. In embodiment 21, the compound of any one of embodiments 1 to 19 and sub-embodiment contained therein, or a pharmaceutically acceptable salt thereof is wherein $R^9$ and $R^{13}$ are amino.

21A. In embodiment 21A, the compound of any one of embodiments 1 to 19 and sub-embodiment contained therein, or a pharmaceutically acceptable salt thereof is wherein $R^9$ and $R^{13}$ are methyl.

21B. In embodiment 21B, the compound of any one of embodiments 1 to 19 and sub-embodiment contained therein, or a pharmaceutically acceptable salt thereof is wherein $R^9$ and $R^{13}$ are independently hydrogen, alkyl, or amino.

22. In embodiment 22, the compound of any one of embodiments 1 to 21B and sub-embodiments contained therein, or a pharmaceutically acceptable salt thereof is wherein L is S.

23. In embodiment 23, the compound of any one of embodiments 1 to 21B and sub-embodiments contained therein, or a pharmaceutically acceptable salt thereof is wherein L is S(O) or S(O)$_2$.

24. In embodiment 24, the compound of any one of embodiments 1 to 21B and sub-embodiments contained therein, or a pharmaceutically acceptable salt thereof is wherein L is bond.

25. In embodiment 25, the compound of any one of embodiments 1 to 24 and sub-embodiments contained therein, or a pharmaceutically acceptable salt thereof is wherein L is $CR^7R^8$ where $R^5$ and $R^6$ are independently hydrogen or alkyl. In one sub-embodiment, of embodiment 10, L is CH$_2$. In another sub-embodiment of embodiment 10, L is C(CH$_3$)$_2$.

26. In embodiment 26, the compound of any one of embodiments 1 to 3, 6-8, and 10 to 25 and sub-embodiments contained therein, or a pharmaceutically acceptable salt thereof is wherein $R^{10}$ is hydroxyalkyl. In a first sub-embodiment of embodiment 11, $R^{10}$ is hydroxymethyl.

27. In embodiment 27, the compound of any one of embodiments 1 to 3, 6-8, and 10 to 25 and sub-embodiments contained therein, or a pharmaceutically acceptable salt thereof is wherein $R^{10}$ is alkylsulfonyl. In a first sub-embodiment of embodiment 27, $R^2$ is methylsulfonyl or ethylsulfonyl.

27A. In embodiment 27A, the compound of any one of embodiments 1 to 3, 6-8, and 10 to 25 and sub-embodiments contained therein, or a pharmaceutically acceptable salt thereof is wherein $R^{10}$ is hydrogen.

28. In embodiment 28, the compound of any one of embodiments 11 to 25 and sub-embodiments contained therein, or a pharmaceutically acceptable salt thereof is wherein $R^{14}$ is hydrogen.

29. In embodiment 29, the compound of any one of embodiments 11 to 25 and sub-embodiments contained therein, or a pharmaceutically acceptable salt thereof is wherein $R^{14}$ is -alkyl. In a first subembodiment, $R^{14}$ is methyl.

30. In embodiment 30, the compound of any one of embodiments 1 to 29 and sub-embodiments contained therein, or a pharmaceutically acceptable salt thereof is wherein:

$R^{11}$ and $R^{15}$ are selected from amino and aminoalkyl; and $R^{12}$ and $R^{16}$ are selected from hydrogen, cyano, halo, alkyl, haloalkyl, alkoxy, haloalkoxy, cycloalkyl, aryl, heterocyclyl, and heteroaryl, where alkyl, cycloalkyl, aryl, heterocyclyl and heteroaryl are optionally substituted with one to three substituents independently selected from alkyl, halo, haloalkyl, haloalkoxy, alkoxy, and cyano. In a sub-embodiment of embodiment 30, $R^{11}$ and $R^{15}$ are aminomethyl, and $R^{12}$ and $R^{16}$ are methyl.

31. In embodiment 31, the compound of any one of embodiments 1 to 29 and sub-embodiments contained therein, or a pharmaceutically acceptable salt thereof is wherein: $R^{11}$ and $R^{12}$, and $R^{15}$ and $R^{16}$ together with the carbon atom to which they are attached form a ring of formula (c):

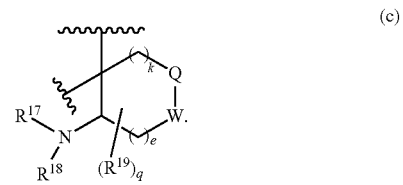

In a first subembodiment of embodiment 31, ring of formula (c) is:

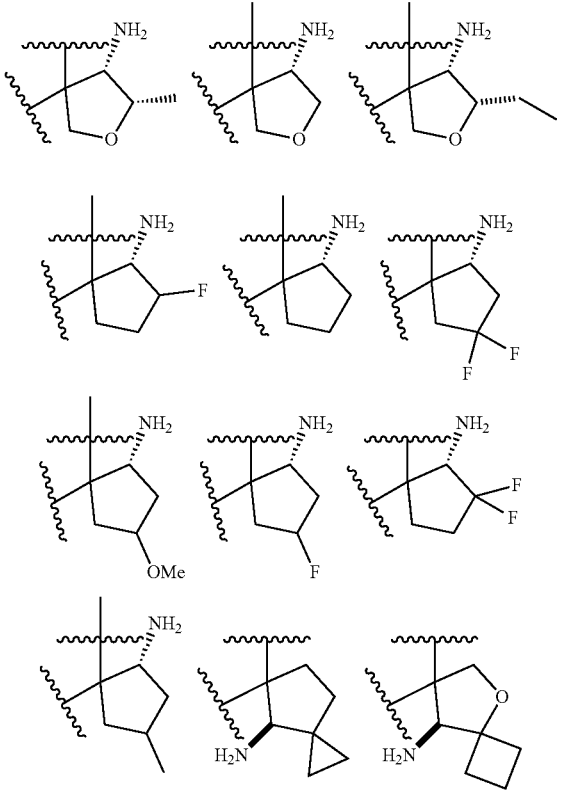

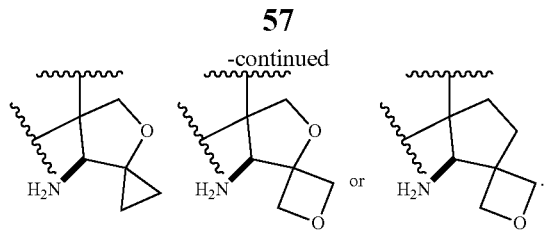

In a second subembodiment of embodiment 31, ring of formula (c) is

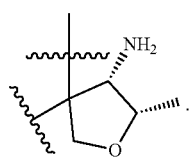

32. In embodiment 32, the compound of any one of 1 to 29 and sub-embodiments contained therein, or a pharmaceutically acceptable salt thereof is wherein $R^{11}$ and $R^{12}$, and $R^{15}$ and $R^{16}$ together with the carbon atom to which they are attached form a ring of formula (c):

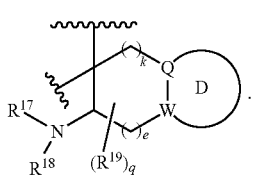

In a first embodiment of embodiment 32, ring of formula (c) is:

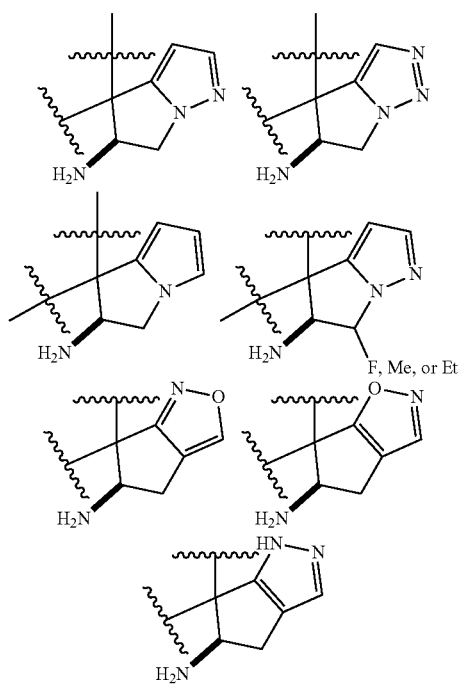

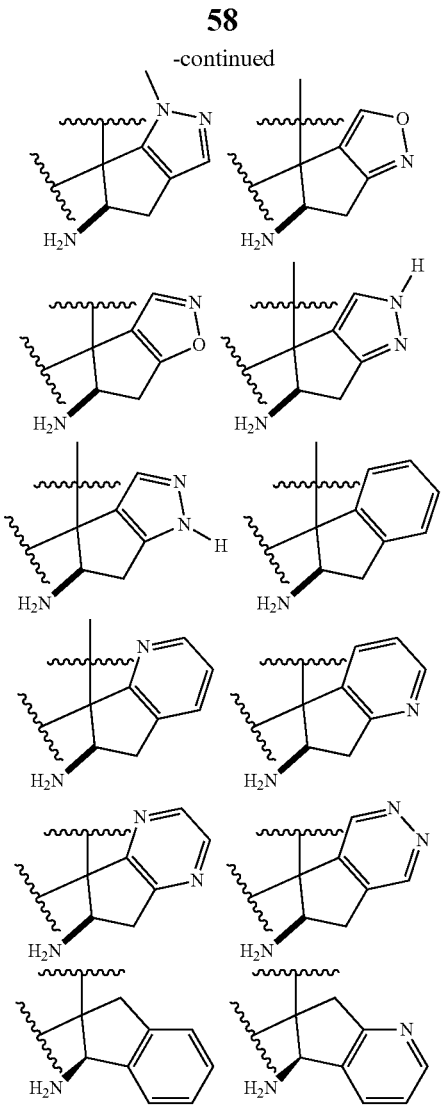

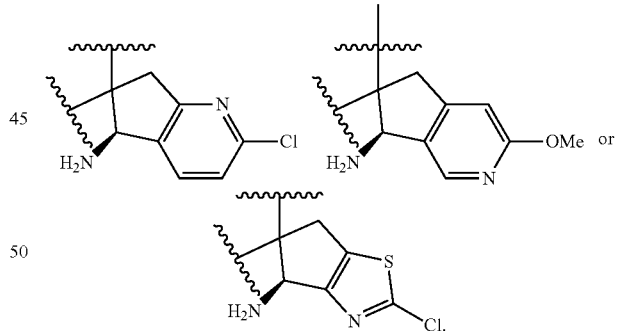

33. In embodiment 33, the compound of any one of embodiments 1 to 32 and sub-embodiments contained therein, or a pharmaceutically acceptable salt thereof is wherein $R^1$, $R^2$, $R^3$, and $R^4$ are independently selected from hydrogen, alkyl, halo, haloalkyl, haloalkoxy, alkoxy, cyano, or hydroxy, amino. In a first subembodiment 33, one of $R^1$, $R^2$, $R^3$, and $R^4$ is hydrogen and the remaining three of $R^1$, $R^2$, $R^3$, and $R^4$ are independently selected from hydrogen, methyl, fluoro, methoxy, hydroxy, or amino. In a second subembodiment 33, two or three of $R^1$, $R^2$, $R^3$, and $R^4$ are hydrogen and the remaining one or two of $R^1$, $R^2$, $R^3$, and $R^4$ are independently selected from hydrogen, methyl, fluoro, methoxy, hydroxy, or amino. In a third subembodiment 33, $R^1$, $R^2$, $R^3$, and $R^4$ are hydrogen.

34. In embodiment 34, the compound of any one of embodiments 1 to 32 and sub-embodiments contained therein, or a pharmaceutically acceptable salt thereof is wherein $R^5$ is hydrogen, alkyl, halo, or amino and $R^6$ is hydrogen, alkyl, halo, haloalkyl, haloalkoxy, alkoxy, hydroxy, or cyano.

35. In embodiment 35, the compound of any one of embodiments 1 to 32 and sub-embodiments contained therein, or a pharmaceutically acceptable salt thereof is wherein $R^5$ is hydrogen, chloro, methyl, or amino and R is hydrogen, methyl, chloro, trifluoromethyl, trifluoromethoxy, or methoxy.

36. In embodiment 34, the compound of any one of embodiments 1 to 32 and sub-embodiments contained therein, or a pharmaceutically acceptable salt thereof is $R^5$ and $R^6$ are hydrogen.

It is understood that the embodiments set forth above include all combination of embodiments and subembodiments listed therein. For example, the ring of formula (c) listed in embodiment 31 and first and second sub-embodiments of embodiment 31, can independently be combined with one or more of the embodiments 1-30 and 32-36 and/or subembodiments contained therein.

Additional embodiments include Embodiments 37-63 below:

37. A compound of Formula (I'):

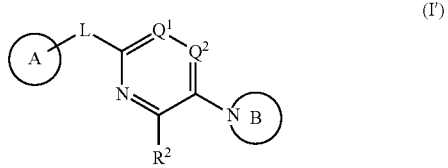

wherein:
A is

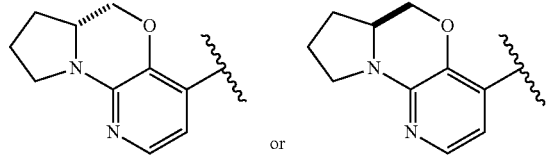

substituted with $R^a$, $R^b$, and/or $R^c$ wherein $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, alkoxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —S(O)R, S(O)$_2$R, —C(O)R, —OR', —NR'C(O)R, —NR'SO$_2$R, —OC(O)NR'R", —C(O)NR'R", —S(O)$_2$NR'R", —NR'R", or —NR'C(O)C(O)R where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R" are independently hydrogen, alkyl, hydroxyalkyl, alkoxyalkyl, aminoalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl or R' and R" together with the nitrogen atom to which they are attached form optionally substituted heterocyclyl; or when $R^c$ and $R^a$ are attached to the same carbon of cycloalkyl or fused heteroaryl ring, then $R^c$ and $R^a$ together with the carbon atom to which they are attached form cycloalkylene or heterocyclylene;

or A is has the structure (d):

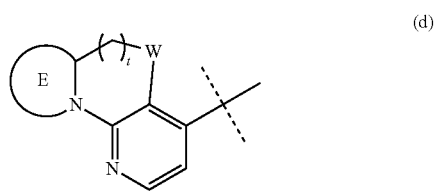

where:
t is 0, 1 or 2;
ring E is 4 to 7 membered heterocycle containing 1 or 2 heteroatoms independently selected from O, N, S, and SO$_2$ where the remaining atoms are carbon; and W is O, CH$_2$, or N; substituted with $R^a$, $R^b$, and/or $R^c$ wherein $R^a$ and $R^b$ are independently selected from hydrogen, amino, alkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, or alkoxy; or when $R^a$ and $R^c$ are attached to the same carbon atom, $R^a$ and $R^c$ together with the carbon atom to which they are attached form cycloalkylene or heterocyclylene $Q^1$ is N or CR wherein $R^1$ is hydrogen or deuterium;
$Q^2$ is N or CH, or CD;
$R^2$ is alkyl, halo, hydroxy, hydroxyalkyl, —CD$_2$OH, alkylsulfoxide, alkylsulfonyl, aminosulfonyl, aminocarbonyl, carboxy, cyano, or alkoxycarbonyl;
L is bond, O, S, S(O), S(O)$_2$, or CR$^5$R$^6$ where $R^5$ and $R^6$ are independently hydrogen or alkyl;
and

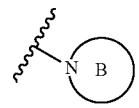

s a ring of formula (a) or (b):

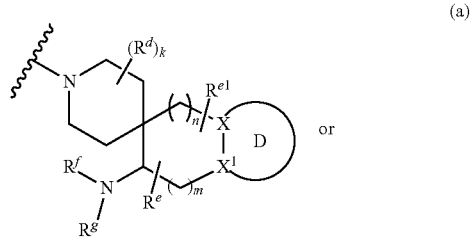

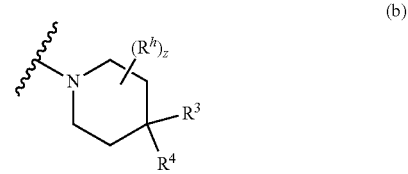

wherein:
  m is 0, 1; or 2;
  n is 0, 1, or 2 wherein when n is 2 then one of the $CH_2$ can be replaced with O, S, or $SO_2$; provided m+n is 1, 2, or 3;
  k is 0, 1 or 2;
  z is 0, 1, or 2;
  each $R^d$ is independently hydrogen, alkyl, or halogen;
  $R^e$ and $R^{e1}$ are independently hydrogen, alkyl, halogen, haloalkyl, alkoxy, haloalkoxy, hydroxy, hydroxyalkyl, cyano or oxo; or
  when $R^e$ and $R^{e1}$ are attached to the same carbon atom, then $R^e$ and $R^{e1}$ together with the carbon atom to which they are attached form cycloalkylene or heterocyclylene;
  $R^f$ and $R^g$ are independently hydrogen, alkyl, or haloalkyl;
  each $R^h$ is independently alkyl, halo, haloalkyl, alkoxy, hydroxyalkyl, alkoxyalkyl, hydroxy, cyano, or oxo; or
  when one $R^h$ is connected to carbon 2 or 3 of the piperidine (b) ring and the second $R^h$ is attached to carbon 5 or 6 of the piperidine (b) ring, the nitrogen atom being position 1, then the first and second $R^h$ combine to form alkylene chain;
  ring D is phenyl or a 5 or 6 membered heteroaryl ring which, including X and $X^1$, contains one to three heteroatoms independently selected from N, O, and S and ring D can optionally be substituted with one or two groups independently selected from alkyl, halo, haloalkyl, alkoxy, haloalkoxy, hydroxy, hydroxyalkyl, cyano, amino, aminoalkyl, carboxy, cycloalkyl, heterocyclyl, heteroaryl, and acylamino;
  X and $X^1$ are independently N or C provided only one of X and $X^1$ can be N;
  $R^3$ is amino or aminoalkyl;
  $R^4$ is alkyl, cycloalkylalkyl, halo, hydroxy, amino, alkoxycarbonyl, hydroxyalkyl, alkoxyalkyl, arylalkyl, heterocyclalkyl, cycloalkylalkyl, heterocyclalkyl, 5 or 6 membered heteroaryl, or 4 to 6 membered heterocyclyl wherein heteroaryl or heterocyclyl by itself or as part of aralkyl or heteroaralkyl is substituted with $R^i$ and/or $R^j$ independently selected from hydrogen, alkyl, halo, haloalkyl, haloalkoxy, alkoxy, hydroxy, cyano, amino, aminoalkyl, alkylsulfoxide, or alkylsulfonyl; or
  $R^3$ and $R^4$ together with the carbon atom to which they are attached form a ring of formula (c):

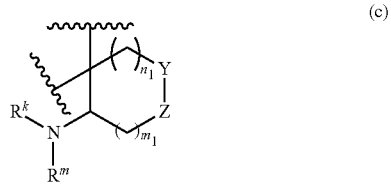

(c)

wherein:
  m1 is 0, 1; or 2;
  n1 is 0, 1, or 2; provided m1+n1 is 1, 2, or 3;
  $R^k$ and $R^m$ are independently hydrogen, alkyl, or haloalkyl;
  one of Y and Z is $CH_2$, O, S, S(O), $S(O)_2$, or NH; and the other of X and Y is $CH_2$; and wherein ring of formula (c) is substituted with R" and/or $R^o$ independently selected from hydrogen, alkyl, alkyldienyl, alkenyl, halo, haloalkyl, haloalkoxy, alkoxy, hydroxy, cyano, alkylsulfoxide, alkylsulfonyl, oxo, cycloalkyl, heterocyclyl, and heteroaryl; or when R" and $R^o$ are attached to the same carbon atom, then R" and $R^o$ together with the carbon atom to which they are attached form cycloalkylene or heterocyclylene; or
  a pharmaceutically acceptable salt thereof.

38. The compound of embodiment 37 having a structure of Formula (I'A):

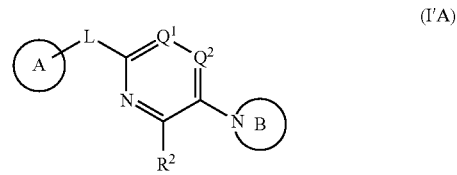

(I'A)

wherein:
  A is

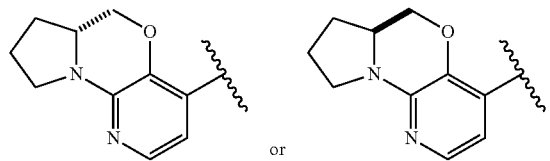

or substituted with $R^a$, $R^b$, and/or $R^c$ wherein $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —S(O)R, $S(O)_2R$, —C(O)R, —NR'C(O)R, —NR'$SO_2$R, —C(O)NR'R", —$S(O)_2$NR'R", —NR'R", or —NR'C(O)C(O)R where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R" are independently hydrogen, alkyl, hydroxyalkyl, alkoxyalkyl, aminoalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl or R' and R" together with the nitrogen atom to which they are attached form optionally substituted heterocyclyl; or when $R^c$ and $R^a$ are attached to the same carbon of cycloalkyl or fused heteroaryl ring, then $R^c$ and $R^a$ together with the carbon atom to which they are attached form cycloalkylene or heterocyclylene;
  A has the structure (d):

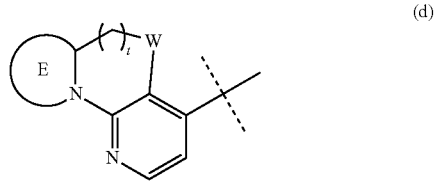

(d)

where:

t is 0, 1 or 2;

ring E is 4 to 7 membered heterocycle containing 1 or 2 heteroatoms independently selected from O, N, S, and $SO_2$ where the remaining atoms are carbon; and W is O, $CH_2$, or N; optionally substituted with $R^a$, $R^b$, and/or $R^c$ wherein $R^a$ and $R^b$ are independently selected from hydrogen, amino, alkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^o$ is hydrogen, alkyl, halo, hydroxy, or alkoxy; or when $R^a$ and $R^c$ are attached to the same carbon atom, $R^a$ and $R^c$ together with the carbon atom to which they are attached form cycloalkylene or heterocyclylene;

$Q^1$ is N or $CR^1$ wherein $R^1$ is hydrogen or deuterium;

$Q^2$ is N or CH, or CD;

$R^2$ is alkyl, halo, hydroxy, hydroxyalkyl, —$CD_2OH$, alkylsulfoxide, alkylsulfonyl, aminosulfonyl, aminocarbonyl, carboxy, cyano, or alkoxycarbonyl;

L is bond, O, S, S(O), $S(O)_2$, or $CR^5R^6$ where $R^5$ and $R^6$ are independently hydrogen or alkyl; and

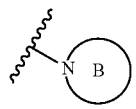

is a ring of formula (a) or (b):

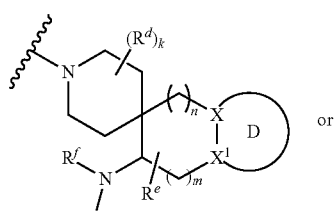

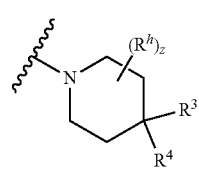

wherein:

m is 0, 1; or 2;

n is 0, 1, or 2; provided m+n is 1, 2, or 3;

k is 0, 1 or 2 z is 0, 1, or 2 each $R^d$ is independently hydrogen, alkyl, or halogen;

$R^e$ is hydrogen, alkyl, halogen, haloalkyl, alkoxy, haloalkoxy, hydroxy, hydroxyalkyl, cyano or oxo;

$R^f$ and $R^g$ are independently hydrogen, alkyl, or haloalkyl;

each $R^h$ is independently alkyl, halo, haloalkyl, alkoxy, hydroxyalkyl, alkoxyalkyl, hydroxy, cyano, or oxo; or when one $R^h$ is connected to carbon 2 or 3 of the piperidine (b) ring and the second $R^h$ is attached to carbon 5 or 6 of the piperidine (b) ring, the nitrogen atom being position 1, then the first and second $R^h$ combine to form alkylene chain;

ring D is phenyl or a 5 or 6 membered heteroaryl ring which, including X and $X^1$, contains one to three heteroatoms independently selected from N, O, and S and ring D can optionally be substituted with one or two groups independently selected from alkyl, halo, haloalkyl, alkoxy, haloalkoxy, hydroxy, hydroxyalkyl, cyano, amino, aminoalkyl, carboxy, cycloalkyl, heterocyclyl, heteroaryl, and acylamino;

X and $X^1$ are independently N or C provided only one of X and $X^1$ can be N;

$R^3$ is amino or aminoalkyl;

$R^4$ is alkyl, cycloalkylalkyl, halo, hydroxy, amino, alkoxycarbonyl, hydroxyalkyl, alkoxyalkyl, arylalkyl, heterocyclalkyl, cycloalkylalkyl, heterocyclalkyl, 5 or 6 membered heteroaryl, or 4 to 6 membered heterocyclyl wherein heteroaryl or heterocyclyl by itself or as part of aralkyl or heteroaralkyl is substituted with $R^i$ and/or $R^j$ independently selected from hydrogen, alkyl, halo, haloalkyl, haloalkoxy, alkoxy, hydroxy, cyano, amino, aminoalkyl, alkylsulfoxide, or alkylsulfonyl; or $R^3$ and $R^4$ together with the carbon atom to which they are attached form a ring of formula (c):

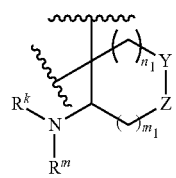

wherein:

m1 is 0, 1; or 2;

n1 is 0, 1, or 2; provided m1+n1 is 1, 2, or 3;

$R^k$ and $R^m$ are independently hydrogen, alkyl, or haloalkyl;

one of Y and Z is $CH_2$, O, S, S(O), $S(O)_2$, or NH; and the other of X and Y is $CH_2$; and wherein ring of formula (c) is substituted with $R^n$ and/or $R^o$ independently selected from hydrogen, alkyl, alkyldienyl, alkenyl, halo, haloalkyl, haloalkoxy, alkoxy, hydroxy, cyano, alkylsulfoxide, alkylsulfonyl, oxo, cycloalkyl, heterocyclyl, and heteroaryl; or a pharmaceutically acceptable salt thereof.

39. A compound of Formula (I'B):

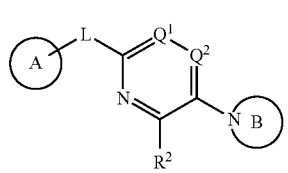

wherein:

A is

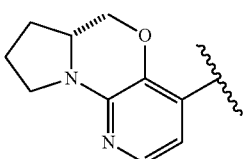 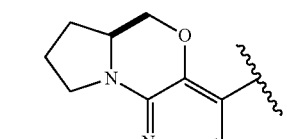

substituted with $R^a$, $R^b$, and/or $R^c$ wherein $R^a$ and $R^b$ are independently selected from hydrogen, alkyl, halo, haloalkyl, alkoxy, haloalkoxy, hydroxy, hydroxyalkyl, cyano, aminoalkyl, carboxy, and alkoxycarbonyl and $R^o$ is hydrogen, alkyl, halo, hydroxy, alkoxy, optionally substituted heterocyclyl, optionally substituted aryl, optionally substituted heteroaryl, —S(O)R, S(O)$_2$R, —C(O)R, —NR'C(O)R, —NR'SO$_2$R, —C(O)NR'R", —S(O)$_2$NR'R", —NR'R", or —NR'C(O)C(O)R where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R" are independently hydrogen, alkyl, hydroxyalkyl, alkoxyalkyl, aminoalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl or R' and R" together with the nitrogen atom to which they are attached form optionally substituted heterocyclyl;

$Q^1$ is N or $CR^1$ wherein $R^1$ is hydrogen or deuterium;

$Q^2$ is N or CH, or CD;

$R^2$ is alkyl, halo, hydroxy, hydroxyalkyl, —CD$_2$OH, alkylsulfoxide, alkylsulfonyl, aminosulfonyl, aminocarbonyl, carboxy, cyano, or alkoxycarbonyl;

L is bond, O, S, S(O), S(O)$_2$, or $CR^5R^6$ where $R^5$ and $R^6$ are independently hydrogen or alkyl;

and

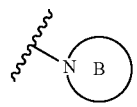

is a ring of formula (a) or (b):

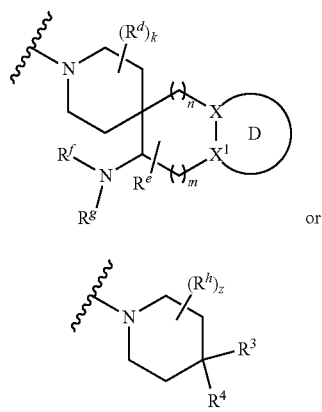

wherein:

m is 0, 1; or 2;

n is 0, 1, or 2; provided m+n is 1, 2, or 3;

k is 0, 1 or 2 z is 0, 1, or 2 each $R^d$ is independently hydrogen, alkyl, or halogen;

$R^e$ is hydrogen, alkyl, halogen, haloalkyl, alkoxy, haloalkoxy, hydroxy, hydroxyalkyl, cyano or oxo;

$R^f$ and $R^g$ are independently hydrogen, alkyl, or haloalkyl;

each $R^h$ is independently alkyl, halo, haloalkyl, alkoxy, hydroxyalkyl, alkoxyalkyl, hydroxy, cyano, or oxo; or when one $R^h$ is connected to carbon 2 or 3 of the piperidine (b) ring and the second $R^h$ is attached to carbon 5 or 6 of the piperidine (b) ring, the nitrogen atom being position 1, then the first and second $R^h$ combine to form alkylene chain;

ring D is phenyl or a 5 or 6 membered heteroaryl ring which, including X and $X^1$, contains one to three heteroatoms independently selected from N, O, and S and ring D can optionally be substituted with one or two groups independently selected from alkyl, halo, haloalkyl, alkoxy, haloalkoxy, hydroxy, hydroxyalkyl, cyano, amino, aminoalkyl, carboxy, cycloalkyl, heterocyclyl, heteroaryl, and acylamino;

X and $X^1$ are independently N or C provided only one of X and $X^1$ can be N;

$R^3$ is amino or aminoalkyl;

$R^4$ is alkyl, cycloalkylalkyl, halo, hydroxy, amino, alkoxycarbonyl, hydroxyalkyl, alkoxyalkyl, arylalkyl, heterocyclalkyl, cycloalkylalkyl, heterocyclalkyl, 5 or 6 membered heteroaryl, or 4 to 6 membered heterocyclyl wherein heteroaryl or heterocyclyl by itself or as part of aralkyl or heteroaralkyl is substituted with $R^i$ and/or $R^j$ independently selected from hydrogen, alkyl, halo, haloalkyl, haloalkoxy, alkoxy, hydroxy, cyano, amino, aminoalkyl, alkylsulfoxide, or alkylsulfonyl; or $R^3$ and $R^4$ together with the carbon atom to which they are attached form a ring of formula (c):

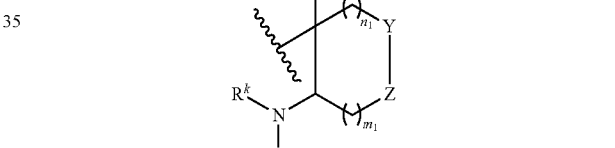

wherein:

m1 is 0, 1; or 2;

n1 is 0, 1, or 2; provided m1+n1 is 1, 2, or 3;

$R^k$ and $R^m$ are independently hydrogen, alkyl, or haloalkyl;

one of Y and Z is CH$_2$, O, S, S(O), S(O)$_2$, or NH; and the other of X and Y is CH$_2$; and wherein ring of formula (c) is substituted with $R^n$ and/or $R^o$ independently selected from hydrogen, alkyl, halo, haloalkyl, haloalkoxy, alkoxy, hydroxy, cyano, alkylsulfoxide, alkylsulfonyl, oxo, cycloalkyl, heterocyclyl, and heteroaryl; or a pharmaceutically acceptable salt thereof.

40. A compound of Formula (I'C):

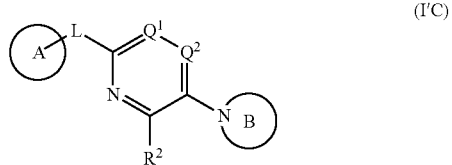

wherein:

A is

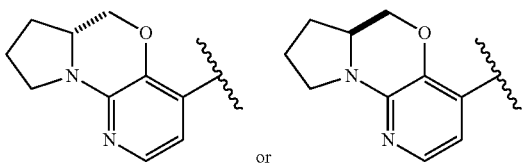

substituted with $R^a$, $R^b$, and/or $R^c$ wherein $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —NHCOR, or —NR'R'' where R is alkyl, cycloalkyl, optionally substituted heterocyclyl, optionally substituted aryl, optionally substituted heteroaryl, or optionally substituted heteroaralkyl, and R' and R'' are independently hydrogen or alkyl or R' and R'' together with the nitrogen atom to which they are attached form optionally substituted heterocyclyl; or when $R^c$ and $R^a$ are attached to the same carbon of cycloalkyl or fused heteroaryl ring, then $R^c$ and $R^a$ together with the carbon atom to which they are attached form cycloalkylene or heterocyclylene;

A has the structure (d):

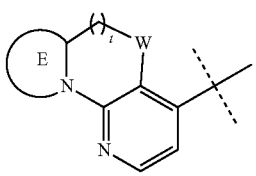

where:

t is 0, 1 or 2;

ring E is 4 to 7 membered heterocycle containing 1 or 2 heteroatoms independently selected from O, N, S, and $SO_2$ where the remaining atoms are carbon; and W is O, $CH_2$, or N; optionally substituted with $R^a$, $R^b$, and/or $R^c$ wherein $R^a$ and $R^b$ are independently selected from hydrogen, amino, alkyl, alkyldienyl, alkenyl, halo, haloalkyl, alkoxy, haloalkoxy, hydroxy, hydroxyalkyl, cyano, aminoalkyl, carboxy, and alkoxycarbonyl and R is hydrogen, alkyl, halo, hydroxy, or alkoxy; or when $R^a$ and $R^c$ are attached to the same carbon atom, $R^a$ and $R^c$ together with the carbon atom to which they are attached form cycloalkylene or heterocyclylene.

$Q^1$ is N or CR wherein $R^1$ is hydrogen or deuterium;

$Q^2$ is N, CH, or CD;

$R^2$ is alkyl, halo, hydroxy, hydroxyalkyl, —$CD_2OH$, alkylsulfoxide, alkylsulfonyl, aminosulfonyl, aminocarbonyl, carboxy, cyano, or alkoxycarbonyl;

L is bond, O, S, SO, $SO_2$, or $CR^5R^6$ where $R^5$ and $R^6$ are independently hydrogen or alkyl;

and

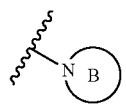

is a ring of formula (a) or (b):

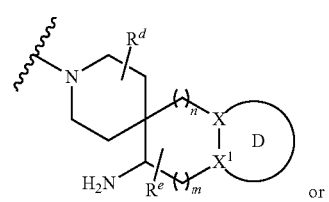

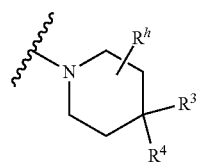

wherein:

m is 0, 1; or 2;

n is 0, 1, or 2; provided m+n is 1, 2, or 3;

$R^d$ is hydrogen or alkyl;

$R^e$ is hydrogen, alkyl, halogen, or oxo;

$R^h$ is independently alkyl, halo, haloalkyl, alkoxy, hydroxyalkyl, alkoxyalkyl, hydroxy, cyano, or oxo;

ring D is phenyl or a 5 or 6 membered heteroaryl ring which, including X and $X^1$, contains one to three heteroatoms independently selected from N, O, or S and ring D can optionally be substituted with alkyl;

X and $X^1$ are independently N or C provided only one of X and $X^1$ can be N;

$R^3$ is amino or aminoalkyl;

$R^4$ is alkyl, cycloalkylalkyl, halo, hydroxy, amino, alkoxycarbonyl, hydroxyalkyl, alkoxyalkyl, 5 or 6 membered heteroaryl, or 4 to 6 membered heterocyclyl wherein heteroaryl or heterocyclyl is substituted with $R^i$ and/or $R^j$ independently selected from hydrogen, alkyl, halo, haloalkyl, haloalkoxy, alkoxy, hydroxy, cyano, alkylsulfoxide, or alkylsulfonyl; or $R^3$ and $R^4$ together with the carbon atom to which they are attached form a ring of formula (c):

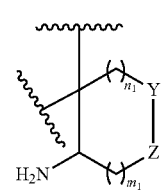

wherein:

m1 is 0, 1; or 2;

n1 is 0, 1, or 2; provided m1+n1 is 1, 2, or 3;

one of Y and Z is $CH_2$, O, S, SO, $SO_2$, or NH; and the other of X and Y is $CH_2$; and wherein ring of formula (c) is substituted with $R^n$ and/or $R^o$ independently selected from hydrogen, alkyl, alkyldienyl, alkenyl, halo, haloalkyl, haloalkoxy, alkoxy, hydroxy, cyano, alkylsulfoxide, alkylsulfonyl, or oxo; or a pharmaceutically acceptable salt thereof.

41. A compound of Formula (I'D):

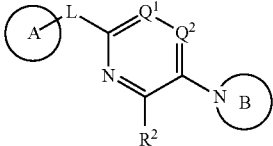

(I'D)

wherein:

A is

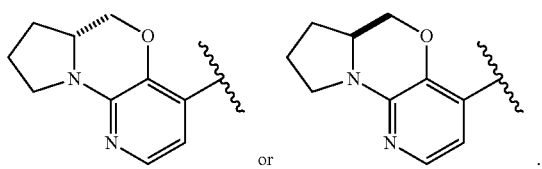

substituted with $R^a$, $R^b$, and/or $R^c$ wherein $R^a$ and $R^b$ are independently selected from hydrogen, alkyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —NHCOR, or —NR'R" where R is alkyl, cycloalkyl, optionally substituted heterocyclyl, optionally substituted aryl, optionally substituted heteroaryl, or optionally substituted heteroaralkyl, and R' and R" are independently hydrogen or alkyl or R' and R" together with the nitrogen atom to which they are attached form optionally substituted heterocyclyl;

$Q^1$ is N or CR wherein $R^1$ is hydrogen or deuterium;

$Q^2$ is N, CH, or CD;

$R^2$ is alkyl, halo, hydroxy, hydroxyalkyl, —CD$_2$OH, alkylsulfoxide, alkylsulfonyl, aminosulfonyl, aminocarbonyl, carboxy, cyano, or alkoxycarbonyl;

L is bond, O, S, SO, SO$_2$, or CR$^5$R$^6$ where $R^5$ and $R^6$ are independently hydrogen or alkyl;

and

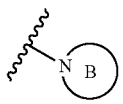

is a ring of formula (a) or (b):

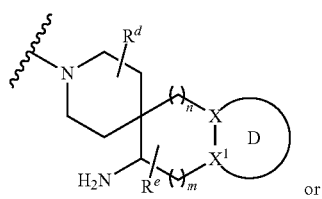

(a)

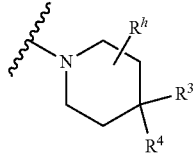

(b)

wherein:
m is 0, 1; or 2;
n is 0, 1, or 2; provided m+n is 1, 2, or 3;
$R^d$ is hydrogen or alkyl;
$R^e$ is hydrogen, alkyl, halogen, or oxo;
$R^h$ is independently alkyl, halo, haloalkyl, alkoxy, hydroxyalkyl, alkoxyalkyl, hydroxy, cyano, or oxo;
ring D is phenyl or a 5 or 6 membered heteroaryl ring which, including X and $X^1$, contains one to three heteroatoms independently selected from N, O, or S and ring D can optionally be substituted with alkyl;
X and $X^1$ are independently N or C provided only one of X and $X^1$ can be N;
$R^3$ is amino or aminoalkyl;
$R^4$ is alkyl, cycloalkylalkyl, halo, hydroxy, amino, alkoxycarbonyl, hydroxyalkyl, alkoxyalkyl, 5 or 6 membered heteroaryl, or 4 to 6 membered heterocyclyl wherein heteroaryl or heterocyclyl is substituted with $R^i$ and/or $R^j$ independently selected from hydrogen, alkyl, halo, haloalkyl, haloalkoxy, alkoxy, hydroxy, cyano, alkylsulfoxide, or alkylsulfonyl; or
$R^3$ and $R^4$ together with the carbon atom to which they are attached form a ring of formula (c):

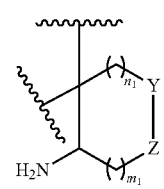

(c)

wherein:
m1 is 0, 1; or 2;
n1 is 0, 1, or 2; provided m1+n1 is 1, 2, or 3;
one of Y and Z is CH$_2$, O, S, SO, SO$_2$, or NH; and the other of X and Y is CH$_2$; and wherein ring of formula (c) is substituted with $R^n$ and/or $R^o$ independently selected from hydrogen, alkyl, halo, haloalkyl, haloalkoxy, alkoxy, hydroxy, cyano, alkylsulfoxide, alkylsulfonyl, or oxo; or
a pharmaceutically acceptable salt thereof.

42. In embodiment 42, the compound of any one of embodiments 37 to 41, or a pharmaceutically acceptable salt thereof has the structure of formula (III'):

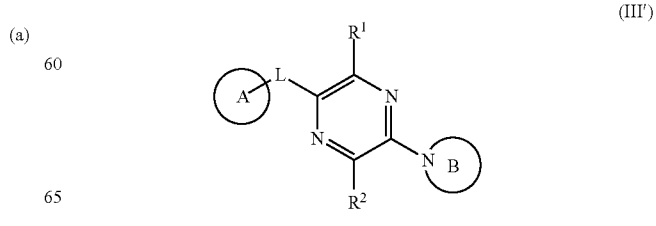

(III')

43. In embodiment 43, the compound of any one of embodiments 37 to 41, or a pharmaceutically acceptable salt thereof has the structure of formula (IV'):

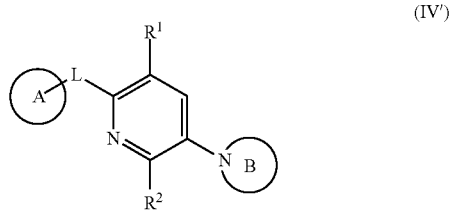
(IV')

44. In embodiment 44, the compound of any one of embodiments 37 to 41, or a pharmaceutically acceptable salt thereof has the structure of formula (V') or (VI'):

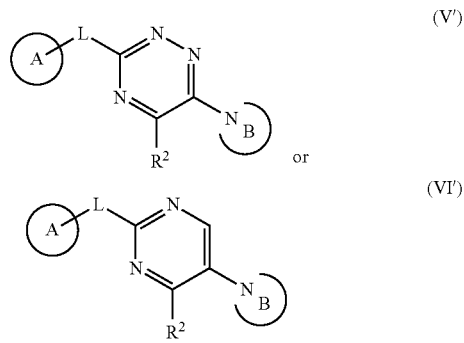

In one sub-embodiment of embodiment 4, the compound or a pharmaceutically acceptable salt thereof has structure (V). In another sub-embodiment of embodiment 4, the compound or a pharmaceutically acceptable salt thereof has structure (VI).

45. In embodiment 45, the compound of any one of embodiments 37 to 43 and sub-embodiments contained therein, or a pharmaceutically acceptable salt thereof is wherein $R^1$ is hydrogen.

46. In embodiment 46, the compound of any one of embodiments 37 to 43 and sub-embodiment contained therein, or a pharmaceutically acceptable salt thereof is wherein $R^1$ is deuterium.

47. In embodiment 7, the compound of any one of embodiments 37 to 46 and sub-embodiments contained therein, or a pharmaceutically acceptable salt thereof is wherein L is S.

48. In embodiment 8, the compound of any one of embodiments 37 to 46 and sub-embodiments contained therein, or a pharmaceutically acceptable salt thereof is wherein L is S(O) or S(O)$_2$.

49. In embodiment 49, the compound of any one of embodiments 37 to 46 and sub-embodiments contained therein, or a pharmaceutically acceptable salt thereof is wherein L is bond.

50. In embodiment 50, the compound of any one of embodiments 37 to 46 and sub-embodiments contained therein, or a pharmaceutically acceptable salt thereof is wherein L is $CR^5R^6$ where $R^5$ and $R^6$ are independently hydrogen or alkyl. In one sub-embodiment, of embodiment 50, L is $CH_2$. In another sub-embodiment of embodiment 50, L is $C(CH_3)_2$.

51. In embodiment 11, the compound of any one of embodiments 37 to 50 and sub-embodiments contained therein, or a pharmaceutically acceptable salt thereof is wherein $R^2$ is hydroxyalkyl. In a first sub-embodiment of embodiment 51, $R^2$ is hydroxymethyl.

52. In embodiment 52, the compound of any one of embodiments 37 to 50 and sub-embodiments contained therein, or a pharmaceutically acceptable salt thereof is wherein $R^2$ is alkylsulfonyl. In a first sub-embodiment of embodiment 52, $R^2$ is methylsulfonyl or ethylsulfonyl.

53. In embodiment 53, the compound of any one of embodiments 37 to 50 and sub-embodiments contained therein, or a pharmaceutically acceptable salt thereof is wherein $R^2$ is alkylsulfoxide. In a first sub-embodiment of embodiment 53, $R^2$ is methylsulfoxide, ethylsulfoxide, or isopropylsulfoxide. In a second sub-embodiment of embodiment 53, $R^2$ is methylsulfoxide.

54. In embodiment 54, the compound of any one of embodiments 37 to 50 and sub-embodiments contained therein, or a pharmaceutically acceptable salt thereof is wherein $R^2$ is -CD$_2$OH.

55. In embodiment 55, the compound of any one of embodiments 37 to 50 and sub-embodiments contained therein, or a pharmaceutically acceptable salt thereof is wherein $R^2$ is alkoxycarbonyl, aminosulfonyl or aminocarbonyl. In a first sub-embodiment of embodiment 55, $R^2$ is —S(O)$_2$NH$_2$. In a second sub-embodiment of embodiment 55, $R^2$ is —CONH$_2$. In a third sub-embodiment of embodiment 55, $R^2$ is —C(O)CH$_3$.

56. In embodiment 16, the compound of any one of embodiments 37 to 50 and sub-embodiments contained therein, or a pharmaceutically acceptable salt thereof is wherein $R^2$ is hydroxy.

57. In embodiment 57, the compound of any one of embodiments 37 to 50 and sub-embodiments contained therein, or a pharmaceutically acceptable salt thereof is wherein $R^2$ is halo. In a sub-embodiment of embodiment 17, $R^2$ is chloro.

58. In embodiment 58, the compound of any one of embodiments 37 to 57 and sub-embodiments contained therein, or a pharmaceutically acceptable salt thereof is wherein:

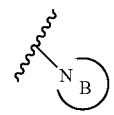

is a ring of formula (a):

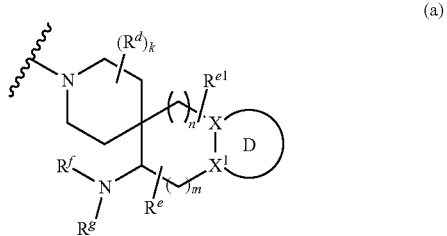
(a)

wherein:

m is 0, 1; or 2;

n is 0, 1, or 2 wherein when n is 2 then one of the $CH_2$ can be replaced with O, S, or $SO_2$; provided m+n is 1, 2, or 3;

k is 0, 1 or 2 z is 0, 1, or 2 each $R^d$ is independently hydrogen, alkyl, or halogen;

$R^e$ and $R^{e1}$ are independently hydrogen, alkyl, halogen, haloalkyl, alkoxy, haloalkoxy, hydroxy, hydroxyalkyl, cyano or oxo; or when $R^e$ and $R^{e1}$ are attached to the same carbon atom, then $R^e$ and $R^{e1}$ together with the carbon atom to which they are attached form cycloalkylene or heterocyclylene.

In a first embodiment of embodiment 58,

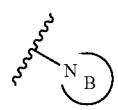

is a ring of formula:

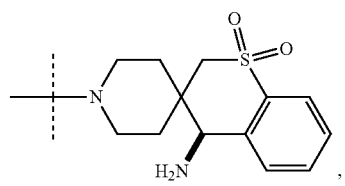

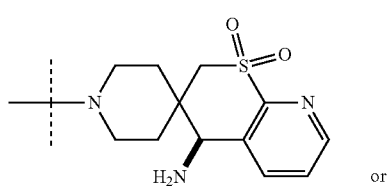

or

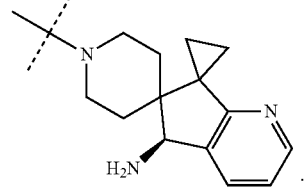

59. In embodiment 59, the compound of any one of embodiments 37 to 57 and sub-embodiments contained therein, or a pharmaceutically acceptable salt thereof is wherein:

is a ring of formula (a):

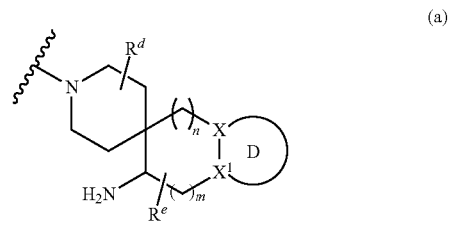

In a first sub-embodiment of embodiment 59,

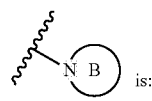 is:

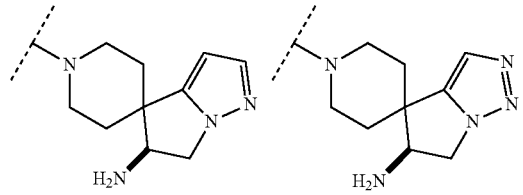

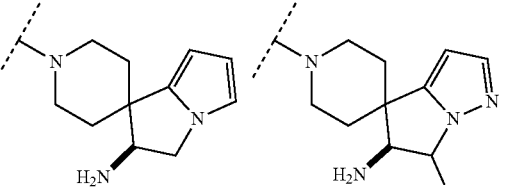

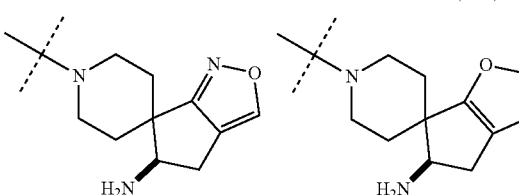

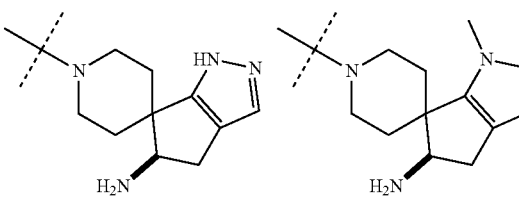

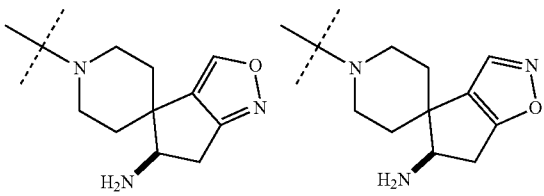

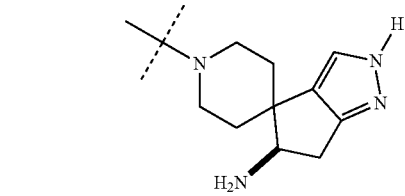

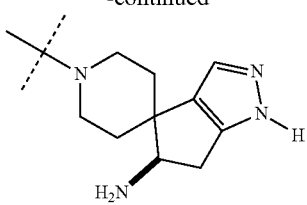
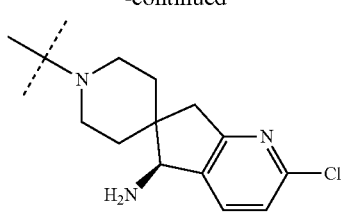
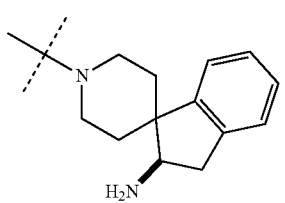
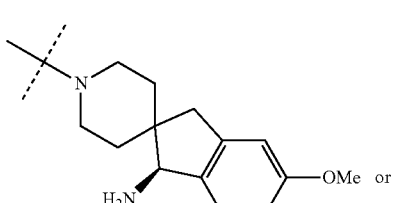
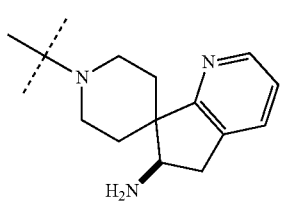
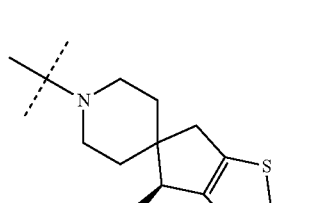
In a second sub-embodiment of embodiment 59,
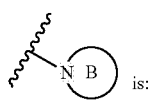 is:
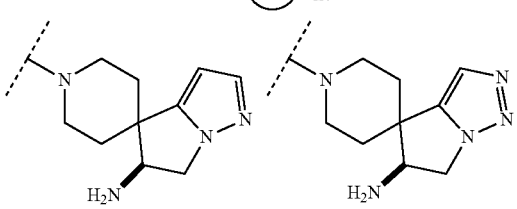
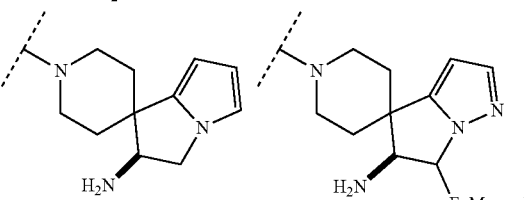
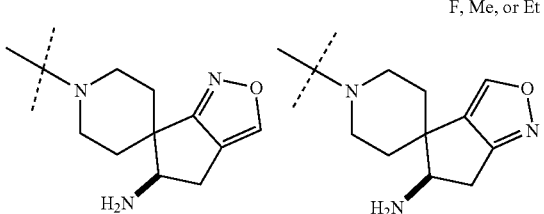
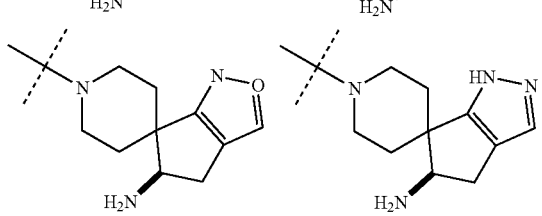

77
-continued

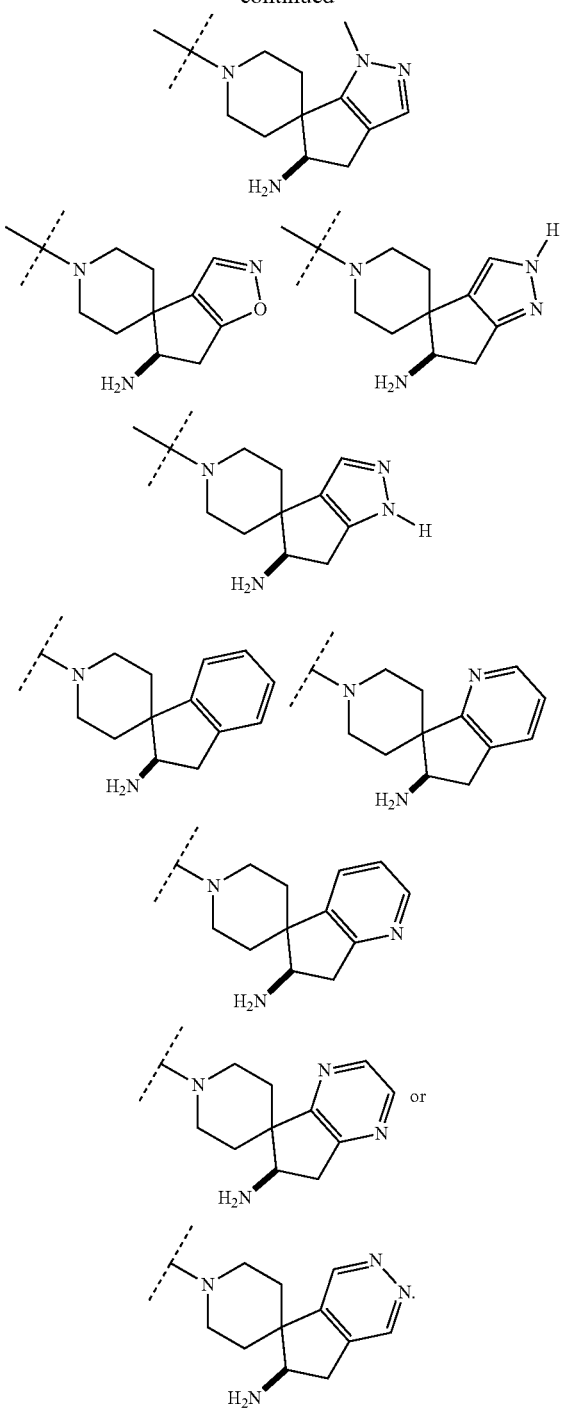

In a third sub-embodiment of embodiment 59

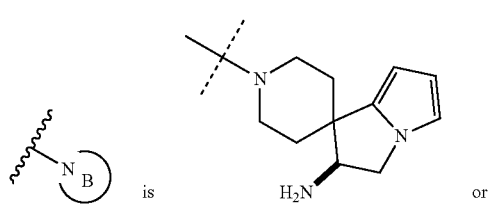

78
-continued

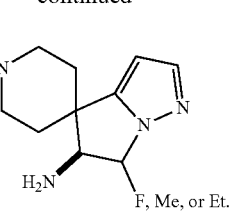

60. In embodiment 60, the compound of any one of embodiments 37 to 57 and sub-embodiments contained therein, or a pharmaceutically acceptable salt thereof is wherein

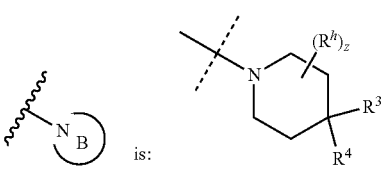

(b)

preferably where z is 1, and
where $R^3$ is amino or aminoalkyl; and
$R^4$ is alkyl, cycloalkylalkyl, halo, hydroxy, amino, alkoxycarbonyl, hydroxyalkyl, alkoxyalkyl, 5 or 6 membered heteroaryl, or 4 to 6 membered heterocyclyl wherein heteroaryl or heterocyclyl is substituted with $R^i$ and/or $R^j$ independently selected from hydrogen, alkyl, halo, haloalkyl, haloalkoxy, alkoxy, hydroxy, cyano, alkylsulfoxide, or alkylsulfonyl. In a sub-embodiment of embodiment 20, z is 0, $R^3$ is aminomethyl, and $R^4$ is methyl.

61. In embodiment 61, the compound of any one of embodiments 37 to 57 and sub-embodiments contained therein, or a pharmaceutically acceptable salt thereof is wherein

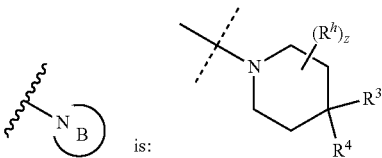

(b)

preferably where z is 1, and
where $R^3$ and $R^4$ together with the carbon atom to which they are attached form a ring of formula (c):

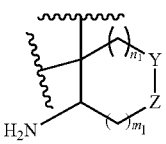

(c)

wherein:
m1 is 0, 1; or 2;
n1 is 0, 1, or 2; provided m1+n1 is 1, 2, or 3;
$R^k$ and $R^m$ are independently hydrogen, alkyl, or haloalkyl;

one of Y and Z is CH$_2$, O, S, S(O), S(O)$_2$, or NH; and the other of X and Y is CH$_2$; and wherein ring of formula (c) is substituted with R" and/or R° independently selected from hydrogen, alkyl, alkyldienyl, alkenyl, halo, haloalkyl, haloalkoxy, alkoxy, hydroxy, cyano, alkylsulfoxide, alkylsulfonyl, oxo, cycloalkyl, heterocyclyl, and heteroaryl; or when R" and R° are attached to the same carbon atom, then R" and R° together with the carbon atom to which they are attached form cycloalkylene or heterocyclylene;

In a first subembodiment of embodiment 61,

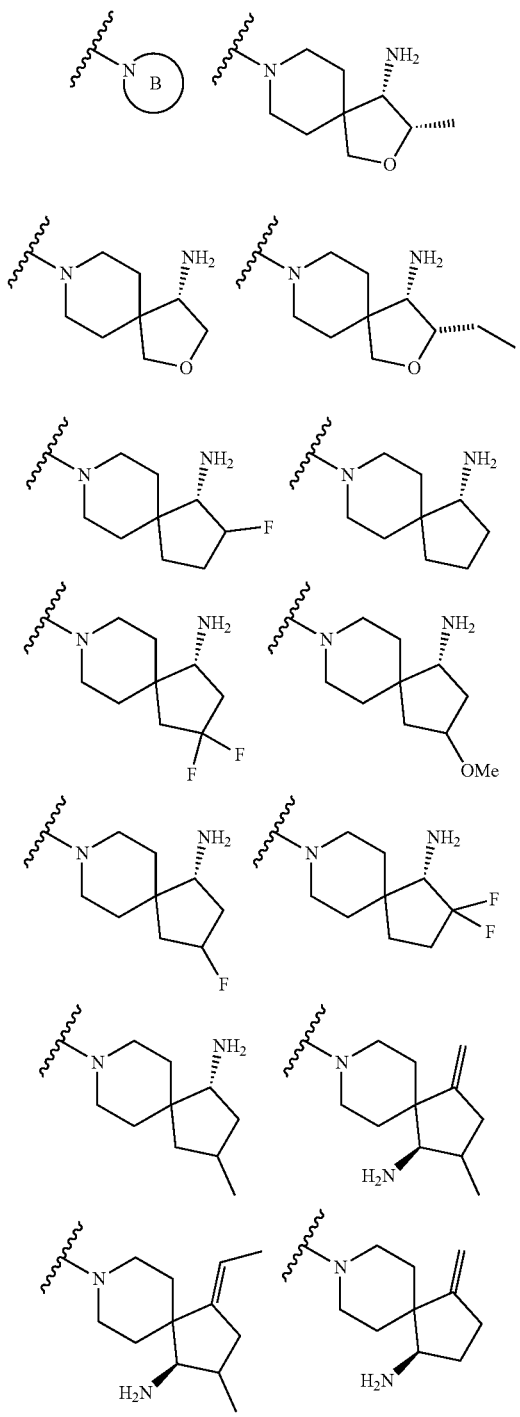

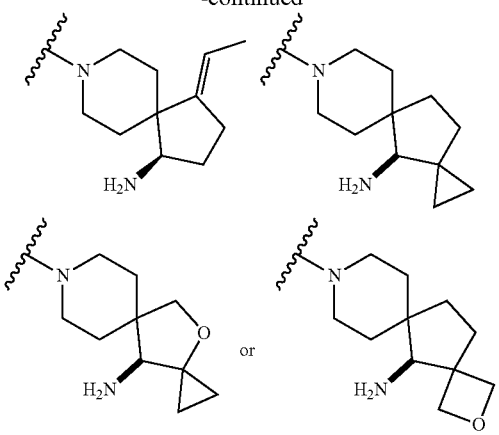

62. In embodiment 62, the compound of any one of embodiments 37 to 57 and sub-embodiments contained therein, or a pharmaceutically acceptable salt thereof is wherein

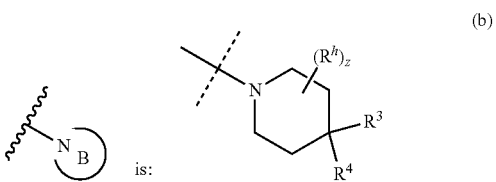

preferably where z is 1, and where R$^3$ and R$^4$ together with the carbon atom to which they are attached form a ring of formula (c):

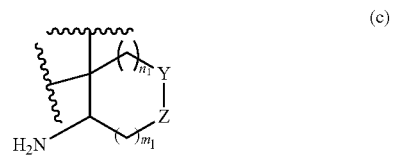

wherein:
m1 is 0, 1; or 2;
n1 is 0, 1, or 2; provided m1+n1 is 1, 2, or 3;
R$^k$ and R$^m$ are independently hydrogen, alkyl, or haloalkyl;
one of Y and Z is CH$_2$, O, S, S(O), S(O)$_2$, or NH; and the other of X and Y is CH$_2$; and wherein ring of formula (c) is substituted with R" and/or R° independently selected from hydrogen, alkyl, alkyldienyl, alkenyl, halo, haloalkyl, haloalkoxy, alkoxy, hydroxy, cyano, alkylsulfoxide, alkylsulfonyl, oxo, cycloalkyl, heterocyclyl and heteroaryl.

In a first sub-embodiment of embodiment 62,

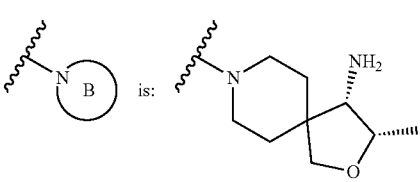

-continued
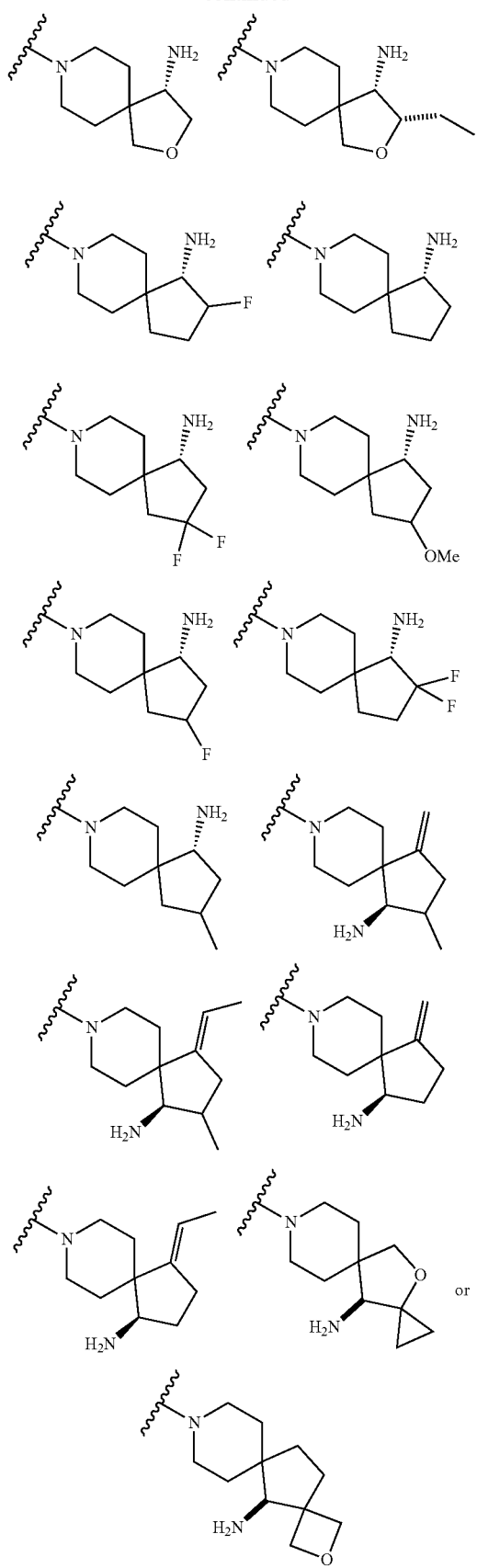
In a second subembodiment of embodiment 62,
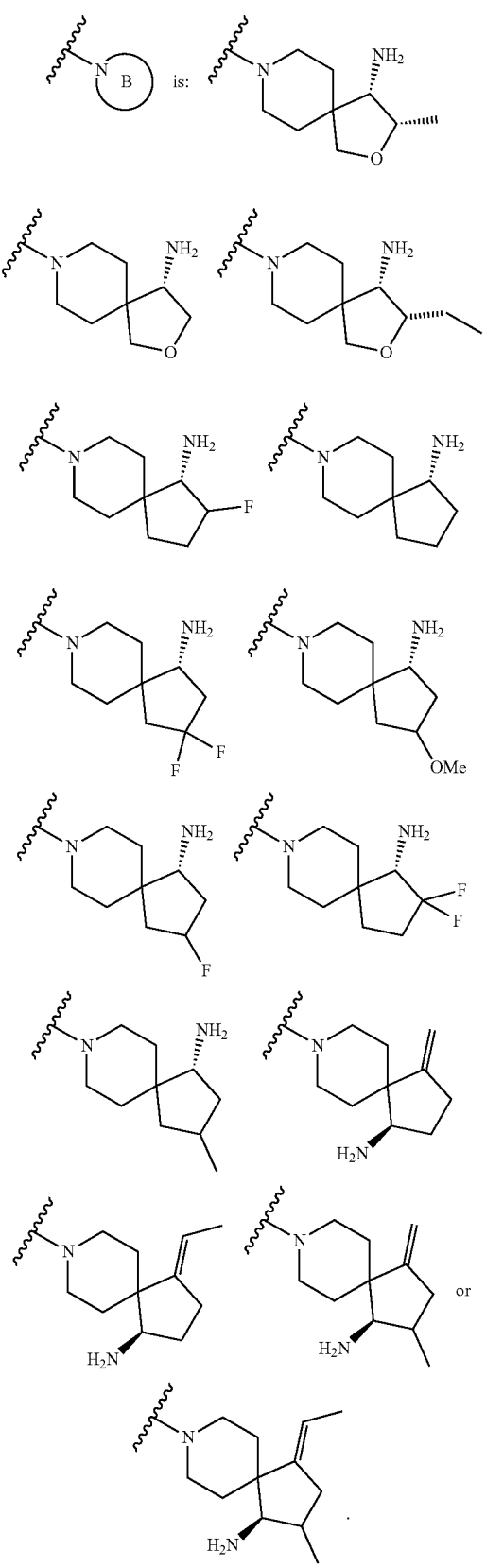

In a third sub-embodiment of embodiment 62,

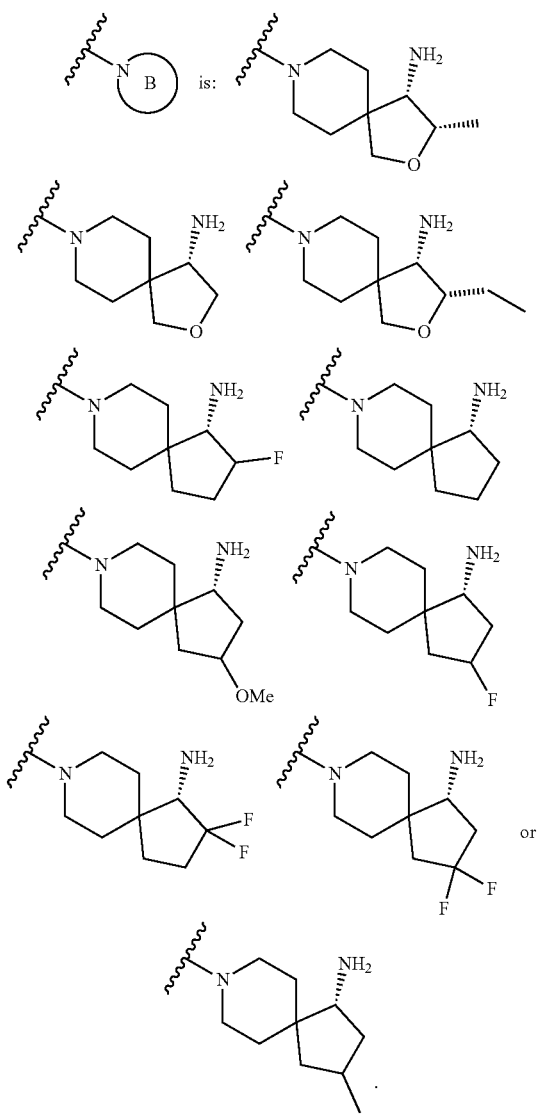

In a fourth sub-embodiment of embodiment 62,

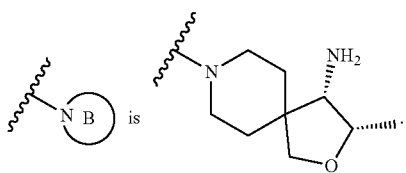

63. In embodiment 63, the compound of any one of embodiments 37 to 60 and sub-embodiments contained therein, or a pharmaceutically acceptable salt thereof $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —S(O)R, S(O)$_2$R, —C(O)R, —NR'C(O)R, —NR'SO$_2$R, —C(O)NR'R", —S(O)$_2$NR'R", —NR'R", or —NR'C(O)C(O)R where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R" are independently hydrogen, alkyl, hydroxyalkyl, alkoxyalkyl, aminoalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl or R' and R" together with the nitrogen atom to which they are attached form optionally substituted heterocyclyl; or when $R^c$ and $R^a$ are attached to the same carbon of cycloalkyl or fused heteroaryl ring, then $R^c$ and $R^a$ together with the carbon atom to which they are attached form cycloalkylene or heterocyclylene.

In a first sub-embodiment of embodiment 63, $R^a$ and $R^b$ are independently selected from hydrogen, alkyl, amino, cycloalkyl, alkyldienyl, alkenyl, halo, haloalkyl, alkoxy, haloalkoxy, hydroxy, and cyano and $R^c$ is hydrogen or —NR'R" where R' and R" are independently hydrogen, alkyl, hydroxyalkyl, alkoxyalkyl, aminoalkyl, or optionally substituted heterocyclyl.

In a second sub-embodiment of embodiment 63, $R^a$ and $R^b$ are independently selected from hydrogen, alkyl, halo, haloalkyl, alkoxy, haloalkoxy, hydroxy, and cyano and R is hydrogen or —NR'R" where R' and R" are independently hydrogen, alkyl, hydroxyalkyl, alkoxyalkyl, aminoalkyl, or optionally substituted heterocyclyl.

In a third sub-embodiment of embodiment 63, $R^a$ and $R^b$ are independently selected from hydrogen, alkyl, halo, haloalkyl, alkoxy, haloalkoxy, hydroxy, and cyano and R is hydrogen or —NR'R" where R' and R" are independently hydrogen, alkyl, hydroxyalkyl, alkoxyalkyl, aminoalkyl, or optionally substituted heterocyclyl.

In a fourth sub-embodiment of embodiment 63, $R^a$ and $R^b$ are independently selected from hydrogen, methyl, ethyl, methoxy, ethoxy, chloro, fluoro, difluoromethyl, trifluoromethyl, difluoromethoxy, trifluoromethoxy, hydroxy, or cyano, and $R^c$ is hydrogen.

In a fifth sub-embodiment of embodiment 63, and first subembodiment therein, ring A has the structure (d):

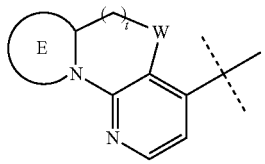

(d)

where:
t is 0, 1 or 2;
ring E is 4 to 7 membered heterocycle containing 1 or 2 heteroatoms independently selected from O, N, S, and SO$_2$ where the remaining atoms are carbon; and W is O, CH$_2$, or N; substituted with $R^a$, $R^b$, and/or $R^c$ wherein $R^a$ and $R^b$ are independently selected from hydrogen, amino, alkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, or alkoxy; or when $R^a$ and $R^c$ are attached to the same carbon atom, $R^a$ and $R^c$ together with the carbon atom to which they are attached form cycloalkylene or heterocyclylene.

In a first embodiment, of the fifth sub-embodiment, ring A is
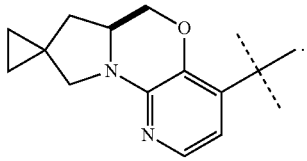
In a second embodiment, of the fourth sub-embodiment, ring A is:
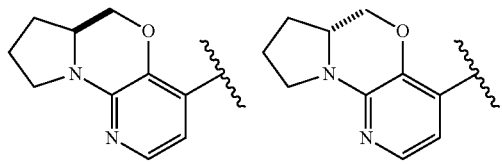
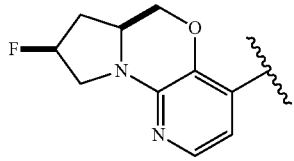
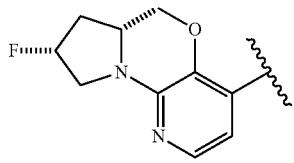
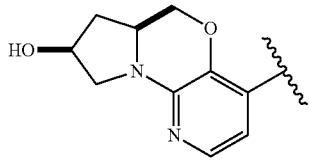
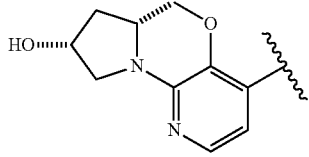
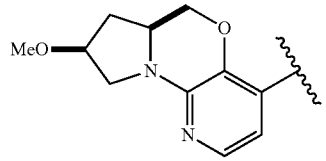
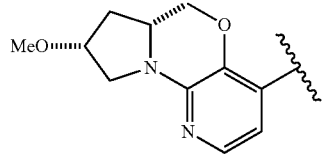
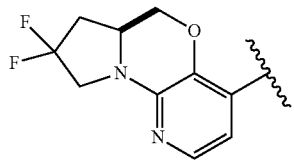
-continued
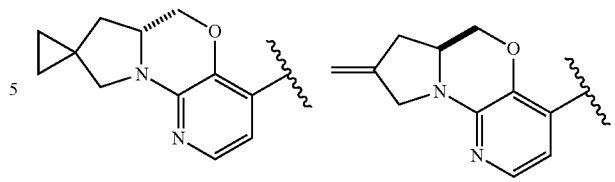
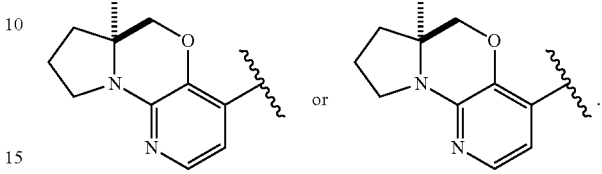
In a second embodiment of the fifth sub-embodiment, ring A is:
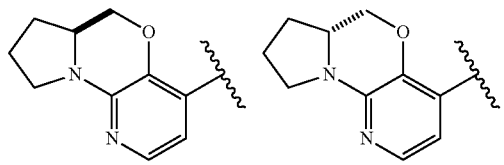
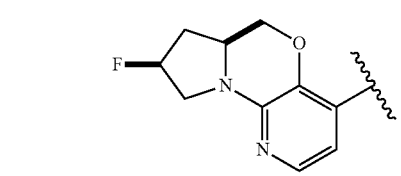
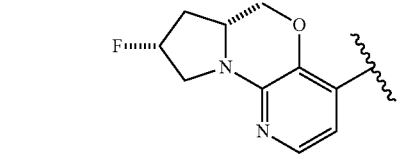
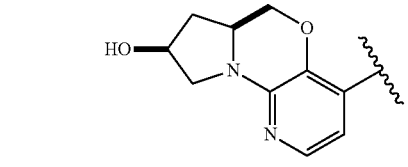
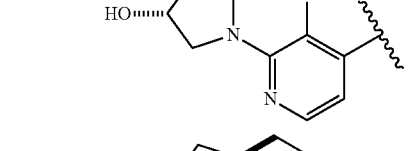
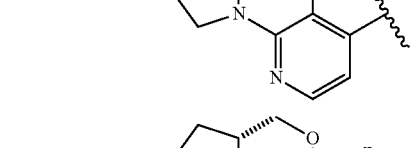

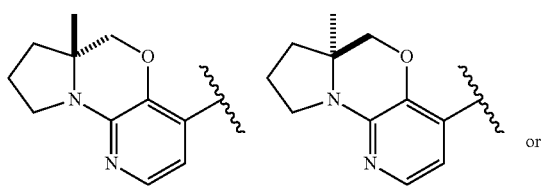
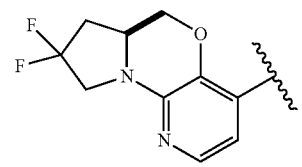
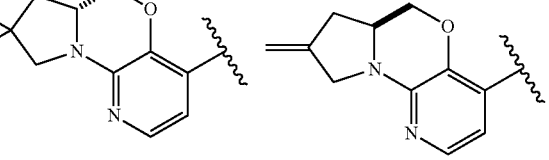
In an sixth subembodiment of embodiment 63, ring A is:
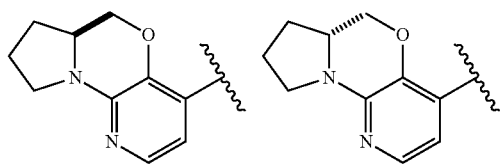
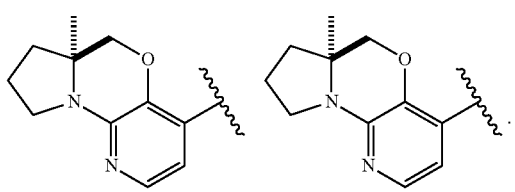
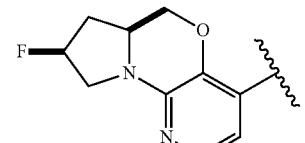
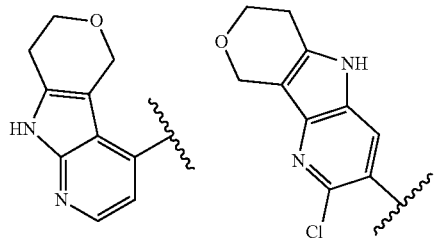
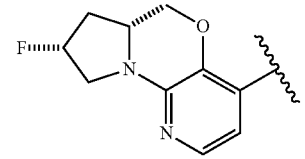
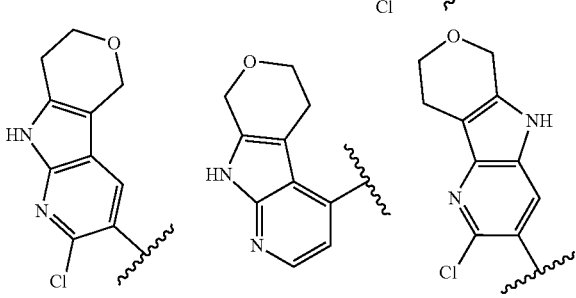
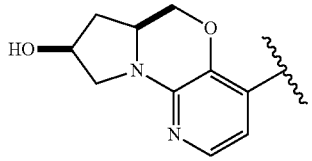
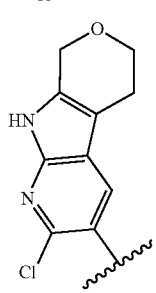
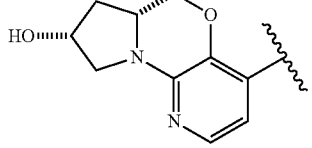
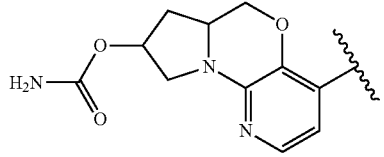
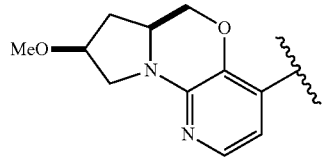
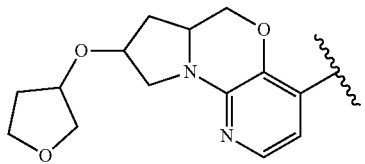
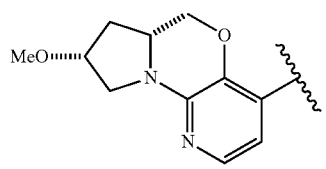

-continued

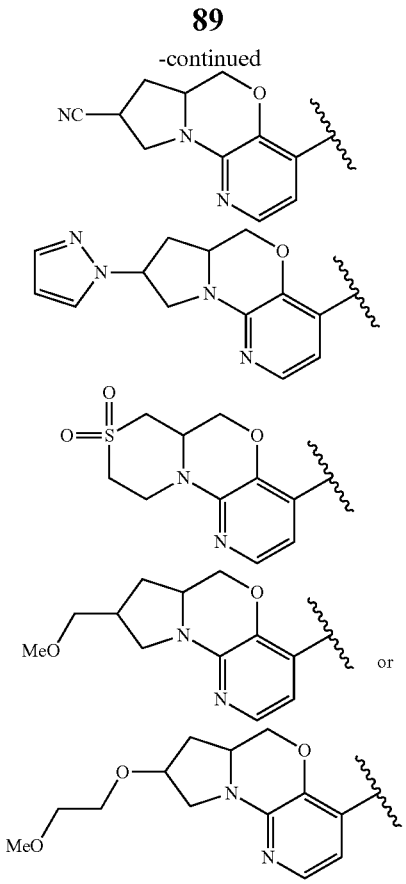

It is understood that the embodiments 37 to 63 set forth above include all combination of embodiments and subembodiments listed therein. For example, the ring Alisted in fifth sub-embodiment of embodiment 63, can independently be combined with one or more of the embodiments 35 to 62 and/or subembodiments contained therein.

Additional Embodiments include embodiments 66 to 112 below:

66. A compound of Formula (I):

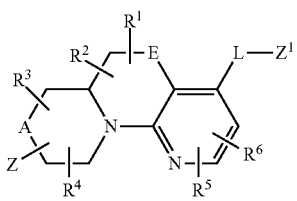

(I)

wherein:

A and E are independently selected from a bond, $CH_2$, O, NH, S, and $S(O)_2$;

Z is hydrogen, alkyl, halo, haloalkyl, haloalkoxy, cyano, cycloalkyl, heterocyclyl, heteroaryl (wherein cycloalkyl, heterocyclyl, and heteroaryl are optionally substituted with one to three halo), —O(alk)$_y$R$^a$, —O(alk)OR$^b$, —S(O)R$^c$, —S(O)$_2$R$^d$, —NR$^e$C(O) R$^f$, —NR$^g$SO$_2$R$^h$, —OC(O)NR$^i$R$^j$, —C(O)NR$^k$R$^m$, —S(O)$_2$NR$^n$R$^o$, —NR$^p$R$^q$, —NR$^r$C(O)C(O)R$^s$ or —Y-M (wherein Y is bond, O, or $SO_2$ and M is alkyl, haloalkyl, cycloalkyl, heterocyclyl, or heteroaryl wherein alkyl, haloalkyl, cycloalkyl, heterocyclyl and heteroaryl are substituted with —O(alk)$_y$R$^a$, —O(alk)OR$^b$, —S(O)R$^c$, —S(O)$_2$R$^d$, —NR$^e$C(O)R$^f$, —NR$^g$SO$_2$R$^h$, —OC(O)NR$^i$R$^j$, —C(O)NR$^k$R$^m$, —S(O)$_2$NR$^n$R$^o$, —NR$^p$R$^q$, or —NR$^r$C(O)C(O)R$^s$ and cycloalkyl, heterocyclyl, and heteroaryl are optionally further substituted with 1 to 3 halo);

wherein each y is 0 or 1, each alk is alkylene, and each R$^c$, R$^d$, R$^f$, R$^h$, and R$^s$ are independently alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; and each R$^a$, R$^b$, R$^e$, R$^g$, R$^i$, Rj, R$^k$, R$^m$, R$^n$, R$^o$, R$^p$, R$^q$, R$^r$, and R$^s$ are independently hydrogen, alkyl, cycloalkyl, cycloalkylalkyl, hydroxyalkyl, alkoxyalkyl, aminoalkyl, optionally substituted heterocyclyl, optionally substituted heterocyclylalkyl, optionally substituted aryl, optionally substituted aralkyl, optionally substituted heteroaryl, or optionally substituted heteroaralkyl; or, independently of each other, each R$^i$ and R$^j$, R$^k$ and R$^m$, R$^n$ and R$^o$, and R$^p$ and R$^q$, together with the nitrogen atom to which they are attached form optionally substituted heterocyclyl;

R$^1$, R$^2$, R$^3$, and R$^4$ are independently selected from hydrogen, alkyl, cycloalkyl, halo, haloalkyl, haloalkoxy, alkoxy, cyano, hydroxy, hydroxyalkyl, amino, and aminoalkyl;

or one of R$^1$ and R$^2$ and R$^3$ and R$^4$, when attached to the same carbon, combine to form oxo, alkyldienyl, 3 to 6 membered cycloalkylene, or 4 to 6 membered optionally substituted heterocyclylene;

R$^5$ and R$^6$ are independently selected from hydrogen, alkyl, cycloalkyl, halo, haloalkyl, haloalkoxy, alkoxy, hydroxy, cyano, hydroxylalkyl, amino, and aminoalkyl, or wherein one of R$^5$ and R$^6$ is optionally substituted heterocyclyl and the other R$^5$ and R$^6$ is selected from hydrogen, alkyl, cycloalkyl, halo, haloalkyl, haloalkoxy, alkoxy, hydroxy, cyano, hydroxylalkyl, amino, and aminoalkyl;

L is bond, O, S, S(O), S(O)$_2$, or CR$^7$R$^8$ where R$^7$ and R$^8$ are independently hydrogen or alkyl;

Z$^1$ is a group of formula (a) or (b):

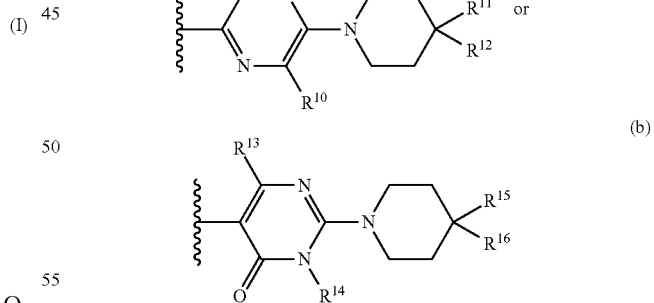

wherein:

R$^9$ is hydrogen, alkyl, halo, hydroxy, amino, or haloalkyl;

R$^{10}$ is hydrogen, alkyl, halo, hydroxy, hydroxyalkyl, —CD$_2$OH, alkylsulfoxide, alkylsulfonyl, amino, aminoalkyl, aminosulfonyl, aminocarbonyl, carboxy, cyano, or alkoxycarbonyl;

R$^{13}$ is hydrogen, alkyl, halo, hydroxy, amino, or haloalkyl;

R$^{14}$ is hydrogen, alkyl, or haloalkyl;

R$^{11}$ and R$^{15}$ are selected from amino and aminoalkyl;

$R^{12}$ and $R^{16}$ are selected from hydrogen, cyano, halo, alkyl, haloalkyl, alkoxy, haloalkoxy, cycloalkyl, aryl, heterocyclyl, and heteroaryl, where alkyl, cycloalkyl, aryl, heterocyclyl and heteroaryl are optionally substituted with one to three substituents independently selected from alkyl, halo, haloalkyl, haloalkoxy, alkoxy, and cyano;

or $R^{11}$ and $R^{12}$, and $R^{15}$ and $R^{16}$ together with the carbon atom to which they are attached form a ring of formula (c):

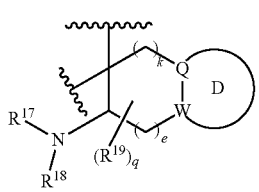

(c)

wherein:
e is 0, 1; or 2;
k is 0, 1, or 2 provided e+k is 1, 2, or 3;
q is 0, 1, or 2, or 3;
$R^{17}$ and $R^{18}$ are independently selected from hydrogen, alkyl, cycloalkyl and haloalkyl;
each $R^{19}$ is independently selected from hydrogen, alkyl, halo, haloalkyl, haloalkoxy, alkoxy, hydroxy, cyano, alkylsulfoxide, alkylsulfonyl, oxo, cycloalkyl, optionally substituted heterocyclyl, and optionally substituted heteroaryl; or
when two $R^{19}$ groups are attached to the same carbon atom, the two $R^{19}$ groups together with the carbon atom to which they are attached form cycloalkylene or heterocyclylene.
ring D is absent or present; wherein:
(i) when ring D is absent, then one of Q and W is $CH_2$, O, S, S(O), S(O)$_2$, or NH; and the other of Q and W is $CH_2$; and
(ii) when ring D is present, then Q and W are independently N or C provided only one of Q and W is N; and ring D is phenyl or a 5 or 6 membered heteroaryl ring which, including Q and W, contains one to three heteroatoms independently selected from N, O, and S and ring D is optionally be substituted with one or two substituents independently selected from alkyl, cycloalkyl, halo, haloalkyl, alkoxy, haloalkoxy, hydroxy, hydroxyalkyl, cyano, amino, aminoalkyl, carboxy, and optionally substituted heterocyclyl; or a pharmaceutically acceptable salt thereof.

67. The compound of embodiment 66, or a pharmaceutically acceptable salt thereof is wherein the compound has a structure of formula (II):

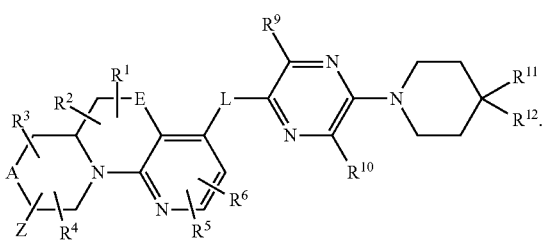

(II)

68. The compound of embodiment 67 or 68, and or a pharmaceutically acceptable salt thereof is wherein the compound has a structure of Formula (IIA):

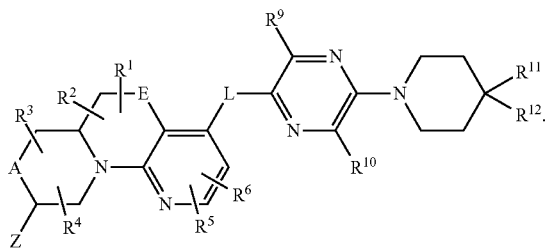

(IIA)

69. The compound of embodiment 66, or a pharmaceutically acceptable salt thereof is wherein the compound has a structure of formula (III):

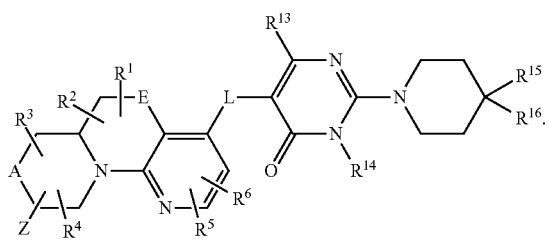

(III)

70. The compound of embodiment 66 or 69, or a pharmaceutically acceptable salt thereof is wherein the compound has structure of Formula (IIIA):

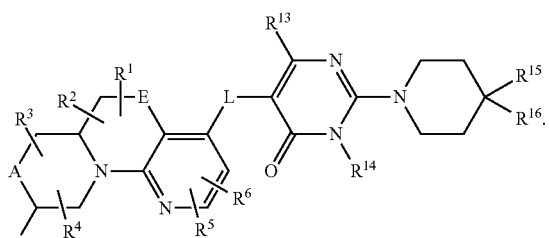

(IIIA)

71. The compound of any one of embodiments 66 to 70, or a pharmaceutically acceptable salt thereof wherein E is O and A is $CH_2$ or bond.

72. The compound of any one of embodiments 66 to 70, or a pharmaceutically acceptable salt thereof wherein E is O and A is bond.

73. The compound of embodiment 68, or a pharmaceutically acceptable salt thereof has a structure of formula (IIB):

(IIB)

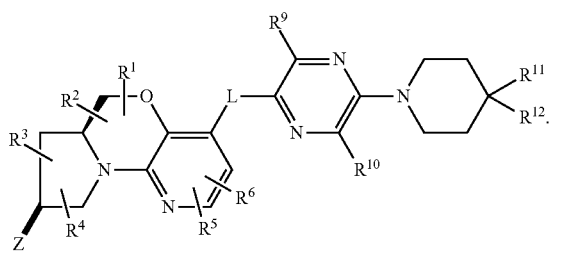

74. The compound of embodiment 70, or a pharmaceutically acceptable salt thereof has the structure of formula (IIIB):

(IIIB)

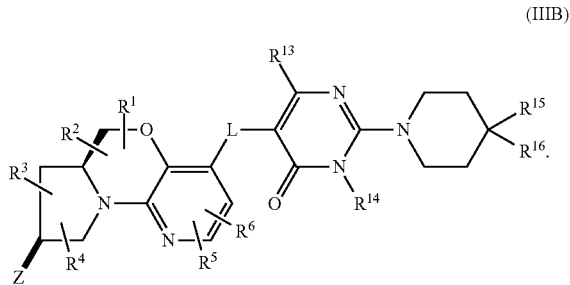

75. The compound of any one of embodiments 66 to 74, or a pharmaceutically acceptable salt thereof wherein Z is hydrogen, alkyl, halo, haloalkyl, haloalkoxy, cyano, cycloalkyl, heterocyclyl, heteroaryl (wherein cycloalkyl, heterocyclyl, and heteroaryl are optionally substituted with one to three halo), —O(alk)$_y$R$^a$, —O(alk)OR$^b$, —S(O)$_2$R$^d$, —OC(O)NR$^i$R$^j$, —S(O)$_2$NR$^n$R$^o$, —NR$^p$R$^q$, or —Y-M (wherein Y is bond, O, or SO$_2$ and M is alkyl, haloalkyl, cycloalkyl, heterocyclyl, or heteroaryl wherein alkyl, haloalkyl, cycloalkyl, heterocyclyl and heteroaryl are substituted with —O(alk)$_y$R$^a$, —O(alk)OR$^b$, —S(O)$_2$R$^d$, or —NR$^p$R$^q$ and cycloalkyl, heterocyclyl, and heteroaryl are optionally further substituted with 1 to 3 halo).

76. The compound of any one of embodiments 66 to 74, or a pharmaceutically acceptable salt thereof wherein Z is —Y-M (wherein Y is bond or O and M is alkyl, haloalkyl, cycloalkyl, heterocyclyl, or heteroaryl wherein alkyl, haloalkyl, cycloalkyl, heterocyclyl and heteroaryl are substituted with —O(alk)OR$^b$, —S(O)$_2$R$^d$, —NR$^e$C(O)R$^f$, —NR$^g$SO$_2$R$^h$, —OC(O)NR$^i$R$^j$, —C(O)NR$^k$R$^m$, or —S(O)$_2$NR$^n$R$^o$.

77. The compound of any one of embodiments 66 to 74, or a pharmaceutically acceptable salt thereof wherein Z is —Y-M (wherein Y is bond and M is alkyl, haloalkyl, cycloalkyl, heterocyclyl, or heteroaryl wherein alkyl, haloalkyl, cycloalkyl, heterocyclyl and heteroaryl are substituted with —O—R$^a$ where R$^a$ is alkyl, cycloalkyl, cycloalkylalkyl, aminoalkyl, optionally substituted heterocyclyl, optionally substituted heterocyclylalkyl, optionally substituted aryl, or optionally substituted heteroaryl.

78. The compound of any one of embodiments 66 to 74, or a pharmaceutically acceptable salt thereof wherein Z is —Y-M (wherein Y is bond and M is alkyl, haloalkyl, cycloalkyl, heterocyclyl, or heteroaryl wherein alkyl, haloalkyl, cycloalkyl, heterocyclyl and heteroaryl are substituted with —O(alk)OR$^a$ where R$^a$ is alkyl, cycloalkyl, cycloalkylalkyl, aminoalkyl, optionally substituted heterocyclyl, optionally substituted heterocyclylalkyl, optionally substituted aryl, or optionally substituted heteroaryl.

79. The compound of any one of embodiments 66 to 74, or a pharmaceutically acceptable salt thereof wherein Z is —OR$^a$ where R$^a$ is alkyl, cycloalkyl, cycloalkylalkyl, aminoalkyl, optionally substituted heterocyclyl, optionally substituted heterocyclylalkyl, optionally substituted aryl, or optionally substituted heteroaryl.

80. The compound of any one of embodiments 66 to 74, or a pharmaceutically acceptable salt thereof wherein Z is —O(alk)OR$^b$ where R$^b$ is alkyl, cycloalkyl, cycloalkylalkyl, aminoalkyl, optionally substituted heterocyclyl, optionally substituted heterocyclylalkyl, optionally substituted aryl, or optionally substituted heteroaryl.

81. The compound of any one of embodiments 66 to 74, or a pharmaceutically acceptable salt thereof wherein Z is hydrogen, fluoro, cyano, methoxy, hydroxy, cyclopentyloxy, tetrahydrofuran-3-yloxy, oxetan-3-yloxy, methoxymethyloxy, methoxyethyloxy, methylsulfonyl, aminocarbonyloxy, pyrazol-1-yl, hydroxymethyl, methoxymethyl, ethoxymethyl, methoxymethyloxymethyl, ethoxymethyloxymethyl, methoxyethyloxymethyl, cyclopropylmethyloxy, or oxetan-3-ylmethyloxymethyl.

82. The compound of any one of embodiments 66 to 74, or a pharmaceutically acceptable salt thereof wherein Z is methoxymethyloxy, methoxyethyloxy, methoxymethyl, methoxymethyloxymethyl, ethoxymethyloxymethyl, methoxyethyloxymethyl, cyclopropylmethyloxy, or oxetan-3-ylmethyloxymethyl.

83. The compound of any one of embodiments 66 to 74, or a pharmaceutically acceptable salt thereof wherein Z is methoxymethyl, methoxymethyloxymethyl, ethoxymethyloxymethyl, methoxyethyloxymethyl, cyclopropylmethyloxymethyl, or oxetan-3-ylmethyloxymethyl.

84. The compound of any one of embodiments 66 to 74, or a pharmaceutically acceptable salt thereof wherein Z is fluoro.

85. The compound of any one of embodiments 66 to 84, or a pharmaceutically acceptable salt thereof wherein R$^9$ and R$^{13}$ are hydrogen.

86. The compound of any one of embodiments 66 to 84, or a pharmaceutically acceptable salt thereof wherein R$^9$ and R$^{13}$ are amino.

87. The compound of any one of embodiments 66 to 84, or a pharmaceutically acceptable salt thereof wherein R$^9$ and R$^{13}$ are amino.

88. The compound of any one of embodiments 66 to 84, or a pharmaceutically acceptable salt thereof wherein R$^9$ and R$^{13}$ are methyl.

89. The compound of any one of embodiments 66 to 84, or a pharmaceutically acceptable salt thereof wherein R$^9$ and R$^{13}$ are independently hydrogen, alkyl, or amino.

90. The compound of any one of embodiments 66 to 89, or a pharmaceutically acceptable salt thereof wherein L is S.

91. The compound of any one of embodiments 66 to 89, or a pharmaceutically acceptable salt thereof wherein L is S(O) or S(O)$_2$.

92. The compound of any one of embodiments 66 to 89, or a pharmaceutically acceptable salt thereof wherein L is bond.

93. The compound of any one of embodiments 66 to 89, or a pharmaceutically acceptable salt thereof wherein L is CR$^7$R$^8$ where R$^5$ and R$^6$ are independently hydrogen or alkyl.

94. The compound of any one of embodiments 66 to 68, 71 to 73 and 75 to 93, or a pharmaceutically acceptable salt thereof wherein $R^{10}$ is hydroxyalkyl.

95. The compound of any one of embodiments 66 to 68, 71 to 73 and 75 to 93, or a pharmaceutically acceptable salt thereof wherein $R^{10}$ is hydroxymethyl.

96. The compound of any one of embodiments 66, 69 to 72, and 74 to 93, or a pharmaceutically acceptable salt thereof is wherein $R^{14}$ is hydrogen or methyl.

97. The compound of any one of embodiments 66 to 96, or a pharmaceutically acceptable salt thereof wherein:
$R^{11}$ and $R^{15}$ are selected from amino and aminoalkyl; and $R^{12}$ and $R^{16}$ are independently selected from hydrogen, cyano, halo, alkyl, haloalkyl, alkoxy, haloalkoxy, cycloalkyl, aryl, heterocyclyl, and heteroaryl, where alkyl, cycloalkyl, aryl, heterocyclyl and heteroaryl are optionally substituted with one to three substituents independently selected from alkyl, halo, haloalkyl, haloalkoxy, alkoxy, and cyano.

98. The compound of embodiments 97, or a pharmaceutically acceptable salt thereof wherein $R^1$ and $R^{15}$ are aminomethyl and $R^{12}$ and $R^{16}$ are methyl.

99. The compound of any one of embodiments 66 to 96, or a pharmaceutically acceptable salt thereof wherein $R^1$ and $R^{12}$, and $R^{15}$ and $R^{16}$ together with the carbon atom to which they are attached form a ring of formula (c):

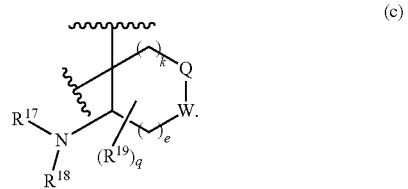

(c)

100. The compound of embodiment 99, or a pharmaceutically acceptable salt thereof wherein ring of formula (c) is:

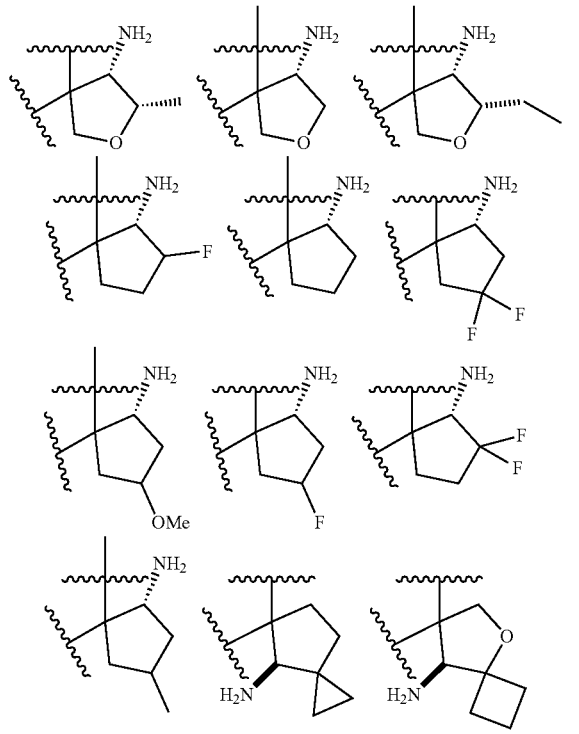

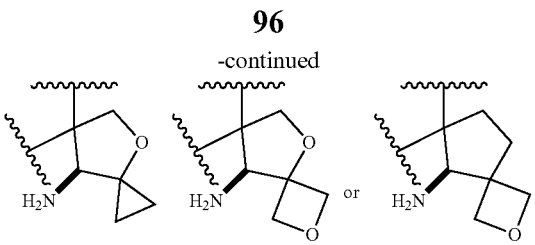

101. The compound of any one of embodiments 66 to 96, or a pharmaceutically acceptable salt thereof wherein $R^1$ and $R^{12}$, and $R^{15}$ and $R^{16}$ together with the carbon atom to which they are attached form a ring of formula (c):

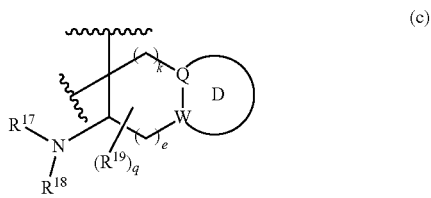

(c)

102. The compound of embodiment 101, or a pharmaceutically acceptable salt thereof wherein ring of formula (c) is:

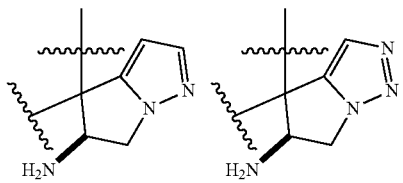

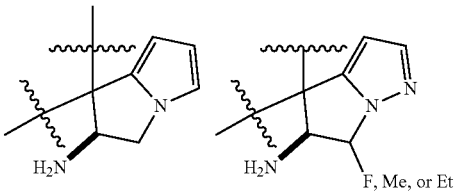

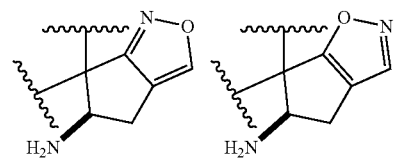

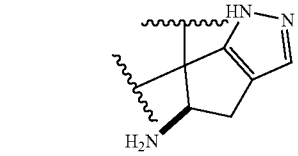

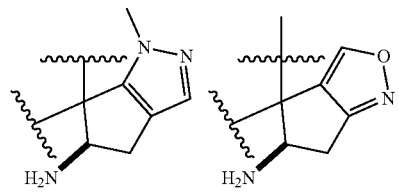

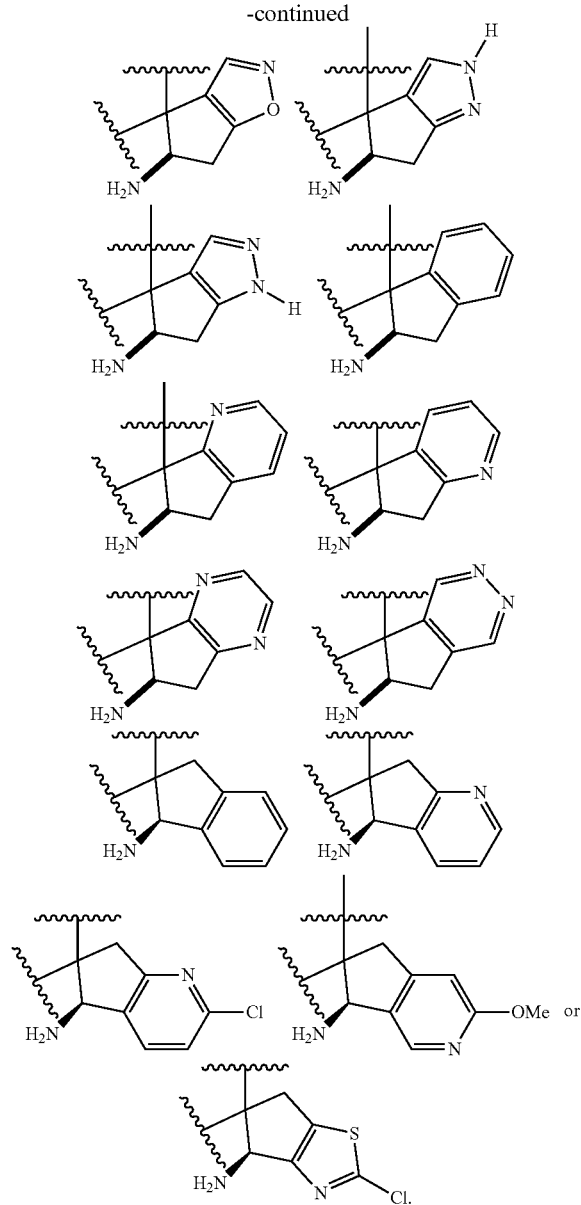

103. The compound of any one of embodiments 66 to 102, or a pharmaceutically acceptable salt thereof wherein $R^1$, $R^2$, $R^3$, and $R^4$ are independently selected from hydrogen, alkyl, halo, haloalkyl, haloalkoxy, alkoxy, cyano, and hydroxy, amino.

104. The compound of embodiment 103, or a pharmaceutically acceptable salt thereof wherein $R^1$, $R^2$, $R^3$, and $R^4$ is hydrogen and the remaining three of $R^1$, $R^2$, $R^3$, and $R^4$ are independently selected from hydrogen, methyl, fluoro, methoxy, hydroxy, and amino.

105. The compound of embodiment 103, or a pharmaceutically acceptable salt thereof wherein $R^1$, $R^2$, $R^3$, and $R^4$ are hydrogen.

106. The compound of any one of embodiments 66 to 105, or a pharmaceutically acceptable salt wherein $R^5$ is hydrogen, alkyl, halo, or amino and $R^6$ is hydrogen, alkyl, halo, haloalkyl, haloalkoxy, alkoxy, hydroxy, or cyano.

107. The compound of embodiment 106, or a pharmaceutically acceptable salt thereof wherein $R^5$ and $R^6$ are hydrogen.

108. A pharmaceutical composition comprising a compound, or a pharmaceutically acceptable salt thereof, of any one of embodiments 66 to 107 and a pharmaceutically acceptable excipient.

109. A method of treating a disease treatable by inhibition of SHP2 in a patient which method comprises administering to the patient, preferably a patient in need of such treatment, a therapeutically effective amount of a compound, or a pharmaceutically acceptable salt thereof, of any one of embodiments 66 to 107 or which method comprises administering to the patient, preferably a patient in need of such treatment, a pharmaceutical composition comprising a compound, or a pharmaceutically acceptable salt thereof, of any one of embodiments 66 to 107 and a pharmaceutically acceptable excipient.

110. The method of embodiment 109 wherein the disease is cancer.

111. The method of embodiment 110 wherein the cancer is selected from lung, stomach, liver, colon, kidney, breast, pancreatitis, juvenile myelomonocytic leukemias, neurolastoma, melanoma, and acute myeloid leukemia.

112. The method of embodiment 109 wherein the disease is selected from Noonan syndrome and Leopard syndrome.

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

General Synthetic Scheme

Compounds of Formula (I), (IA), (IB), or (IC) in which, L is S and other groups are as defined in Summary can be prepared as illustrated and described in Scheme 1 below.

Scheme 1

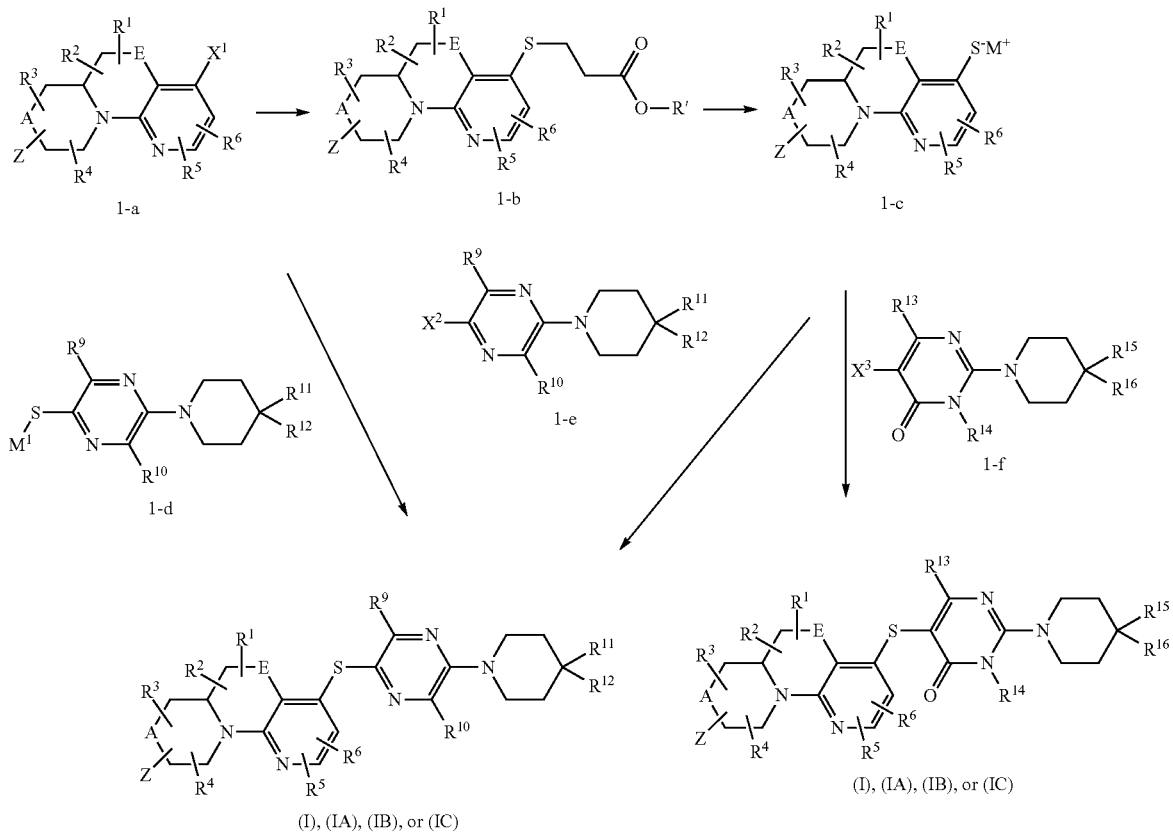

(I), (IA), (IB), or (IC)        (I), (IA), (IB), or (IC)

Coupling of a compound of formula 1-a, where $X^1$ is halogen, where Z, $R^1$, $R^2$, $R^3$, $R^4$, $R^5$, and $R^6$ are as defined in the Summary or a precursor group thereof and E and A are as defined in the Summary, with a compound of formula 1-d where $M^1$ is metal such as sodium or potassium, in the presence of transition metal catalyst such as $Pd_2(dba)_3$ and xantphos under standard coupling condition provides compounds of Formula (I). If a compound of formula 1-a is substituted with an amino group, then the amino group can be protected with a suitable protecting group such as t-butyl carbamate prior to the coupling reaction. Removal of the amino protecting group by methods well known in the art then provides a compound of Formula (I), (IA), (IB), or (IC)

Alternatively, compounds of Formula (I), (IA), (IB), or (IC) can be prepared by reacting compound of formula 1-a with 3-mercaptopropanoate ester in the presence of transition metal catalyst such as $Pd_2(dba)_3$ and xantphos under standard coupling condition to provide a compound of formula 1-b where R' is an alkyl group such as 3-methylheptane. Treatment of a compound of formula 1-b with a base such as potassium t-butoxide, sodium t-butoxide, sodium methoxide, and the like, provides a compound of formula 1-c as a thiosalt, where $M^+$ is a metal ion such as potassium or sodium. Coupling of 1-c with a compound of formula 1-e or formula 1-f where $X^2$ or $X^3$ is halo provides a compound of Formula (I), (IA), (IB), or (IC) where Z1 is a group of formula (a) or (b), respectively.

Compounds of formula 1-a where $X^1$ is halogen, E is O, and A, E, Z, $R^1$, $R^2$, $R^3$, $R^4$, $R^5$, $R^6$, are as defined in Summary or a precursor group thereof, can be prepared as illustrated and described in Methods 1 and 2 below.

Method (1):

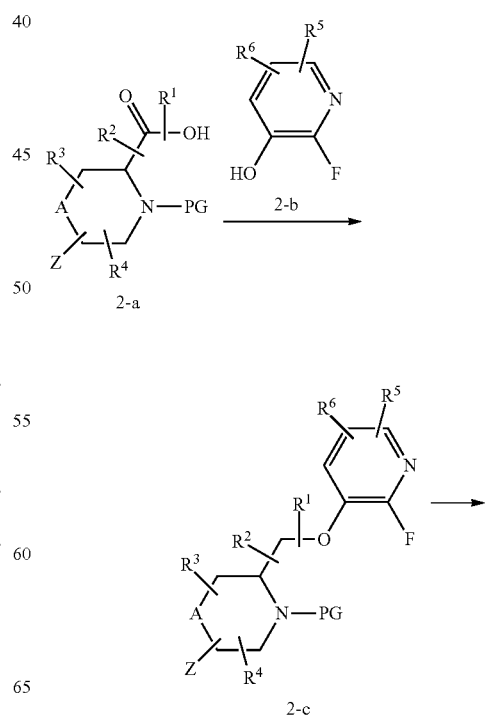

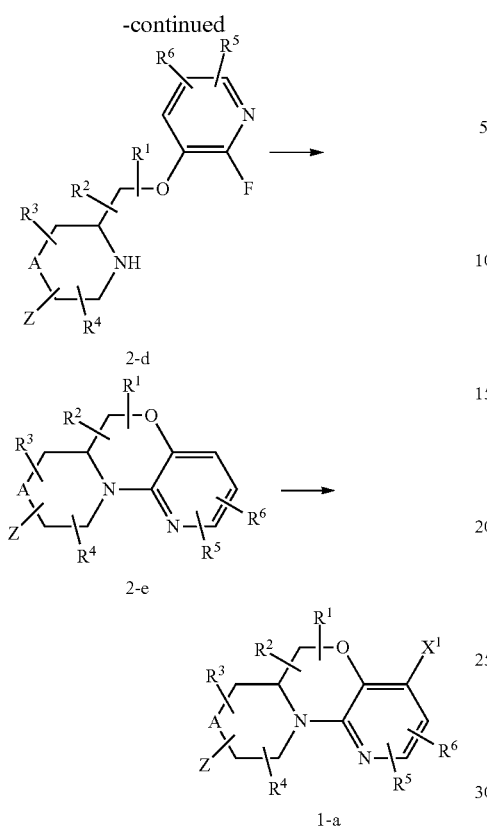

2-d 2-e 1-a

Coupling a compound of formula 2-b in which $R^5$ and $R^6$ are as defined in Summary or a precursor group thereof with an alcohol of formula 2-a where PG is a suitable amino protecting group such as Boc, under Mitsunobu condition, for example, using diethyl azodicarboxylate and triphenyl phosphine provides a compound of formula 2-c. Compounds of formula 2-b are commercially available or they can be prepared by methods well known in the art. For example, 2-fluoropyridin-3-ol is commercially available. Compounds of formula 2-a are commercially available or they can be prepared by methods well known in the art. For example, tert-butyl (S)-2-(hydroxymethyl)pyrrolidine-1-carboxylate, tert-butyl (R)-2-(hydroxymethyl)pyrrolidine-1-carboxylate, tert-butyl (2S,4S)-4-fluoro-2-(hydroxymethyl)-pyrrolidine-1-carboxylate, tert-butyl (2S,4R)-4-fluoro-2-(hydroxymethyl)pyrrolidine-1-carboxylate, tert-butyl (S)-4,4-difluoro-2-(hydroxymethyl)pyrrolidine-1-carboxylate, tert-butyl (2S,4R)-2-(hydroxymethyl)-4-methoxypyrrolidine-1-carboxylate, tert-butyl (2S,4S)-2-(hydroxymethyl)-4-methoxypyrrolidine-1-carboxylate, tert-butyl (S)-6-(hydroxymethyl)-5-azaspiro[2.4]heptane-5-carboxylate, tert-butyl (R)-3-(hydroxymethyl)morpholine-4-carboxylate, tert-butyl (S)-3-(hydroxymethyl)morpholine-4-carboxylate, tert-butyl (R)-2-(hydroxymethyl)azetidine-1-carboxylate, tert-butyl (S)-2-(hydroxymethyl)azetidine-1-carboxylate are commercially available.

Removal of the amino protecting group provides a compound of formula 2-d. For example, Boc group can be cleaved under acidic condition such HCl in dioxane. Cyclization of compound 2-d with a base such as $K_2CO_3$, sodium carbonate, and the like, provides a compound of formula 2-e. Lithiation of compound 2-e using alkyl lithium such n-BuLi, followed by trapping with iodine provides a compound of formula 1-a.

Method (2)

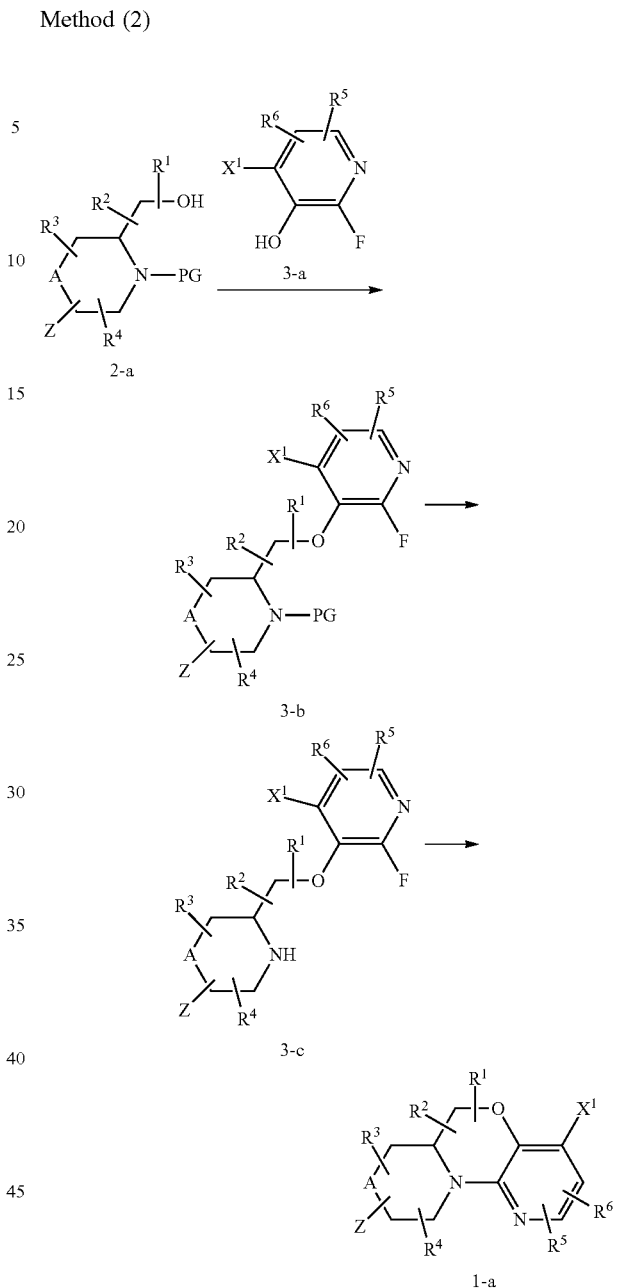

3-a 3-b 3-c 1-a

Alternatively, coupling a compound of formula 3-a where $X^1$ is halogen, $R^5$ and $R^6$ are as defined in summary and an alcohol of formula 2-a where PG is an amino protecting group such as Boc, under Mitsunobu condition, for example, using diethyl azodicarboxylate and triphenyl phosphine provides a compound of formula 3-b. Compounds of formula 3-a are commercially available or they can be prepared by methods well known in the art. For example, 2-fluoro-4-iodopyridin-3-ol is commercially available. Compound 3-c is converted to a compound of formula 1-a as described in Scheme 1 above.

Utility

The Src Homolgy-2 phosphatase (SHP2) is a protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways. SHP2 mediates activation of Erk1 and Erk2 (Erk1/2, Erk) MAP kinases by receptor tyrosine kinases such as ErbB1, ErbB2 and c-Met.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive conformation, inhibiting its own activity via a binding network involving residues from both the N-SH2 and PTP domains. In response to growth factor stimulation, SHP2 binds to specific tyrosine-phosphorylated sites on docking proteins such as Gab1 and Gab2 via its SH2 domains. This induces a conformational change that results in SHP2 activation.

Mutations in PTPN11 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

Noonan Syndrome (NS) and Leopard Syndrome (LS): PTPN11 mutations cause LS (multiple lentigenes, electrocardiographic conduction abnormalities, ocular hypertelorism, pulmonic stenosis, abnormal genitalia, retardation of growth, sensorineural deafness) and NS (congenital anomalies including cardiac defects, craniofacial abnormalities and short stature). Both disorders are part of a family of autosomal dominant syndromes caused by germline mutations in components of the RAS/RAF/MEK/ERK mitogen activating protein kinase pathway, required for normal cell growth and differentiation. Aberrant regulation of this pathway has profound effects, particularly on cardiac development, resulting in various abnormalities, including valvuloseptal defects and/or hypertrophic cardiomyopathy (HCM). Perturbations of the MAPK signaling pathway have been established as central to these disorders and several candidate genes along this pathway have been identified in humans, including mutations in KRAS, NRAS, SOS1, RAF1, BRAF, MEK1, MEK2, SHOC2, and CBL. The gene most commonly mutated in NS and LS is PTPN11. Germline mutations in PTPN11 (SHP2) are found in ~50% of the cases with NS and nearly all patients with LS that shares certain features with NS. For NS, Y62D and Y63C substitutions in the protein are largely invariant and are among the most common mutations. Both these mutations affect the catalytically inactive conformation of SHP2 without perturbing the binding of the phosphatase to its phosphorylated signaling partners.

Juvenile Myelomonocytic Leukemias (JMML):—Somatic mutations in PTPN11(SHP2) occur in about 35% of the patients with JMML, a childhood myeloproliferative disorder (MPD). These gain-of-function mutations are typically point mutations in the N-SH2 domain or in the phosphatase domain, which prevent self-inhibition between the catalytic domain and the N-SH2 domain, resulting in SHP2 activity.

Acute Myeloid Leukemia: PTPN11 mutations have been identified in: ~10% of pediatric acute leukemias, such as myelodysplastic syndrome (MDS); ~7% of B cell acute lymphoblastic leukemia (B-ALL); and ~4% of acute myeloid leukemia (AML).

NS and leukemia mutations cause changes in amino acids located at the interface formed by the N-SH2 and PTP domains in the self-inhibited SHP2 conformation, disrupting the inhibitory intramolecular interaction, leading to hyperactivity of the catalytic domain.

SHP2 acts as a positive regulator in receptor tyrosine kinase (RTK) signaling. Cancers containing RTK alterations (EGFR amp, Her2 amp, FGFR amp, Met 31"15, translocated/activated RTK, i.e. ALK, BCR/ABL) include Esophageal, Breast, Lung, Colon, Gastric, Glioma, Head and Neck cancers.

Esophageal cancer (or oesophageal cancer) is a malignancy of the esophagus. There are various subtypes, primarily squamous cell cancer (<50%) and adenocarcinoma. There is a high rate of RTK expression in esophageal adenocarcinoma and squamous cell cancer. A SHP2 inhibitor of the invention can, therefore, be employed for innovative treatment strategies.

Breast cancer is a major type of cancer and a leading cause of death in women, where patients develop resistance to current drugs. There are four major subtypes of breast cancers including luminal A, luminal B, Her2 like, and triple negative/Basal-like. Triple negative breast cancer (TNBC) is an aggressive breast cancer lacking specific targeted therapy. Epidermal growth factor receptor I (EGFR) has emerged as a promising target in TNBC. Inhibition of Her2 as well as EGFR via SHP2 may be a promising therapy in breast cancer.

Lung Cancer—NSCLC is currently a major cause of cancer-related mortality, accounting for about 85% of lung cancers (predominantly adenocarcinomas and squamous cell carcinomas). Although cytotoxic chemotherapy remains an important part of treatment, targeted therapies based on genetic alterations such as EGFR and ALK in the tumor are more likely to benefit from a targeted therapy.

Colon Cancer—Approximately 30% to 50% of colorectal tumors are known to have a mutated (abnormal) KRAS, and BRAF mutations occur in 10 to 15% of colorectal cancers. For a subset of patients whose colorectal tumors have been demonstrated to over express EGFR, these patients exhibit a favorable clinical response to anti-EGFR therapy.

Gastic Cancer is one of the most prevalent cancer types. Aberrant expression of tyrosine kinases, as reflected by the aberrant tyrosine phosphorylation in gastric cancer cells, is known in the art. Three receptor-tyrosine kinases, c-met (HGF receptor), FGF receptor 2, and erbB2/neu are frequently amplified in gastric carcinomas. Thus, subversion of different signal pathways may contribute to the progression of different types of gastric cancers.

Neuroblastoma is a pediatric tumor of the developing sympathetic nervous system, accounting for about 8% of childhood cancers. Genomic alterations of the anaplastic lymphoma kinase (ALK) gene have been postulated to contribute to neuroblastoma pathogenesis.

Squamous-cell carcinoma of the head and neck (SCCHN). High levels of EGFR expression are correlated with poor prognosis and resistance to radiation therapy in a variety of cancers, mostly in squamous-cell carcinoma of the head and neck (SCCHN). Blocking of the EGFR signaling results in inhibition of the stimulation of the receptor, cell proliferation, and reduced invasiveness and metastases. The EGFR is, therefore, a prime target for new anticancer therapy in SCCHN.

The present invention relates to compounds capable of inhibiting the activity of SHP2. The invention further provides a process for the preparation of compounds of the invention and pharmaceutical preparations comprising such compounds. Another aspect of the present invention relates to a method of treating SHP2-mediated disorders comprising the step of administering to a patient in need thereof a therapeutically effective amount of a compound of formula I as defined in the Summary.

In certain embodiments, the present invention relates to the aforementioned method, wherein said SHP2-mediated disorders are cancers selected from, but not limited to: JMML; AML; MDS; B-ALL; neuroblastoma; esophageal; breast cancer; lung cancer; colon cancer; Gastric cancer, Head and Neck cancer.

The compounds of the present invention may also be useful in the treatment of other diseases or conditions related to the aberrant activity of SHP2. Thus, as a further aspect, the invention relates to a method of treatment of a disorder selected from: NS; LS; JMML; AML; MDS; B-ALL; neuroblastoma; esophageal; breast cancer; lung cancer; colon cancer; gastric cancer; head and neck cancer.

A SHP2 inhibitor of the present invention may be usefully combined with another pharmacologically active compound, or with two or more other pharmacologically active compounds, particularly in the treatment of cancer. For example, a compound of the current invention or a pharmaceutically acceptable salt thereof, as defined above, may be administered simultaneously, sequentially or separately in combination with one or more agents selected from chemotherapy agents, for example, mitotic inhibitors such as a taxane, a *vinca* alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine. Such combinations may offer significant advantages, including synergistic activity, in therapy.

In certain embodiments, the present invention relates to the aforementioned method, wherein said compound is administered parenterally.

In certain embodiments, the present invention relates to the aforementioned method, wherein said compound is administered intramuscularly, intravenously, subcutaneously, orally, pulmonary, intrathecally, topically or intranasally.

In certain embodiments, the present invention relates to the aforementioned method, wherein said compound is administered systemically.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

In another aspect, the present invention relates to a method of treating an SHP2-mediated disorder, comprising the step of: administering to a patient in need thereof a therapeutically effective amount of a chemotherapeutic agent in combination with a therapeutically effective amount of a compound of formula I as defined in the Summary. In addition to human cancer, inhibition of SHP2 also has the therapeutic potential for treatment of systemic lupus erythematosus, rheumatoid arthritis and fibrosis.

Testing

The SHP2 inhibitory activity of the compounds of Formula (I), (IA), (IB), and (IC) can be tested using the in vitro assay described in Biological Examples 1 below.

Pharmaceutical Compositions

In general, the compounds of this disclosure will be administered in a therapeutically effective amount by any of the accepted modes of administration for agents that serve similar utilities. Therapeutically effective amounts of compounds this disclosure may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the patient, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance.

The compositions are comprised of in general, a compound of this disclosure in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhaler or insufflator. Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

Combinations and Combination Therapies

The compounds of this disclosure may be used in combination with one or more other drugs in the treatment of diseases or conditions for which compounds of this disclosure or the other drugs may have utility. Such other drug(s) may be administered, by a route and in an amount commonly used therefore, contemporaneously or sequentially with a compound of Formula (I). When a compound of this disclosure is used contemporaneously with one or more other drugs, a pharmaceutical composition in unit dosage form containing such other drugs and the compound of Formula (I) is preferred. However, the combination therapy may also include therapies in which the compound of this disclosure and one or more other drugs are administered on different overlapping schedules. It is also contemplated that when used in combination with one or more other active ingredients, the compounds of Formula (I) and the other active ingredients may be used in lower doses than when each is used singly.

Accordingly, the pharmaceutical compositions of Formula (I) also include those that contain one or more other drugs, in addition to a compound of Formula (I).

The above combinations include combinations of a compound of this disclosure not only with one other drug, but also with two or more other active drugs. Likewise, a compound of this disclosure may be used in combination with other drugs that are used in the prevention, treatment, control, amelioration, or reduction of risk of the diseases or conditions for which a compound of this disclosure is useful. Such other drugs may be administered, by a route and in an amount commonly used therefore, contemporaneously or sequentially with a compound of Formula (I). When a compound of this disclosure is used contemporaneously with one or more other drugs, a pharmaceutical composition containing such other drugs in addition to the compound of this disclosure can be used. Accordingly, the pharmaceutical compositions of Formula (I) also include those that also contain one or more other active ingredients, in addition to a compound of this disclosure. The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of this disclosure in any combination with one or more other anti-cancer agents including but not limited to:

MAP kinase pathway (RAS/RAF/MEK/ERK) inhibitors including but not limited to: Vemurafanib (PLX4032), Dabrafenib, Encorafenib (LGX818), TQ-B3233, XL-518 (Cas No. 1029872-29-4, available from ACC Corp); trametinib, selumetinib (AZD6244), TQ-B3234, PD184352, PD325901, TAK-733, pimasertinib, binimetinib, refametinib, cobimetinib (GDC-0973), AZD8330, BVD-523, LTT462, Ulixertinib, AMG510, ARS853, and any RAS inhibitors disclosed in patents WO2016049565, WO2016164675, WO2016168540, WO2017015562, WO2017058728, WO2017058768, WO2017058792, WO2017058805, WO2017058807, WO2017058902, WO2017058915, WO2017070256, WO2017087528, WO2017100546, WO2017172979, WO2017201161, WO2018064510, WO2018068017, WO2018119183.

CSF1R inhibitors (PLX3397, LY3022855, etc.) and CSF1R antibodies (IMC-054, RG7155)TGF beta receptor kinase inhibitor such as LY2157299.

BTK inhibitor such as ibrutinib; BCR-ABL inhibitors: Imatinib (Gleevec®); Inilotinib hydrochloride; Nilotinib (Tasigna®); Dasatinib (BMS-345825); Bosutinib (SKI-606); Ponatinib (AP24534); Bafetinib (INNO406); Danusertib (PHA-739358), AT9283 (CAS 1133385-83-7); Saracatinib (AZD0530); and A/-[2-[(15,4R)-6-[[4-(Cyclobutylarmno)-5-(trifluoromethyl)-2-pyrimidinyl]amino]-1,2,3,4-tetrahydronaphthalen-1,4-imin-9-yl]-2-oxoethyl]-acetamide (PF-03814735, CAS 942487-16-3).

ALK inhibitors: PF-2341066 (XALKOPJ®; crizotinib); 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamine; GSK1838705 A; CH5424802; Ceritinib (ZYKADIA); TQ-B3139, TQ-B3101 PI3K inhibitors: 4-[2-(1H-Indazol-4-yl)-6-[[4-(methylsulfonyl)piperazin-1-yl]methyl]thieno[3,2-d]pyrimidin-4-yl]moφholine (also known as GDC 0941 and described in PCT Publication Nos. WO 09/036082 and WO 09/055730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806).

Vascular Endothelial Growth Factor (VEGF) receptor inhibitors: Bevacizumab (sold under the trademark Avastin® by Genentech/Roche), axitinib, (N-methyl-2-[[3-[(E)-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide, and described in PCT Publication No. WO 02/066470), pasireotide (also known as SOM230, and described in PCT Publication No. WO 02/010192), sorafenib (sold under the tradename Nexavar®); AL-2846 MET inhibitor such as foretinib, carbozantinib, or crizotinib.

FLT3 inhibitors—sunitinib malate (sold under the tradename Sutent® by Pfizer); PKC412 (midostaurin); tanutinib, sorafenib, lestaurtinib, KW-2449, quizartinib (AC220) and crenolanib.

Epidermal growth factor receptor (EGFR) inhibitors: Gefitnib (sold under the tradename Iressa®), N-[4-[(3-Chloro-4-fluorophenyl)amino]-7-[[(3"S")-tetrahydro-3-furanyl]oxy]-6-quinazolinyl]-4(dimethylamino)-2-butenamide, sold under the tradename Tovok® by Boehringer Ingelheim), cetuximab (sold under the tradename Erbitux® by Bristol-Myers Squibb), panitumumab (sold under the tradename Vectibix® by Amgen).

HER2 receptor inhibitors: Trastuzumab (sold under the trademark Herceptin® by Genentech/Roche), neratinib (also known as HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443), lapatinib or lapatinib ditosylate (sold under the trademark Tykerb® by GlaxoSmithKline); Trastuzumab emtansine (in the United States, ado-trastuzumab emtansine, trade name Kadcyla)—an antibody-drug conjugate consisting of the monoclonal antibody trastuzumab (Herceptin) linked to the cytotoxic agent mertansine (DM1);

HER dimerization inhibitors: Pertuzumab (sold under the trademark Omnitarg®, by Genentech).

CD20 antibodies: Rituximab (sold under the trademarks Riuxan® and MabThera® by Genentech/Roche), tositumomab (sold under the trademarks Bexxar® by GlaxoSmithKline), ofatumumab (sold under the trademark Arzerra® by GlaxoSmithKline).

Tyrosine kinase inhibitors: Erlotinib hydrochloride (sold under the trademark Tarceva® by Genentech/Roche), Linifanib (N-[4-(3-amino-1H-indazol-4-yl)phenyl]-N'-(2-fluoro-5-methylphenyl)urea, also known as ABT 869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl)propoxy]quinoline-3-car bonitrile, also known as SKI-606, and described in U.S. Pat. No. 6,780,996), dasatinib (sold under the tradename Sprycel® by Bristol-Myers Squibb), armala (also known as pazopanib, sold under the tradename Votrient® by GlaxoSmithKline), imatinib and imatinib mesylate (sold under the tradenames Gilvec® and Gleevec® by Novartis).

DNA Synthesis inhibitors: Capecitabine (sold under the trademark Xeloda® by Roche), gemcitabine hydrochloride (sold under the trademark Gemzar® by Eli Lilly and Company), nelarabine ((2R3S,4R,5R)-2-(2-amino-6-methoxypurin-9-yl)-5-(hydroxymethyl)oxolane-3,4-diol, sold under the tradenames Arranon® and Atriance® by GlaxoSmithKline).

Antineoplastic agents: oxaliplatin (sold under the tradename Eloxatin® ay Sanofi-Aventis and described in U.S. Pat. No. 4,169,846).

Human Granulocyte colony-stimulating factor (G-CSF) modulators: Filgrastim (sold under the tradename Neupogen® by Amgen).

Immunomodulators: Afutuzumab (available from Roche®), pegfilgrastim (sold under the tradename Neulasta® by Amgen), lenalidomide (also known as CC-5013, sold under the tradename Revlimid®), thalidomide (sold under the tradename Thalomid®);

CD40 inhibitors: Dacetuzumab (also known as SGN-40 or huS2C6, available from Seattle Genetics, Inc); Pro-apoptotic receptor agonists (PARAs): Dulanermin (also known as AMG-951, available from Amgen/Genentech).

Hedgehog antagonists: 2-chloro-N-[4-chloro-3-(2-pyridinyl)phenyl]-4-(methylsulfonyl)-benzamide (also known as GDC-0449, and described in PCT Publication No. WO 06/028958);

Phospholipase A2 inhibitors: Anagrelide (sold under the tradename Agrylin®);

BCL-2 inhibitors: 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386);

MCl-1 inhibitors: MIK665, S64315, AMG 397, and AZD5991;

Aromatase inhibitors: Exemestane (sold under the trademark Aromasin® by Pfizer), letrozole (sold under the tradename Femara® by Novartis), anastrozole (sold under the tradename Arimidex®);

Topoisomerase I inhibitors: Irinotecan (sold under the trademark Camptosar® by Pfizer), topotecan hydrochloride (sold under the tradename Hycamtin® by GlaxoSmithKline);

Topoisomerase II inhibitors: etoposide (also known as VP-16 and Etoposide phosphate, sold under the tradenames Toposar®, VePesid® and Etopophos®), teniposide (also known as VM-26, sold under the tradename Vumon®);

mTOR inhibitors: Temsirolimus (sold under the tradename Torisel® by Pfizer), ridaforolimus (formally known as deferolimus, (1R,2R,4S)-4-[(2R)-2[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0 4'9]hexatriaconta-16,24,26,28-tetraen-12-yl]propyl]-2-methoxycyclohexyl dimethylphosphinate, also known as AP23573 and MK8669, and described in PCT Publication No. WO 03/064383), everolimus (sold under the tradename Afinitor® by Novartis);

Proteasome inhibitor such as carfilzomib, MLN9708, delanzomib, or bortezomib

BET inhibitors such as INCB054329, OTX015, CPI-0610; LSD1 inhibitors such as GSK2979552, INCB059872; HIF-2a inhibitors such as PT2977 and PT2385;

Osteoclastic bone resorption inhibitors: 1-Hydroxy-2-imidazol-1-yl-phosphonoethyl) phosphonic acid monohydrate (sold under the tradename Zometa® by Novartis); CD33 Antibody Drug Conjugates: Gemtuzumab ozogamicin (sold under the tradename Mylotarg® by Pfizer/Wyeth);

CD22 Antibody Drug Conjugates: Inotuzumab ozogamicin (also referred to as CMC-544 and WAY-207294, available from Hangzhou Sage Chemical Co., Ltd.);

CD20 Antibody Drug Conjugates: Ibritumomab tiuxetan (sold under the tradename Zevalin®);

Somatostain analogs: octreotide acetate, sold under the tradenames Sandostatin® and Sandostatin LAR®);

Synthetic Interleukin-11 (IL-11): oprelvekin (sold under the tradename Neumega® by Pfizer/Wyeth);

Synthetic erythropoietin: Darbepoetin alfa (sold under the tradename Aranesp® by Amgen);

Receptor Activator for Nuclear Factor κ B (RANK) inhibitors: Denosumab (sold under the tradename Prolia® by Amgen);

Thrombopoietin mimetic peptibodies: Romiplostim (sold under the tradename Nplate® by Amgen;

Cell growth stimulators: Palifermin (sold under the tradename Kepivance® by Amgen);

Anti-Insulin-like Growth Factor-1 receptor (IGF-1R) antibodies: Figitumumab (also known as CP-751,871, available from ACC Corp), robatumumab (CAS No. 934235-44-6);

Anti-CS1 antibodies: Elotuzumab (HuLuc63, CAS No. 915296-00-3);

CD52 antibodies: Alemtuzumab (sold under the tradename Campath®);

Histone deacetylase inhibitors (HDI): Voninostat (sold under the tradename Zolinza® by Merck);

Alkylating agents: Temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, sold under the tradename Thioplex®; Biologic response modifiers: bacillus calmette-guerin (sold under the tradenames theraCys® and TICE® BCG), denileukin diftitox (sold under the tradename Ontak®);

Anti-tumor antibiotics: doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), mitomycin C (sold under the tradename Mutamycin®);

Anti-microtubule agents: Estramustine (sold under the tradename Emcyl®);

Cathepsin K inhibitors: Odanacatib (also know as MK-0822, N-(1-cyanocyclopropyl)-4-fluoro-N2-{(1S)-2,2,2-trifluoro-1-[4'-(methylsulfonyl)biphenyl-4-yl]ethyl}-L-leucinamide, available from Lanzhou Chon Chemicals, ACC Corp., and ChemieTek, and described in PCT Publication no. WO 03/075836); Epothilone B analogs: Ixabepilone (sold under the tradename Lxempra® by Bristol-Myers Squibb);

Heat Shock Protein (HSP) inhibitors: Tanespimycin (17-allylamino-17-demethoxygeldanamycin, also known as KOS-953 and 17-AAG, available from SIGMA, and described in U.S. Pat. No. 4,261,989), NVP-HSP990, AUY922, AT13387, STA-9090, Debio 0932, KW-2478, XL888, CNF2024, TAS-116

TpoR agonists: Eltrombopag (sold under the tradenames Promacta® and Revolade® by GlaxoSmithKline);

Anti-mitotic agents: Docetaxel (sold under the tradename Taxotere® by Sanofi-Aventis); Adrenal steroid inhibitors: aminoglutethimide (sold under the tradename Cytadren®);

Anti-androgens: Nilutamide (sold under the tradenames Nilandron® and Anandron®), bicalutamide (sold under tradename Casodex®), flutamide (sold under the tradename Fulexin™);

Androgens: Fluoxymesterone (sold under the tradename Halotestin®);

Proteasome inhibitors: Bortezomib (sold under the tradename Velcade®);

CDK (CDK1, CDK2, CDK3, CDK5, CDK7, CDK8, or CDK9) inhibitors including but not limited to Alvocidib (pan-CDK inhibitor, also known as flavopirdol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002);

CDK4/6 inhibitors pabociclib, ribociclib, abemaciclib, and Trilaciclib; CDK9 inhibtiors AZD 4573, P276-00, AT7519M, TP-1287;

Gonadotropin-releasing hormone (GnRH) receptor agonists: Leuprolide or leuprolide acetate (sold under the tradenames Viadure® by Bayer AG, Eligard® by Sanofi-Aventis and Lupron® by Abbott Lab);

Taxane anti-neoplastic agents: Cabazitaxel (1-hydroxy-7,10-dimethoxy-9-oxo-5,20-epoxytax-11-ene-2α,4,13α-triyl-4-acetate-2-benzoate-13-[(2R,3S)-3-{[(tert-butoxy)carbonyl]amino}-2-hydroxy-3-phenylpropanoate), larotaxel ((2α,3ξ,4α,5β,7α,10β,13α)-4,10-bis(acetyloxy)-13-({(2R,3S)-3-[(tert-butoxycarbonyl) amino]-2-hydroxy-3-phenylpropanoyl}oxy)-1-hydroxy-9-oxo-5,20-epoxy-7,19-cyclotax-11-en-2-yl benzoate);

5HT1a receptor agonists: Xaliproden (also known as SR57746, 1-[2-(2-naphthyl)ethyl]-4-[3-(trifluoromethyl)phenyl]-1,2,3,6-tetrahydropyridine, and described in U.S. Pat. No. 5,266,573); HPC vaccines: Cervarix® sold by GlaxoSmithKline, Gardasil® sold by Merck; Iron Chelating agents: Deferasinox (sold under the tradename Exjade® by Novartis);

Anti-metabolites: Claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodim (MTX), sold under the tradenames Rheumatrex® and Trexall™), pentostatin (sold under the tradename Nipent®);

Bisphosphonates: Pamidronate (sold under the tradename Aredia®), zoledronic acid (sold under the tradename Zometa®); Demethylating agents: 5-azacitidine (sold under the tradename Vidaza®), decitabine (sold under the tradename Dacogen®);

Plant Alkaloids: Paclitaxel protein-bound (sold under the tradename Abraxane®), vinblastine (also known as vinblastine sulfate, vincaleukoblastine and VLB, sold under the tradenames Alkaban-AQ® and Velban®), vincristine (also known as vincristine sulfate, LCR, and VCR, sold under the tradenames Oncovin® and Vincasar Pfs®), vinorelbine (sold under the tradename Navelbine®), paclitaxel (sold under the tradenames Taxol and Onxal™);

Retinoids: Ali tretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Clarus®, Decutan®, Isotane®, Izotech®, Oratane®, Isotret®, and Sotret®), bexarotene (sold under the tradename Targretin®);

Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®);

Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®);

[00209] Estrogen receptor downregulators: Fulvestrant (sold under the tradename Faslodex®);

Anti-estrogens: tamoxifen (sold under the tradename Novaldex®); Toremifene (sold under the tradename Fareston®);

Selective estrogen receptor modulators (SERMs): Raloxifene (sold under the tradename Evista®);

Leutinizing hormone releasing hormone (LHRH) agonists: Goserelin (sold under the tradename Zoladex®); Progesterones: megestrol (also known as megestrol acetate, sold under the tradename Megace®);

Miscellaneous cytotoxic agents: Arsenic trioxide (sold under the tradename Trisenox®), asparaginase (also known as L-asparaginase, *Erwinia* L-asparaginase, sold under the tradenames Elspar® and Kidrolase®);

One or more additional immune checkpoint inhibitors can be used in combination with a compound as described herein for treatment of SHP2-associated diseases, disorders or conditions. Exemplary immune checkpoint inhibitors include inhibitors (smack molecules or biologics) against immune checkpoint molecules such as CD27, CD28, CD40, CD122, CD96, CD73, CD39, CD47, OX40, GITR, CSF1R, JAK, PI3K delta, PI3K gamma, TAM kinase, arginase, CD137 (also known as 4-1BB), ICOS, A2AR, A2BR, HIF-2a, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR, CD137 and STING. In some embodiments, the immune checkpoint molecule is an inhibitory checkpoint molecule selected from B7-H3, B7-H4, BTLA, CTLA-4, IDO, TDO, Arginase, KIR, LAG3, PD-1, TIM3, CD96, TIGIT and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, or pembrolizumab or PDR001. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MED14736, MPDL3280A (also known as RG7446), or MSB0010718C. In some embodiments, the anti-PD-L1 monoclonal antibody is MPDL3280A (atezolizumab) or MED14736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab. In some embodiments, the inhibitor of an immune checkpoint molecule is an inhibitor of LAG3, e.g., an anti-LAG3 antibody. In some embodiments, the anti-LAG3 antibody is BMS-986016 or LAG525. In some embodiments, the inhibitor of an immune checkpoint molecule is an inhibitor of GITR, e.g., an anti-GITR antibody. In some embodiments, the anti-GITR antibody is TRX518 or, MK-4166, INCAGN01876 or MK-1248. In some embodiments, the inhibitor of an immune checkpoint molecule is an inhibitor of OX40, e.g., an anti-OX40 antibody or OX40L fusion protein. In some embodiments, the anti-OX40 antibody is MEDI0562 or, INCAGN01949, GSK2831781, GSK-3174998, MOXR-0916, PF-04518600 or LAG525. In some embodiments, the OX40L fusion protein is MEDI6383

Compounds of the invention can also be used to increase or enhance an immune response, including increasing the immune response to an antigen; to improve immunization, including increasing vaccine efficacy; and to increase inflammation. In some embodiments, the compounds of the invention can be sued to enhance the immune response to vaccines including, but not limited, *Listeria* vaccines, oncolytic viarl vaccines, and cancer vaccines such as GVAX® (granulocyte-macrophage colony-stimulating factor (GM-CF) gene-transfected tumor cell vaccine). Anti-cancer vaccines include dendritic cells, synthetic peptides, DNA vaccines and recombinant viruses. Other immune-modulatory agents also include those that block immune cell migration such as antagonists to chemokine receptors, including CCR2 and CCR4; Sting agonists and Toll receptor agonists.

Other anti-cancer agents also include those that augment the immune system such as adjuvants or adoptive T cell transfer. Compounds of this application may be effective in combination with CAR (Chimeric antigen receptor) T cell treatment as a booster for T cell activation A compound of the invention can also be used in combination with the following adjunct therapies:

Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid).

EXAMPLES

The following preparations of intermediates (References) compounds of Formula (I) are given to enable those skilled in the art to more clearly understand and to practice the present disclosure. They should not be considered as limiting the scope of the disclosure, but merely as being illustrative and representative thereof.

Reference 1

Synthesis of (5S)-5,6-dihydrospiro[piperidine-4,4-pyrrolo[1,2-b]pyrazol]-5-amine dihydrochloride

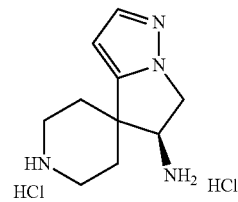 [SMILES: N[C@@H]1Cn2nccc2C12CCNCC2 ; Cl ; Cl]

Step 1: 1-[1-[(tert-butoxy)(hydroxy)methyl]-4-[hydroxy(methoxy)methyl]piperidin-4-yl]ethan-1-ol

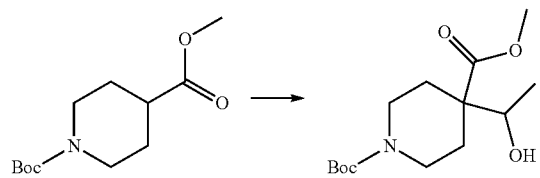 [SMILES: COC(=O)C1CCN(C(=O)OC(C)(C)C)CC1 ; COC(=O)C1(C(C)O)CCN(C(=O)OC(C)(C)C)CC1]

To a solution of [1-[(tert-butoxy)(hydroxy)methyl]piperidin-4-yl](methoxy)methanol (20 g, 80.86 mmol, 1.0 equiv) in THF (200 mL) at −78° C. was added LDA (48.52 mL, 97.03 mmol, 1.2 equiv) dropwise under nitrogen atmosphere. After stirring for 1.5 h at −78° C.~−60° C., to the above mixture was added acetaldehyde (5.34 g, 121.29 mmol, 1.5 equiv) dropwise over 5 minutes at −78° C. and the resulting mixture was stirred for additional 2 h at −78° C.~−40° C. The reaction mixture was then poured into sat. NH$_4$Cl aq. solution and extracted with EtOAc. The organic layer was washed with brine, dried over anhydrous Na$_2$SO$_4$ and concentrated. The residue was purified by silica gel column chromatography (EtOAc/PE, 0-50%) to afford 12 g (50.9% yield) of the title compound as light yellow oil.

Step 2: 1-tert-butyl 4-methyl 4-[1-(trifluoromethanesulfonyloxy)ethyl]piperidine-1,4-dicarboxylate

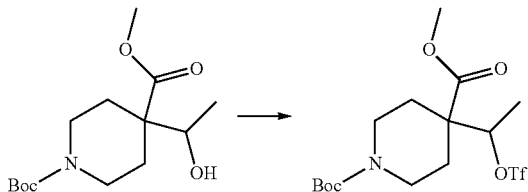 [SMILES: COC(=O)C1(C(C)O)CCN(C(=O)OC(C)(C)C)CC1 ; COC(=O)C1(C(C)OS(=O)(=O)C(F)(F)F)CCN(C(=O)OC(C)(C)C)CC1]

To a solution of 1-tert-butyl 4-methyl 4-(1-hydroxyethyl)piperidine-1,4-dicarboxylate (9.5 g, 33.06 mmol, 1 equiv) in DCM (100 mL) were added pyridine (10.4 g, 131.48 mmol, 4.0 equiv) and (trifluoromethane)sulfonyl trifluoromethanesulfonate (18.7 g, 66.27 mmol, 2.0 equiv) dropwise at 0° C. under nitrogen atmosphere. After stirring for 2 h at 0° C., the reaction mixture was quenched with water at 0° C. The resulting mixture was extracted with CH$_2$Cl$_2$. The organic layer was washed with brine, dried over anhydrous Na$_2$SO$_4$ and concentrated under reduced pressure to give 20 g (crude) of the title compound. This crude product was used directly in next step without further purification.

Step 3: 1-tert-butyl 4-methyl 4-ethenylpiperidine-1,4-dicarboxylate

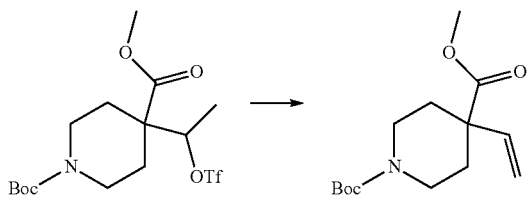 [SMILES: COC(=O)C1(C(C)OS(=O)(=O)C(F)(F)F)CCN(C(=O)OC(C)(C)C)CC1 ; C=CC1(C(=O)OC)CCN(C(=O)OC(C)(C)C)CC1]

To a stirred solution of 1-tert-butyl 4-methyl 4-[1-(trifluoromethanesulfonyloxy)-ethyl]piperidine-1,4-dicarboxylate (20 g, crude) in DCM (300 mL) was added DBU (28.50 mL, 187.18 mmol) at rt under nitrogen atmosphere. After stirring for 4 h at rt, the reaction mixture was concentrated under reduced pressure and the residue was purified by silica gel column chromatography (EtOAc/PE, 6%) to afford the title compound (4.5 g, 55.2% yield for two steps) as light yellow oil.

Step 4: 1-[(tert-butoxy)carbonyl]-4-ethenylpiperidine-4-carboxylic acid

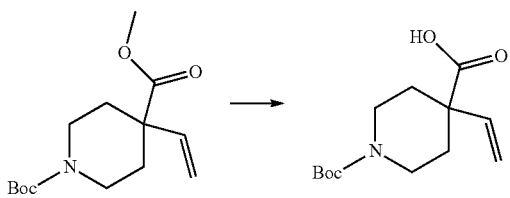 [SMILES: C=CC1(C(=O)OC)CCN(C(=O)OC(C)(C)C)CC1 ; C=CC1(C(=O)O)CCN(C(=O)OC(C)(C)C)CC1]

To a solution of 1-tert-butyl 4-methyl 4-ethenylpiperidine-1,4-dicarboxylate (4.8 g, 17.82 mmol, 1.0 equiv) in MeOH (40 mL) were added water (10 mL) and LiOH (2.35 g, 98.01 mmol, 5.5 equiv) at room temperature. After stirring for 16 h at rt, the mixture was acidified to pH=5 with 0.5 M HCl aq. solution. The reaction mixture was then extracted with CH$_2$Cl$_2$. The combined organic layers were washed with brine, dried over anhydrous Na$_2$SO$_4$ and concentrated to give the title compound (4.5 g, 98.9% yield) as a light yellow oil which was used for next step without further purification.

Step 5: tert-butyl 4-ethenyl-4-[methoxy(methyl)carbamoyl]piperidine-1-carboxylate

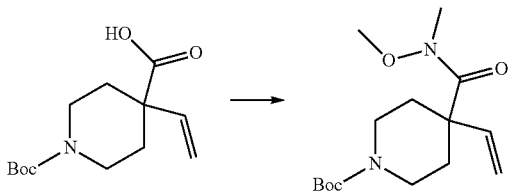 [SMILES: C=CC1(C(=O)O)CCN(C(=O)OC(C)(C)C)CC1 ; C=CC1(C(=O)N(C)OC)CCN(C(=O)OC(C)(C)C)CC1]

To a solution of 1-[(tert-butoxy)carbonyl]-4-ethenylpiperidine-4-carboxylic acid (4.5 g, 17.62 mmol, 1.0 equiv) and methoxy(methyl)amine (1.61 g, 26.43 mmol, 1.5 equiv) in DCM (70 mL) were added HATU (13.40 g, 35.25 mmol, 2.0 equiv) and Et$_3$N (5.35 g, 52.86 mmol, 3.0 equiv) at rt under nitrogen atmosphere. After stirring for 12 h at rt, the reaction mixture was quenched with water at room temperature and extracted with DCM. The organic layer was washed with brine, dried over anhydrous Na$_2$SO$_4$ and concentrated. The residue was purified by silica gel column chromatography (EtOAc/PE, 5%) to afford the title compound (5 g, 95% yield) as a white solid.

Step 6: tert-butyl 4-acetyl-4-ethenylpiperidine-1-carboxylate

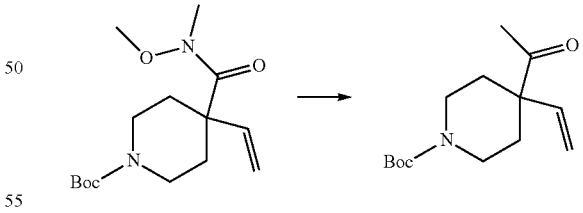

To a solution of tert-butyl 4-ethenyl-4-[methoxy(methyl)carbamoyl]piperidine-1-carboxylate (5 g, 16.75 mmol, 1.0 equiv) in THF (60 mL) was added 2.5 M CH$_3$MgBr (16.76 mL, 41.89 mmol, 2.50 equiv) dropwise at 0° C. under nitrogen atmosphere. After stirring for 12 h at rt, the reaction was quenched with sat. NH$_4$Cl aq. solution at 0° C. and the mixture was extracted with EtOAc. The organic layer was washed with brine, dried over anhydrous Na$_2$SO$_4$ and concentrated. The residue was purified by silica gel column chromatography (EtOAc/PE, 1/3) to afford the title compound (3.5 g, 82.4% yield) as light yellow oil.

Step 7: tert-butyl 4-[(2Z)-3-(dimethylamino)prop-2-enoyl]-4-ethenylpiperidine-1-carboxylate

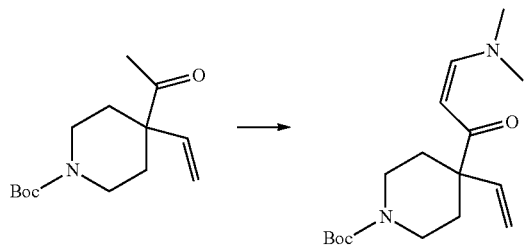 [SMILES: C=CC1(C(C)=O)CCN(C(=O)OC(C)(C)C)CC1 ; C=CC1(C(=O)/C=C\N(C)C)CCN(C(=O)OC(C)(C)C)CC1]

A solution of tert-butyl 4-acetyl-4-ethenylpiperidine-1-carboxylate (2.2 g, 8.68 mmol, 1.0 equiv) in [(tert-butoxy)(dimethylamino)methyl]dimethylamine (2 mL, 9.69 mmol, 1.1 equiv.) was stirred for 4 h at 100° C. under nitrogen atmosphere. The reaction mixture was concentrated under reduced pressure. The residue was purified by silica gel column chromatography, eluted with PE/EtOAc (1:1) to afford the title compound (1.6 g, 59.7% yield) as light yellow oil.

Step 8: tert-butyl 4-ethenyl-4-(1H-pyrazol-5-yl)piperidine-1-carboxylate

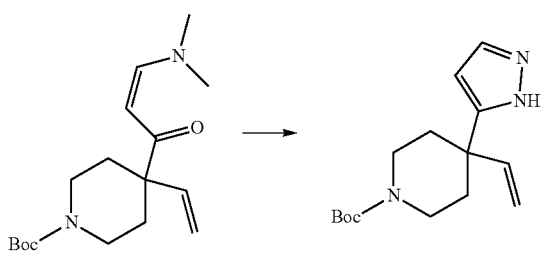 [SMILES: C=CC1(C(=O)/C=C\N(C)C)CCN(C(=O)OC(C)(C)C)CC1 ; C=CC1(c2ccn[nH]2)CCN(C(=O)OC(C)(C)C)CC1]

To a stirred solution of tert-butyl 4-[(2Z)-3-(dimethylamino)prop-2-enoyl]-4-ethenylpiperidine-1-carboxylate (2.2 g, 7.13 mmol, 1.0 equiv.) in EtOH (50 mL) was added hydrazine monohydrate (0.54 g, 10.78 mmol, 1.5 equiv) at 25° C. under nitrogen atmosphere. After stirring for 16 h at 25° C., the reaction was quenched with water and the resulting mixture was extracted with DCM. The organic layer was washed with brine, dried over anhydrous $Na_2SO_4$ and concentrated. The residue was purified by silica gel column chromatography, eluted with EtOAc/PE (30%-60%) to afford the title compound (1.6 g, 80.8% yield) as a white solid.

Step 9: tert-butyl 4-(oxiran-2-yl)-4-(1H-pyrazol-5-yl)piperidine-1-carboxylate

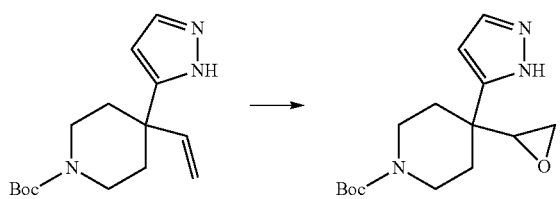 [SMILES: C=CC1(c2ccn[nH]2)CCN(C(=O)OC(C)(C)C)CC1 ; CC(C)(C)OC(=O)N1CCC(c2ccn[nH]2)(C2CO2)CC1]

To a stirred mixture of tert-butyl 4-ethenyl-4-(1H-pyrazol-5-yl)piperidine-1-carboxylate (2 g, 7.2 mmol, 1.0 equiv) and methyltrioxorhenium(VII) (179.72 mg, 0.72 mmol, 0.1 equiv) in DCM (30 mL) were added pyridine (228.14 mg, 2.88 mmol, 0.4 equiv) and $H_2O_2$ (30%) (1.23 g, 10.85 mmol, 1.5 equiv) at rt. After stirring for 16 h at rt, the reaction was quenched with water and extracted with DCM. The organic layer was washed with brine, dried over anhydrous $Na_2SO_4$ and concentrated. The residue was purified by silica gel column chromatography, eluted with EtOAc/PE (30%-60%) to afford the tittle compound (0.8 g, 37.82%) as a white solid.

Step 10: tert-butyl 5-hydroxy-5,6-dihydrospiro[piperidine-4,4-pyrrolo[1,2-b]pyrazole]-1-carboxylate

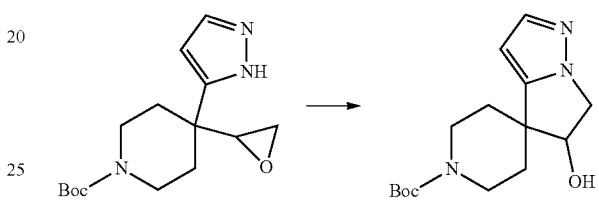

To a stirred solution of tert-butyl 4-(oxiran-2-yl)-4-(1H-pyrazol-5-yl)piperidine-1-carboxylate (0.7 g, 2.38 mmol, 1.0 equiv) in THF (10 mL) were added LiBr (0.62 g, 7.15 mmol, 3.0 equiv) and $CH_3COOH$ (0.43 g, 7.15 mmol, 3.0 equiv) at room temperature. After stirring for 16 h at rt, the reaction mixture was stirred at 45° C. for 8 h. After cooling to rt, the reaction mixture was quenched with sat. $NaHCO_3$ aq. solution and the mixture was extracted with EtOAc. The organic layer was washed with brine, dried over anhydrous $Na_2SO_4$ and concentrated. The residue was purified by silica gel column chromatography, eluted with EtOAc/PE (30%-100%) to afford the title compound (0.4 g, 57.1% yield) as a white solid.

Step 11: tert-butyl 5-oxo-5,6-dihydrospiro[piperidine-4,4-pyrrolo[1,2-b]pyrazole]-1-carboxylate

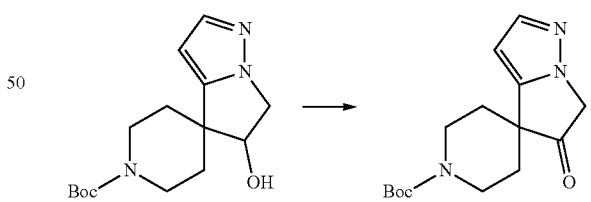

To a solution of tert-butyl 5-hydroxy-5,6-dihydrospiro[piperidine-4,4-pyrrolo[1,2-b]pyrazole]-1-carboxylate (0.4 g, 1.36 mmol, 1.0 equiv) in DCM (8 mL) was added Dess-Martin (0.87 g, 2.04 mmol, 1.5 equiv) at rt. After stirring for 4 h at room temperature, the reaction mixture was quenched with sat. $NaHCO_3$ aq. solution at room temperature and extracted with DCM. The organic layer was washed with brine, dried over anhydrous $Na_2SO_4$ and concentrated. The residue was purified by silica gel column chromatography (EtOAc/PE, 20%-60%) to afford the title compound (0.36 g, 90.62%) as a white solid.

Step 12: tert-butyl (S)-5-[(R)-2-methylpropane-2-sulfinyl)amino]-5,6-dihydrospiro[piperidine-4,4-pyrrolo[1,2-b]pyrazole]-1-carboxylate

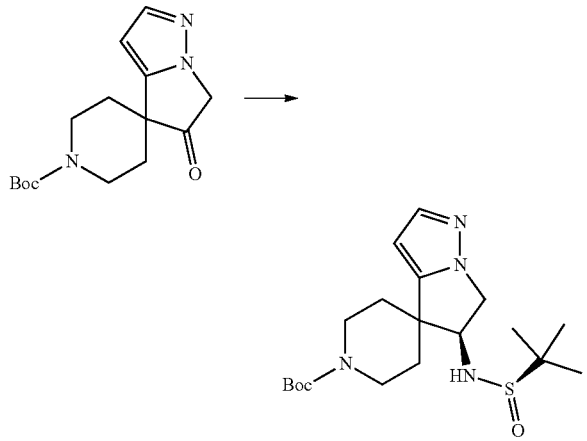

To a solution of tert-butyl 5-oxo-5,6-dihydrospiro[piperidine-4,4-pyrrolo[1,2-b]pyrazole]-1-carboxylate (0.36 g, 1.23 mmol, 1.0 equiv.) in THF (6 mL) was added (R)-2-methylpropane-2-sulfinamide (0.30 g, 2.47 mmol, 2.0 equiv.) and Ti(OEt)₄ (1.13 g, 4.94 mmol, 4.0 equiv.) at rt under nitrogen atmosphere. After stirring for 4 hrs at 75° C., the reaction mixture was cooled to −20° C. To the above mixture was added MeOH (1 mL) and LiBH₄ (40.38 mg, 1.85 mmol, 1.50 equiv) at −20° C. After stirring for additional 6 h at 0° C., the reaction mixture was quenched with sat. NH₄Cl aq. solution at 0° C. The mixture was then filtered and the filter cake was washed with EtOAc. The filtrate was concentrated under reduced pressure and the residue was dissolved in MeOH (3 mL). To the above mixture was added LiBH₄ (80.75 mg, 3.71 mmol, 3.0 equiv) at room temperature. The resulting mixture was stirred for additional 8 h at 45° C. The reaction mixture was quenched with sat. NH₄Cl aq. solution at 0° C. The resulting mixture was extracted with EtOAc. The organic layer was washed with brine, dried over anhydrous Na₂SO₄ and concentrated under reduced pressure. The residue was purified by silica gel column chromatography, eluted with EtOAc/PE (30%-70%) to afford the title compound (200 mg, 40.8% yield) as a white solid.

Step 13: (5S)-5,6-dihydrospiro[piperidine-4,4-pyrrolo[1,2-b]pyrazol]-5-amine dihydrochloride

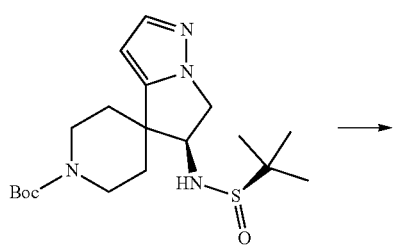

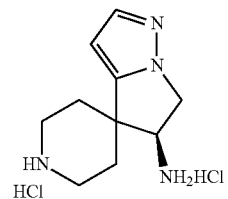

To a stirred solution of tert-butyl (S)-5-[(R)-2-methylpropane-2-sulfinyl)amino]-5,6-dihydrospiro[piperidine-4,4-pyrrolo[1,2-b]pyrazole]-1-carboxylate (100 mg, 0.252 mmol, 1.0 equiv) in 1,4-dioxane (0.5 mL) was added the solution of HCl in dioxane (4 M, 0.50 mL) dropwise at room temperature. After stirring for 30 mins at rt, the reaction mixture was concentrated under reduced pressure. To the residue was added Et₂O (1 mL) and the precipitate was collected by filtration to afford the title compound (60 mg, 89.7% yield) as a white solid.

Example 1

Synthesis of (3-((3S,4S)-4-amino-3-methyl-2-oxa-8-azaspiro[4.5]decan-8-yl)-6-(((S)-6a,7,8,9-tetrahydro-6H-pyrido[3,2-b]pyrrolo[1,2-d][1,4]oxazin-4-yl)thio)pyrazin-2-yl)methanol

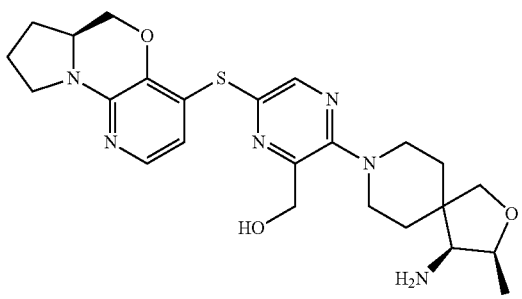 [SMILES: C[C@@H]1OCC2(CCN(c3ncc(Sc4ccnc5c4OC[C@@H]4CCCN54)nc3CO)CC2)[C@@H]1N]

Step 1: tert-butyl (2S)-2-[[(2-fluoropyridin-3-yl)oxy]methyl]pyrrolidine-1-carboxylate

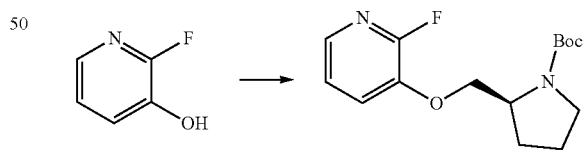

To a stirred mixture of 2-fluoropyridin-3-ol (1 g, 8.84 mmol, 1.00 equiv.) and tert-butyl (2S)-2-(hydroxylmethyl)prrolidine-1-carboxylate (2.14 g, 10.61 mmol, 1.2 equiv.) in THF (15 mL) were added PPh₃ (3.48 g, 13.26 mmol, 1.50 equiv) and DEAD (2.31 g, 13.26 mmol, 1.5 equiv.) at room temperature under nitrogen atmosphere. After stirring for 16 h at room temperature, the reaction mixture was concentrated under reduced pressure. The residue was purified by silica gel column chromatography, eluted with PE/EtOAc (15:1) to afford the title compound (2.5 g, 95.4% yield) as a light yellow oil.

Step 2: 2-fluoro-3-[[(2S)-pyrrolidin-2-yl]methoxy]pyridine dihydrochloride

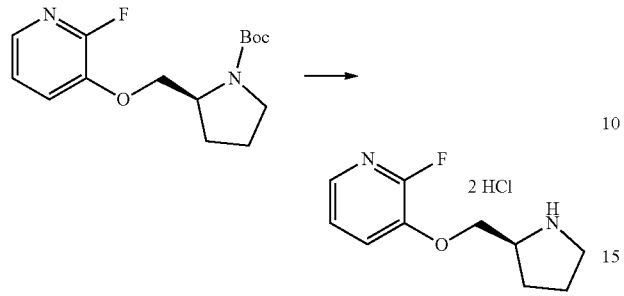

To a stirred solution of tert-butyl (2S)-2-[[(2-fluoropyridin-3-yl)oxy]methyl]-pyrrolidine-1-carboxylate (2500 mg, 8.43 mmol, 1.00 equiv) in DCM (15 mL) was added hydrogen chloride (4 M in dioxane) (15 mL) at room temperature. After stirring at rt for 4 h, the reaction mixture was concentrated under vacuum to afford the title compound (2.20 g, 96.8% yield) as a white solid.

Step 3: (S)-6a,7,8,9-tetrahydro-6H-pyrido[3,2-b]pyrrolo[1,2-d][1,4]oxazine

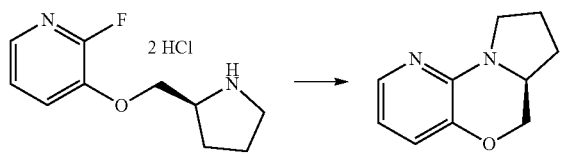 [SMILES: Fc1ncccc1OC[C@@H]1CCCN1 ; c1cnc2c(c1)OC[C@@H]1CCCN21]

To a stirred solution of 2-fluoro-3-[[(2S)-pyrrolidin-2-yl]methoxy]pyridine dihydrochloride (2.20 g, 8.17 mmol, 1.00 equiv) in ethanol (50 mL) was added K$_2$CO$_3$ (5.64 g, 40.87 mmol, 5.00 equiv) at room temperature and the resulting mixture was stirred for 12 h at 65° C. The mixture was then filtered and the filtrate was concentrated under reduced pressure. The residue was purified by silica gel column chromatography, eluted with PE/EtOAc (3:1) to afford the title compound (1.34 g, 93% yield) as colorless oil.

Step 4: (S)-4-iodo-6a,7,8,9-tetrahydro-6H-pyrido[3,2-b]pyrrolo[1,2-d][1,4]oxazine

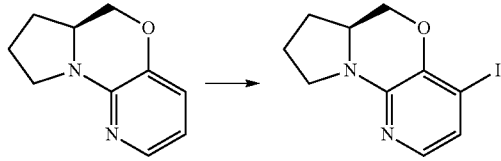 [SMILES: c1cnc2c(c1)OC[C@@H]1CCCN21 ; Ic1ccnc2c1OC[C@@H]1CCCN21]

To a stirred solution of (S)-6a,7,8,9-tetrahydro-6H-pyrido[3,2-b]pyrrolo[1,2-d][1,4]oxazine (600 mg, 3.41 mmol, 1.00 equiv) in THF (15 mL) was added dropwise n-butyllithium solution (2.5 M in hexane, 3.4 mL, 8.5 mmol, 2.50 equiv) at −78° C. under N$_2$ atmosphere. The reaction mixture was allowed to warm to 0° C. and stirred for 1.5 h. To the above mixture was added to a solution of I$_2$ (950.60 mg, 3.74 mmol, 1.10 equiv) in THF (2 mL) dropwise at −78° C. The resulting mixture was allowed to warm to room temperature and stirred for 2 h at room temperature. The reaction mixture was quenched with sat. NH$_4$Cl aq. solution and diluted with EtOAc. The organic layer was washed with brine, dried over anhydrous Na$_2$SO$_4$. After filtration, the filtrate was concentrated under reduced pressure. The residue was purified by silica gel column chromatography, eluted with PE/EtOAc (3:1) to afford the title compound (700 mg, 68% yield) as a yellow solid.

Step 5: 2-ethylhexyl 3-(((S)-6a,7,8,9-tetrahydro-6H-pyrido[3,2-b]pyrrolo[1,2-d][1,4]oxazin-4-yl)thio)propanoate

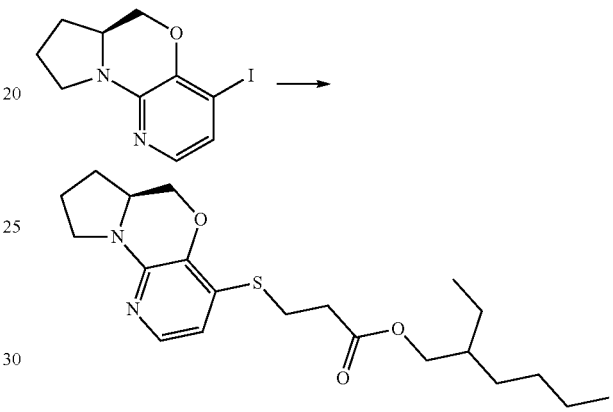

To a stirred mixture of (S)-4-iodo-6a,7,8,9-tetrahydro-6H-pyrido[3,2-b]pyrrolo[1,2-d][1,4]oxazine (150.00 mg, 0.496 mmol, 1.00 equiv), 2-ethylhexyl 3-sulfanylpropanoate (162.62 mg, 0.745 mmol, 1.50 equiv), Pd$_2$(dba)$_3$ (22.73 mg, 0.025 mmol, 0.05 equiv) and Xantphos (14.36 mg, 0.025 mmol, 0.05 equiv) in 1,4-dioxane (2 mL) was added DIEA (192.51 mg, 1.489 mmol, 3.00 equiv) at room temperature under nitrogen atmosphere. After stirring for 1 h at 90° C., the reaction mixture was concentrated under reduced pressure. The residue was purified by silica gel column chromatography, eluted with EtOAc/PE (0-30%) to afford the title compound (160 mg, 82% yield) as a light yellow solid.

Step 6: potassium (S)-6a,7,8,9-tetrahydro-6H-pyrido[3,2-b]pyrrolo[1,2-d][1,4]oxazine-4-thiolate

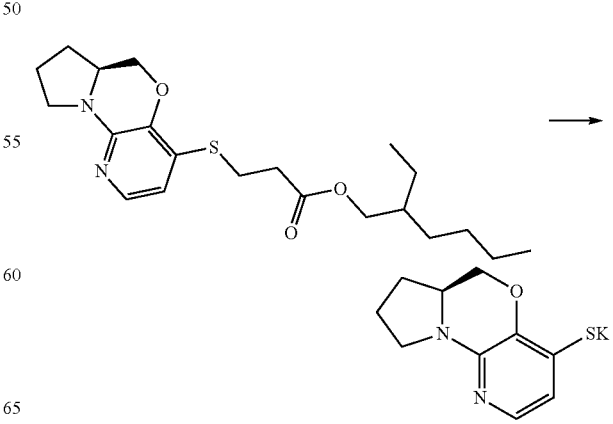

To a stirred solution of 2-ethylhexyl 3-(((S)-6a,7,8,9-tetrahydro-6H-pyrido[3,2-b]-pyrrolo[1,2-d][1,4]oxazin-4-yl)thio)propanoate (140.00 mg, 0.357 mmol, 1.0 equiv) in THF (2 mL) was added 1.0 M t-BuOK (0.43 mL, 0.43 mmol, 1.20 equiv) at −10° C. After stirring for 0.5 h at 0° C., the reaction mixture was diluted with petroleum ether. The precipitated solids were collected by filtration and washed with ethyl acetate to afford the title compound (75 mg, 85% yield) as a light yellow solid.

Step 7: methyl 6-bromo-3-[(3S,4S)-4-[[(tert-butoxy)carbonyl]amino]-3-methyl-2-oxa-8-azaspiro[4.5]decan-8-yl]pyrazine-2-carboxylate

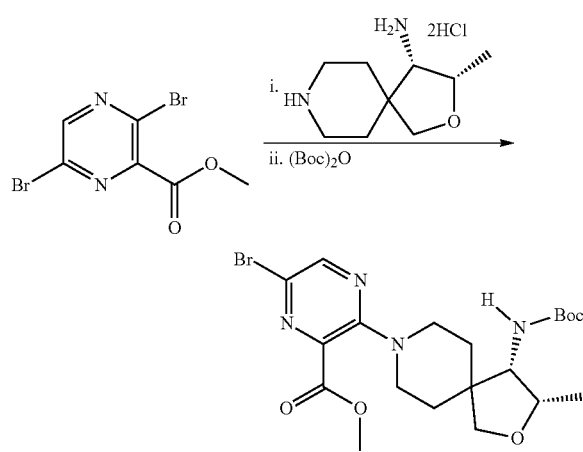

A solution of methyl 3,6-dibromopyrazine-2-carboxylate (500 mg, 1.690 mmol, 1 equiv), (3S,4S)-3-methyl-2-oxa-8-azaspiro[4.5]decan-4-amine dihydrochloride (493.05 mg, 2.028 mmol, 1.2 equiv) and DIEA (1091.88 mg, 8.448 mmol, 5.0 equiv) in DMA (10 mL) was stirred for 2 h at 55° C. Di-tert-butyl dicarbonate (552.33 mg, 2.531 mmol, 1.5 equiv) was then added and the resulting mixture was stirred for 2 h at room temperature. The reaction mixture was diluted with water and extracted with EtOAc. The organic layer was washed with water and brine, dried over anhydrous Na₂SO₄ and concentrated. The residue was purified by silica gel column chromatography, eluted with PE/EtOAc=1:1 to afford the title compound (615 mg, 2 steps yield 75%) as yellow oil.

Step 8: tert-butyl N-[(3S,4S)-8-[5-bromo-3-(hydroxymethyl)pyrazin-2-yl]-3-methyl-2-oxa-8-azaspiro[4.5]decan-4-yl]carbamate

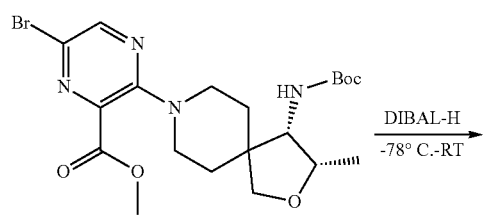

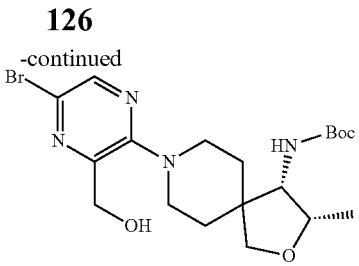

To a stirred solution of methyl 6-bromo-3-[(3S,4S)-4-[[(tert-butoxy)carbonyl]-amino]-3-methyl-2-oxa-8-azaspiro[4.5]decan-8-yl]pyrazine-2-carboxylate (150 mg, 0.309 mmol, 1 equiv) in DCM (3.75 mL) was added DIBAL-H (1.0 M in DCM, 1.24 mL, 1.240 mmol, 4.01 equiv) dropwise at −78° C. under nitrogen atmosphere. The resulting mixture was stirred for 30 min at −78° C. under nitrogen atmosphere, warmed to rt then quenched by adding sat. Rochelle's salt aq. solution. The resulting mixture was extracted with EtOAc. The organic layer was washed with brine, dried over anhydrous Na₂SO₄ and concentrated. The residue was purified by silica gel column chromatography, eluted with EtOAc/PE (0-50%) to afford the title compound (65 mg, 46%) as a yellow solid.

Step 9: tert-butyl ((3S,4S)-8-(3-(hydroxymethyl)-5-(((S)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-yl)carbamate

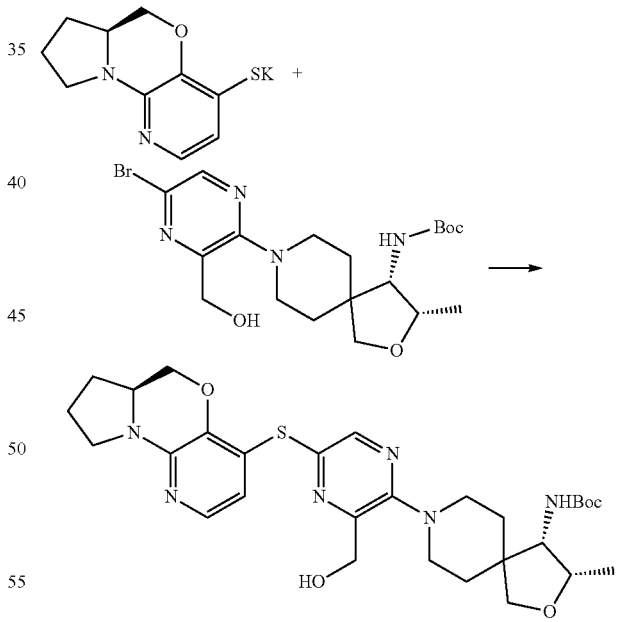

To a stirred mixture of tert-butyl N-[(3S,4S)-8-[5-bromo-3-(hydroxymethyl)pyrazin-2-yl]-3-methyl-2-oxa-8-azaspiro[4.5]decan-4-yl]carbamate (25.00 mg, 0.055 mmol, 1.00 equiv), potassium (S)-6a,7,8,9-tetrahydro-6H-pyrido[3,2-b]pyrrolo[1,2-d][1,4]oxazine-4-thiolate (20.20 mg, 0.082 mmol, 1.50 equiv), Pd₂(dba)₃ (15.02 mg, 0.0164 mmol, 0.30 equiv) and Xantphos (9.49 mg, 0.0164 mmol, 0.30 equiv) in 1,4-dioxane (1 mL) was added DIEA (21.19 mg, 0.164 mmol, 3.00 equiv) at room temperature under nitrogen atmosphere. After stirring for 1.5 h at 100° C., the reaction mixture was concentrated under reduced pressure.

The residue was purified by silica gel column chromatography, eluted with EtOAc/PE (50%-100%) to afford the title compound (25 mg, 78% yield) as a light yellow solid.

Step 10: (3-((3S,4S)-4-amino-3-methyl-2-oxa-8-azaspiro[4.5]decan-8-yl)-6-(((S)-6a,7,8,9-tetrahydro-6H-pyrido[3,2-b]pyrrolo[1,2-d][1,4]oxazin-4-yl)thio)pyrazin-2-yl)methanol formate

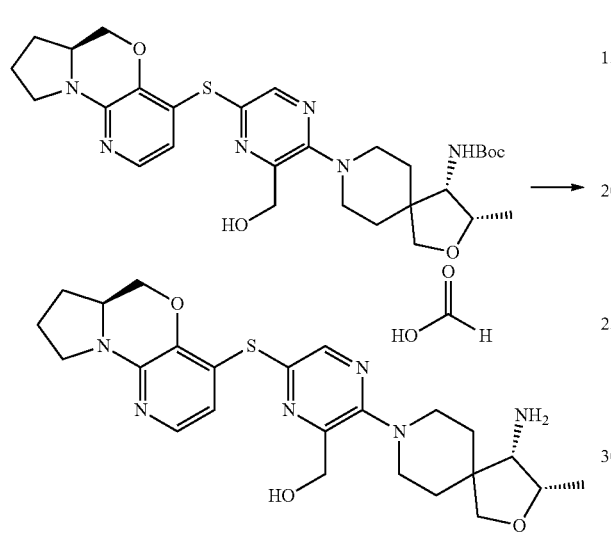

To a stirred solution of tert-butyl ((3S,4S)-8-(3-(hydroxymethyl)-5-(((S)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-yl)carbamate (20.00 mg, 0.034 mmol, 1.0 equiv) in DCM (1.5 mL) was added TFA (0.3 mL) at room temperature. After stirring for 5 h at room temperature, the reaction mixture was concentrated under reduced pressure. The crude product was purified by Prep-HPLC to afford the title compound (7 mg, 39% yield) as a light yellow solid. MS (ES, m/z): [M+1]$^+$=485.2.

Example 2

Synthesis of (3-((3S,4S)-4-amino-3-methyl-2-oxa-8-azaspiro[4.5]decan-8-yl)-6-(((R)-6a,7,8,9-tetrahydro-6H-pyrido[3,2-b]pyrrolo[1,2-d][1,4]oxazin-4-yl)thio)pyrazin-2-yl)methanol

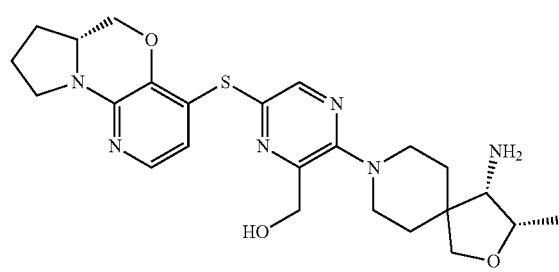 [SMILES: C[C@@H]1OCC2(CCN(c3ncc(Sc4ccnc5c4OC[C@H]4CCCN54)nc3CO)CC2)[C@@H]1N]

Compound 2 was synthesized by the method described in Example 1 using tert-butyl (2R)-2-(hydroxylmethyl)prroli-dine-1-carboxylate instead of tert-butyl (2S)-2-(hydroxylmethyl)-prrolidine-1-carboxylate in Step 1. MS (ES, m/z): [M+1]$^+$=485.3.

Example 3

Synthesis of (3-((3S,4S)-4-amino-3-methyl-2-oxa-8-azaspiro[4.5]decan-8-yl)-6-((((6aS,8S)-8-fluoro-6a,7,8,9-tetrahydro-6H-pyrido[3,2-b]pyrrolo[1,2-d][1,4]oxazin-4-yl)thio)pyrazin-2-yl)methanol

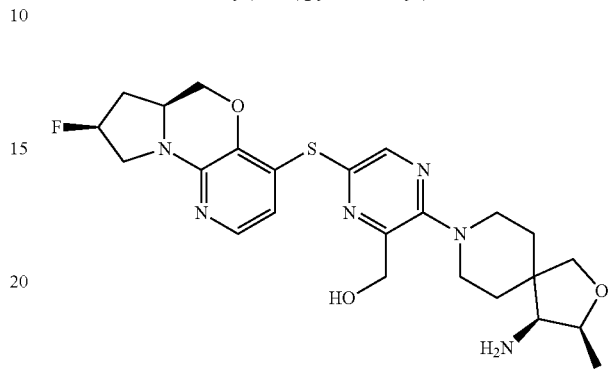

Step 1: tert-butyl(2S,4S)-4-fluoro-2-(hydroxymethyl)pyrrolidine-1-carboxylate

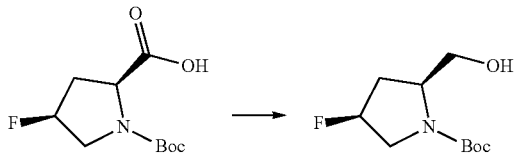 [SMILES: CC(C)(C)OC(=O)N1C[C@@H](F)C[C@H]1C(=O)O ; CC(C)(C)OC(=O)N1C[C@@H](F)C[C@H]1CO]

To a stirred solution of (2S,4S)-1-(tert-butoxycarbonyl)-4-fluoropyrrolidine-2-carboxylic acid (2.33 g, 9.99 mmol, 1.0 equiv) in THF (25 mL) was added BH$_3$-Me$_2$S (2.8 mL, 29.5 mmol, 3.0 equiv) dropwise at 0-5° C. under nitrogen atmosphere and the resulting mixture was stirred overnight at room temperature. The mixture was cooled to 0° C. and quenched with MeOH. The resulting mixture was concentrated under reduced pressure and the residue was purified by silica gel column chromatography, eluted with EtOAc/PE (1/1) to give the title compound (2.0 g, 91.3%).

Step 2: tert-butyl(2S,4S)-4-fluoro-2-[[(2-fluoro-4-iodopyridin-3-yl)oxy]methyl]pyrrolidine-1-carboxylate

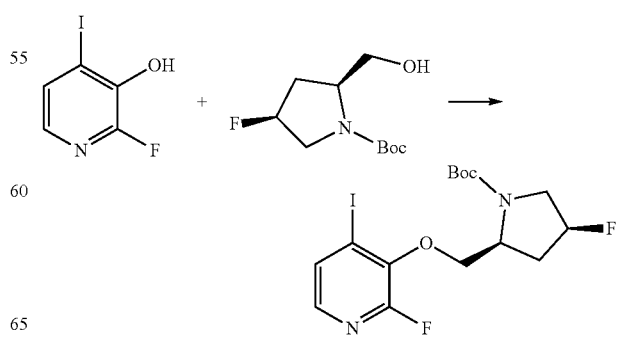

To a stirred solution of 2-fluoro-4-iodopyridin-3-ol (436 mg, 1.82 mmol, 1.0 equiv), tert-butyl (2S,4S)-4-fluoro-2-(hydroxymethyl)pyrrolidine-1-carboxylate (400 mg, 1.82 mmol, 1.0 equiv) and PPh₃ (717 mg, 2.73 mmol, 1.5 equiv) in THF (4.00 mL) was added DEAD (476 mg, 2.73 mmol, 1.5 equiv) dropwise at 0° C. under nitrogen atmosphere. The resulting mixture was stirred overnight at room temperature under nitrogen atmosphere. The reaction mixture was quenched with water and the resulting mixture was extracted with EtOAc. The combined organic layers were washed with water and brine, dried over anhydrous Na₂SO₄ and concentrated. The residue was purified by silica gel column chromatography, eluted with EtOAc/PE (0-50%), to afford the title compound (610 mg, 75.5%).

Step 3: 2-fluoro-3-(((2S,4S)-4-fluoropyrrolidin-2-yl)methoxy)-4-iodopyridine hydrochloride

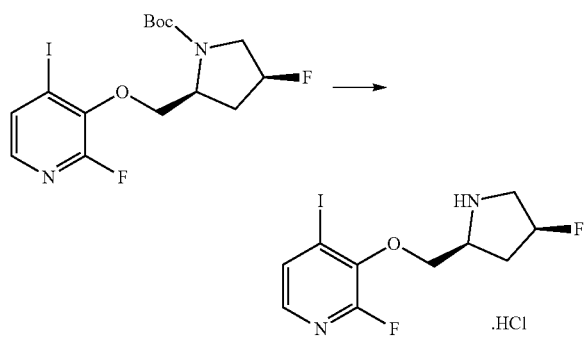

To a stirred solution of tert-butyl (2S,4S)-4-fluoro-2-[[(2-fluoro-4-iodopyridin-3-yl)oxy]methyl]pyrrolidine-1-carboxylate (560 mg, 1.272 mmol, 1.0 equiv) in 1,4-dioxane (5 mL) was added a solution of 3.3 M HCl in 1,4-dioxane (5 mL, 16.5 mmol, 13 equiv) dropwise at 0° C. After stirring at room temperature for 1 hour, the reaction mixture was concentrated under reduced pressure and the residue was triturated with Et₂O. The solid was collected by filtration and dried under vacuum to give product as HCl salt (375 mg, 78.3%).

Step 4: (6aS,8S)-8-fluoro-4-iodo-6a,7,8,9-tetrahydro-6H-pyrido[3,2-b]pyrrolo[1,2-d][1,4]oxazine

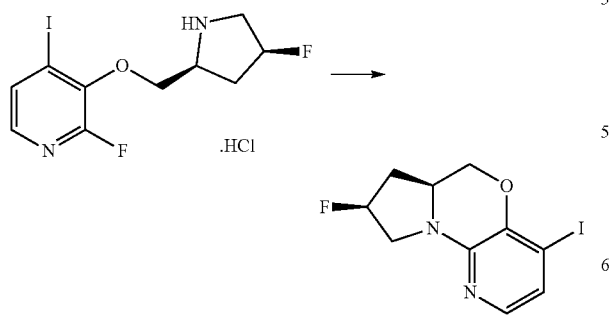

A mixture of 2-fluoro-3-(((2S,4S)-4-fluoropyrrolidin-2-yl)methoxy)-4-iodopyridine hydrochloride (370 mg, 0.983 mmol, 1.0 equiv) and K₂CO3 (407 mg, 2.95 mmol, 3.0 equiv) in EtOH (4 mL) was stirred for 2 h at 60° C. The resulting mixture was diluted with water and extracted with EtOAc. The combined organic layers were washed with water and brine, dried over anhydrous Na₂SO₄ and concentrated. The residue was purified by silica gel column chromatography, eluted with EtOAc/PE (0-30%), to afford the title compound (245 mg, 77.9%).

Step 5: 2-ethylhexyl 3-([5-[(3S,4S)-4-[(tert-butoxycarbonyl)amino]-3-methyl-2-oxa-8-azaspiro[4.5]decan-8-yl]-6-(hydroxymethyl)pyrazin-2-yl]sulfanyl)propanoate

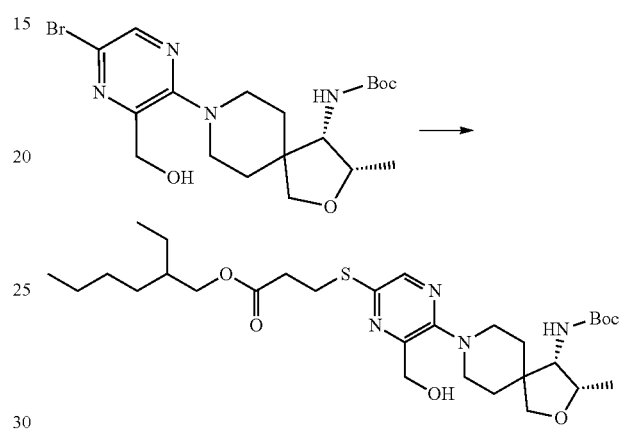

A solution of tert-butyl N-[(3S,4S)-8-[5-bromo-3-(hydroxymethyl)pyrazin-2-yl]-3-methyl-2-oxa-8-azaspiro[4.5]decan-4-yl]carbamate (580.0 mg, 1.27 mmol, 1.0 equiv), 2-ethylhexyl 3-sulfanylpropanoate (332.29 mg, 1.52 mmol, 1.2 equiv), Pd₂(dba)₃ (116.1 mg, 0.127 mmol, 0.10 equiv), XantPhos (73.38 mg, 0.127 mmol, 0.10 equiv) and DIEA (491.69 mg, 3.804 mmol, 3.00 equiv) in 1,4-dioxane (12.0 mL) was stirred for 1 h at 100° C. under nitrogen atmosphere. The resulting mixture was concentrated under vacuum and the residue was purified by silica gel column chromatography, eluted with EtOAc/PE (0-50%), to afford the title compound (600 mg, 79.54%).

Step 6: sodium 5-((3S,4S)-4-((tert-butoxycarbonyl)amino)-3-methyl-2-oxa-8-azaspiro[4.5]-decan-8-yl)-6-(hydroxymethyl)pyrazine-2-thiolate

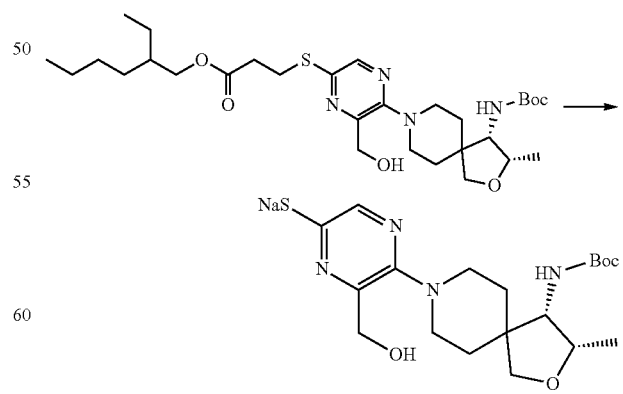

To a stirred solution of 2-ethylhexyl 3-([5-[(3S,4S)-4-[(tert-butoxycarbonyl)amino]-3-methyl-2-oxa-8-azaspiro[4.5]decan-8-yl]-6-(hydroxymethyl)pyrazin-2-yl]sulfanyl)

propanoate (680.0 mg, 1.14 mmol, 1.0 equiv) in CH₃OH (6.80 mL) was added CH₃ONa (247.04 mg, 1.372 mmol, 1.20 equiv, 30% in MeOH) dropwise at 5° C. After stirring at rt for 16 h, the reaction mixture was concentrated under vacuum and the residue was triturated with Et₂O to afford the title compound (390 mg, crude)), which was used for next step without further purification.

Step 7: tert-butyl ((3S,4S)-8-(5-(((6aS,8S)-8-fluoro-6a,7,8,9-tetrahydro-6H-pyrido[3,2-b]pyrrolo[1,2-d][1,4]oxazin-4-yl)thio)-3-(hydroxymethyl)pyrazin-2-yl)-3-methyl-2-oxa-8-azaspiro[4.5]decan-4-yl) carbamate

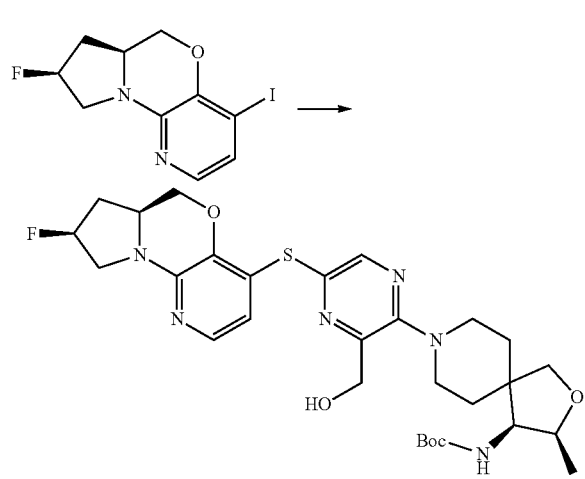

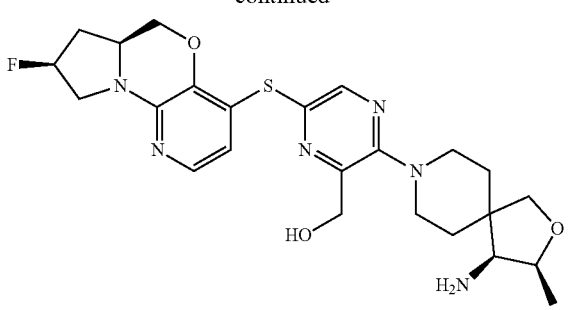

A solution of (6aS,8S)-8-fluoro-4-iodo-6a,7,8,9-tetrahydro-6H-pyrido[3,2-b]pyrrolo[1,2-d][1,4]oxazine (30.00 mg, 0.094 mmol, 1.0 equiv), sodium 5-((3S,4S)-4-((tert-butoxycarbonyl)amino)-3-methyl-2-oxa-8-azaspiro[4.5]decan-8-yl)-6-(hydroxymethyl)pyrazine-2-thiolate (48.64 mg, 0.112 mmol, 1.2 equiv), Pd₂(dba)₃ (25.75 mg, 0.028 mmol, 0.30 equiv), XantPhos (16.27 mg, 0.028 mmol, 0.30 equiv) and DIEA (36.34 mg, 0.281 mmol, 3.00 equiv) in dioxane (0.90 mL) was stirred for 1 h at 80° C. under nitrogen atmosphere. After cooling to rt, the reaction mixture was diluted with water, extracted with EtOAc. The organic layer was washed with water and brine, dried over Na₂SO₄ and concentrated. The residue was purified by silica gel column chromatography, eluted with MeOH/CH₂Cl₂ (0-10%), to afford the title compound (32 mg, 56.4%).

Step 8: (3-((S)-4-amino-2-oxa-8-azaspiro[4.5]decan-8-yl)-6-(((6aS,8S)-8-fluoro-6a,7,8,9-tetrahydro-6H-pyrido[3,2-b]pyrrolo[1,2-d][1,4]oxazin-4-yl)thio)pyrazin-2-yl)methanol

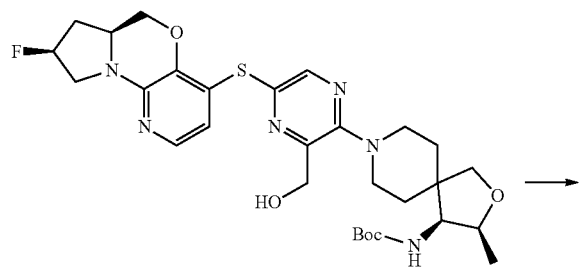

To a solution tert-butyl ((3S,4S)-8-(5-(((6aS,8S)-8-fluoro-6a,7,8,9-tetrahydro-6H-pyrido[3,2-b]pyrrolo[1,2-d][1,4]oxazin-4-yl)thio)-3-(hydroxymethyl)pyrazin-2-yl)-3-methyl-2-oxa-8-azaspiro[4.5]decan-4-yl)carbamate (26 mg, 0.043 mmol, 1.00 equiv) in DCM (1.2 mL) was added TFA (0.4 mL, 5.23 mmol, 122 equiv) dropwise at 5° C. After stirring at rt for 1 h, the reaction mixture was concentrated under vacuum and the residue was purified by Prep-HPLC to give the title compound (3.1 mg, 14.30%). MS (ES, m/z): [M+1]⁺=503.2.

Example 4

Synthesis of (3-((3S,4S)-4-amino-3-methyl-2-oxa-8-azaspiro[4.5]decan-8-yl)-6-(((6aS,8R)-8-fluoro-6a,7,8,9-tetrahydro-6H-pyrido[3,2-b]pyrrolo[1,2-d][1,4]oxazin-4-yl)thio)pyrazin-2-yl)methanol

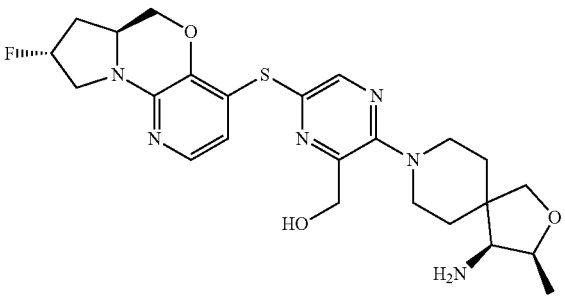 [SMILES: C[C@@H]1OCC2(CCN(c3ncc(Sc4ccnc5c4OC[C@@H]4C[C@@H](F)CN54)nc3CO)CC2)[C@@H]1N]

The title compound was synthesized by the method described in Example 3 using (2S,4R)-1-(tert-butoxycarbonyl)-4-fluoropyrrolidine-2-carboxylic acid in Step 1. MS (ES, m/z): [M+1]⁺=503.3.

Example 5

Synthesis of (3-((3S,4S)-4-amino-3-methyl-2-oxa-8-azaspiro[4.5]decan-8-yl)-6-(((6aS,8S)-8-methoxy-6a,7,8,9-tetrahydro-6H-pyrido[3,2-b]pyrrolo[1,2-d][1,4]oxazin-4-yl)thio)pyrazin-2-yl)methanol

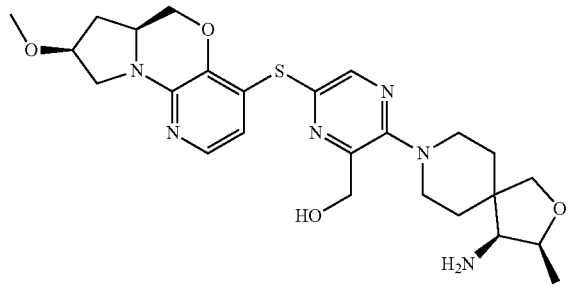 [SMILES: CO[C@H]1C[C@H]2COc3c(Sc4cnc(N5CCC6(CC5)CO[C@@H](C)[C@H]6N)c(CO)n4)ccnc3N2C1]

Step 1: 1-tert-butyl 2-methyl (2S,4S)-4-[(tert-butyldimethylsilyl)oxy]pyrrolidine-1,2-dicarboxylate

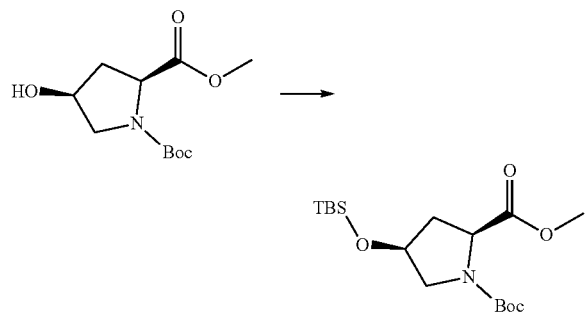

To a stirred solution of 1-tert-butyl 2-methyl (2S,4S)-4-hydroxypyrrolidine-1,2-dicarboxylate (6.0 g, 24.46 mmol, 1.0 equiv) and imidazole (2.5 g, 36.72 mmol, 1.50 equiv) in DCM (60 mL) was added TBS-Cl (5.53 g, 36.69 mmol, 1.50 equiv) in portions at 0-5° C. After stirring overnight at room temperature, the reaction mixture was quenched with MeOH and water, and the resulting mixture was extracted with EtOAc. The combined organic layers were washed with water and brine, dried over anhydrous Na₂SO₄ and concentrated. The residue was purified by silica gel column chromatography, eluted with EtOAc/PE (0-10%), to afford the title compound (9.0 g, 102.3%).

Step 2: tert-butyl(2S,4S)-4-[(tert-butyldimethylsilyl)oxy]-2-(hydroxymethyl)pyrrolidine-1-carboxylate

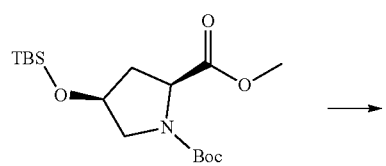

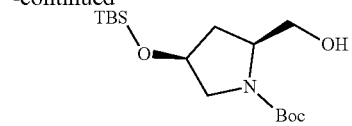

To a stirred mixture of 1-tert-butyl 2-methyl (2S,4S)-4-[(tert-butyldimethylsilyl)oxy]-pyrrolidine-1,2-dicarboxylate (3.0 g, 8.344 mmol, 1.0 equiv) in THF (30 mL) was added LiAlH₄ (475 mg, 12.516 mmol, 1.50 equiv) in portions at 0° C. under nitrogen atmosphere and the resulting mixture was stirred for 2 h at room temperature under nitrogen atmosphere. After cooling to 0° C., the reaction mixture was quenched with sat. aq. Na₂SO₄ solution. The resulting mixture was filtered and the filtrate was concentrated under reduced pressure. The residue was purified by silica gel column chromatography, eluted with EtOAc/PE (0-100%), to afford the title compound (1.6 g, 57.8%).

Step 3: tert-butyl (2S,4S)-4-[(tert-butyldimethylsilyl)oxy]-2-[[(2-fluoro-4-iodopyridin-3-yl)oxy]methyl]pyrrolidine-1-carboxylate

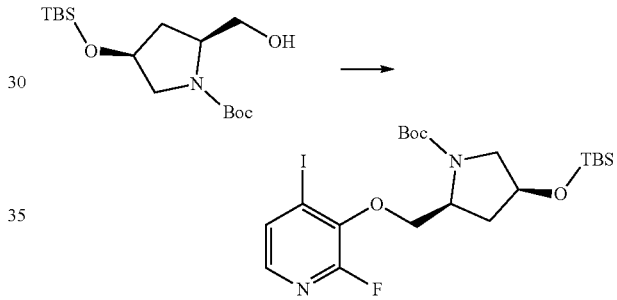

To a stirred mixture of 2-fluoro-4-iodopyridin-3-ol (400 mg, 1.674 mmol, 1.0 equiv), tert-butyl (2S,4S)-4-[(tert-butyldimethylsilyl)oxy]-2-(hydroxymethyl)pyrrolidine-1-carboxylate (555 mg, 1.674 mmol, 1.00 equiv) and PPh₃ (658 mg, 2.511 mmol, 1.50 equiv) in THF (4 mL) was added DEAD (437 mg, 2.51 mmol, 1.50 equiv) dropwise at 0° C. under nitrogen atmosphere. The resulting mixture was stirred for 2 h at room temperature under nitrogen atmosphere, then quenched with water at 0° C. and extracted with EtOAc. The combined organic layers were washed with water and brine, dried over anhydrous Na₂SO₄ and concentrated. The residue was purified by silica gel column chromatography, eluted with EtOAc/PE (0-30%), to afford the title compound (735 mg, 79.4%).

Step 4: (3S,5S)-5-[[(2-fluoro-4-iodopyridin-3-yl)oxy]methyl]pyrrolidin-3-ol hydrochloride

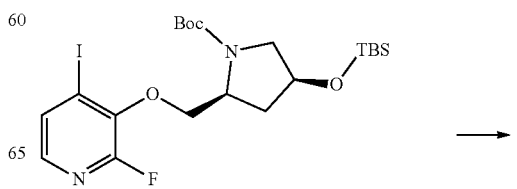

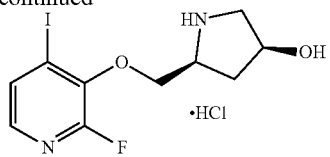

To a stirred solution of tert-butyl (2S,4S)-4-[(tert-butyldimethylsilyl)oxy]-2-[[(2-fluoro-4-iodopyridin-3-yl)oxy]methyl]pyrrolidine-1-carboxylate (750 mg, 1.357 mmol, 1.0 equiv) was added a solution of 3.0 M HCl in 1,4-dioxane (5 mL, 15 mmol, 11 equiv) dropwise at 0-5° C. After stirring at room temperature for 1 h, the reaction mixture was concentrated under reduced pressure and the residue was triturated with Et$_2$O. The precipitates were collected by filtration and dried under reduced pressure to give the title compound (400 mg, 78.7%).

Step 5: (6aS,8S)-4-iodo-6a,7,8,9-tetrahydro-6H-pyrido[3,2-b]pyrrolo[1,2-d][1,4]oxazin-8-ol

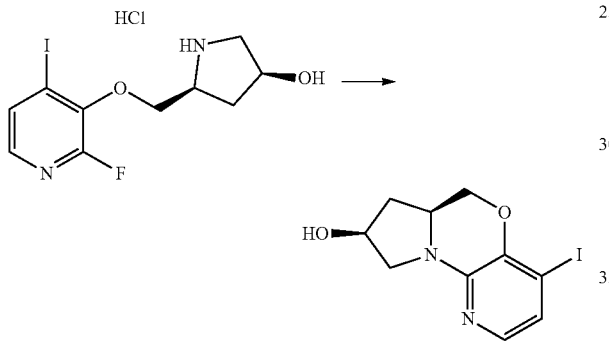

A mixture of (3S,5S)-5-[[(2-fluoro-4-iodopyridin-3-yl)oxy]methyl]pyrrolidin-3-ol hydrochloride (400 mg, 1.068 mmol, 1.00 equiv) and K$_2$CO3 (443 mg, 3.205 mmol, 3.00 equiv) in EtOH (4 mL) was stirred for 2 h at 60° C. After cooling to rt, the resulting mixture was diluted with water and extracted with EtOAc. The combined organic layers were washed with water and brine, dried over anhydrous Na$_2$SO$_4$ and concentrated. The residue was purified by silica gel column chromatography, eluted with EtOAc/PE (0-40%), to afford the title compound (300 mg, 88.3%).

Step 6: (6aS,8S)-4-iodo-8-methoxy-6a,7,8,9-tetrahydro-6H-pyrido[3,2-b]pyrrolo[1,2-d][1,4]oxazine

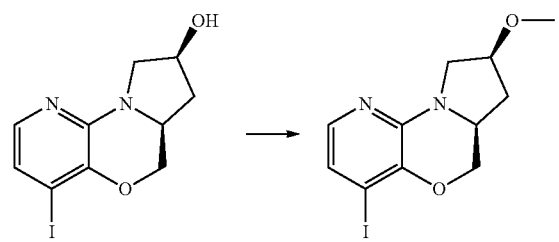 [SMILES: O[C@H]1C[C@H]2COc3c(I)ccnc3N2C1 ; CO[C@H]1C[C@H]2COc3c(I)ccnc3N2C1]

To a stirred solution of (6aS,8S)-4-iodo-6a,7,8,9-tetrahydro-6H-pyrido[3,2-b]pyrrolo[1,2-d][1,4]oxazin-8-ol (100.00 mg, 0.314 mmol, 1.0 equiv) and Ag$_2$O (364.23 mg, 1.572 mmol, 5.0 equiv) in DMF (1.00 mL) was added MeI (133.86 mg, 0.943 mmol, 3.00 equiv) dropwise at room temperature and the resulting mixture was stirred for 4 h at 50° C. After cooling to room temperature, the reaction mixture was filtered. The filtrate was washed with H$_2$O and brine, dried over anhydrous Na$_2$SO$_4$ and concentrated. The residue was purified by silica gel column chromatography, eluted with PE/EA (2/1), to afford the title compound (89 mg, 85.2%).

Step 7: tert-butyl((3S,4S)-8-(3-(hydroxymethyl)-5-(((6aS,8S)-8-methoxy-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-yl)carbamate

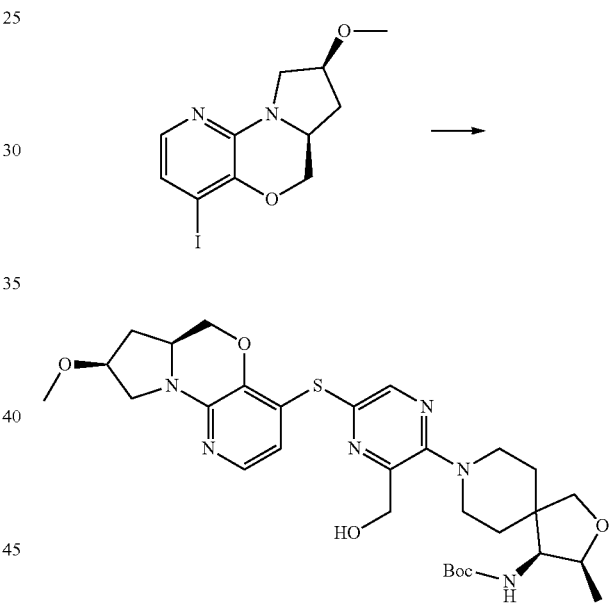

To a stirred mixture of (6aS,8S)-4-iodo-8-methoxy-6a,7,8,9-tetrahydro-6H-pyrido[3,2-b]pyrrolo[1,2-d][1,4]oxazine (30.00 mg, 0.090 mmol, 1.0 equiv) and tert-butyl N-[(3S,4S)-8-[3-(hydroxymethyl)-5-sulfanylpyrazin-2-yl]-3-methyl-2-oxa-8-azaspiro[4.5]decan-4-yl]carbamate (37.08 mg, 0.090 mmol, 1.0 equiv) in dioxane (0.30 mL) were added Pd$_2$(dba)$_3$ (24.81 mg, 0.027 mmol, 0.30 equiv), Xantphos (15.68 mg, 0.027 mmol, 0.30 equiv) and DIEA (35.02 mg, 0.271 mmol, 3.0 equiv) at room temperature under N$_2$ atmosphere. The resulting mixture was stirred for 1 h at 80° C. under N$_2$ atmosphere. After cooling to room temperature, the reaction mixture was concentrated under vacuum and the residue was purified by silica gel column chromatography, eluted with DCM/MeOH (10/1), to afford the title compound (25 mg, 45.6%).

Step 8: (3-((3S,4S)-4-amino-3-methyl-2-oxa-8-azaspiro[4.5]decan-8-yl)-6-(((6aS,8S)-8-methoxy-6a,7,8,9-tetrahydro-6H-pyrido[3,2-b]pyrrolo[1,2-d][1,4]oxazin-4-yl)thio)pyrazin-2-yl)methanol formate

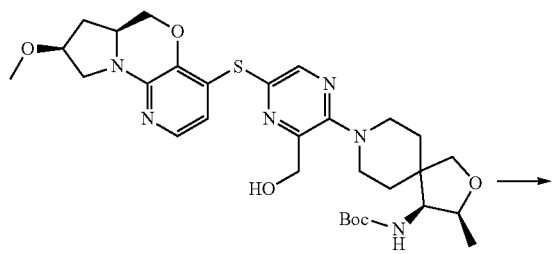

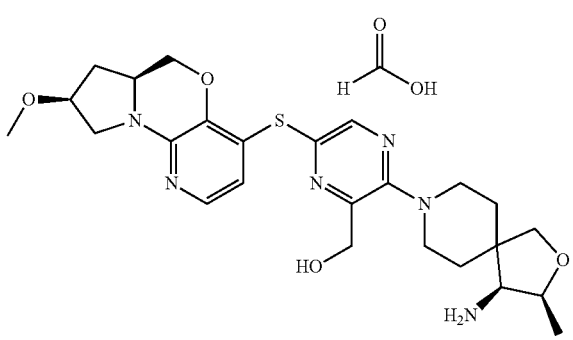

TFA (1.3 mL) was added to a solution of tert-butyl ((3S,4S)-8-(3-(hydroxymethyl)-5-(((6aS,8S)-8-methoxy-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-yl)carbamate (130.0 mg, 0.21 mmol, 1.0 equiv) in DCM (3.0 mL) at room temperature. After stirring at rt for 2 h, the reaction solution was concentrated and the residue was purified by Prep-HPLC to give product (19 mg, 16.1%). MS (ES, m/z): [M+1]$^+$=515.3.

Example 6

Synthesis of (3-((3S,4S)-4-amino-3-methyl-2-oxa-8-azaspiro[4.5]decan-8-yl)-6-(((6aS,8R)-8-methoxy-6a,7,8,9-tetrahydro-6H-pyrido[3,2-b]pyrrolo[1,2-d][1,4]oxazin-4-yl)thio)pyrazin-2-yl)methanol

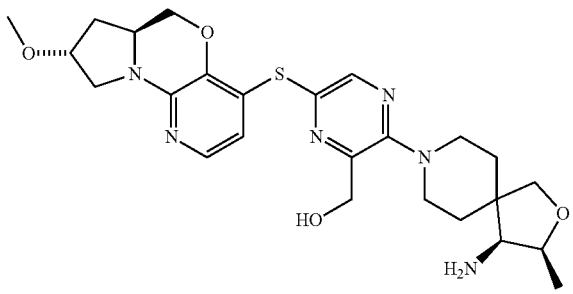 [SMILES: CO[C@@H]1C[C@H]2COc3c(Sc4cnc(N5CCC6(CC5)CO[C@@H](C)[C@H]6N)c(CO)n4)ccnc3N2C1]

Step 1: (6aS,8R)-4-iodo-8-methoxy-6a,7,8,9-tetrahydro-6H-pyrido[3,2-b]pyrrolo[1,2-d][1,4]oxazine

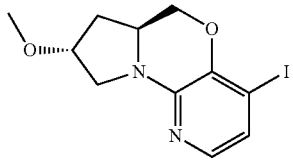 [SMILES: CO[C@@H]1C[C@H]2COc3c(I)ccnc3N2C1]

Compound (6aS,8R)-4-iodo-8-methoxy-6a,7,8,9-tetrahydro-6H-pyrido[3,2-b]pyrrolo[1,2-d][1,4]oxazine was synthesized by the method described in Example 5, Steps 1-6 using 1-(tert-butyl) 2-methyl (2S,4S)-4-hydroxypyrrolidine-1,2-dicarboxylate in Step 1.

Step 2: (3-((3S,4S)-4-amino-3-methyl-2-oxa-8-azaspiro[4.5]decan-8-yl)-6-(((6aS,8R)-8-methoxy-6a,7,8,9-tetrahydro-6H-pyrido[3,2-b]pyrrolo[1,2-d][1,4]oxazin-4-yl)thio)pyrazin-2-yl)methanol

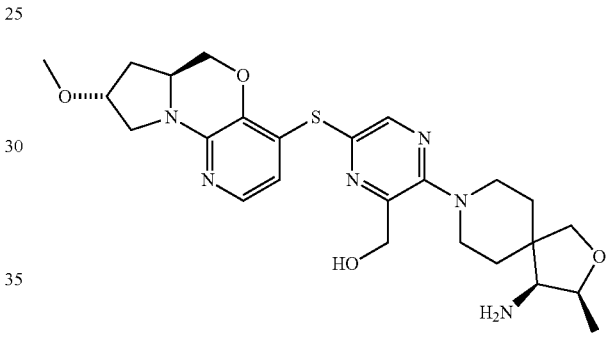

(3-((3S,4S)-4-Amino-3-methyl-2-oxa-8-azaspiro[4.5]decan-8-yl)-6-(((6aS,8R)-8-methoxy-6a,7,8,9-tetrahydro-6H-pyrido[3,2-b]pyrrolo[1,2-d][1,4]oxazin-4-yl)thio)pyrazin-2-yl)methanol was synthesized by proceeding analogously as described in Example 5, Steps 7-8. MS (ES, m/z): [M+1]$^+$= 515.3.

Example 7

Synthesis of (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-ol

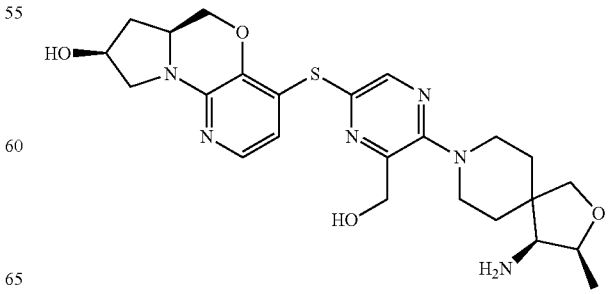

The title compound was synthesized by the method as described in Example 5, Steps 7-8 using (6aS,8S)-4-iodo-6a,7,8,9-tetrahydro-6H-pyrido[3,2-b]pyrrolo[1,2-d][1,4]oxazin-8-ol in Step 7. MS (ES, m/z): [M+1]⁺=501.3.

Example 8

Synthesis of (6aS,8R)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-ol

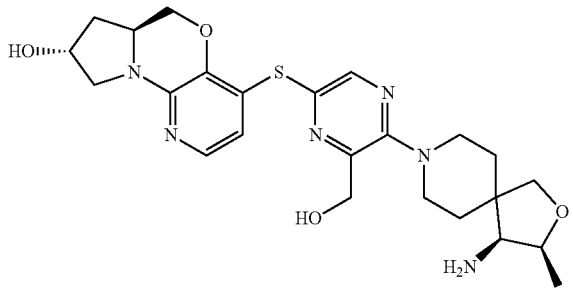 [SMILES: C[C@@H]1OCC2(CCN(c3ncc(Sc4ccnc5c4OC[C@@H]4C[C@@H](O)CN54)nc3CO)CC2)[C@@H]1N]

The title compound was synthesized by proceeding analogously as described in Example 7. MS (ES, m/z): [M+1]⁺=501.3.

Example 9

Synthesis of (3-((3S,4S)-4-amino-3-methyl-2-oxa-8-azaspiro[4.5]decan-8-yl)-6-(((6aR,8R)-8-methoxy-6a,7,8,9-tetrahydro-6H-pyrido[3,2-b]pyrrolo[1,2-d][1,4]oxazin-4-yl)thio)pyrazin-2-yl)methanol

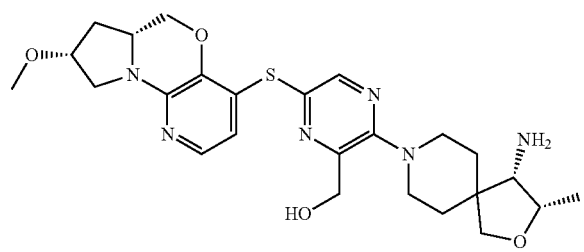

The title compound was synthesized by proceeding analogously as described in Example 5, Steps 2-8 using 1-tert-butyl 2-methyl (2R,4R)-4-methoxy-pyrrolidine-1,2-dicarboxylate in Step 2. MS (ES, m/z): [M+1]⁺=515.3.

Example 10

Synthesis of (3-((3S,4S)-4-amino-3-methyl-2-oxa-8-azaspiro[4.5]decan-8-yl)-6-(((6aR,8S)-8-methoxy-6a,7,8,9-tetrahydro-6H-pyrido[3,2-b]pyrrolo[1,2-d][1,4]oxazin-4-yl)thio)pyrazin-2-yl)methanol

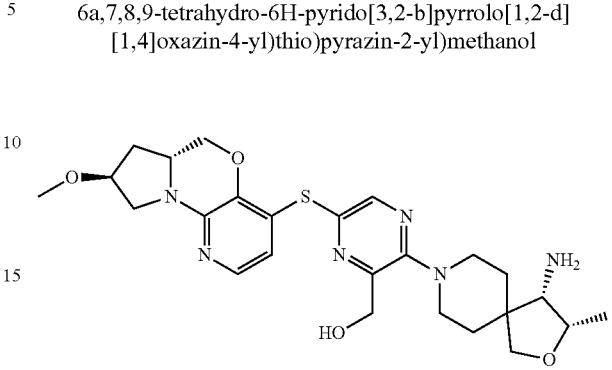

The title compound was synthesized by proceeding analogously as described in Example 5 Steps 2-8 using tert-butyl (2R,4S)-2-(hydroxymethyl)-4-methoxypyrrolidine-1-carboxylate in Step 2. MS (ES, m/z): [M+1]⁺=515.2.

Example 11

Synthesis of (3-((3S,4S)-4-amino-3-methyl-2-oxa-8-azaspiro[4.5]decan-8-yl)-6-(((6aS,8S)-8-(((S)-tetrahydrofuran-3-yl)oxy)-6a,7,8,9-tetrahydro-6H-pyrido[3,2-b]pyrrolo[1,2-d][1,4]oxazin-4-yl)thio)pyrazin-2-yl)methanol

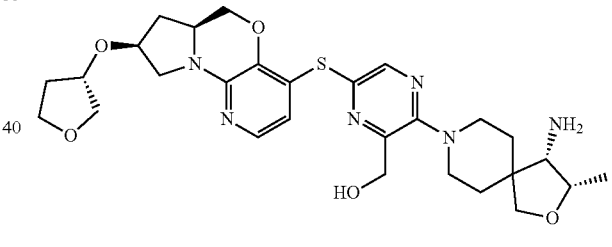

Step 1: (6aS,8S)-4-iodo-8-(((S)-tetrahydrofuran-3-yl)oxy)-6a,7,8,9-tetrahydro-6H-pyrido[3,2-b]pyrrolo[1,2-d][1,4]oxazine

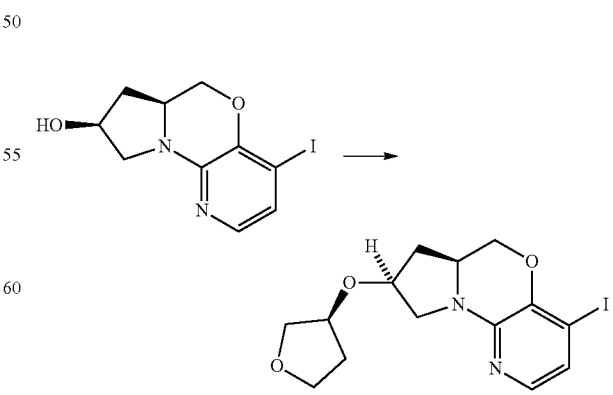

To a stirred solution of (3R)-oxolan-3-yl 4-methylbenzenesulfonate (457 mg, 1.886 mmol, 3 equiv) and (6aS,8S)-

4-iodo-6a,7,8,9-tetrahydro-6H-pyrido[3,2-b]pyrrolo[1,2-d][1,4]oxazin-8-ol (200 mg, 0.629 mmol, 1.00 equiv) in DMF (2.00 mL) was added NaH (88 mg, 2.200 mmol, 3.5 equiv, 60%) in portions at 0° C. under nitrogen atmosphere and the resulting mixture was stirred overnight at room temperature under nitrogen atmosphere. After cooling to 0° C., the reaction was quenched with water and the resulting mixture was diluted with water and extracted with EtOAc. The combined organic layers were washed with water and brine, dried over anhydrous Na₂SO₄ and concentrated. The residue was purified by Prep-TLC (EtOAc 100%) to afford the title compound (70 mg, 28.7%).

Step 2: (3-((3S,4S)-4-amino-3-methyl-2-oxa-8-azaspiro[4.5]decan-8-yl)-6-(((6aS,8S)-8-(((S)-tetrahydrofuran-3-yl)oxy)-6a,7,8,9-tetrahydro-6H-pyrido[3,2-b]pyrrolo[1,2-d][1,4]oxazin-4-yl)thio)pyrazin-2-yl)methanol

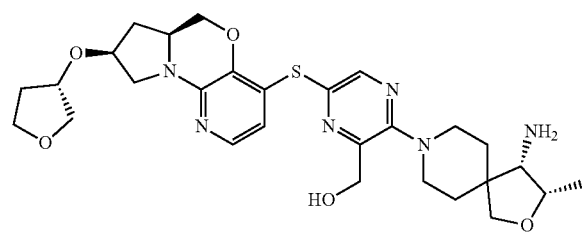 [SMILES: C[C@@H]1OCC2(CCN(c3ncc(Sc4ccnc5c4OC[C@@H]4C[C@H](O[C@H]6CCOC6)CN54)nc3CO)CC2)[C@@H]1N]

The title compound was synthesized from (6aS,8S)-4-iodo-8-(((S)-tetrahydrofuran-3-yl)oxy)-6a,7,8,9-tetrahydro-6H-pyrido[3,2-b]pyrrolo[1,2-d][1,4]oxazine by proceeding analogously as described in Example 5, Steps 7-8. MS (ES, m/z): [M+1]⁺=571.3.

Example 12

Synthesis of (3-((3S,4S)-4-amino-3-methyl-2-oxa-8-azaspiro[4.5]decan-8-yl)-6-(((6aS,8S)-8-(((R)-tetrahydrofuran-3-yl)oxy)-6a,7,8,9-tetrahydro-6H-pyrido[3,2-b]pyrrolo[1,2-d][1,4]oxazin-4-yl)thio)pyrazin-2-yl)methanol

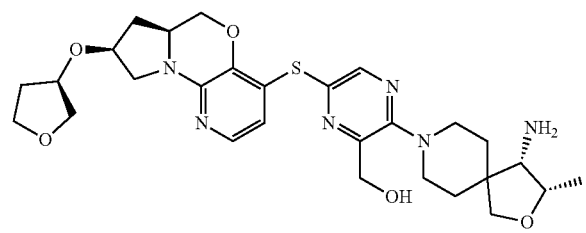 [SMILES: C[C@@H]1OCC2(CCN(c3ncc(Sc4ccnc5c4OC[C@@H]4C[C@H](O[C@@H]6CCOC6)CN54)nc3CO)CC2)[C@@H]1N]

The title compound was synthesized from (3S)-oxolan-3-yl 4-methylbenzenesulfonate by proceeding analogously as described in Example 11. MS (ES, m/z): [M+1]⁺=571.3.

Example 13

Synthesis of (3-((3S,4S)-4-amino-3-methyl-2-oxa-8-azaspiro[4.5]decan-8-yl)-6-(((6aS,8S)-8-(oxetan-3-yloxy)-6a,7,8,9-tetrahydro-6H-pyrido[3,2-b]pyrrolo[1,2-d][1,4]oxazin-4-yl)thio)pyrazin-2-yl)methanol

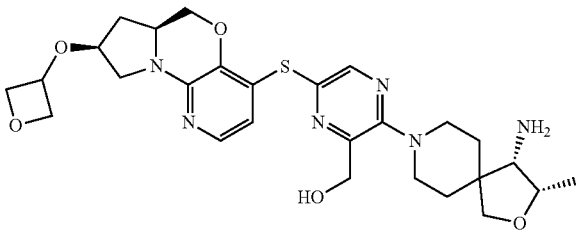 [SMILES: C[C@@H]1OCC2(CCN(c3ncc(Sc4ccnc5c4OC[C@@H]4C[C@H](OC6COC6)CN54)nc3CO)CC2)[C@@H]1N]

Step 1: (6aS,8R)-4-iodo-6a,7,8,9-tetrahydro-6H-pyrido[3,2-b]pyrrolo[1,2-d][1,4]oxazin-8-yl trifluoromethanesulfonate

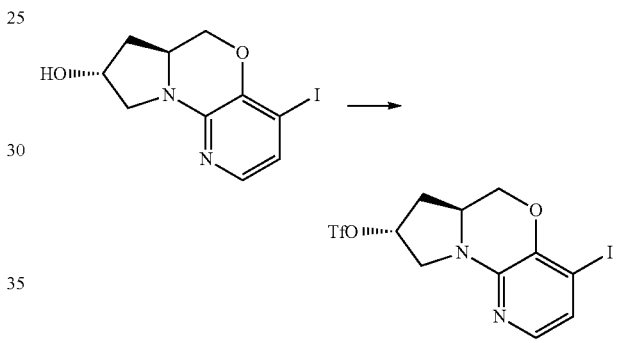

To a stirred solution of (6aS,8R)-4-iodo-6a,7,8,9-tetrahydro-6H-pyrido[3,2-b]-pyrrolo[1,2-d][1,4]oxazin-8-ol (400 mg, 1.257 mmol, 1.00 equiv) and DIEA (244 mg, 1.886 mmol, 1.50 equiv) in DCM (4.00 mL) was added Tf₂O (426 mg, 1.509 mmol, 1.20 equiv) dropwise at 5° C. The reaction solution was stirred at 5° C. for 30 min and then concentrated under vacuum. The residue was purified by silica gel column chromatography, eluted with EtOAc/PE (0-40%) to afford the title compound (300 mg, 53.0%) as a white solid.

Step 2: (6aS,8S)-4-iodo-8-(oxetan-3-yloxy)-6a,7,8,9-tetrahydro-6H-pyrido[3,2-b]pyrrolo[1,2-d][1,4]oxazine

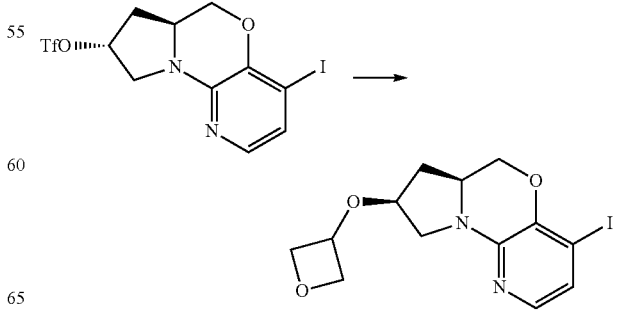

To a stirred solution of oxetan-3-ol (99 mg, 1.336 mmol, 2.00 equiv) in DMF (3.00 mL) was added 60% NaH (67 mg, 1.67 mmol, 2.50 equiv) at 5° C. The mixture was stirred at this temperature for 1 h. (6aS,8R)-4-Iodo-6a,7,8,9-tetrahydro-6H-pyrido[3,2-b]pyrrolo[1,2-d][1,4]oxazin-8-yl trifluoromethanesulfonate (300.00 mg, 0.666 mmol, 1.00 equiv) was added at 20° C. The resulting mixture was allowed to warm to 50° C. and stirred for 10 min. The reaction was quenched with water at 5° C. and the resulting mixture was extracted with EtOAc. The combined organic layers were washed with water and brine, dried over anhydrous $Na_2SO_4$. After filtration, the filtrate was concentrated under reduced pressure. The residue was purified by silica gel column chromatography, eluted with EtOAc/PE (0-100%) to afford the title compound (20 mg, 8.0%) as a white solid.

Step 3: (3-((3S,4S)-4-amino-3-methyl-2-oxa-8-azaspiro[4.5]decan-8-yl)-6-((((6aS,8S)-8-(oxetan-3-yloxy)-6a,7,8,9-tetrahydro-6H-pyrido[3,2-b]pyrrolo[1,2-d][1,4]oxazin-4-yl)thio)pyrazin-2-yl)methanol

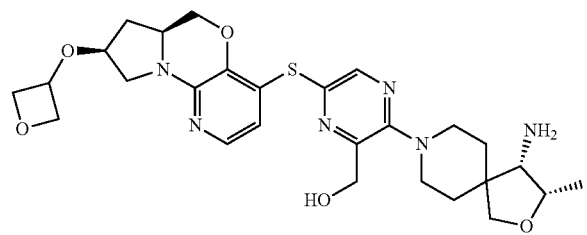 [SMILES: C[C@@H]1OCC2(CCN(c3ncc(Sc4ccnc5c4OC[C@@H]4C[C@H](OC6COC6)CN54)nc3CO)CC2)[C@@H]1N]

The title compound was synthesized by proceeding analogously as described in Example 5 Steps 7-8 using (6aS,8S)-4-iodo-8-(oxetan-3-yloxy)-6a,7,8,9-tetrahydro-6H-pyrido[3,2-b]pyrrolo[1,2-d][1,4]oxazine in Step 7. MS (ES, m/z): $[M+1]^+$=557.3.

Example 14

Synthesis of (3-((3S,4S)-4-amino-3-methyl-2-oxa-8-azaspiro[4.5]decan-8-yl)-6-((((6aS,8S)-8-(methoxymethoxy)-6a,7,8,9-tetrahydro-6H-pyrido[3,2-b]pyrrolo[1,2-d][1,4]oxazin-4-yl)thio)pyrazin-2-yl)methanol

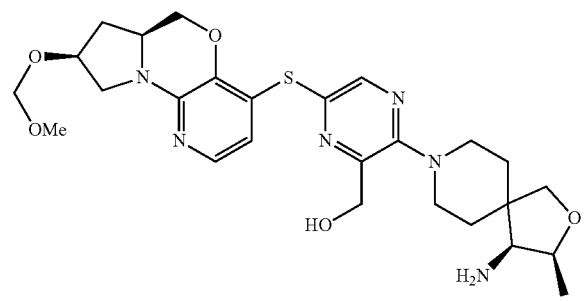 [SMILES: COCO[C@H]1C[C@H]2COc3c(Sc4cnc(N5CCC6(CC5)CO[C@@H](C)[C@H]6N)c(CO)n4)ccnc3N2C1]

Step 1: (6aS,8S)-4-iodo-8-(methoxymethoxy)-6a,7,8,9-tetrahydro-6H-pyrido[3,2-b]pyrrolo[1,2-d][1,4]oxazine

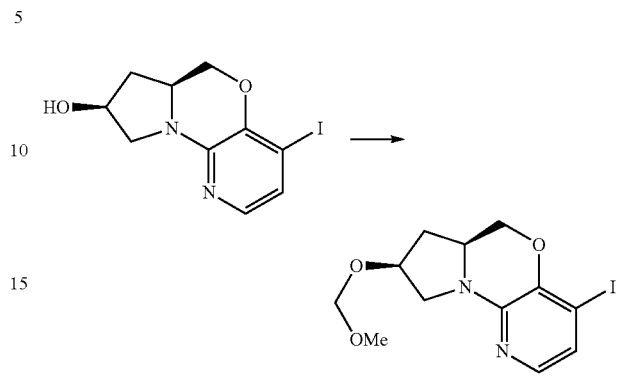

To a stirred solution of (6aS,8S)-4-iodo-6a,7,8,9-tetrahydro-6H-pyrido[3,2-b]pyrrolo[1,2-d]-[1,4]oxazin-8-ol (60 mg, 0.189 mmol, 1.00 equiv) and DIEA (49 mg, 0.377 mmol, 2.00 equiv) in DME (1.00 mL) was added bromo(methoxy)methane (35.35 mg, 0.283 mmol, 1.50 equiv) dropwise at room temperature under $N_2$ atmosphere. The resulting mixture was stirred for 4 h at room temperature under $N_2$ atmosphere and then quenched with $H_2O$. The resulting mixture was extracted with EA and the combined organic layers were dried over anhydrous $Na_2SO_4$. After filtration, the filtrate was concentrated under reduced pressure. The residue was purified by silica gel column chromatography, eluted with PE/EA (1/1) to afford the title compound (50 mg, 73.2%) as a light yellow solid.

Step 2: (3-((3S,4S)-4-amino-3-methyl-2-oxa-8-azaspiro[4.5]decan-8-yl)-6-((((6aS,8S)-8-(methoxymethoxy)-6a,7,8,9-tetrahydro-6H-pyrido[3,2-b]pyrrolo[1,2-d][1,4]oxazin-4-yl)thio)pyrazin-2-yl)methanol

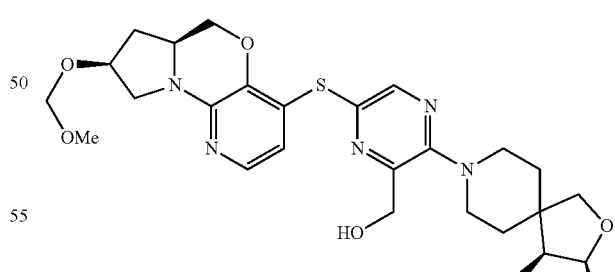

The title compound was synthesized by proceeding analogously as described in Example 5 Steps 7-8 using tert-butyl ((3S,4S)-8-(3-(hydroxymethyl)-5-((((6aS,8S)-8-(methoxymethoxy)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-yl)carbamate in Step 7. MS (ES, m/z): $[M+1]^+$=545.2.

Example 15

Synthesis of (3-((3S,4S)-4-amino-3-methyl-2-oxa-8-azaspiro[4.5]decan-8-yl)-6-(((6aS,8S)-8-(2-methoxyethoxy)-6a,7,8,9-tetrahydro-6H-pyrido[3,2-b]pyrrolo[1,2-d][1,4]oxazin-4-yl)thio)pyrazin-2-yl)methanol

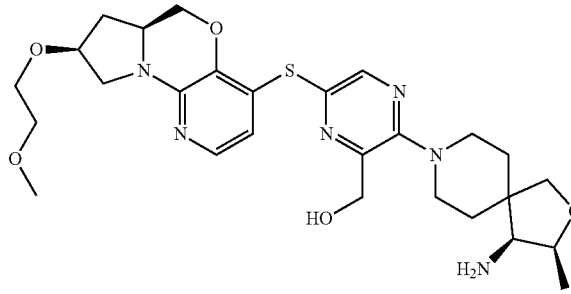

The title compound was synthesized by proceeding analogously as described in Example 14 using 2-bromoethyl methyl ether in Step 1. MS (ES, m/z): [M+1]$^+$=559.3.

Example 16

Synthesis of (3-((3S,4S)-4-amino-3-methyl-2-oxa-8-azaspiro[4.5]decan-8-yl)-6-(((6aS,8S)-8-(cyclopropylmethoxy)-6a,7,8,9-tetrahydro-6H-pyrido[3,2-b]pyrrolo[1,2-d][1,4]oxazin-4-yl)thio)pyrazin-2-yl)methanol

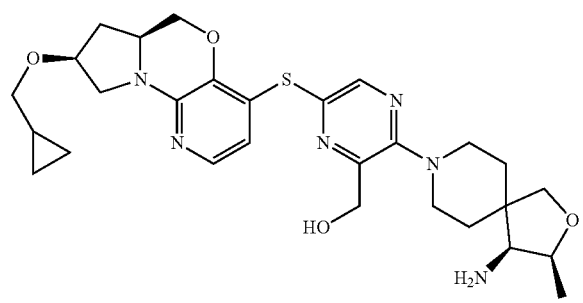 [SMILES: C[C@@H]1OCC2(CCN(c3ncc(Sc4ccnc5c4OC[C@@H]4C[C@H](OCC6CC6)CN54)nc3CO)CC2)[C@@H]1N]

The title compound was synthesized by proceeding analogously as described in Example 14 using (bromomethyl)cyclopropane r in Step 1. MS (ES, m/z): [M+1]$^+$=555.4.

Example 17

Synthesis of (3-((3S,4S)-4-amino-3-methyl-2-oxa-8-azaspiro[4.5]decan-8-yl)-6-(((S)-6a',7'-dihydro-6'H,9'H-spiro[cyclopropane-1,8'-pyrido[3,2-b]pyrrolo[1,2-d][1,4]oxazin]-4'-yl)thio)pyrazin-2-yl)methanol

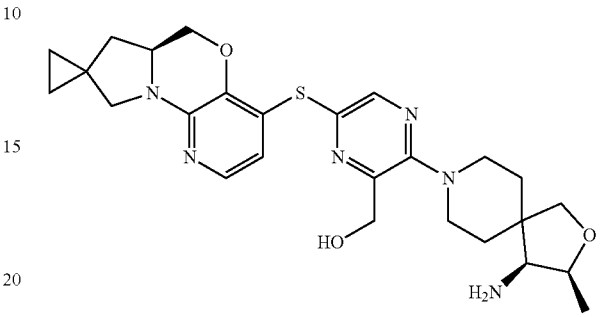

Step 1: (S)-4'-iodo-6a',7'-dihydro-6'H,9'H-spiro[cyclopropane-1,8'-pyrido[3,2-b]pyrrolo[1,2-d]-[1,4]oxazine]

Compound (S)-4'-iodo-6a',7'-dihydro-6'H,9'H-spiro[cyclopropane-1,8'-pyrido[3,2-b]pyrrolo[1,2-d][1,4]oxazine] was synthesized by proceeding analogously as described in Example 1, Steps 1-4 using 5-tert-butyl 6-methyl (6S)-5-azaspiro[2.4]heptane-5,6-dicarboxylate in Step 1.

Step 2: (3-((3S,4S)-4-amino-3-methyl-2-oxa-8-azaspiro[4.5]decan-8-yl)-6-(((S)-6a',7'-dihydro-6'H,9'H-spiro[cyclopropane-1,8'-pyrido[3,2-b]pyrrolo[1,2-d][1,4]oxazin]-4'-yl)thio)pyrazin-2-yl)methanol

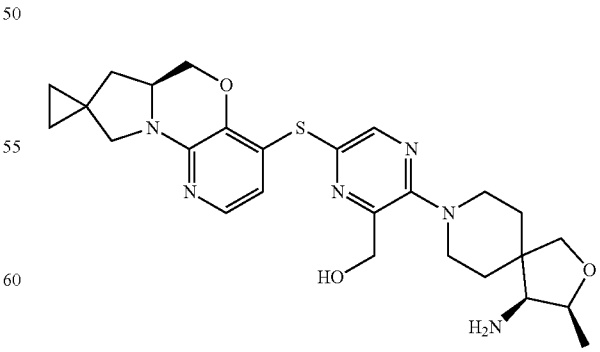

The title compound was synthesized by proceeding analogously as described in Example 1, Steps 5-8. MS (ES, m/z): [M+1]$^+$=511.3.

Example 18 and 19

Synthesis of (6aS,8S)-4-((5-((3S,4S)-4-amino-3-methyl-2-oxa-8-azaspiro[4.5]decan-8-yl)-6-(hydroxymethyl)pyrazin-2-yl)thio)-8-methyl-6a,7,8,9-tetrahydro-6H-pyrido[3,2-b]-pyrrolo[1,2-d][1,4]oxazin-8-ol and (6aS,8R)-4-((5-((3S,4S)-4-amino-3-methyl-2-oxa-8-azaspiro[4.5]decan-8-yl)-6-(hydroxymethyl)pyrazin-2-yl)thio)-8-methyl-6a,7,8,9-tetrahydro-6H-pyrido[3,2-b]pyrrolo[1,2-d][1,4]oxazin-8-ol

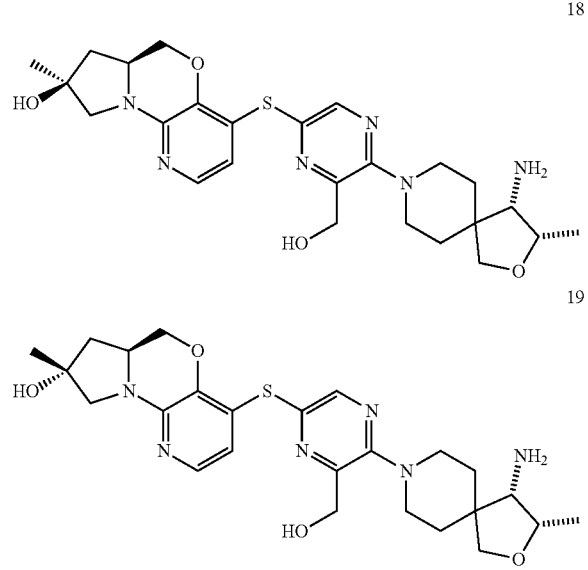

stereochemistry of the tertiary alcohol arbitrarily assigned in 18 and 19

Step 1: (S)-4-iodo-6a,7-dihydro-6H-pyrido[3,2-b]pyrrolo[1,2-d][1,4]oxazin-8(9H)-one

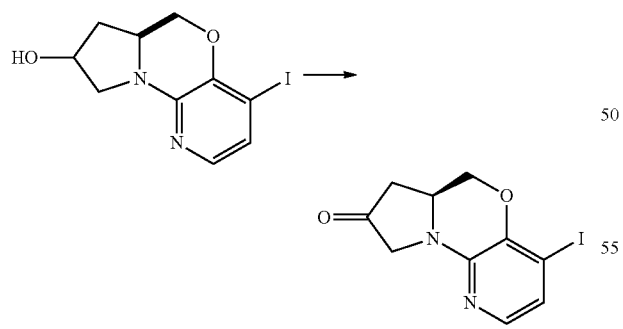

To a stirred solution of oxalyl chloride (209.47 mg, 1.650 mmol, 1.5 equiv) in DCM (1.4 mL) was added DMSO (257.89 mg, 3.301 mmol, 3.0 equiv) in DCM (0.2 mL) dropwise at −78° C. under nitrogen atmosphere and stirred at this temperature for 30 min. To the above solution was added a solution of (6aS)-4-iodo-6a,7,8,9-tetrahydro-6H-pyrido[3,2-b]pyrrolo[1,2-d][1,4]oxazin-8-ol (350.00 mg, 1.100 mmol, 1.00 equiv) in DCM (2.0 mL) at −78° C. After stirring at −78° C. for 30 min, DIEA (853.1 mg, 6.6 mmol, 6.0 equiv) was added dropwise at −78° C. The resulting mixture was stirred for additional 30 min at −78° C., then warmed to room temperature over 30 min. After stirring at rt for 10 min, the reaction mixture was cooled to 5° C. and quenched by addition of sat. NH₄Cl aq. solution at 5° C. The resulting mixture was extracted with EtOAc and the combined organic layers were washed with brine, dried over anhydrous Na₂SO₄ and concentrated to afford the title compound (250 mg, 71.8%).

Step 2: 2-ethylhexyl 3-(((S)-8-oxo-6a,7,8,9-tetrahydro-6H-pyrido[3,2-b]pyrrolo[1,2-d][1,4]-oxazin-4-yl)thio)propanoate

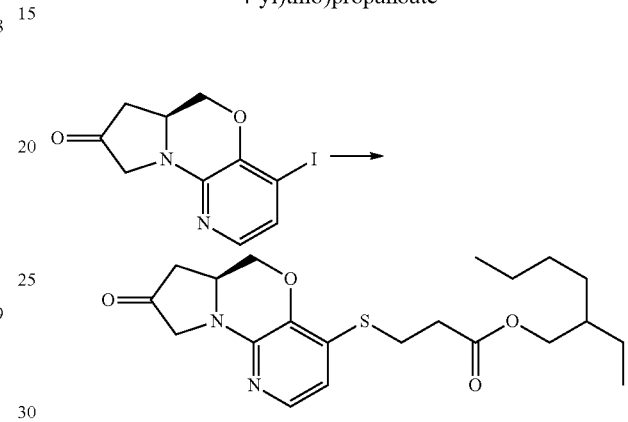

A solution of (S)-4-iodo-6a,7-dihydro-6H-pyrido[3,2-b]pyrrolo[1,2-d][1,4]oxazin-8(9H)-one (220.00 mg, 0.696 mmol, 1.00 equiv), 2-ethylhexyl 3-sulfanylpropanoate (182.37 mg, 0.835 mmol, 1.20 equiv), Pd₂(dba)₃ (63.73 mg, 0.070 mmol, 0.10 equiv), XantPhos (40.27 mg, 0.070 mmol, 0.10 equiv) and DIEA (269.85 mg, 2.088 mmol, 3.00 equiv) in dioxane (4.40 mL) was stirred for 1 h at 100° C. under nitrogen atmosphere. The resulting mixture was concentrated under vacuum and the residue was purified by silica gel column chromatography, eluted with EtOAc/PE (0-50%), to afford the title compound (280 mg, 99%).

Step 3: 2-ethylhexyl 3-(((6aS)-8-hydroxy-8-methyl-6a,7,8,9-tetrahydro-6H-pyrido[3,2-b]-pyrrolo[1,2-d][1,4]oxazin-4-yl)thio)propanoate

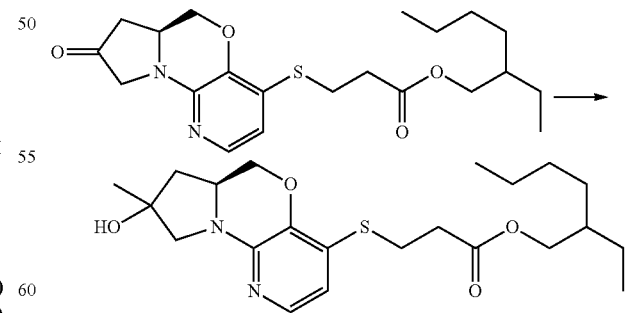

To a stirred solution of 2-ethylhexyl 3-(((S)-8-oxo-6a,7,8,9-tetrahydro-6H-pyrido[3,2-b]pyrrolo[1,2-d][1,4]oxazin-4-yl)thio)propanoate (160 mg, 0.394 mmol, 1.00 equiv) in THF (1.60 mL) was added 2.0 M bromo(methyl)magnesium (0.24 mL, 0.48 mmol, 1.22 equiv) dropwise at 5° C. under nitrogen atmosphere and the resulting mixture was stirred at 5° C. for 1 h. The reaction was quenched by addition of sat. NH₄Cl aq. solution at 5° C. and extracted with EtOAc. The combined organic layers were washed with brine, dried over anhydrous Na₂SO₄ and concentrated. The residue was purified by silica gel column chromatography, eluted with EtOAc/PE (0-100%), to afford the title compound (90 mg, 54.1%).

Step 4: (6aS,8S)-4-((5-((3S,4S)-4-amino-3-methyl-2-oxa-8-azaspiro[4.5]decan-8-yl)-6-(hydroxymethyl)pyrazin-2-yl)thio)-8-methyl-6a,7,8,9-tetrahydro-6H-pyrido[3,2-b]-pyrrolo[1,2-d][1,4]oxazin-8-ol and (6aS,8R)-4-((5-((3S,4S)-4-amino-3-methyl-2-oxa-8-azaspiro[4.5]decan-8-yl)-6-(hydroxymethyl)pyrazin-2-yl)thio)-8-methyl-6a,7,8,9-tetrahydro-6H-pyrido[3,2-b]pyrrolo[1,2-d][1,4]oxazin-8-ol

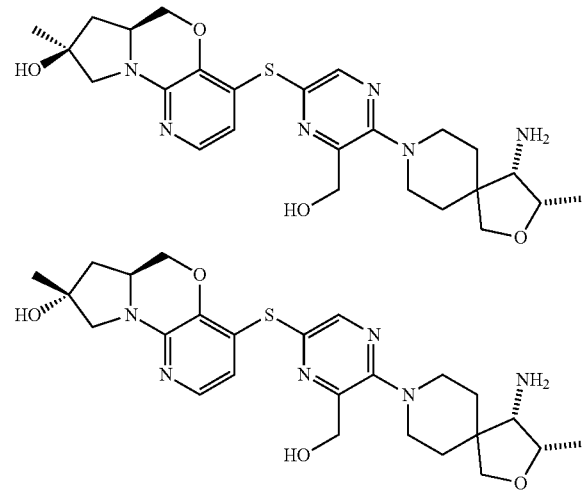

The title compounds were synthesized from 2-ethylhexyl 3-(((6aS)-8-hydroxy-8-methyl-6a,7,8,9-tetrahydro-6H-pyrido[3,2-b]pyrrolo[1,2-d][1,4]oxazin-4-yl)thio)propanoate by proceeding analogously as described in Example 1, Steps 6-8. MS (ES, m/z): [M+1]⁺=515.3.

Example 20

Synthesis of (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazine-8-carbonitrile

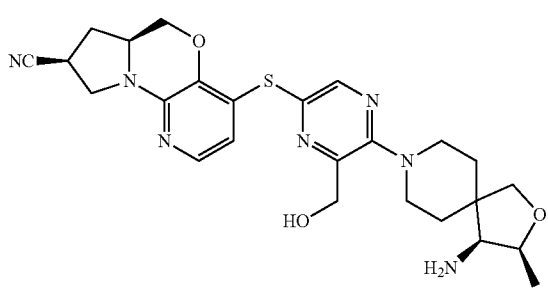 [SMILES: C[C@@H]1OCC2(CCN(c3ncc(Sc4ccnc5c4OC[C@@H]4C[C@H](C#N)CN54)nc3CO)CC2)[C@@H]1N]

Step 1: (6aS,8R)-4-iodo-6a,7,8,9-tetrahydro-6H-pyrido[3,2-b]pyrrolo[1,2-d][1,4]oxazin-8-yl methanesulfonate

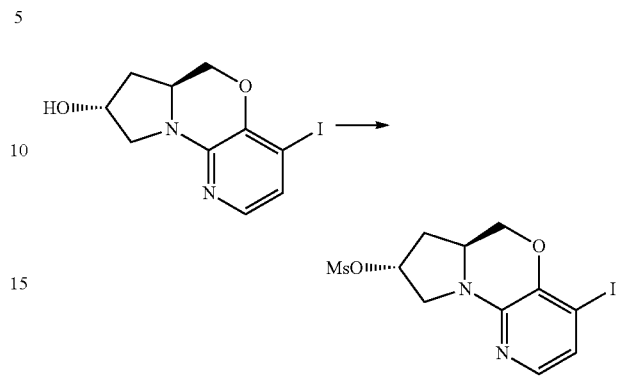

To a stirred solution of (6aS,8R)-4-iodo-6a,7,8,9-tetrahydro-6H-pyrido[3,2-b]pyrrolo[1,2-d][1,4]oxazin-8-ol (400.00 mg, 1.257 mmol, 1.00 equiv) in DCM (6.00 mL) were added TEA (190.86 mg, 1.886 mmol, 1.50 equiv) and MsCl (172.85 mg, 1.509 mmol, 1.20 equiv) at room temperature. After stirring for 16 h at room temperature, the reaction mixture was cooled to 0° C. and quenched with water. The resulting mixture was extracted with EtOAc and the combined organic layers were washed with brine, dried over anhydrous Na₂SO₄ and concentrated. The residue was purified by silica gel column chromatography, eluted with EtOAc/PE (0-50%) to afford the title compound (450 mg, 90.3%).

Step 2: (6aS,8S)-4-iodo-6a,7,8,9-tetrahydro-6H-pyrido[3,2-b]pyrrolo[1,2-d][1,4]oxazine-8-carbonitrile

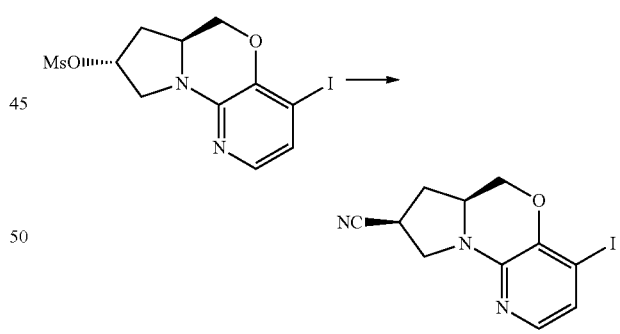

To a stirred solution of (6aS,8R)-4-iodo-6a,7,8,9-tetrahydro-6H-pyrido[3,2-b]pyrrolo[1,2-d][1,4]oxazin-8-yl methanesulfonate (300.00 mg, 0.757 mmol, 1.00 equiv) in DMF (5.00 mL) was added NaCN (55.66 mg, 1.136 mmol, 1.50 equiv) at room temperature. After stirring at 75° C. for 16 h, the reaction mixture was cooled at room temperature and quenched with water. The mixture was then extracted with EtOAc and the combined organic layers were washed with brine, dried over anhydrous Na₂SO₄ and concentrated. The residue was purified by silica gel column chromatography, eluted with EtOAc/PE (0-50%), to afford the title compound (140 mg, 56.5%).

Step 3: (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]-oxazine-8-carbonitrile

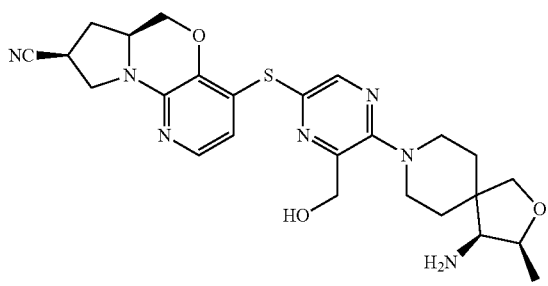 [SMILES: C[C@@H]1OCC2(CCN(c3ncc(Sc4ccnc5c4OC[C@@H]4C[C@H](C#N)CN54)nc3CO)CC2)[C@@H]1N]

The compound was synthesized from (6aS,8S)-4-iodo-6a,7,8,9-tetrahydro-6H-pyrido[3,2-b]pyrrolo[1,2-d][1,4]oxazine-8-carbonitrile by proceeding analogously as described in Example 5, Steps 7-8. [M+1]$^+$=510.2.

Example 21

Synthesis of (3-((3S,4S)-4-amino-3-methyl-2-oxa-8-azaspiro[4.5]decan-8-yl)-6-((((6aS,8S)-8-(methylsulfonyl)-6a,7,8,9-tetrahydro-6H-pyrido[3,2-b]pyrrolo[1,2-d][1,4]oxazin-4-yl)thio)pyrazin-2-yl)methanol

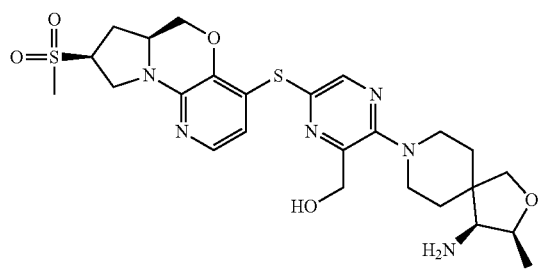 [SMILES: C[C@@H]1OCC2(CCN(c3ncc(Sc4ccnc5c4OC[C@@H]4C[C@H](S(C)(=O)=O)CN54)nc3CO)CC2)[C@@H]1N]

Step 1: 1-tert-butyl 2-methyl (2S,4R)-4-(methanesulfonyloxy)pyrrolidine-1,2-dicarboxylate

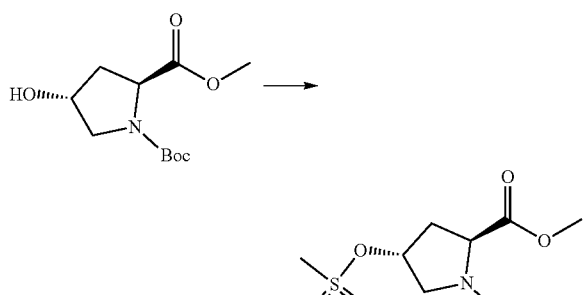

To a stirred solution of 1-tert-butyl 2-methyl (2S,4R)-4-hydroxypyrrolidine-1,2-dicarboxylate (9 g, 36.7 mmol, 1.0 equiv) and TEA (7.43 g, 73.4 mmol, 2.0 equiv) in DCM (100 mL) was added MsCl (5 g, 43.6 mmol, 1.2 equiv) dropwise at 0° C. and the resulting mixture was stirred for 1 h at 0° C. The reaction was quenched with water and extracted with DCM. The combined organic layers were washed with water and brine, dried over anhydrous Na$_2$SO$_4$ and concentrated. The residue was purified by silica gel column chromatography, eluted with EtOAc/PE (0-50%), to afford the title compound (10.5 g, 88.5%).

Step 2: 1-(tert-butyl) 2-methyl (2R,4R)-4-methoxypyrrolidine-1,2-dicarboxylate

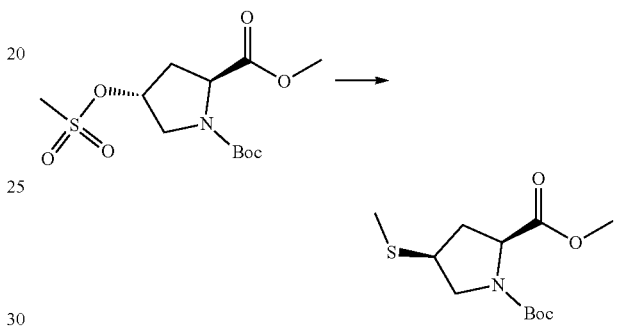

A solution of 1-tert-butyl 2-methyl (2S,4R)-4-(methanesulfonyloxy)pyrrolidine-1,2-dicarboxylate (4.30 g, 13.298 mmol, 1.00 equiv) in dry DMF (20.00 mL) was added NaSCH$_3$ (1.07 g, 15.27 mmol, 1.07 equiv) at 30° C. After stirring overnight at rt, the reaction mixture was poured into water and extracted with EtOAc. The combined organic layers were washed with water and brine, dried over Na$_2$SO$_4$ and concentrated. The residue was purified by silica gel column chromatography, eluted with PE/EA (1/1) to afford the title compound (4 g, 109.2%).

Step 3: tert-butyl (2S,4S)-2-(hydroxymethyl)-4-(methylthio)pyrrolidine-1-carboxylate

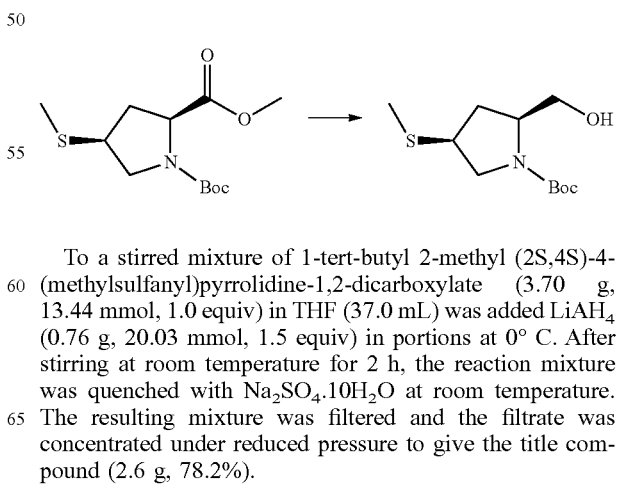

To a stirred mixture of 1-tert-butyl 2-methyl (2S,4S)-4-(methylsulfanyl)pyrrolidine-1,2-dicarboxylate (3.70 g, 13.44 mmol, 1.0 equiv) in THF (37.0 mL) was added LiAH$_4$ (0.76 g, 20.03 mmol, 1.5 equiv) in portions at 0° C. After stirring at room temperature for 2 h, the reaction mixture was quenched with Na$_2$SO$_4$.10H$_2$O at room temperature. The resulting mixture was filtered and the filtrate was concentrated under reduced pressure to give the title compound (2.6 g, 78.2%).

Step 4: tert-butyl (2S,4S)-2-(hydroxymethyl)-4-(methylsulfonyl)pyrrolidine-1-carboxylate

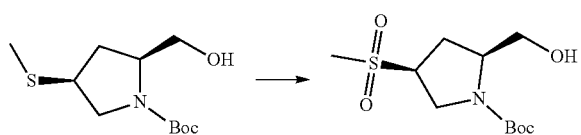 [SMILES: CS[C@H]1C[C@@H](CO)N(C(=O)OC(C)(C)C)C1 ; CC(C)(C)OC(=O)N1C[C@@H](S(C)(=O)=O)C[C@H]1CO]

To a stirred solution of tert-butyl (2S,4S)-2-(hydroxymethyl)-4-(methylsulfanyl)-pyrrolidine-1-carboxylate (3.70 g, 14.959 mmol, 1.00 equiv) in DCM (40 mL) at room temperature was added m-CPBA (77%12.91 g, 57.60 mmol, 3.85 equiv) in portions over 5 h. The resulting mixture was diluted with DCM and washed with sat. aq. NaHCO₃ solution and brine, dried over anhydrous Na₂SO₄ and concentrated. The residue was purified by silica gel column chromatography, eluted with DCM/MeOH (20/1), to afford the title compound (1 g, 23.9%).

Step 5: (3-(((3S,4S)-4-amino-3-methyl-2-oxa-8-azaspiro[4.5]decan-8-yl)-6-(((6aS,8S)-8-(methylsulfonyl)-6a,7,8,9-tetrahydro-6H-pyrido[3,2-b]pyrrolo[1,2-d][1,4]oxazin-4-yl)thio)pyrazin-2-yl)methanol

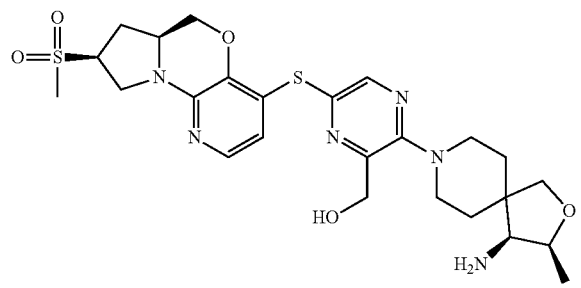 [SMILES: C[C@@H]1OCC2(CCN(c3ncc(Sc4ccnc5c4OC[C@@H]4C[C@H](S(C)(=O)=O)CN54)nc3CO)CC2)[C@@H]1N]

The title compound was synthesized tert-butyl (2S,4S)-2-(hydroxymethyl)-4-(methylsulfonyl)pyrrolidine-1-carboxylate by the method described in Example 1, Steps 2-8. MS (ES, m/z): [M+1]⁺=563.3.

Example 22

Synthesis of (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d]-[1,4]oxazin-8-ylcarbamate

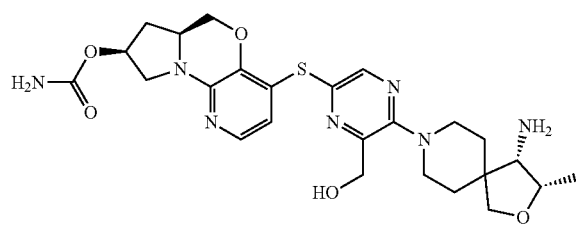 [SMILES: C[C@@H]1OCC2(CCN(c3ncc(Sc4ccnc5c4OC[C@@H]4C[C@H](OC(N)=O)CN54)nc3CO)CC2)[C@@H]1N]

Step 1: (6aS,8S)-4-iodo-6a,7,8,9-tetrahydro-6H-pyrido[3,2-b]pyrrolo[1,2-d][1,4]oxazin-8-yl carbamate

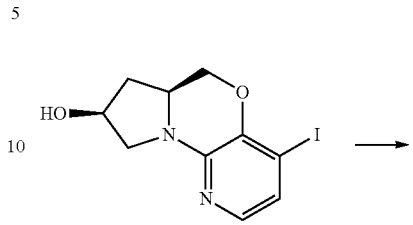

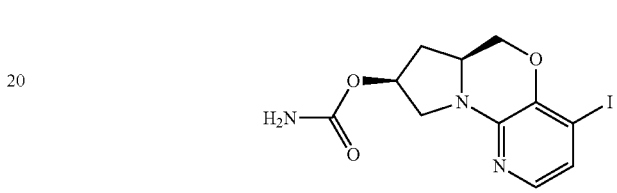

To a stirred solution of (6aS,8S)-4-iodo-6a,7,8,9-tetrahydro-6H-pyrido[3,2-b]pyrrolo[1,2-d][1,4]oxazin-8-ol (150.0 mg, 0.472 mmol, 1.0 equiv) in DCM (1.80 mL) was added trichloroethanecarbonyl isocyanate (222.08 mg, 1.179 mmol, 2.5 equiv) dropwise at 5° C. and the resulting mixture was stirred at this temperature for about 30 min. To the above solution, K₂CO3 (129.88 mg, 0.940 mmol, 2.0 equiv) and MeOH (1.80 mL) were added at room temperature and the resulting mixture was stirred for additional 6 h at room temperature. The mixture was diluted with water and extracted with EtOAc. The combined organic layers were washed with brine, dried over anhydrous Na₂SO₄ and concentrated. The residue was purified by silica gel column chromatography, eluted with EtOAc/PE (0-100%) to afford the title compound (100 mg, 58.7%).

Step 2: (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]-oxazin-8-yl carbamate

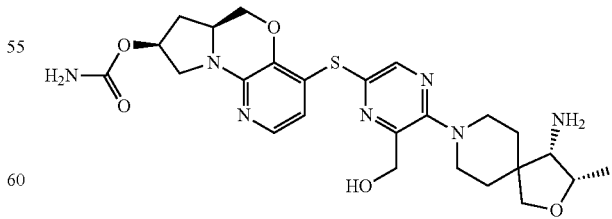

The title compound was synthesized from tert-butyl (2S,4S)-2-(hydroxymethyl)-4-(methylsulfonyl)pyrrolidine-1-carboxylate by proceeding analogously as described in Example 5, Steps 7-8. MS (ES, m/z): [M+1]⁺=544.3.

Example 23

Synthesis of (6aS,8R)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-ylcarbamate

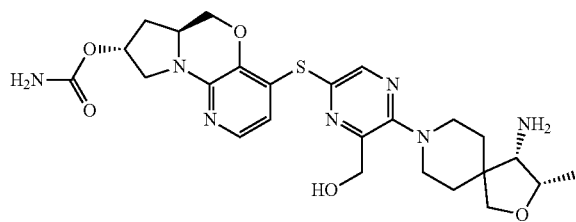 [SMILES: C[C@@H]1OCC2(CCN(c3ncc(Sc4ccnc5c4OC[C@@H]4C[C@@H](OC(N)=O)CN54)nc3CO)CC2)[C@@H]1N]

The title compound was synthesized from ((6aS,8R)-4-iodo-6a,7,8,9-tetrahydro-6H-pyrido[3,2-b]pyrrolo[1,2-d][1,4]oxazin-8-ol by as described in example 22. MS (ES, m/z): [M+1]$^+$=544.2.

Example 24

Synthesis of (6-(((6aS,8S)-8-(1H-pyrazol-1-yl)-6a,7,8,9-tetrahydro-6H-pyrido[3,2-b]-pyrrolo[1,2-d][1,4]oxazin-4-yl)thio)-3-((3S,4S)-4-amino-3-methyl-2-oxa-8-azaspiro[4.5]decan-8-yl)pyrazin-2-yl)methanol

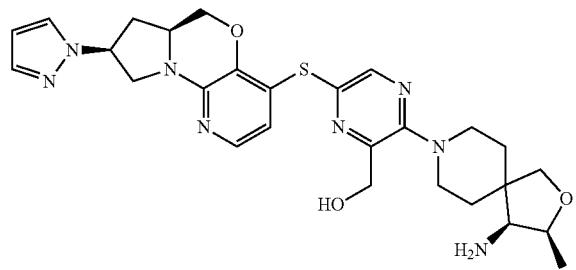 [SMILES: C[C@@H]1OCC2(CCN(c3ncc(Sc4ccnc5c4OC[C@@H]4C[C@H](n6cccn6)CN54)nc3CO)CC2)[C@@H]1N]

Step 1: (6aS,8S)-4-iodo-8-(1H-pyrazol-1-yl)-6a,7,8,9-tetrahydro-6H-pyrido[3,2-b]-pyrrolo[1,2-d][1,4]oxazine

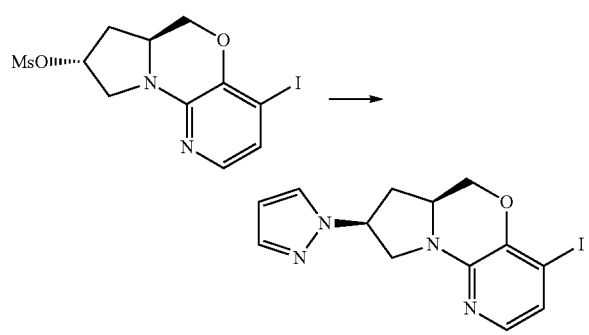

To a stirred solution of pyrazole (17.18 mg, 0.252 mmol, 1.0 equiv) in DMF (0.75 mL) was added NaH (20.19 mg, 0.505 mmol, 2.0 equiv, 60%) in portions at 5° C. and the resulting mixture was stirred at 5° C. for 1 h. To the above mixture was added (6aS,8R)-4-iodo-6a,7,8,9-tetrahydro-6H-pyrido[3,2-b]pyrrolo[1,2-d][1,4]oxazin-8-yl methanesulfonate (100.00 mg, 0.252 mmol, 1.00 equiv) at room temperature and the resulting mixture was stirred at 50° C. After cooling to 0° C., the reaction was quenched by addition of water and then extracted with EtOAc. The combined organic layers were washed with water, brine, dried over anhydrous Na$_2$SO$_4$ and concentrated. The residue was purified by silica gel column chromatography, eluted with EtOAc/PE (0-100%), to afford the title compound (60 mg, 64.5%).

Step 2: (6-(((6aS,8S)-8-(1H-pyrazol-1-yl)-6a,7,8,9-tetrahydro-6H-pyrido[3,2-b]pyrrolo[1,2-d][1,4]oxazin-4-yl)thio)-3-((3S,4S)-4-amino-3-methyl-2-oxa-8-azaspiro[4.5]decan-8-yl)pyrazin-2-yl)methanol

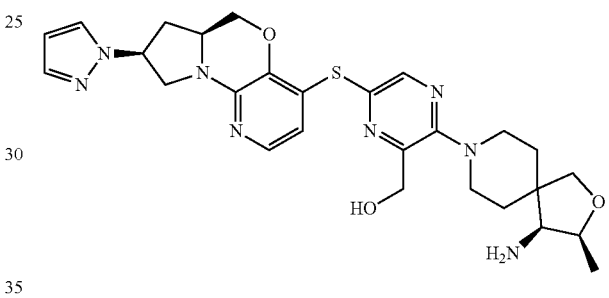

The title compound was synthesized from (6aS,8S)-4-iodo-8-(1H-pyrazol-1-yl)-6a,7,8,9-tetrahydro-6H-pyrido[3,2-b]pyrrolo[1,2-d][1,4]oxazine by proceeding analogously described in Example 5, Steps 7-8. MS (ES, m/z): [M+1]$^+$=551.3

Example 25

Synthesis of (6-(((6aS,8R)-8-(1H-pyrazol-1-yl)-6a,7,8,9-tetrahydro-6H-pyrido[3,2-b]-pyrrolo[1,2-d][1,4]oxazin-4-yl)thio)-3-((3S,4S)-4-amino-3-methyl-2-oxa-8-azaspiro[4.5]decan-8-yl)pyrazin-2-yl)methanol

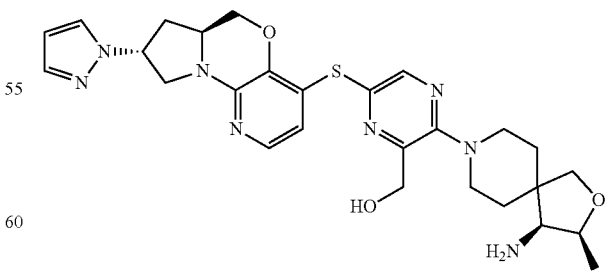

The title compound was synthesized from (6aS,8S)-4-iodo-6a,7,8,9-tetrahydro-6H-pyrido[3,2-b]pyrrolo[1,2-d][1,4]oxazin-8-yl methanesulfonate by the method described in Example 24. MS (ES, m/z): [M+1]$^+$=551.3.

Example 26 and 27

Synthesis of (3-((3S,4S)-4-amino-3-methyl-2-oxa-8-azaspiro[4.5]decan-8-yl)-6-(((R)-6a,7,9,10-tetrahydro-6H-[1,4]oxazino[4,3-d]pyrido[3,2-b][1,4]oxazin-4-yl)thio)pyrazin-2-yl)methanol and (3-((3S,4S)-4-amino-3-methyl-2-oxa-8-azaspiro[4.5]decan-8-yl)-6-(((S)-6a,7,9,10-tetrahydro-6H-[1,4]oxazino[4,3-d]pyrido[3,2-b][1,4]oxazin-4-yl)thio)pyrazin-2-yl)methanol

26

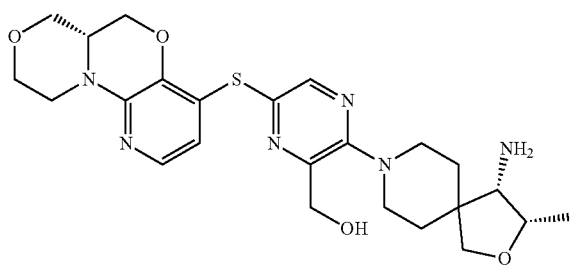

27

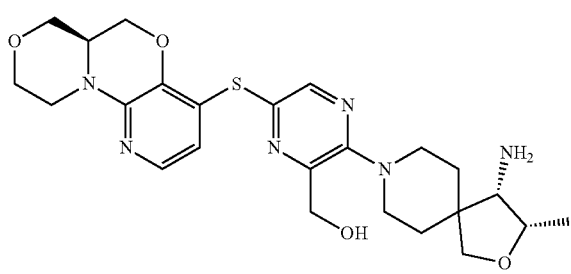

The title compounds were synthesized by proceeding analogously as described in Example 5, Steps 2-8 using tert-butyl 3-(hydroxymethyl)morpholine-4-carboxylate in Step 2. MS (ES, m/z): [M+1]$^+$=501.2.

Example 28

Synthesis of 4-((5-((3S,4S)-4-amino-3-methyl-2-oxa-8-azaspiro[4.5]decan-8-yl)-6-(hydroxymethyl)pyrazin-2-yl)thio)-6a,7,9,10-tetrahydro-6H-pyrido[3,2-b][1,4]thiazino[4,3-d][1,4]oxazine 8,8-dioxide

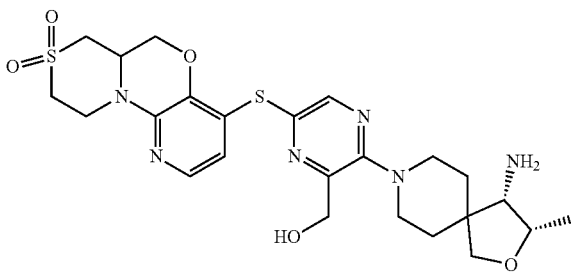 [SMILES: C[C@@H]1OCC2(CCN(c3ncc(Sc4ccnc5c4OCC4CS(=O)(=O)CCN54)nc3CO)CC2)[C@@H]1N]

Step 1: 4-(tert-butoxycarbonyl)thiomorpholine-3-carboxylic acid

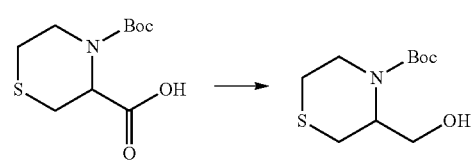 [SMILES: CC(C)(C)OC(=O)N1CCSCC1C(=O)O ; CC(C)(C)OC(=O)N1CCSCC1CO]

To a stirred solution of thiomorpholine-3-carboxylic acid (3000 mg, 20.382 mmol, 1.00 equiv) and Et$_3$N (4125 mg, 40.764 mmol, 2.00 equiv) in DCM (50.00 mL) was added Boc$_2$O (6672 mg, 30.57 mmol, 1.50 equiv) in portions at room temperature under N$_2$ atmosphere. The resulting mixture was stirred for 16 h at room temperature under N$_2$ atmosphere and then diluted with water and extracted with DCM. The combined organic layers were dried over anhydrous Na$_2$SO$_4$ and concentrated. The residue was purified by silica gel column chromatography, eluted with DCM/MeOH (10/1) to afford the title compound (3.2 g, 63.5%) as light yellow oil.

Step 2: tert-butyl 3-(hydroxymethyl)thiomorpholine-4-carboxylate

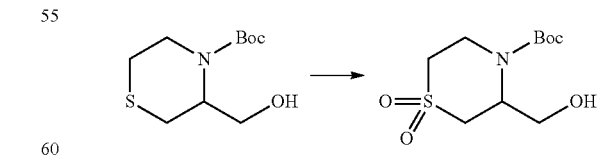

To a stirred solution of 4-(tert-butoxycarbonyl)thiomorpholine-3-carboxylic acid (2000 mg, 8.087 mmol, 1.00 equiv) in THF (20 mL) was added 1M BH$_3$-THF (16.18 mL, 16.180 mmol, 2.00 equiv) dropwise at 0° C. under N$_2$ atmosphere. The resulting mixture was stirred for 16 h at 45° C. under N$_2$ atmosphere and then quenched with MeOH at 0° C. The resulting mixture was concentrated under vacuum and the residue was purified by silica gel column chromatography, eluted with DCM/MeOH (10/1) to afford the title compound (1.8 g, 95.4%) as light yellow oil.

Step 3: tert-butyl 3-(hydroxymethyl)thiomorpholine-4-carboxylate 1,1-dioxide A solution of tert-butyl 3-(hydroxymethyl)thiomorpholine-4-carboxylate (500 mg, 2.143 mmol, 1.00 equiv) and m-CPBA (77%, 851 mg, 3.78 mmol, 1.77 equiv) in DCM (10 mL) was stirred for 16 h at room temperature under N$_2$ atmosphere. The reaction was quenched with saturated NaHCO$_3$ (5 mL) at room temperature. The resulting mixture was extracted with DCM. The combined organic layers were washed with saturated NaHCO$_3$, dried over anhydrous Na$_2$SO$_4$. After filtration, the filtrate was concentrated under reduced pressure. The residue was purified by silica gel column chromatography, eluted with DCM/MeOH (10/1) to afford the title compound (400 mg, 70.4%) as light yellow oil.

Step 4: 3-(hydroxymethyl)thiomorpholine 1,1-dioxide; trifluoroacetic acid

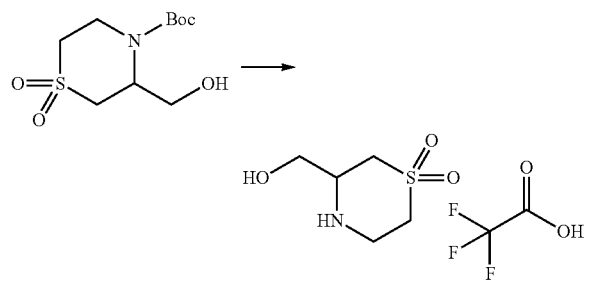

To a stirred solution of tert-butyl 3-(hydroxymethyl)thiomorpholine-4-carboxylate 1,1-dioxide (180 mg, 0.678 mmol, 1.00 equiv) in DCM (5.0 mL) was added TFA (3.868 g, 33.921 mmol, 50.00 equiv) at room temperature. The resulting mixture was stirred for 2 h at room temperature. The resulting mixture was concentrated under reduced pressure to afford the title compound (170 mg, 89.74%) as a white solid.

Step 5: 4-iodo-6a,7,9,10-tetrahydro-6H-pyrido[3,2-b][1,4]thiazino[4,3-d][1,4]oxazine 8,8-dioxide

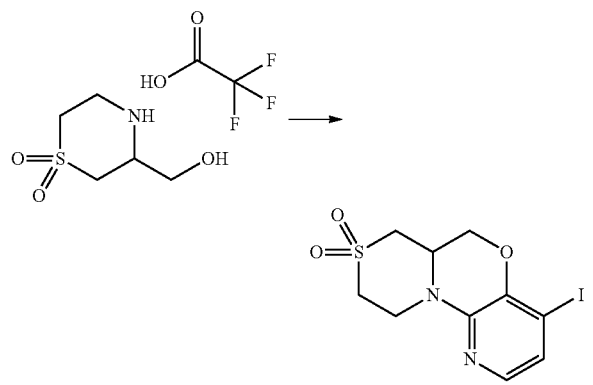

To a stirred solution of 3-(hydroxymethyl)thiomorpholine 1,1-dioxide trifluoroacetic acid (180 mg, 0.645 mmol, 1.00 equiv) and 2-fluoro-4-iodopyridin-3-ol (154 mg, 0.645 mmol, 1.00 equiv) in toluene (3.0 mL) were added PPh$_3$ (254 mg, 0.967 mmol, 1.50 equiv) and DEAD (168 mg, 0.967 mmol, 1.50 equiv) at room temperature under nitrogen atmosphere. The resulting mixture was stirred for 16 h at 60° C. under nitrogen atmosphere and then concentrated under reduced pressure. The residue was purified by Prep-TLC (PE/EtOAc 5:1) to afford the title compound (45 mg, 19.1%) as a light yellow solid.

Step 6: 4-((5-((3S,4S)-4-amino-3-methyl-2-oxa-8-azaspiro[4.5]decan-8-yl)-6-(hydroxymethyl)-pyrazin-2-yl)thio)-6a,7,9,10-tetrahydro-6H-pyrido[3,2-b][1,4]thiazino[4,3-d][1,4]oxazine 8,8-dioxide

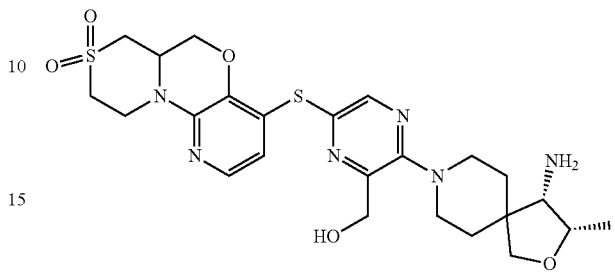

The title compounds were synthesized by proceeding analogously as described in Example 5, Steps 7-8 using 4-iodo-6a,7,9,10-tetrahydro-6H-pyrido[3,2-b][1,4]thiazino[4,3-d][1,4]oxazine 8,8-dioxide in Step 7. MS (ES, m/z): $[M+1]^+$=549.2.

Example 29 and 30

Synthesis of (3-((3S,4S)-4-amino-3-methyl-2-oxa-8-azaspiro[4.5]decan-8-yl)-6-((((6aS,8S)-8-(methoxymethyl)-6a,7,8,9-tetrahydro-6H-pyrido[3,2-b]pyrrolo[1,2-d][1,4]oxazin-4-yl)thio)pyrazin-2-yl)methanol [29] and (3-((3S,4S)-4-amino-3-methyl-2-oxa-8-azaspiro[4.5]decan-8-yl)-6-((((6aS,8R)-8-(methoxymethyl)-6a,7,8,9-tetrahydro-6H-pyrido[3,2-b]pyrrolo[1,2-d][1,4]oxazin-4-yl)thio)pyrazin-2-yl)methanol [30]

29

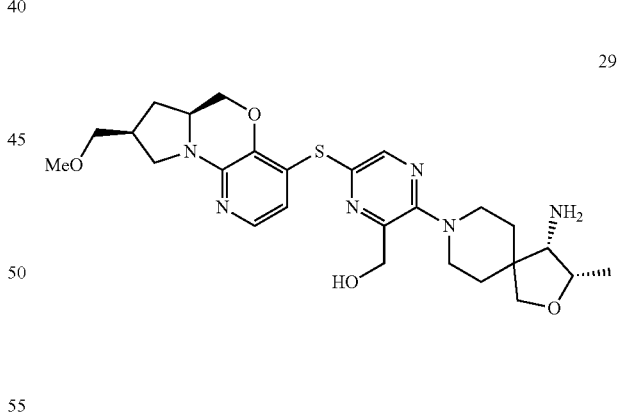

30

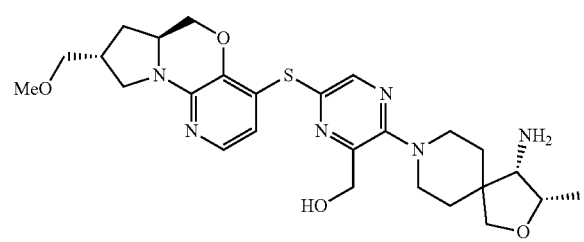

Step 1: 1-(tert-butyl) 2-methyl(S)-4-(methoxymethylene)pyrrolidine-1,2-dicarboxylate

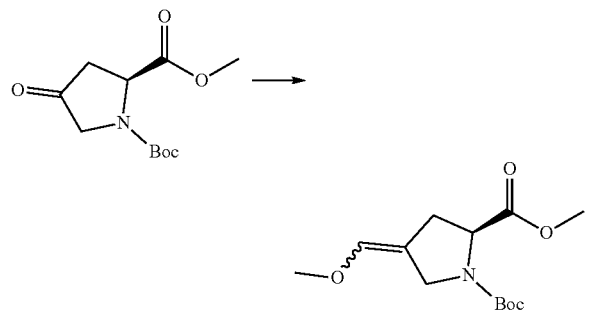

To a stirred mixture of 1-(tert-butyl) 2-methyl (S)-4-oxopyrrolidine-1,2-dicarboxylate (4.00 g, 16.443 mmol, 1.00 equiv) and K$_2$CO3 (1.50 g, 10.853 mmol, 0.66 equiv) in MeOH (80.0 mL) was added dimethyl (1-diazo-2-oxopropyl)phosphonate (9.48 g, 49.330 mmol, 3.00 equiv) at 0° C. under nitrogen atmosphere. After stirring for 12 h at room temperature, the reaction mixture was poured into water and the resulting mixture was extracted with EtOAc. The organic layer was washed with brine, dried over anhydrous Na$_2$SO$_4$ and concentrated. The residue was purified by silica gel column chromatography, eluted with PE/EtOAc (3:1), to afford the title compound (1.45 g, 32.5%) as a light-yellow oil.

Step 2: 1-(tert-butyl) 2-methyl (2S)-4-(methoxymethyl)pyrrolidine-1,2-dicarboxylate

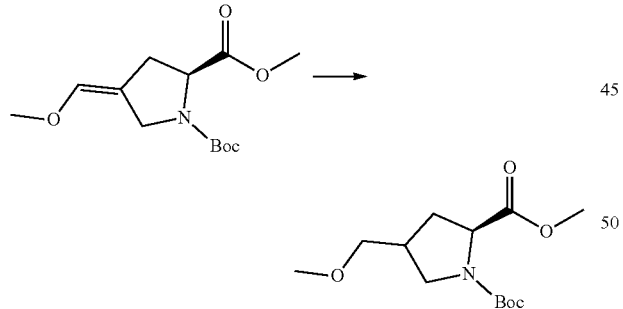

To a stirred solution of 1-(tert-butyl) 2-methyl (S)-4-(methoxymethylene)pyrrolidine-1,2-dicarboxylate (1.45 g, 5.344 mmol, 1.00 equiv) and 10% Pd/C (145 mg) in MeOH (20.0 mL) was added MgO (220 mg, 5.46 mmol, 1.02 equiv) at room temperature under hydrogen atmosphere. After stirring for 2 h at room temperature, the resulting mixture was filtered. The filtrate was concentrated under reduced pressure to afford the title compound (1.35 g, 92.42%) as a light-yellow oil which was used directly in next step without any further purification.

Step 3: tert-butyl (2S)-2-(hydroxymethyl)-4-(methoxymethyl)pyrrolidine-1-carboxylate

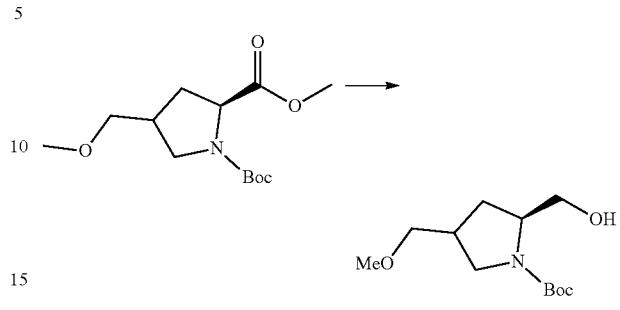

To a stirred solution of 1-(tert-butyl) 2-methyl (2S)-4-(methoxymethyl)pyrrolidine-1,2-dicarboxylate (180 mg, 0.659 mmol, 1.00 equiv) in THF (4.0 mL) was added LiAH$_4$ (37 mg, 0.975 mmol, 1.50 equiv) at room temperature. After stirring for 2 h at room temperature, the resulting mixture was diluted with DCM and quenched with water at 0° C. After filtration, the filter cake was washed with DCM. The organic layer was washed with brine, dried over anhydrous Na$_2$SO$_4$ and concentrated. The residue was purified by silica gel column chromatography, eluted with PE/EtOAc (1:1) to afford the title compound (90 mg, 55.7%) as a light-yellow oil.

Step 4: tert-butyl (2S)-2-(((2-fluoro-4-iodopyridin-3-yl)oxy)methyl)-4-(methoxymethyl)-pyrrolidine-1-carboxylate

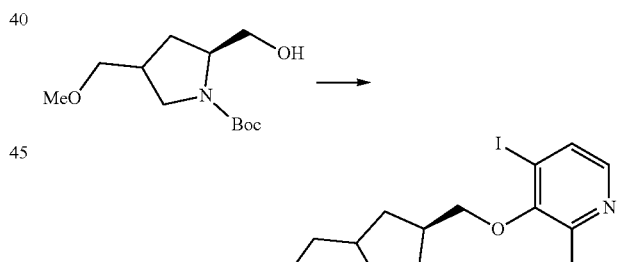

To a stirred solution of tert-butyl (2S)-2-(hydroxymethyl)-4-(methoxymethyl)-pyrrolidine-1-carboxylate (90 mg, 0.367 mmol, 1.00 equiv) and 2-fluoro-4-iodopyridin-3-ol (88 mg, 0.367 mmol, 1.00 equiv) in THF (2.00 mL) were added PPh$_3$ (144 mg, 0.550 mmol, 1.50 equiv) and DEAD (96 mg, 0.55 mmol, 1.50 equiv) at room temperature under nitrogen atmosphere. After stirring for 16 h at room temperature, the reaction mixture was concentrated under reduced pressure. The residue was purified by silica gel column chromatography, eluted with EtOAc/PE (0-60%) to afford the title compound (115 mg, 67.2%) as a light-yellow oil.

Step 5: 2-fluoro-4-iodo-3-(((2S)-4-(methoxymethyl)pyrrolidin-2-yl)methoxy)pyridine hydrogen chloride

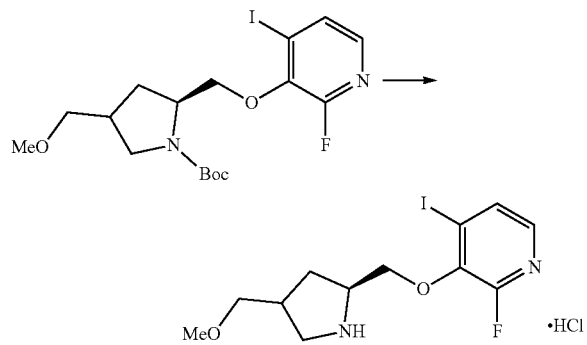

To a stirred solution of tert-butyl (2S)-2-(((2-fluoro-4-iodopyridin-3-yl)oxy)methyl)-4-(methoxymethyl)pyrrolidine-1-carboxylate (115 mg, 0.247 mmol, 1.00 equiv) in dioxane (1.0 mL) was added HCl (4.0 M in dioxane, 0.62 mL, 2.48 mmol, 10.00 equiv) at room temperature. After stirring for 5 h at room temperature, the reaction mixture was concentrated under reduced pressure to afford the title compound (110 mg, crude) as a light yellow solid, which was used directly in next step without further purification. MS (ES, m/z): [M+1]$^+$=367.0.

Step 6: (6aS)-4-iodo-8-(methoxymethyl)-6a,7,8,9-tetrahydro-6H-pyrido[3,2-b]pyrrolo[1,2-d][1,4]oxazine

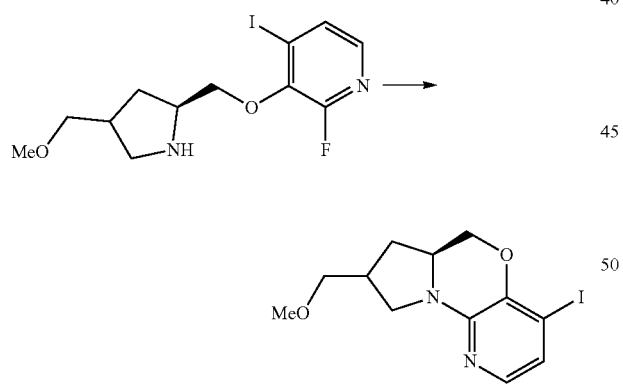

To a stirred solution of 2-fluoro-4-iodo-3-(((2S,4S)-4-(methoxymethyl)pyrrolidin-2-yl)-methoxy)pyridine hydrogen chloride (110 mg, 0.273 mmol, 1.00 equiv) in EtOH (3.0 mL) was added K$_2$CO3 (208 mg, 1.50 mmol, 5.51 equiv) at room temperature. After stirring for 2 h at 60° C., the reaction mixture was concentrated under reduced pressure. The residue was purified by silica gel column chromatography, eluted with EtOAc/PE (0-60%) to afford the title compound (80 mg, 2 steps 93.5%) as a light-yellow oil.

Step 7: tert-butyl((3S,4S)-8-(3-(hydroxymethyl)-5-((((6aS)-8-(methoxymethyl)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-yl)carbamate

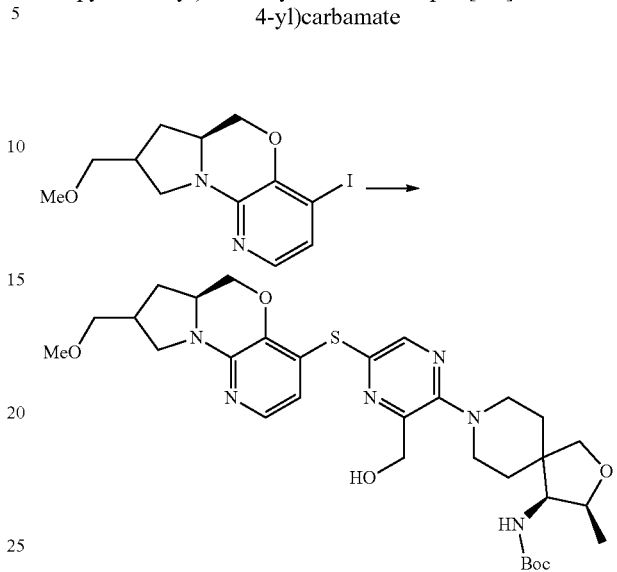

To a stirred mixture of (6aS)-4-iodo-8-(methoxymethyl)-6a,7,8,9-tetrahydro-6H-pyrido-[3,2-b]pyrrolo[1,2-d][1,4]oxazine (80 mg, 0.231 mmol, 1.00 equiv), sodium 5-((3S,4S)-4-((tert-butoxycarbonyl)amino)-3-methyl-2-oxa-8-azaspiro[4.5]decan-8-yl)-6-(hydroxy-methyl)pyrazine-2-thiolate (100 mg, 0.231 mmol, 1.0 equiv), Pd$_2$(dba)$_3$ (63 mg, 0.069 mmol, 0.30 equiv) and XantPhos (40 mg, 0.069 mmol, 0.30 equiv) in dioxane (1.50 mL) was added DIEA (90 mg, 0.693 mmol, 3.00 equiv) at room temperature under nitrogen atmosphere. After stirring for 1 h at 80° C., the reaction mixture was concentrated under reduced pressure. The residue was purified by silica gel column chromatography, eluted with MeOH/DCM (0-10%) to afford the title compound (110 mg, 75.7%) as a yellow solid.

Step 8: (3-((3S,4S)-4-amino-3-methyl-2-oxa-8-azaspiro[4.5]decan-8-yl)-6-((((6aS,8S)-8-(methoxymethyl)-6a,7,8,9-tetrahydro-6H-pyrido[3,2-b]pyrrolo[1,2-d][1,4]oxazin-4-yl)thio)-pyrazin-2-yl)methanol [29] and (3-((3S,4S)-4-amino-3-methyl-2-oxa-8-azaspiro[4.5]decan-8-yl)-6-((((6aS,8R)-8-(methoxymethyl)-6a,7,8,9-tetrahydro-6H-pyrido[3,2-b]pyrrolo[1,2-d][1,4]oxazin-4-yl)thio)pyrazin-2-yl)methanol [30]

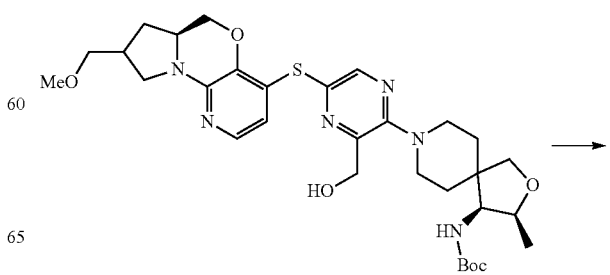

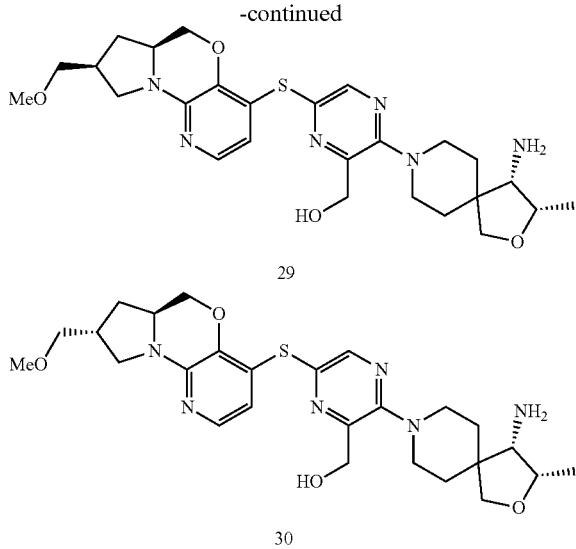

29

30

To a stirred solution of tert-butyl ((3S,4S)-8-(3-(hydroxymethyl)-5-(((6aS,8S)-8-(methoxymethyl)-6a,7,8,9-tetrahydro-6H-pyrido[3,2-b]pyrrolo[1,2-d][1,4]oxazin-4-yl)thio)-pyrazin-2-yl)-3-methyl-2-oxa-8-azaspiro[4.5]decan-4-yl)carbamate (70.00 mg, 0.111 mmol, 1.00 equiv) in DCM (1.0 mL) was added TFA (0.20 mL, 2.61 mmol, 23.5 equiv) at room temperature. After stirring for 2 h at room temperature, the reaction mixture was concentrated under reduced pressure. The mixture was purified by Prep-HPLC to afford 50 mg of crude product. The crude product (50 mg) was further purified by Chiral-HPLC to afford the title compound [29] (9.9 mg, 16.8%), MS (ES, m/z): [M+1]$^+$=529.3 and [30] (5.5 mg, 9.4%) MS (ES, m/z): [M+1]$^+$=529.3; as a white solid.

Example 31

Synthesis of (3-((3S,4S)-4-amino-3-methyl-2-oxa-8-azaspiro[4.5]decan-8-yl)-6-(((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol

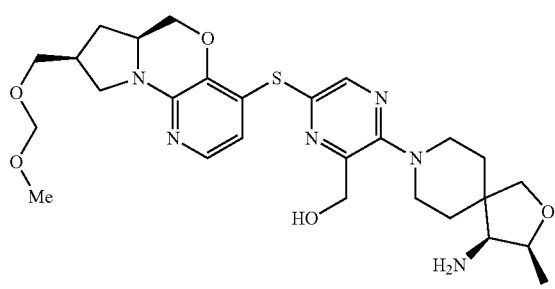 [SMILES: COCOC[C@H]1C[C@H]2COc3c(Sc4cnc(N5CCC6(CC5)CO[C@@H](C)[C@H]6N)c(CO)n4)ccnc3N2C1]

Step 1: tert-butyl (2S,4S)-2-(hydroxymethyl)-4-(methoxymethyl)pyrrolidine-1-carboxylate

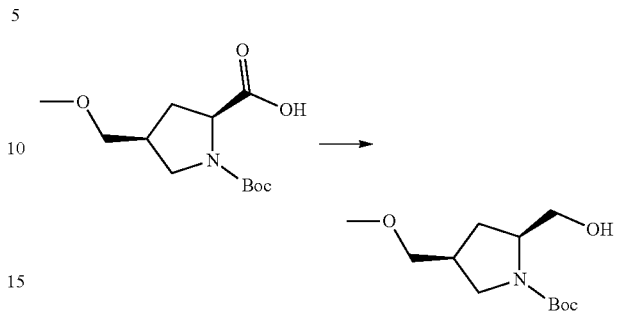

To a stirred solution of (2S,4S)-1-(tert-butoxycarbonyl)-4-(methoxymethyl)pyrrolidine-2-carboxylic acid (180 g, 694.171 mmol, 1.00 equiv) in THF (1.8 L) was added BH$_3$-Me$_2$S (173.00 mL, 1824.073 mmol, 2.63 equiv) dropwise at 0° C. under N$_2$ atmosphere. The resulting mixture was stirred for 16 h at room temperature under N$_2$ atmosphere. The reaction was quenched with MeOH (200 mL) at 0° C. and the resulting mixture was concentrated under reduced pressure. The residue was purified by silica gel column chromatography, eluted with PE/EA (1/1), to afford the title compound (160 g, 94%) as a colorless oil.

Step 2: tert-butyl (2S,4S)-2-(((2-fluoro-4-iodopyridin-3-yl)oxy)methyl)-4-(methoxymethyl)-pyrrolidine-1-carboxylate

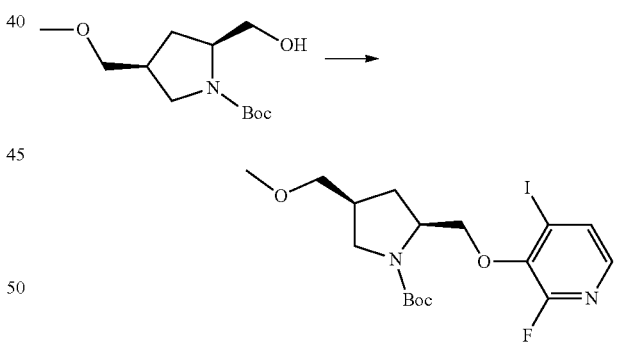

To a stirred solution of tert-butyl (2S,4S)-2-(hydroxymethyl)-4-(methoxymethyl)-pyrrolidine-1-carboxylate (7.0 g, 28.534 mmol, 1.00 equiv), 2-fluoro-4-iodopyridin-3-ol (6.8 g, 28.534 mmol, 1.00 equiv) and PPh$_3$ (11.2 g, 42.7 mmol, 1.50 equiv) in THF (140.00 mL) was added DEAD (7.5 g, 43 mmol, 1.5 equiv) dropwise at rt under N$_2$ atmosphere and the resulting mixture was stirred for 16 h at room temperature. The reaction mixture was then concentrated under reduced pressure and the residue was purified by silica gel column chromatography, eluted with PE/EA (5/1), to afford the title compound (11.5 g, 86.4%) as a light-yellow oil.

Step 3: 2-fluoro-4-iodo-3-(((2S,4S)-4-(methoxymethyl)pyrrolidin-2-yl)methoxy)pyridine dihydrochloride

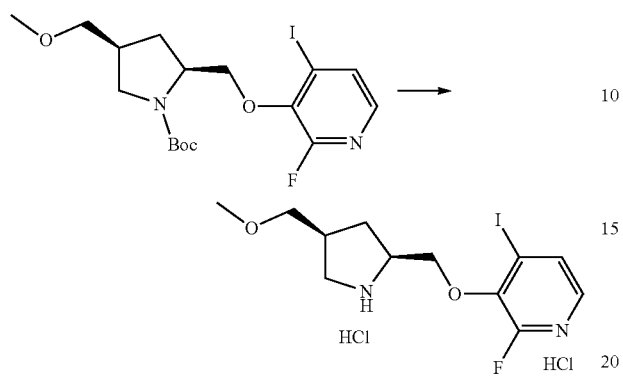

A solution of tert-butyl (2S,4S)-2-(((2-fluoro-4-iodopyridin-3-yl)oxy)methyl)-4-(methoxymethyl)pyrrolidine-1-carboxylate (11.5 g, 24.663 mmol, 1.00 equiv) in 1,4-dioxane (20.0 mL) and 4.0 M HCl in 1,4-dioxane (50.0 mL) was stirred for 3 h at room temperature under $N_2$ atmosphere. The resulting mixture was concentrated under reduced pressure to afford the title compound (14 g, crude) as a light-yellow oil, which was used for next step without further purification.

Step 4: (6aS,8S)-4-iodo-8-(methoxymethyl)-6a,7,8,9-tetrahydro-6H-pyrido[3,2-b]pyrrolo[1,2-d][1,4]oxazine

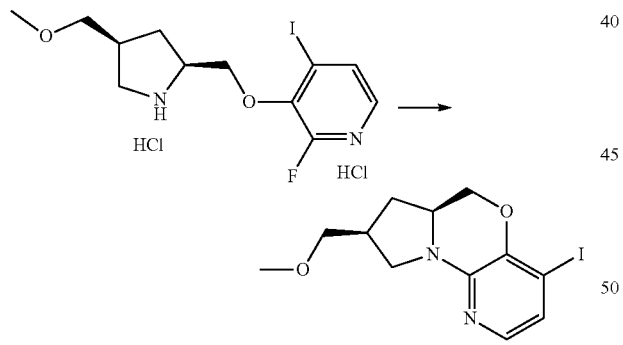

A mixture of crude 2-fluoro-4-iodo-3-(((2S,4S)-4-(methoxymethyl)pyrrolidin-2-yl)-methoxy)pyridine dihydrochloride (14.0 g, 31.88 mmol, 1.00 equiv) and $K_2CO_3$ (15.9 g, 115 mmol, 3.6 equiv) in EtOH (280.0 mL) was stirred for 3 h at 60° C. After cooled at rt, the resulting mixture was filtered and the filter cake was washed with EtOAc. The combined filtrate was concentrated under reduced pressure. The residue was purified by silica gel column chromatography, eluted with PE/EA (2/1), to afford the title compound (6.6 g, 2 steps 77%) as a light yellow solid.

Step 5: ((6aS,8S)-4-iodo-6a,7,8,9-tetrahydro-6H-pyrido[3,2-b]pyrrolo[1,2-d][1,4]oxazin-8-yl)-methanol

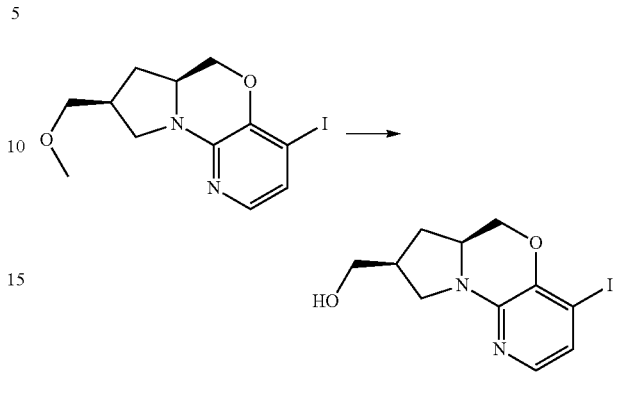

To a stirred mixture of (6aS,8S)-4-iodo-8-(methoxymethyl)-6a,7,8,9-tetrahydro-6H-pyrido[3,2-b]pyrrolo[1,2-d][1,4]oxazine (250 mg, 0.722 mmol, 1.00 equiv) and NaI (357 mg, 2.383 mmol, 3.3 equiv) in $CH_3CN$ (5.00 mL) was added $SiCl_4$ (405 mg, 2.383 mmol, 3.30 equiv) dropwise at room temperature under nitrogen atmosphere. The resulting mixture was stirred for 2 h at 80° C. under nitrogen atmosphere. The mixture was allowed to cool to room temperature, diluted with water, and the pH of the solution was adjusted to pH=8 with saturated $NaHCO_3$ aq solution. The resulting mixture was extracted with DCM and the organic layer was dried over anhydrous $Na_2SO_4$ and concentrated. The residue was purified by silica gel column chromatography, eluted with PE/EtOAc (1:1), to afford the title compound (200 mg, 83.4%) as a yellow solid.

Step 6: (6aS,8S)-4-iodo-8-((methoxymethoxy)methyl)-6a,7,8,9-tetrahydro-6H-pyrido[3,2-b]pyrrolo[1,2-d][1,4] oxazine

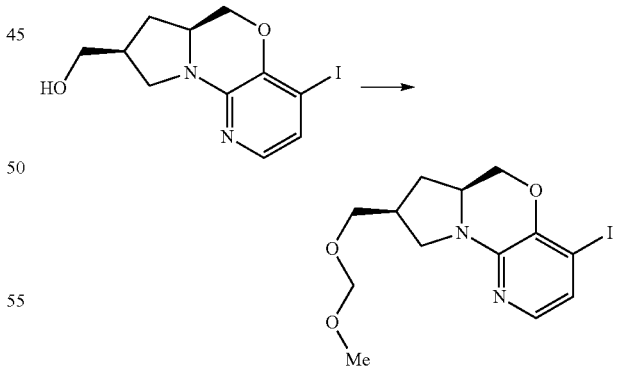

To a stirred solution of ((6aS,8S)-4-iodo-6a,7,8,9-tetrahydro-6H-pyrido[3,2-b]pyrrolo[1,2-d][1,4]oxazin-8-yl) methanol (75 mg, 0.226 mmol, 1.00 equiv) and DIEA (88 mg, 0.68 mmol, 3.0 equiv) in DCM (3.75 mL) was added bromo(methoxy)methane (85 mg, 0.68 mmol, 3.0 equiv) dropwise at room temperature under nitrogen atmosphere. The resulting mixture was stirred for 24 h at room temperature under nitrogen atmosphere. The reaction solution was purified by silica gel column chromatography, eluted with PE/EtOAc (1:1), to afford the title compound (65 mg, 76.5%) as a yellow solid.

Step 7: tert-butyl ((3S,4S)-8-(3-(hydroxymethyl)-5-((((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-yl)carbamate

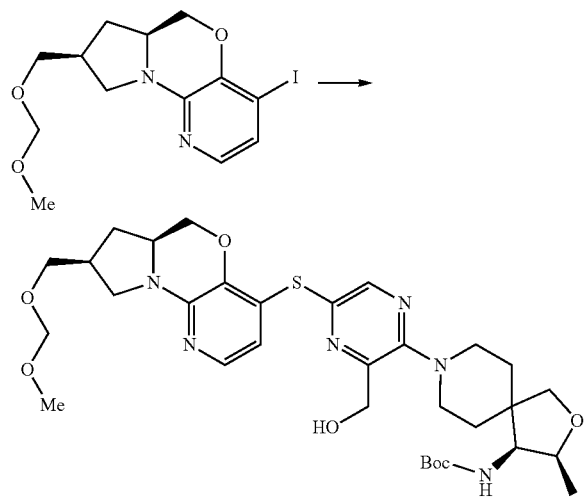

To a stirred mixture of sodium 5-((3S,4S)-4-((tert-butoxycarbonyl)amino)-3-methyl-2-oxa-8-azaspiro[4.5]decan-8-yl)-6-(hydroxymethyl)pyrazine-2-thiolate (55 mg, 0.127 mmol, 1.00 equiv), (6aS,8S)-4-iodo-8-((methoxymethoxy)methyl)-6a,7,8,9-tetrahydro-6H-pyrido[3,2-b]pyrrolo[1,2-d][1,4]oxazine (48 mg, 0.128 mmol, 1 equiv) and XantPhos (22 mg, 0.038 mmol, 0.30 equiv) in dioxane (2.0 mL) were added DIEA (82 mg, 0.63 mmol, 5 equiv) and Pd$_2$(dba)$_3$ (35 mg, 0.038 mmol, 0.30 equiv) in portions at room temperature under nitrogen atmosphere. The resulting mixture was stirred for 1 h at 80° C. under nitrogen atmosphere and then diluted with water and extracted with EtOAc. The organic layer was dried over anhydrous Na$_2$SO$_4$. After filtration, the filtrate was concentrated under reduced pressure and the residue was purified by silica gel column chromatography, eluted with DCM/MeOH (10:1), to afford the title compound (45 mg, 53.8%) as a brown solid.

Step 8: (3-((3S,4S)-4-amino-3-methyl-2-oxa-8-azaspiro[4.5]decan-8-yl)-6-((((6aS,8S)-8-((methoxymethoxy) methyl)-6a,7,8,9-tetrahydro-6H-pyrido[3,2-b]pyrrolo[1,2-d][1,4]oxazin-4-yl)thio)pyrazin-2-yl)methanol

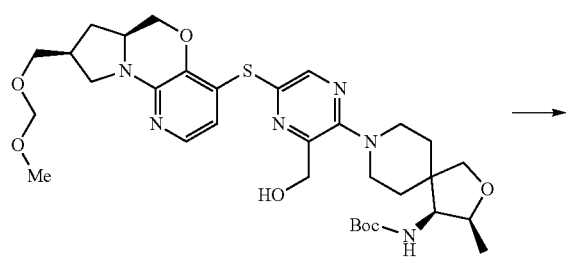

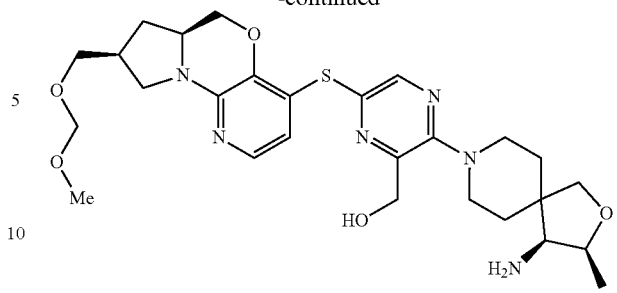

To a stirred solution of tert-butyl ((3S,4S)-8-(3-(hydroxymethyl)-5-((((6aS,8S)-8-((methoxy-methoxy)methyl)-6a,7,8,9-tetrahydro-6H-pyrido[3,2-b]pyrrolo[1,2-d][1,4]oxazin-4-yl)thio)-pyrazin-2-yl)-3-methyl-2-oxa-8-azaspiro[4.5]decan-4-yl)carbamate (35 mg, 0.053 mmol, 1.00 equiv) in DCM (1.80 mL) was added dropwise TFA (0.15 mL) at room temperature. The resulting mixture was stirred for 2 h at room temperature and then basified to pH=8 with ammonia hydroxide aq. solution. The organic solvent was removed under vacuum and the residue was purified by Prep-HPLC to afford the title compound (7 mg, 23.6%) as a white solid. MS (ES, m/z): [M+1]$^+$=559.3.

Example 32

Synthesis of (3-((3S,4S)-4-amino-3-methyl-2-oxa-8-azaspiro[4.5]decan-8-yl)-6-((((6aS,8S)-8-((2-methoxyethoxy)methyl)-6a,7,8,9-tetrahydro-6H-pyrido[3,2-b]pyrrolo[1,2-d][1,4]oxazin-4-yl)thio)pyrazin-2-yl)methanol

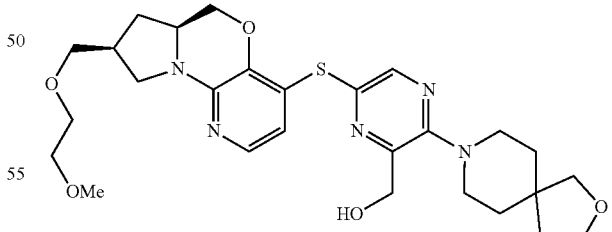

The title compound was synthesized by proceeding analogously as described in Example 31, Steps 6-8 using 1-bromo-2-methoxyethane in Step 6. MS (ES, m/z): [M+1]$^+$= 573.3.

Example 33

Synthesis of (3-((3S,4S)-4-amino-3-methyl-2-oxa-8-azaspiro[4.5]decan-8-yl)-6-(((6aS,8S)-8-((cyclopropylmethoxy)methyl)-6a,7,8,9-tetrahydro-6H-pyrido[3,2-b]pyrrolo[1,2-d][1,4]oxazin-4-yl)thio)pyrazin-2-yl)methanol

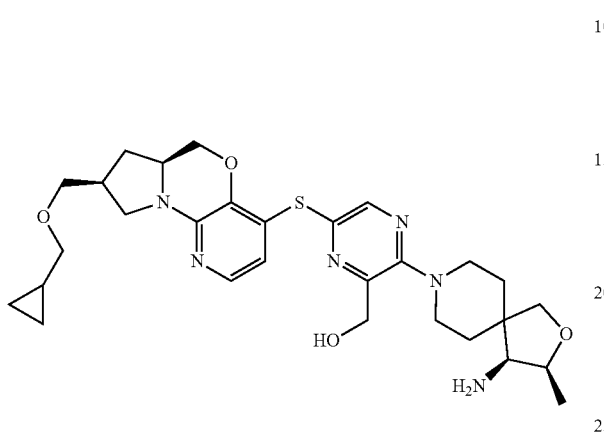

The title compound was synthesized by proceeding analogously as described in Example 31, Steps 6-8 using (bromomethyl)cyclopropane in Step 6. MS (ES, m/z): [M+1]$^+$= 569.3

Example 34

Synthesis of (3-((3S,4S)-4-amino-3-methyl-2-oxa-8-azaspiro[4.5]decan-8-yl)-6-(((6aS,8S)-8-((oxetan-3-ylmethoxy)methyl)-6a,7,8,9-tetrahydro-6H-pyrido[3,2-b]pyrrolo[1,2-d][1,4]oxazin-4-yl)thio)pyrazin-2-yl)methanol

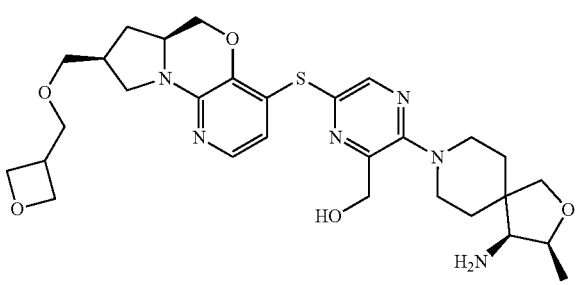 [SMILES: C[C@@H]1OCC2(CCN(c3ncc(Sc4ccnc5c4OC[C@@H]4C[C@H](COCC6COC6)CN54)nc3CO)CC2)[C@@H]1N]

The title compound was synthesized by proceeding analogously as described in Example 31, Steps 6-8 using 3-(bromomethyl)oxetane in Step 6. MS (ES, m/z): [M+1]$^+$=585.3

Example 35

Synthesis of formic acid; (3-((3S,4S)-4-amino-3-methyl-2-oxa-8-azaspiro[4.5]decan-8-yl)-6-(((S)-2-amino-6a,7,8,9-tetrahydro-6H-pyrido[3,2-b]pyrrolo[1,2-d][1,4]oxazin-4-yl)thio)pyrazin-2-yl)methanol

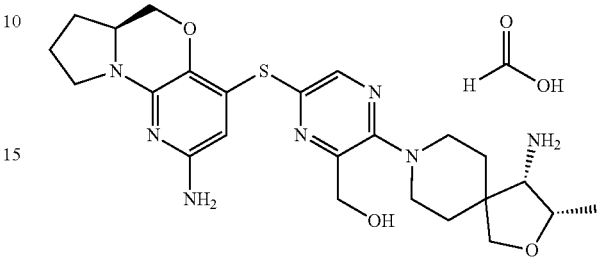

Step 1: 2-fluoro-4-iodo-6-nitropyridin-3-ol

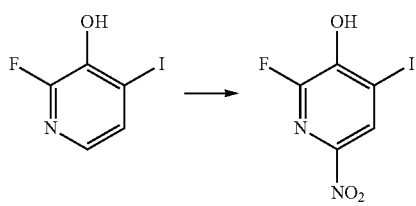 [SMILES: Oc1c(I)ccnc1F ; O=[N+]([O-])c1cc(I)c(O)c(F)n1]

To a stirred solution of 2-fluoro-4-iodopyridin-3-ol (100 mg, 0.418 mmol, 1.00 equiv) and Bu$_4$NNO$_3$ (191 mg, 0.628 mmol, 1.50 equiv) in DCM (2.0 mL) was added TFAA (0.10 mL, 0.595 mmol, 1.42 equiv) dropwise at 0° C. under nitrogen atmosphere and the resulting mixture was stirred for 1 h at 0° C. The reaction was quenched with saturated NH$_4$Cl (aq.) at 0° C. and the resulting mixture was extracted with EtOAc. The combined organic layers were washed with water and brine, dried over anhydrous Na$_2$SO$_4$. After filtration, the filtrate was concentrated under reduced pressure. The residue was purified by silica gel column chromatography, eluted with PE/EtOAc (5:1), to afford the title compound (10 mg, 8.4%) as a yellow solid.

Step 2: tert-butyl(S)-2-(((2-fluoro-4-iodo-6-nitropyridin-3-yl)oxy)methyl)pyrrolidine-1-carboxylate

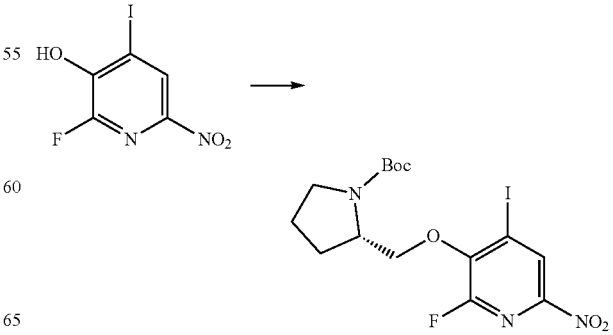

To a stirred solution of 2-fluoro-4-iodo-6-nitropyridin-3-ol (170 mg, 0.599 mmol, 1.00 equiv), tert-butyl(2S)-2-(hydroxymethyl)pyrrolidine-1-carboxylate (180 mg, 0.898 mmol, 1.50 equiv) and PPh$_3$ (235 mg, 0.9 mmol, 1.5 equiv) in THF (2 mL) was added DIAD (181 mg, 0.9 mmol, 1.5 equiv) dropwise at 0° C. under nitrogen atmosphere. The resulting mixture was stirred overnight at 60° C. under nitrogen atmosphere and then quenched with water at room temperature. The resulting mixture was extracted with EtOAc and the combined organic layers were washed with water and brine, dried over anhydrous Na$_2$SO$_4$. After filtration, the filtrate was concentrated under reduced pressure. The residue was purified by silica gel column chromatography, eluted with EtOAc/PE (0-30%) to afford the title compound (50 mg, 17.9%) as a yellow oil.

Step 3: (S)-2-fluoro-4-iodo-6-nitro-3-(pyrrolidin-2-ylmethoxy)pyridine hydrochloride

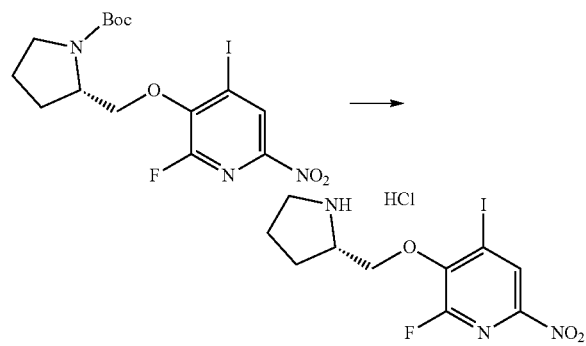

Into a 8 mL sealed tube were added tert-butyl (S)-2-(((2-fluoro-4-iodo-6-nitropyridin-3-yl)oxy)methyl) pyrrolidine-1-carboxylate (50 mg, 0.107 mmol, 1.00 equiv) and a solution of 4 M HCl in 1,4-dioxane (0.50 mL, 2.0 mmol, 18.69 equiv) at 0° C. The reaction solution was stirred for 1 h at room temperature and then concentrated under reduced pressure. The residue was triturated with Et$_2$O to give the crude title product (30 mg) as a yellow oil which was used in the next step directly without further purification.

Step 4: (S)-4-iodo-2-nitro-6a,7,8,9-tetrahydro-6H-pyrido[3,2-b]pyrrolo[1,2-d][1,4]oxazine

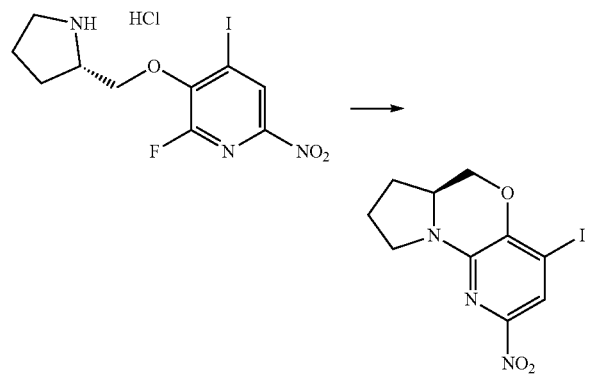

Into an 8 mL sealed tube were added (S)-2-fluoro-4-iodo-6-nitro-3-(pyrrolidin-2-ylmethoxy)pyridine hydrochloride (30 mg, crude), K$_2$CO3 (34 mg, 0.246 mmol) and EtOH (0.30 mL) at room temperature. The resulting mixture was stirred for 2 h at 60° C. and then allowed to cool down to room temperature. The resulting mixture was extracted with EtOAc and the combined organic layers were washed with water and brine, dried over anhydrous Na$_2$SO$_4$. After filtration, the filtrate was concentrated under reduced pressure. The residue was purified by silica gel column chromatography, eluted with PE/EtOAc (5:1) to afford the title compound (13 mg, 2 steps 34.6%) as a yellow solid.

Step 5: (S)-4-iodo-6a,7,8,9-tetrahydro-6H-pyrido[3,2-b]pyrrolo[1,2-d][1,4]oxazin-2-amine

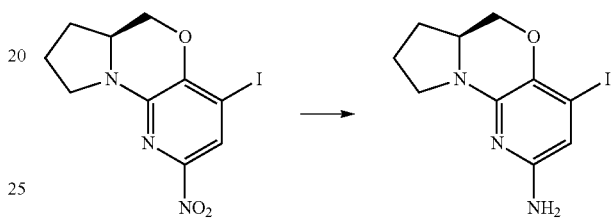

A mixture of (S)-4-iodo-2-nitro-6a,7,8,9-tetrahydro-6H-pyrido[3,2-b]pyrrolo[1,2-d][1,4]oxazine (13 mg, 0.037 mmol, 1.0 equiv), NH$_4$Cl (4 mg, 0.075 mmol, 2.0 equiv) and Fe (4 mg, 0.075 mmol, 2.0 equiv) in EtOH (0.10 mL) and H$_2$O (0.10 mL) was stirred for 2 h at 60° C. The mixture was allowed to cool down to room temperature and filtered. The filter cake was washed with EtOAc and the filtrate was washed with water and brine, dried over anhydrous Na$_2$SO$_4$. After filtration, the filtrate was concentrated under reduced pressure and the residue was purified by silica gel column chromatography, eluted with EtOAc/PE (0-100%), to afford the title compound (9 mg, 75.8%) as a yellow solid.

Step 6: formic acid; (3-((3S,4S)-4-amino-3-methyl-2-oxa-8-azaspiro[4.5]decan-8-yl)-6-(((S)-2-amino-6a,7,8,9-tetrahydro-6H-pyrido[3,2-b]pyrrolo[1,2-d][1,4]oxazin-4-yl)thio)pyrazin-2-yl)methanol

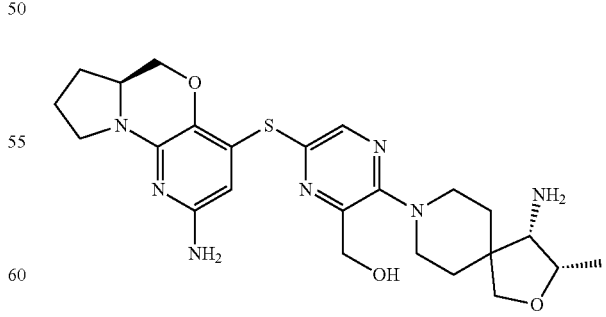

The title compound was synthesized by proceeding analogously as described in Example 5, Steps 7-8 using (S)-4-iodo-6a,7,8,9-tetrahydro-6H-pyrido[3,2-b]pyrrolo[1,2-d][1,4]oxazin-2-amine in Step 7. MS (ES, m/z): [M+1]$^+$=500.3.

Example 36 and 37

Synthesis of (3-((S)-5-amino-5,7-dihydrospiro[cyclopenta[b]pyridine-6,4'-piperidin]-1'-yl)-6-(((6aS,8S)-8-(methoxymethyl)-6a,7,8,9-tetrahydro-6H-pyrido[3,2-b]pyrrolo[1,2-d][1,4]oxazin-4-yl)thio)pyrazin-2-yl)methanol [36] and (3-((S)-5-amino-5,7-dihydrospiro[cyclopenta[b]pyridine-6,4'-piperidin]-1'-yl)-6-(((6aS,8R)-8-(methoxymethyl)-6a,7,8,9-tetrahydro-6H-pyrido[3,2-b]pyrrolo[1,2-d][1,4]oxazin-4-yl)thio)pyrazin-2-yl)methanol [37]

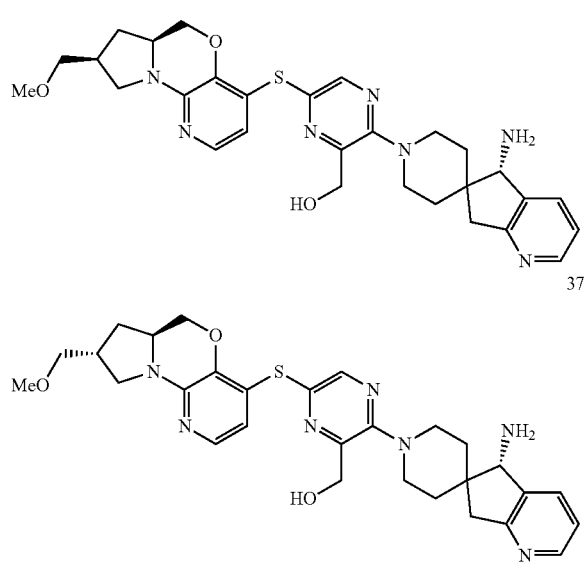

Step 1: 2-ethylhexyl 3-(((6aS)-8-(methoxymethyl)-6a,7,8,9-tetrahydro-6H-pyrido[3,2-b]pyrrolo[1,2-d][1,4]oxazin-4-yl)thio)propanoate

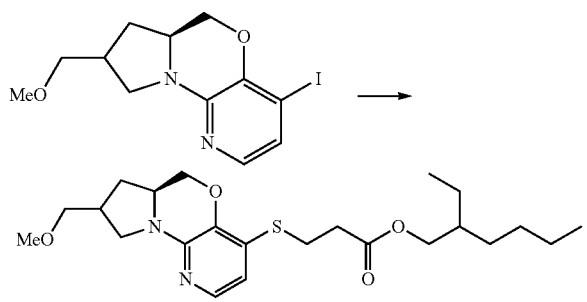

To a stirred mixture of (6aS)-4-iodo-8-(methoxymethyl)-6a,7,8,9-tetrahydro-6H-pyrido[3,2-b]pyrrolo[1,2-d][1,4]oxazine (500 mg, 1.444 mmol, 1.00 equiv), 2-ethylhexyl 3-sulfanylpropanoate (378 mg, 1.733 mmol, 1.20 equiv), Pd$_2$(dba)$_3$ (130 mg, 0.142 mmol, 0.10 equiv) and XantPhos (85 mg, 0.147 mmol, 0.10 equiv) in 1,4-dioxane (7.5 mL) was added DIEA (560 mg, 4.333 mmol, 3.00 equiv) at room temperature under nitrogen atmosphere and the resulting mixture was stirred for 2 h at 85° C. After cooling to rt, the reaction was quenched with water and extracted with EtOAc. The combined organic layers were washed with brine, dried over anhydrous Na$_2$SO$_4$ and concentrated and the residue was purified by silica gel column chromatography, eluted with EtOAc/PE (0-60%), to afford the title compound (500 mg, 79.3%) as a light-yellow oil.

Step 2: sodium (6aS)-8-(methoxymethyl)-6a,7,8,9-tetrahydro-6H-pyrido[3,2-b]pyrrolo[1,2-d][1,4]oxazine-4-thiolate

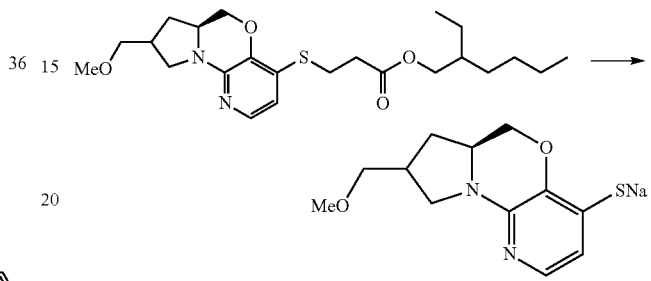

To a stirred solution of 2-ethylhexyl 3-(((6aS)-8-(methoxymethyl)-6a,7,8,9-tetrahydro-6H-pyrido[3,2-b]pyrrolo[1,2-d][1,4]oxazin-4-yl)thio)propanoate (500 mg, 1.145 mmol, 1.00 equiv) in MeOH (10.0 mL) was added NaOMe (68 mg, 1.260 mmol, 1.10 equiv) at room temperature. After stirring for 5 h at room temperature, the reaction mixture was concentrated under vacuum and the residue was triturated with Et$_2$O to afford the title compound (220 mg, 70%) as a yellow solid.

Step 3: (3-chloro-6-(((6aS)-8-(methoxymethyl)-6a,7,8,9-tetrahydro-6H-pyrido[3,2-b]pyrrolo[1,2-d][1,4]oxazin-4-yl)thio)pyrazin-2-yl)methanol

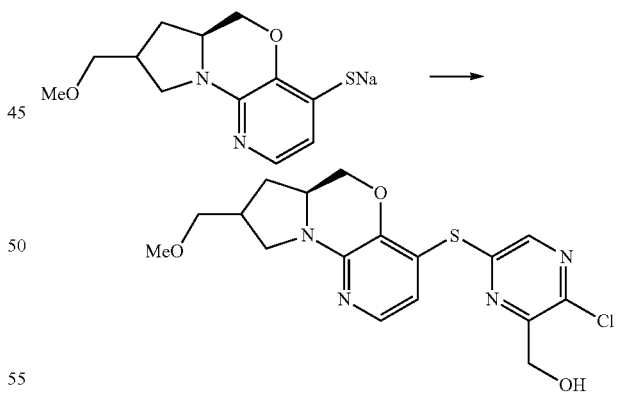

To a stirred mixture of sodium (6aS)-8-(methoxymethyl)-6a,7,8,9-tetrahydro-6H-pyrido[3,2-b]pyrrolo[1,2-d][1,4]oxazine-4-thiolate (100 mg, 0.365 mmol, 1.00 equiv), (6-bromo-3-chloropyrazin-2-yl)methanol (90 mg, 0.40 mmol, 1.10 equiv), Pd$_2$(dba)$_3$ (33 mg, 0.036 mmol, 0.10 equiv) and XantPhos (21 mg, 0.036 mmol, 0.10 equiv) in 1,4-dioxane (2 mL) was added DIEA (141 mg, 1.09 mmol, 3.0 equiv) at room temperature under nitrogen atmosphere. After stirring for 2 h at 85° C., the reaction mixture was concentrated under vacuum and the residue was purified by silica gel column chromatography, eluted with EtOAc/PE (0-60%), to afford the title compound (105 mg, 72.9%) as a light yellow oil.

Step 4: (3-((S)-5-amino-5,7-dihydrospiro[cyclopenta[b]pyridine-6,4'-piperidin]-1'-yl)-6-(((6aS,8S)-8-(methoxy methyl)-6a,7,8,9-tetrahydro-6H-pyrido[3,2-b]pyrrolo[1,2-d][1,4]oxazin-4-yl)thio)pyrazin-2-yl) methanol and (3-((S)-5-amino-5,7-dihydrospiro[cyclopenta[b]pyridine-6,4'-piperidin]-1'-yl)-6-(((6aS,8R)-8-(methoxy methyl)-6a,7,8,9-tetrahydro-6H-pyrido[3,2-b]pyrrolo[1,2-d][1,4]oxazin-4-yl)thio)pyrazin-2-yl)methanol

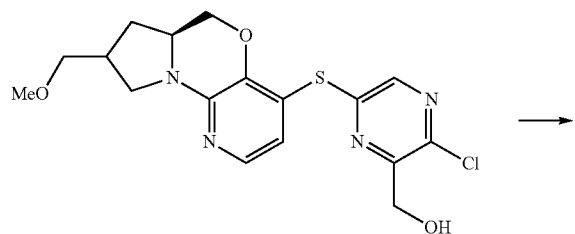

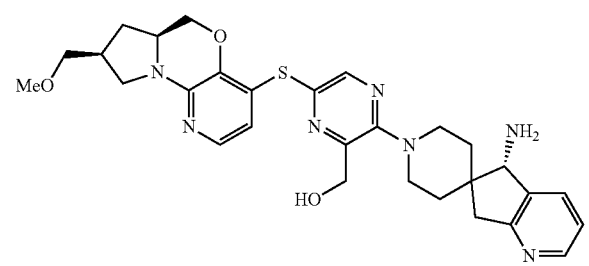

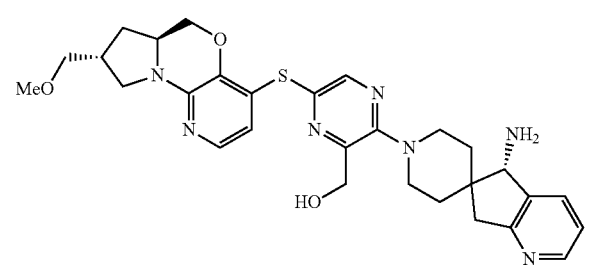

To a stirred mixture of (3-chloro-6-(((6aS)-8-(methoxymethyl)-6a,7,8,9-tetrahydro-6H-pyrido[3,2-b]pyrrolo[1,2-d][1,4]oxazin-4-yl)thio)pyrazin-2-yl)methanol (50 mg, 0.127 mmol, 1.00 equiv) and (S)-5,7-dihydrospiro[cyclopenta[b]pyridine-6,4'-piperidin]-5-amine trihydrochloride (50 mg, 0.159 mmol, 1.25 equiv) in ACN (2.0 mL) was added DIEA (82 mg, 0.63 mmol, 5.0 equiv) at room temperature and the resulting mixture was stirred at 80° C. for 48 h. After cooling to room temperature, the reaction mixture was filtered and the filter cake was washed with MeOH and the combined filtrate was concentrated and the residue was purified by Prep-HPLC to afford the title compounds. MS (ES, m/z): [M+1]$^+$=562.3.

Example 38

Synthesis of (3-((S)-5-amino-13-oxa-9-azadispiro[3.1.5$^6$.2$^4$]tridecan-9-yl)-6-(((6aS,8S)-8-(methoxymethyl)-6a,7,8,9-tetrahydro-6H-pyrido[3,2-b]pyrrolo[1,2-d][1,4]oxazin-4-yl)thio)pyrazin-2-yl)methanol

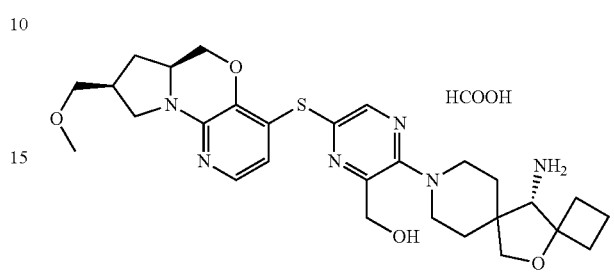

A solution of (3-chloro-6-(((6aS,8S)-8-(methoxymethyl)-6a,7,8,9-tetrahydro-6H-pyrido[3,2-b]pyrrolo[1,2-d][1,4]oxazin-4-yl)thio)pyrazin-2-yl)methanol (35 mg, 0.089 mmol, 1.00 equiv), (S)-13-oxa-9-azadispiro[3.1.5$^6$.2$^4$]tridecan-5-amine dihydrochloride (29 mg, 0.106 mmol, 1.20 equiv) and DIEA (57 mg, 0.443 mmol, 5.00 equiv) in CH$_3$CN (0.56 mL) was stirred for 16 h at 80° C. The reaction mixture was purified by Pre-HPLC to afford the title compound (9.8 mg, 18.4%) as yellow solid. MS (ES, m/z): [M+1]$^+$=555.2.

Example 39 and 40

Synthesis of (3-((S)-5-amino-13-oxa-9-azadispiro[3.1.56.24]tridecan-9-yl)-6-(((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol [39]

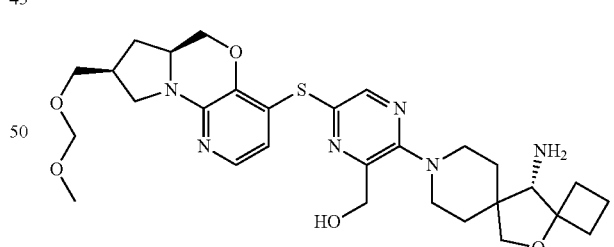

The title compound was synthesized by proceeding analogously as described in Examples 36 and 37, from (6aS,8S)-4-iodo-8-((methoxymethoxy)methyl)-6a,7,8,9-tetrahydro-6H-pyrido[3,2-b]pyrrolo[1,2-d][1,4]oxazine and (S)-13-oxa-9-azadispiro[3.1.5$^6$.2$^4$]tridecan-5-amine dihydrochloride. MS (ES, m/z): [M+1]$^+$=585.3.

179

(3-((3S,4S)-4-Amino-3-methyl-2-oxa-8-azaspiro[4.5]decan-8-yl)-6-((((6aS,8S)-8-((((methoxymethoxy)methyl)-6a,7,8,9-tetrahydro-6H-pyrido[3,2-b]pyrrolo[1,2-d][1,4]oxazin-4-yl)thio)pyrazin-2-yl)methanol [40]

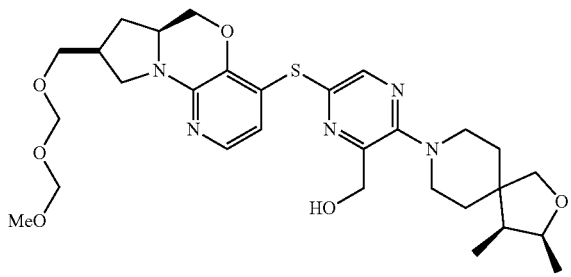 [SMILES: COCOCOC[C@H]1C[C@H]2COc3c(Sc4cnc(N5CCC6(CC5)CO[C@@H](C)[C@H]6C)c(CO)n4)ccnc3N2C1]

was isolated as a side product.

Example 41

Synthesis of (3-((3S,4S)-4-amino-3-methyl-2-azaspiro[4.5]decan-8-yl)-6-((((6aS,8S)-8-(hydroxymethyl)-6a,7,8,9-tetrahydro-6H-pyrido[3,2-b]pyrrolo[1,2-d][1,4]oxazin-4-yl)thio)pyrazin-2-yl)methanol

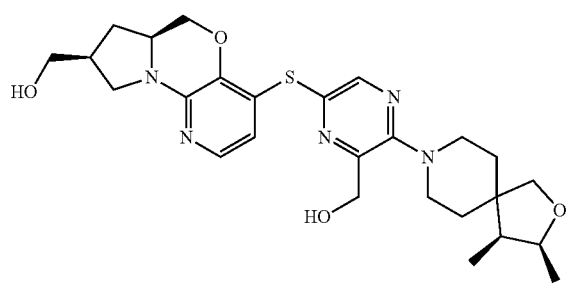 [SMILES: C[C@@H]1OCC2(CCN(c3ncc(Sc4ccnc5c4OC[C@@H]4C[C@H](CO)CN54)nc3CO)CC2)[C@@H]1C]

Step 1: (3-((3S,4S)-4-amino-3-methyl-2-oxa-8-azaspiro[4.5]decan-8-yl)-6-((((6aS,8S)-8-(hydroxymethyl)-6a,7,8,9-tetrahydro-6H-pyrido[3,2-b]pyrrolo[1,2-d][1,4]oxazin-4-yl)thio)pyrazin-2-yl)methanol

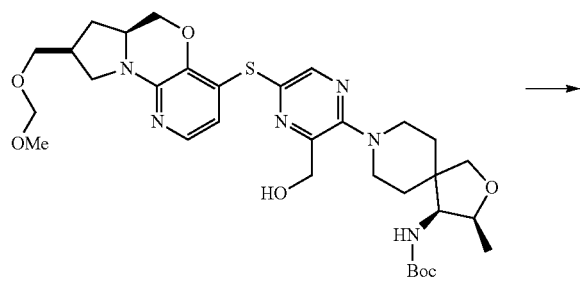

180

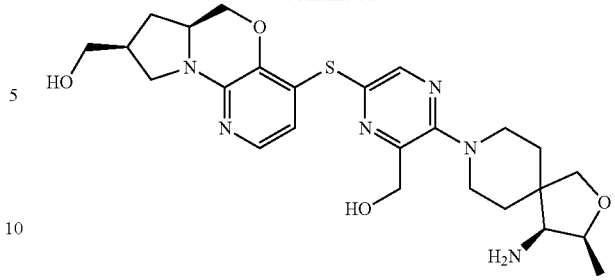

During synthesis of Example 31, compound 42 was also isolated as side product. MS (ES, m/z): $[M+1]^+=515.3$.

Example 42

Synthesis of (3S,4S)-8-(5-((((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-amine

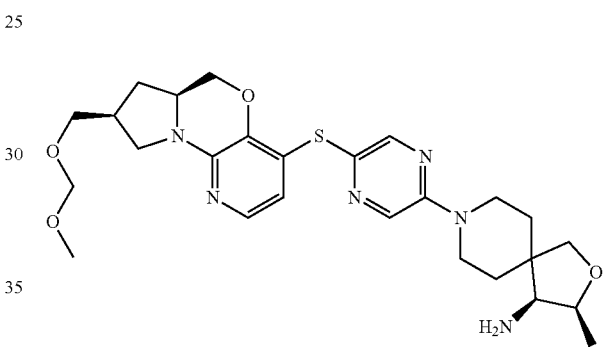

Step 1: (6aS,8S)-4-((5-chloropyrazin-2-yl)thio)-8-((methoxymethoxy)methyl)-6a,7,8,9-tetrahydro-6H-pyrido[3,2-b]pyrrolo[1,2-d][1,4]oxazine

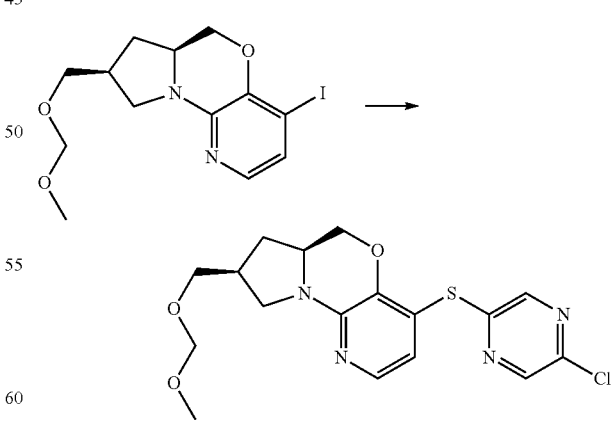

A mixture of (6aS,8S)-4-iodo-8-((methoxymethoxy)methyl)-6a,7,8,9-tetrahydro-6H-pyrido[3,2-b]pyrrolo[1,2-d][1,4]oxazine (90 mg, 0.239 mmol, 1.00 equiv), sodium 5-chloropyrazine-2-thiolate (61 mg, 0.36 mmol, 1.51 equiv) (see WO2016/203406), Pd$_2$(dba)$_3$ (22 mg, 0.024 mmol, 0.10 equiv), Xantphos (14 mg, 0.024 mmol, 0.10 equiv) and DIEA (93 mg, 0.72 mmol, 3.0 equiv) in THF (2 mL) was stirred for 0.5 h at 60° C. under nitrogen atmosphere. The residue was purified by silica gel column chromatography to afford the title compound (93 mg, 98.5%) as brown oil. MS (ES, m/z): [M+1]⁺=395.2.

Step 2: (3S,4S)-8-(5-((((6aS,8S)-8-((methoxymethoxy)methyl)-6a,7,8,9-tetrahydro-6H-pyrido[3,2-b]pyrrolo[1,2-d][1,4]oxazin-4-yl)thio) pyrazin-2-yl)-3-methyl-2-oxa-8-azaspiro[4.5]decan-4-amine

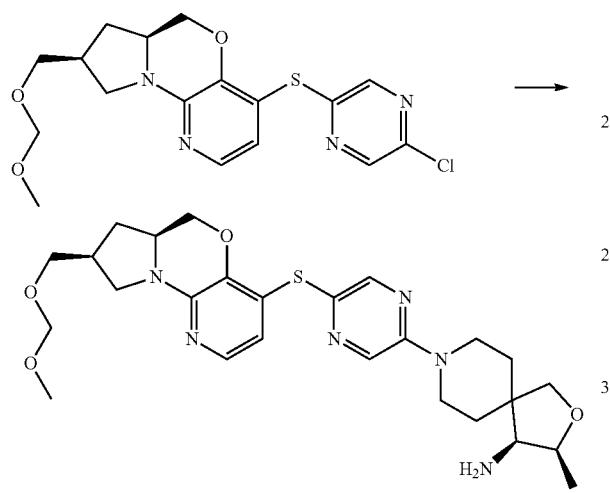

A solution of (6aS,8S)-4-((5-chloropyrazin-2-yl)thio)-8-((methoxymethoxy)methyl)-6a,7,8,9-tetrahydro-6H-pyrido[3,2-b]pyrrolo[1,2-d][1,4]oxazine (40 mg, 0.101 mmol, 1.00 equiv), (3S,4S)-3-methyl-2-oxa-8-azaspiro[4.5]decan-4-amine dihydrochloride (42 mg, 0.173 mmol, 1.70 equiv) and DIEA (65 mg, 0.50 mmol, 5.00 equiv) in CH₃CN (0.40 mL) was stirred for 16 h at 100° C. The residue was purified by Pre-HPLC to afford the title compound (16 mg, 29.9%) as off-white solid. MS (ES, m/z): [M+1]⁺=529.3

Example 43

Synthesis of (3S,4S)-8-(5-((((6aS,8S)-8-(methoxymethyl)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-amine

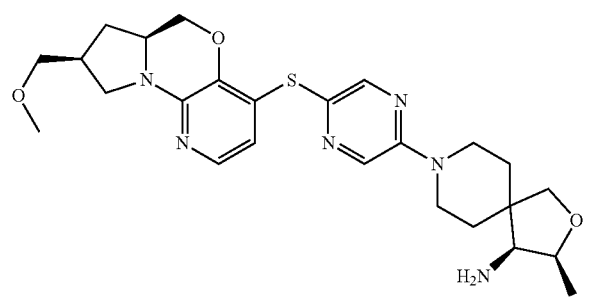 [SMILES: COC[C@H]1C[C@H]2COc3c(Sc4cnc(N5CCC6(CC5)CO[C@@H](C)[C@H]6N)cn4)ccnc3N2C1]

The title compound was synthesized by proceeding analogously as described in Example 42. MS (ES, m/z): [M+1]= 499.3.

Example 44

Synthesis of (3S,4S)-8-(6-amino-5-((((6aS,8S)-8-((methoxymethoxy)methyl)-6a,7,8,9-tetrahydro-6H-pyrido[3,2-b]pyrrolo[1,2-d][1,4]oxazin-4-yl)thio) pyrazin-2-yl)-3-methyl-2-oxa-8-azaspiro[4.5]decan-4-amine

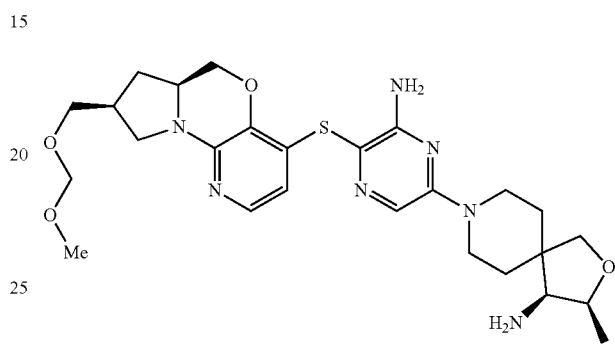

Step 1: 6-chloro-3-((((6aS,8S)-8-((methoxymethoxy) methyl)-6a,7,8,9-tetrahydro-6H-pyrido[3,2-b]pyrrolo [1,2-d][1,4]oxazin-4-yl)thio)pyrazin-2-amine

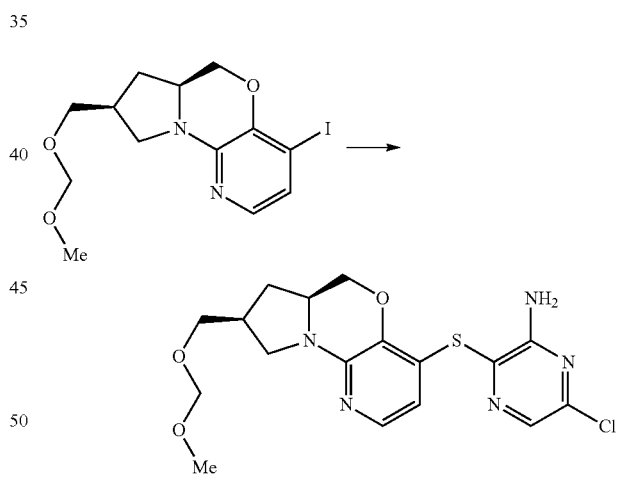

A mixture of (6aS,8S)-4-iodo-8-((methoxymethoxy) methyl)-6a,7,8,9-tetrahydro-6H-pyrido[3,2-b]pyrrolo[1,2-d][1,4]oxazine (90.00 mg, 0.239 mmol, 1.00 equiv), sodium 3-amino-5-chloropyrazine-2-thiolate (60 mg, 0.359 mmol, 1.5 equiv) (see WO2015/107494), Pd₂(dba)₃ (22 mg, 0.024 mmol, 0.1 equiv), Xantphos (14 mg, 0.024 mmol, 0.1 equiv) and DIEA (93 mg, 0.72 mmol, 3.0 equiv) in THF (2.00 mL) was stirred for 0.5 h at 60° C. under nitrogen atmosphere. The residue was purified by silica gel column chromatography and to afford the title compound (93 mg, 98.9%) as a brown oil.

183

Step 2: (3S,4S)-8-(6-amino-5-(((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-amine

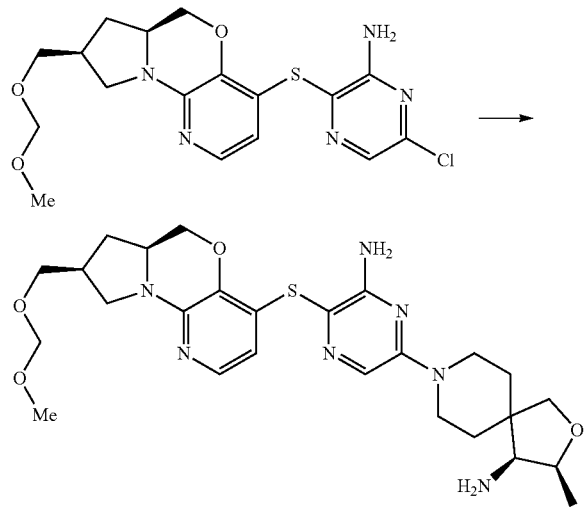

A solution of 6-chloro-3-(((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-amine (40 mg, 0.1 mmol, 1.00 equiv), (3S,4S)-3-methyl-2-oxa-8-azaspiro[4.5]decan-4-amine dihydrochloride (42 mg, 0.17 mmol, 1.76 equiv) and DIEA (65 mg, 0.5 mmol, 5.1 equiv) in CH$_3$CN (0.40 mL) was stirred for 16 h at 100° C. The residue was purified by Pre-HPLC to afford the title compound (16 mg, 30%) as off-white solid. MS (ES, m/z): [M+1]$^+$=544.3.

Example 45

Synthesis of (3S,4S)-8-(6-amino-5-(((6aS,8S)-8-(methoxymethyl)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-amine

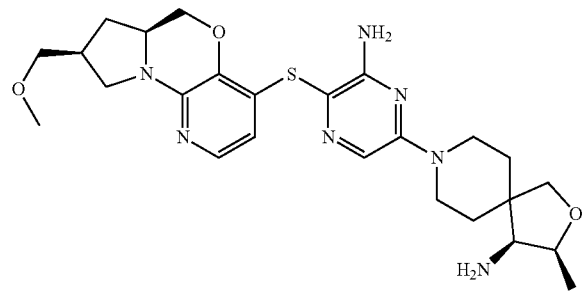 [SMILES: COC[C@H]1C[C@H]2COc3c(Sc4ncc(N5CCC6(CC5)CO[C@@H](C)[C@H]6N)nc4N)ccnc3N2C1]

The title compound was synthesized by proceeding analogously as described in Example 44. MS (ES, m/z): [M+1]$^+$=514.3

184

Example 46

Synthesis of (S)-1'-(5-(((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-5,7-dihydrospiro[cyclopenta[b]pyridine-6,4'-piperidin]-5-amine

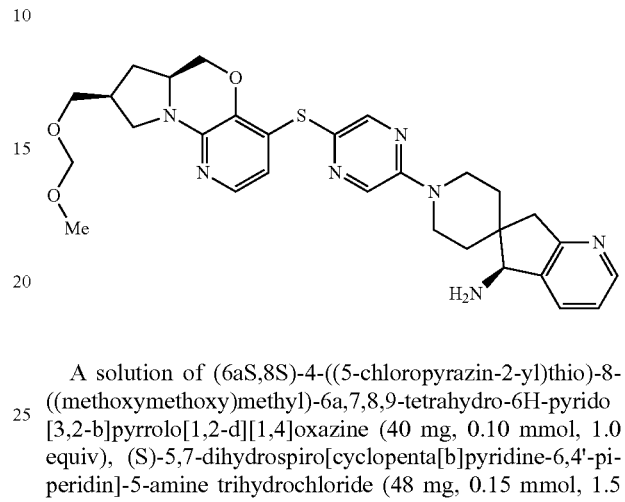

A solution of (6aS,8S)-4-((5-chloropyrazin-2-yl)thio)-8-((methoxymethoxy)methyl)-6a,7,8,9-tetrahydro-6H-pyrido[3,2-b]pyrrolo[1,2-d][1,4]oxazine (40 mg, 0.10 mmol, 1.0 equiv), (S)-5,7-dihydrospiro[cyclopenta[b]pyridine-6,4'-piperidin]-5-amine trihydrochloride (48 mg, 0.15 mmol, 1.5 equiv) and DIEA (65 mg, 0.50 mmol, 5.00 equiv) in CH$_3$CN (0.40 mL) was stirred for 16 h at 100° C. The reaction solution was purified by Pre-HPLC to afford the title compound (12.0 mg, 21.2%) as off-white solid, MS (ES, m/z): [M+1]$^+$=562.3.

Example 47

Synthesis of (S)-1'-(6-amino-5-(((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)-5,7-dihydrospiro[cyclopenta[b]pyridine-6,4'-piperidin]-5-amine

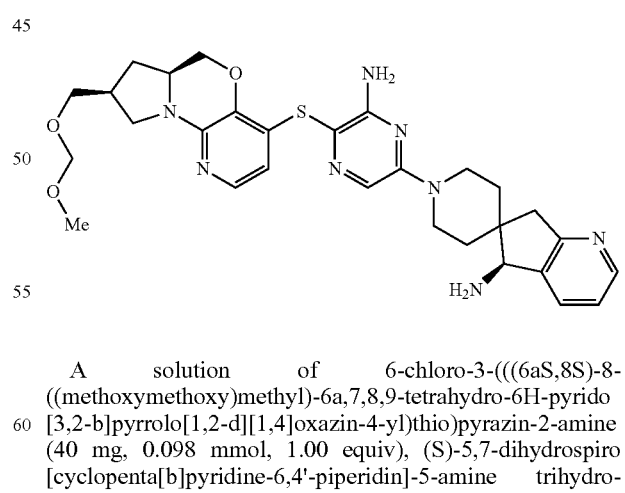

A solution of 6-chloro-3-(((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-amine (40 mg, 0.098 mmol, 1.00 equiv), (S)-5,7-dihydrospiro[cyclopenta[b]pyridine-6,4'-piperidin]-5-amine trihydrochloride (46 mg, 0.147 mmol, 1.50 equiv) and DIEA (63 mg, 0.487 mmol, 5.0 equiv) in CH$_3$CN (0.40 mL) was stirred for 16 h at 100° C. The reaction solution was purified by Pre-HPLC to afford the title compound (16.0 mg, 28.4%) as an off-white solid. MS (ES, m/z): [M+1]$^+$=577.3.

Example 48

Synthesis of (3-((S)-5-amino-5,7-dihydrospiro[cyclopenta[b]pyridine-6,4'-piperidin]-1'-yl)-6-((((6aS,8S)-8-((methoxymethoxy)methyl)-6a,7,8,9-tetrahydro-6H-pyrido[3,2-b]pyrrolo-[1,2-d][1,4]oxazin-4-yl)thio)pyrazin-2-yl)methanol

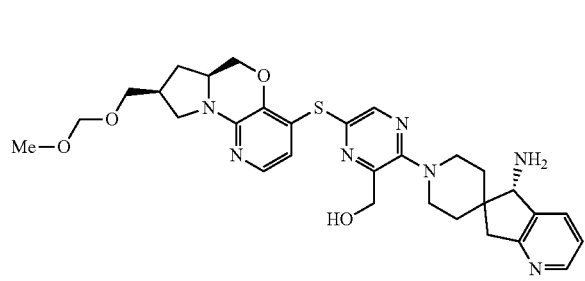 [SMILES: COCOC[C@H]1C[C@H]2COc3c(Sc4cnc(N5CCC6(CC5)Cc5ncccc5[C@H]6N)c(CO)n4)ccnc3N2C1]

To a stirred solution of (S)-5,7-dihydrospiro[cyclopenta[b]pyridine-6,4'-piperidin]-5-amine trihydrochloride (28 mg, 0.09 mmol, 1.53 equiv) and DIEA (38 mg, 0.294 mmol, 5.0 equiv) in ACN (0.5 mL) was added (3-chloro-6-((((6aS,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol (25 mg, 0.059 mmol, 1.00 equiv) at room temperature under nitrogen atmosphere. The resulting mixture was stirred overnight at 100° C. and the mixture was allowed to cool down to room temperature. The crude product was purified by Prep-HPLC to afford the title compound (6.5 mg, 18.67%) as a white solid. MS (ES, m/z): [M+1]⁺=592.3.

Example 49

Synthesis of (3-((3S,4S)-4-amino-3-methyl-2-oxa-8-azaspiro[4.5]decan-8-yl)-6-((((6aS,8S)-8-((methoxymethoxy)methyl)-6a,7,8,9-tetrahydro-6H-pyrido[3,2-b]pyrrolo[1,2-d][1,4]oxazin-4-yl)thio)-5-methylpyrazin-2-yl)methanol

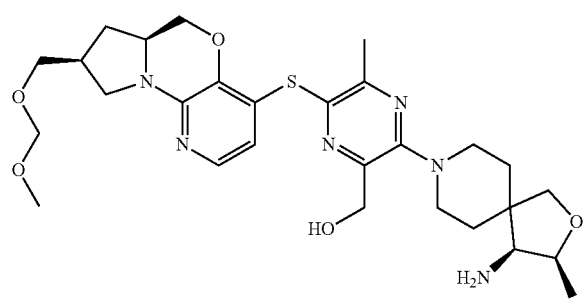 [SMILES: COCOC[C@H]1C[C@H]2COc3c(Sc4nc(CO)c(N5CCC6(CC5)CO[C@@H](C)[C@H]6N)nc4C)ccnc3N2C1]

The title compound was synthesized by proceeding analogously as described in Example 31. MS (ES, m/z): [M+1]⁺= 573.3.

Example 50

Synthesis of (3-((3S,4S)-4-amino-3-methyl-2-oxa-8-azaspiro[4.5]decan-8-yl)-6-((((6aS,8R)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol

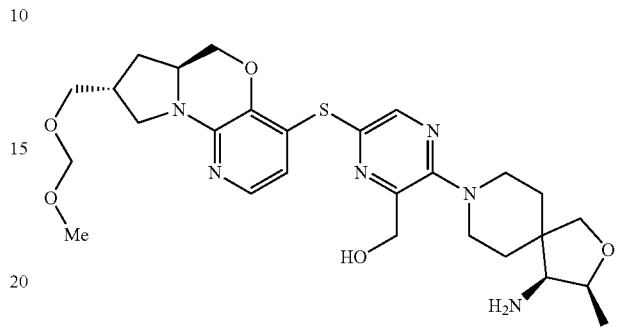

Step 1: (3-chloro-6-((((6aS)-8-((methoxymethoxy)methyl)-6a,7,8,9-tetrahydro-6H-pyrido-[3,2-b]pyrrolo[1,2-d][1,4]oxazin-4-yl)thio)pyrazin-2-yl)methanol

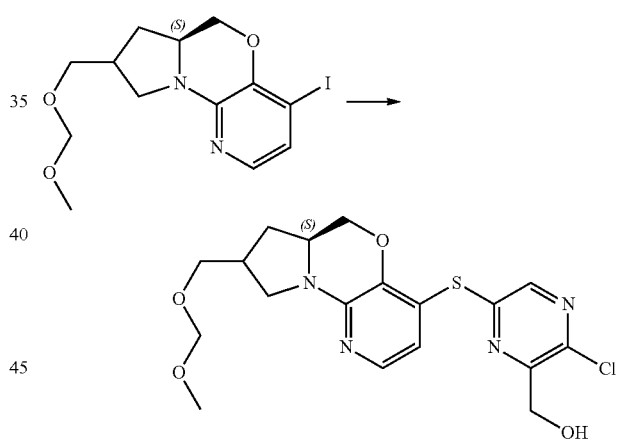

Into a mixture of (6aS)-4-iodo-8-((methoxymethoxy)methyl)-6a,7,8,9-tetrahydro-6H-pyrido[3,2-b]pyrrolo[1,2-d][1,4]oxazine (1.00 g, 2.658 mmol, 1.00 equiv) and sodium 5-chloro-6-(hydroxymethyl)pyrazine-2-thiolate (0.78 g, 3.93 mmol, 1.48 equiv) in THF (10.00 mL) were added XantPhos (0.15 g, 0.26 mmol, 0.10 equiv) and DIEA (1.02 g, 7.892 mmol, 2.97 equiv) at room temperature. Pd₂(dba)₃ (0.12 g, 0.13 mmol, 0.05 equiv) was then added to the solution under nitrogen atmosphere and the resulting mixture was stirred for 1 h at 60° C. under nitrogen atmosphere. The resulting mixture was cooled to rt and filtered and the filtrate was concentrated under reduced pressure and the residue was purified by silica gel column chromatography, eluted with PE/EA (0~100%) to afford product (790 mg, 69.9%).

Step 2: (3-((3S,4S)-4-amino-3-methyl-2-oxa-8-azaspiro[4.5]decan-8-yl)-6-((((6aS,8R)-8-((methoxymethoxy) methyl)-6a,7,8,9-tetrahydro-6H-pyrido[3,2-b]pyrrolo[1,2-d][1,4]oxazin-4-yl)thio)pyrazin-2-yl)methanol

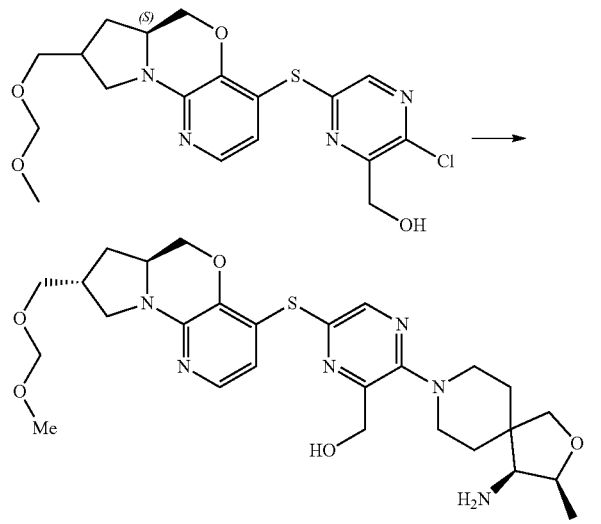

Into a mixture of (3S,4S)-3-methyl-2-oxa-8-azaspiro[4.5]decan-4-amine dihydrochloride (730 mg, 3.002 mmol, 1.72 equiv) and DIEA (1.30 g, 10.06 mmol, 5.77 equiv) in ACN (5 mL) was added (3-chloro-6-((((6aS)-8-((methoxymethoxy)methyl)-6a,7,8,9-tetrahydro-6H-pyrido[3,2-b]pyrrolo[1,2-d][1,4]oxazin-4-yl)thio) pyrazin-2-yl)methanol (740 mg, 1.742 mmol, 1.00 equiv) at room temperature. The resulting mixture was stirred for 16 h at 60° C. under nitrogen atmosphere and then purified by Prep-HPLC and chiral HPLC to afford product. MS (ES, m/z): [M+1]$^+$=559.3.

Example 51 and 52

Synthesis of (3-((3S,4S)-4-amino-3-methyl-2-oxa-8-azaspiro[4.5]decan-8-yl)-6-((((6aR,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol and (3-((3S,4S)-4-amino-3-methyl-2-oxa-8-azaspiro[4.5]decan-8-yl)-6-((((6aR,8R)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol

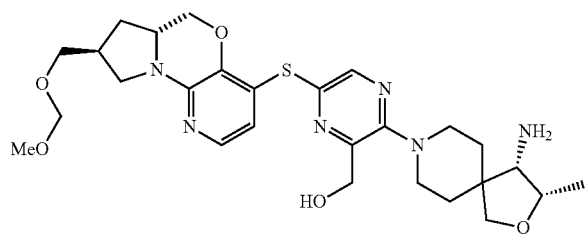

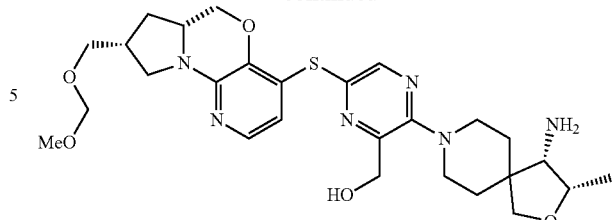

Step 1: (6aR)-4-iodo-8-((methoxymethoxy)methyl)-6a,7,8,9-tetrahydro-6H-pyrido[3,2-b]pyrrolo[1,2-d][1,4]oxazine

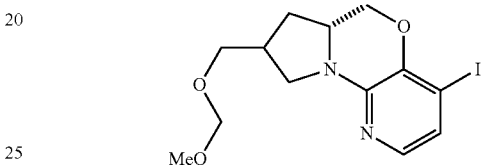

The title compound was synthesized by proceeding analogously as described in Examples 29-30, steps 1-6.

Step 2: (3-((3S,4S)-4-amino-3-methyl-2-oxa-8-azaspiro[4.5]decan-8-yl)-6-((((6aR,8S)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol and (3-((3S,4S)-4-amino-3-methyl-2-oxa-8-azaspiro-[4.5]decan-8-yl)-6-((((6aR,8R)-8-((methoxymethoxy)methyl)-6a,7,8,9-tetrahydro-6H-pyrido[3,2-b]pyrrolo[1,2-d][1,4]oxazin-4-yl)thio)pyrazin-2-yl)methanol

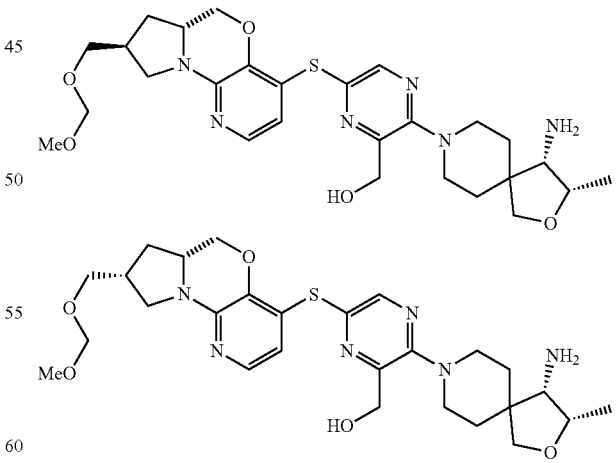

A mixtures of title compounds was synthesized by proceeding analogously as described in Example 31, steps 5-8. The material was then purified by HPLC to give compounds 51 and 52. Compound 51: MS (ES, m/z): [M+1]$^+$=559.3. Compound 52: MS (ES, m/z): [M+1]$^+$=559.3.

Example 53

Synthesis of (3-((3S,4S)-4-amino-3-methyl-2-oxa-8-azaspiro[4.5]decan-8-yl)-6-((6aS,8S)-8-(methoxymethyl)-6a,7,8,9-tetrahydro-6H-pyrido[3,2-b]pyrrolo[1,2-d][1,4]oxazin-4-yl)pyrazin-2-yl)methanol

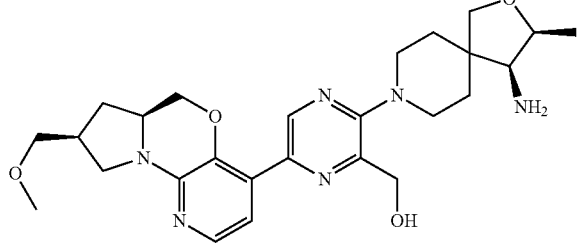

Step 1: ((6aS,8S)-8-(methoxymethyl)-6a,7,8,9-tetrahydro-6H-pyrido[3,2-b]pyrrolo[1,2-d]-[1,4]oxazin-4-yl)boronic acid

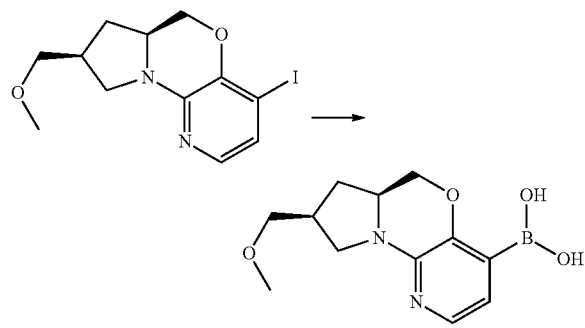

To a stirred solution of (6aS,8S)-4-iodo-8-(methoxymethyl)-6a,7,8,9-tetrahydro-6H-pyrido[3,2-b]pyrrolo[1,2-d][1,4]oxazine (100 mg, 0.289 mmol, 1.00 equiv), 4,4,4',4',5,5,5',5'-octamethyl-2,2'-bi(1,3,2-dioxaborolane) (110 mg, 0.433 mmol, 1.5 equiv), AcOK (57 mg, 0.581 mmol, 2.0 equiv) in toluene (2 mL) was added Pd(dppf)Cl$_2$ (12 mg, 0.0164 mmol, 0.057 equiv) at room temperature under N$_2$ atmosphere. The resulting mixture was stirred for 16 h at 100° C. under N$_2$ atmosphere and the resulting mixture was used directly in next step without further purification.

Step 2: tert-butyl ((3S,4S)-8-(3-(hydroxymethyl)-5-((6aS,8S)-8-(methoxymethyl)-6a,7,8,9-tetrahydro-6H-pyrido[3,2-b]pyrrolo[1,2-d][1,4]oxazin-4-yl)pyrazin-2-yl)-3-methyl-2-oxa-8-azaspiro[4.5]decan-4-yl)carbamate

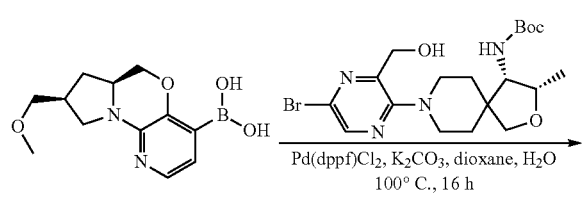

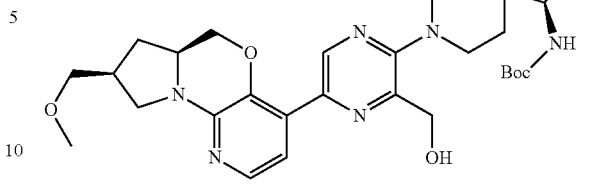

To the mixture of ((6aS,8S)-8-(methoxymethyl)-6a,7,8,9-tetrahydro-6H-pyrido[3,2-b]pyrrolo[1,2-d][1,4]oxazin-4-yl)boronic acid in toluene from last step were added K$_2$CO$_3$ (120 mg, 0.87 mmol, 3.00 equiv), tert-butyl ((3S,4S)-8-(5-bromo-3-(hydroxymethyl)pyrazin-2-yl)-3-methyl-2-oxa-8-azaspiro[4.5]decan-4-yl)carbamate (132 mg, 0.290 mmol, 1.00 equiv), Pd(dppf)Cl$_2$ (12.00 mg, 0.064 mmol, 0.057 equiv) and H$_2$O (0.2 mL) under N$_2$. After stirring for 3 h at 100° C., the resulting mixture was concentrated under reduced pressure. The residue was purified by silica gel column chromatography, eluted with EA, to afford the title compound (70 mg, 40.7%, 2 steps) as a light-yellow oil. MS (ES, m/z): [M+1]=597.3.

Step 3: (3-((3S,4S)-4-amino-3-methyl-2-oxa-8-azaspiro[4.5]decan-8-yl)-6-((6aS,8S)-8-(methoxymethyl)-6a,7,8,9-tetrahydro-6H-pyrido[3,2-b]pyrrolo[1,2-d][1,4]oxazin-4-yl)pyrazin-2-yl)methanol

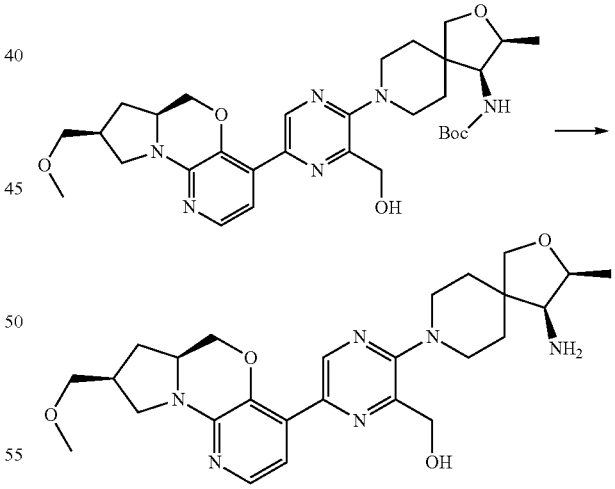

A mixture of tert-butyl ((3S,4S)-8-(3-(hydroxymethyl)-5-((6aS,8S)-8-(methoxymethyl)-6a,7,8,9-tetrahydro-6H-pyrido[3,2-b]pyrrolo[1,2-d][1,4]oxazin-4-yl)pyrazin-2-yl)-3-methyl-2-oxa-8-azaspiro[4.5]decan-4-yl)carbamate (70 mg, 0.117 mmol, 1.00 equiv) in DCM (3 mL) and TFA (1 mL) was stirred at room temperature for 3 h. The resulting mixture was concentrated and purified by Prep-HPLC to afford the title compound (17 mg, 29.3%). MS (ES, m/z): [M+H]$^+$=497.3.

Example 54

Synthesis of (3-((3S,4S)-4-amino-3-methyl-2-oxa-8-azaspiro[4.5]decan-8-yl)-6-((6aS,8S)-8-((methoxymethoxy)methyl)-6a,7,8,9-tetrahydro-6H-pyrido[3,2-b]pyrrolo[1,2-d][1,4]oxazin-4-yl)pyrazin-2-yl)methanol

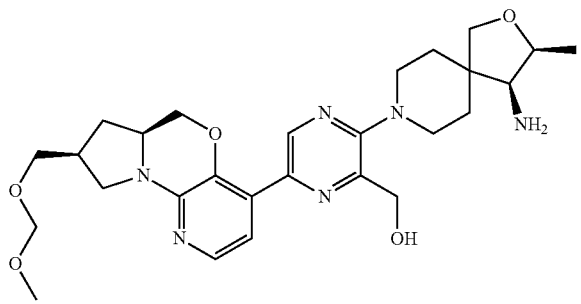 [SMILES: COCOC[C@H]1C[C@H]2COc3c(-c4cnc(N5CCC6(CC5)CO[C@@H](C)[C@H]6N)c(CO)n4)ccnc3N2C1]

The title compound was synthesized by proceeding analogously as described in Example 54. MS (ES, m/z): [M+H]$^+$ =527.3.

Biological Assays

SHP2 Allosteric Inhibition Assay

SHP2 possesses two N-terminal Src homology 2 (SH2) domains, a central protein-tyrosine phosphatase (PTP) domain, and C-terminal tail. At the basal state, SHP2 is auto-inhibited and access of substrates to the catalytic site is blocked by the intermolecular interactions between the SH2 domains and the PTP domain. When bis-tyrosyl-phosphorylated peptides bind to SH2 domain of SHP2, the PTP domain becomes available for substrate recognition and reaction catalysis and SHP2 is allosterically activated. SHP2 catalytic activity can be measured using a fluorogenic artificial substrate DiFMUP.

The phosphatase reactions were carried out at room temperature in 384-well black polystyrene plates (Greiner Bio-One, Cat #784076) using assay buffers containing 60 mM HEPES, pH 7.2, 75 mM NaCl, 75 mM KCl, 1 mM EDTA, 0.05% P-20, and 5 mM DTT.

0.33 nM of SHP2 was co-incubated with of 0.5 µM of bisphos-IRS1 peptide (sequence: H2N-LN(pY)IDLDLV(dPEG8)LST(pY)ASINFQK-amide) and various concentrations of compounds for 30-60 min at room temperature. Then the reaction was initiated by addition of the surrogate substrate DiFMUP (Invitrogen, Cat #D6567, 100 uM final).

The real-time conversion of DiFMUP to DiFMU (6,8-difluoro-7-hydroxyl-4-methyl-coumarin) was measured every 5 min for 30 min using a microplate reader (CLARIOstar, BMG Labtech) with excitation and emission wavelengths of 340 nm and 450 nm, respectively. Initial reaction rates were determined by linear fitting of the data and the inhibitor dose response curves were analyzed using normalized $IC_{50}$ regression curve fitting with control-based normalization.

The $IC_{50}$ value for compounds as numbered in compound Table 1 above are provided below in Table 4 below, where the $IC_{50}$ was measured as 100 nM or less.

TABLE 4

| Compound # from Table 1 | Structure | Shp2 $IC_{50}$ (nM) |
|---|---|---|
| 1 | 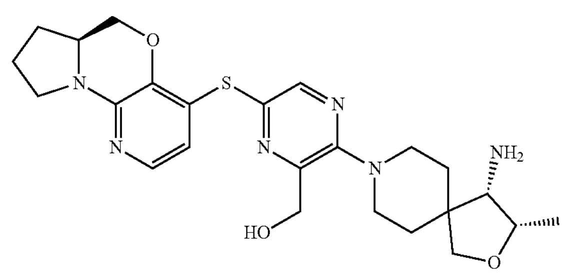 [SMILES: C[C@@H]1OCC2(CCN(c3ncc(Sc4ccnc5c4OC[C@@H]4CCCN54)nc3CO)CC2)[C@@H]1N] | 3 |
| 2 | 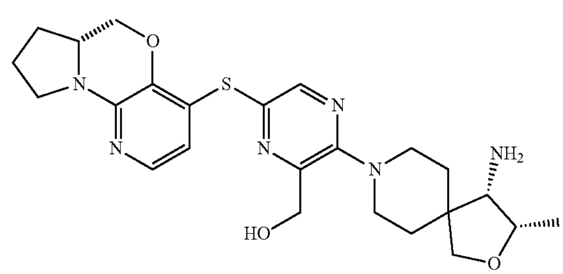 [SMILES: C[C@@H]1OCC2(CCN(c3ncc(Sc4ccnc5c4OC[C@H]4CCCN54)nc3CO)CC2)[C@@H]1N] | 4 |

TABLE 4-continued
| Compound # from Table 1 | Structure | Shp2 IC$_{50}$(nM) |
|---|---|---|
| 3 | 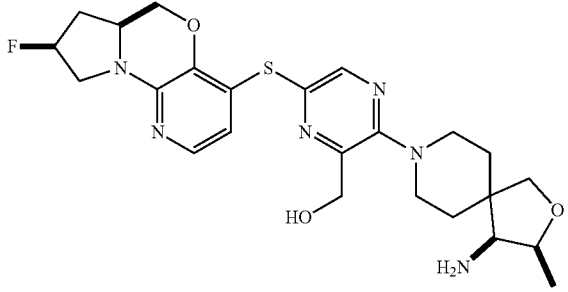 [SMILES: C[C@@H]1OCC2(CCN(c3ncc(Sc4ccnc5c4OC[C@@H]4C[C@H](F)CN54)nc3CO)CC2)[C@@H]1N] | 13 |
| 4 | 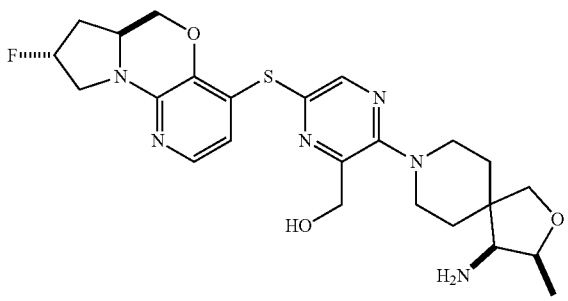 [SMILES: C[C@@H]1OCC2(CCN(c3ncc(Sc4ccnc5c4OC[C@@H]4C[C@@H](F)CN54)nc3CO)CC2)[C@@H]1N] | 5 |
| 5 | 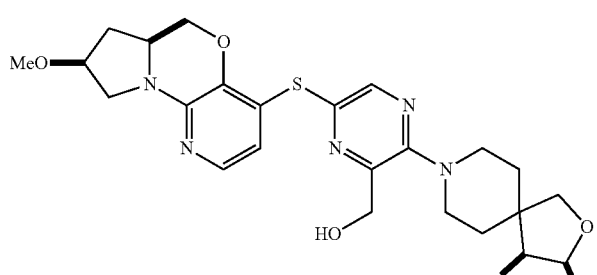 | 8 |
| 6 | 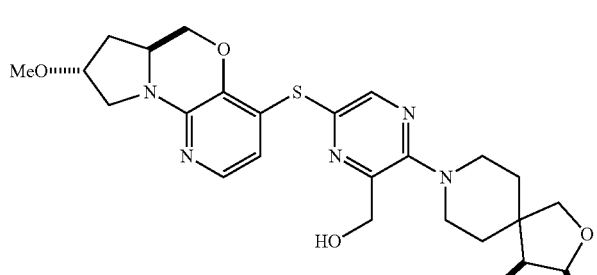 | 6 |
| 7 | 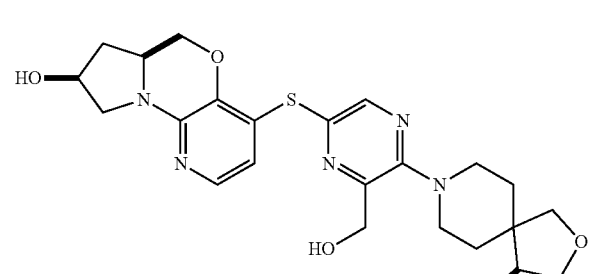 | 6 |

TABLE 4-continued

| Compound # from Table 1 | Structure | Shp2 IC$_{50}$(nM) |
|---|---|---|
| 8 | 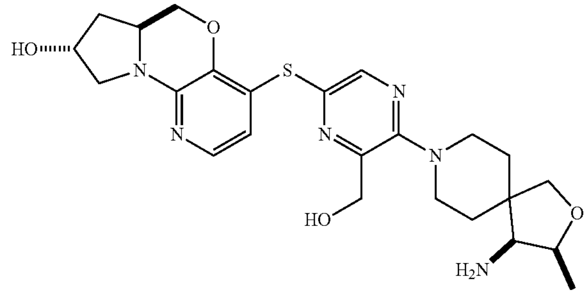 | 8 |
| 9 | 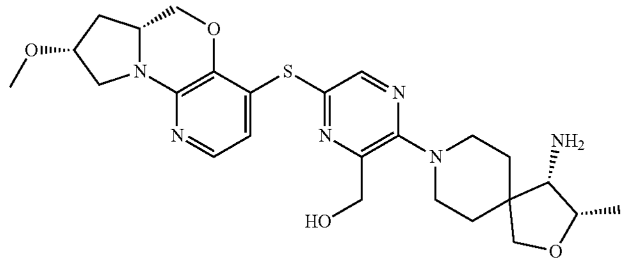 | 8 |
| 10 | 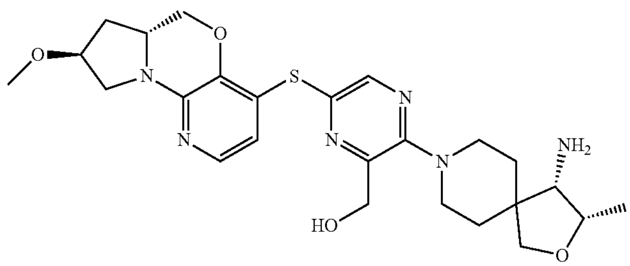 | 10 |
| 11 | 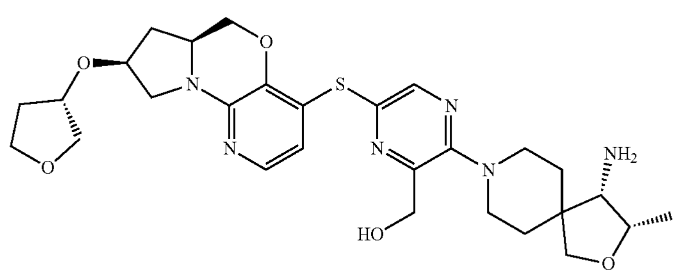 [SMILES: C[C@@H]1OCC2(CCN(c3ncc(Sc4ccnc5c4OC[C@@H]4C[C@H](O[C@H]6CCOC6)CN54)nc3CO)CC2)[C@@H]1N] | 14 |
| 12 | 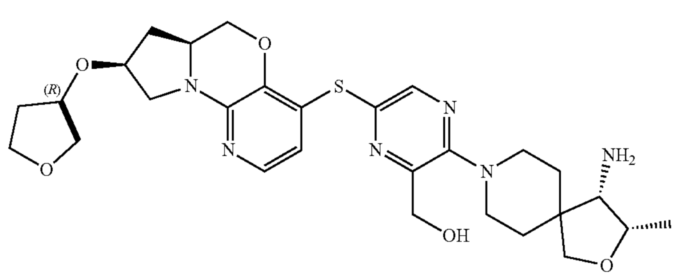 | 12 |

TABLE 4-continued

| Compound # from Table 1 | Structure | Shp2 IC$_{50}$(nM) |
|---|---|---|
| 13 | 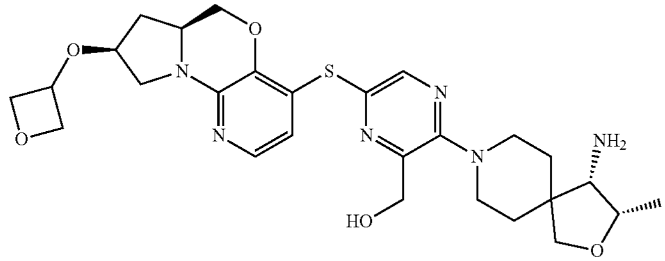 [SMILES: C[C@@H]1OCC2(CCN(c3ncc(Sc4ccnc5c4OC[C@@H]4C[C@H](OC6COC6)CN54)nc3CO)CC2)[C@@H]1N] | 8 |
| 14 | 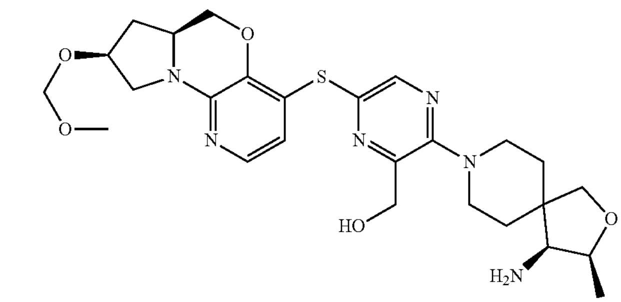 [SMILES: COCO[C@H]1C[C@H]2COc3c(Sc4cnc(N5CCC6(CC5)CO[C@@H](C)[C@H]6N)c(CO)n4)ccnc3N2C1] | 5 |
| 15 | 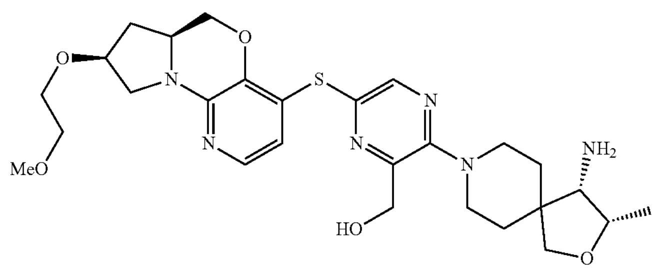 [SMILES: COCCO[C@H]1C[C@H]2COc3c(Sc4cnc(N5CCC6(CC5)CO[C@@H](C)[C@H]6N)c(CO)n4)ccnc3N2C1] | 10 |
| 16 | 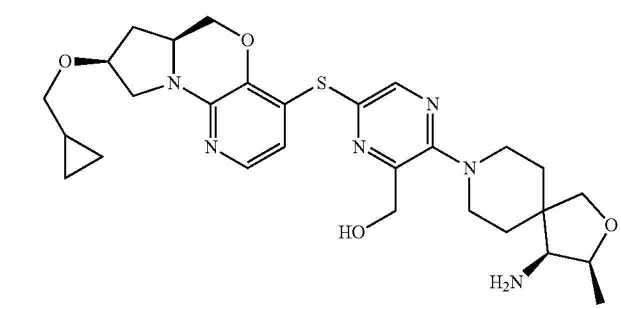 [SMILES: C[C@@H]1OCC2(CCN(c3ncc(Sc4ccnc5c4OC[C@@H]4C[C@H](OCC6CC6)CN54)nc3CO)CC2)[C@@H]1N] | 3 |
| 17 | 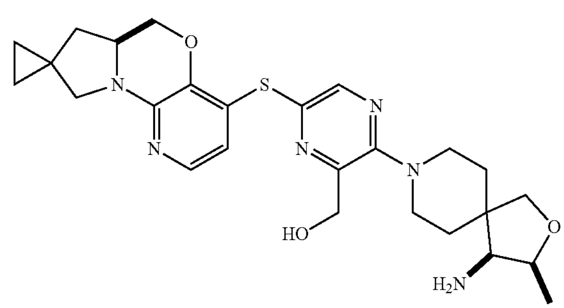 [SMILES: C[C@@H]1OCC2(CCN(c3ncc(Sc4ccnc5c4OC[C@@H]4CC6(CC6)CN54)nc3CO)CC2)[C@@H]1N] | 2 |

TABLE 4-continued

| Compound # from Table 1 | Structure | Shp2 IC$_{50}$(nM) |
|---|---|---|
| 18 | 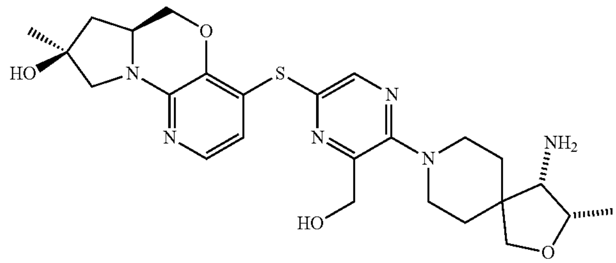 | one of 21 and 22 is 13 and the other is 8 |
| 19 | 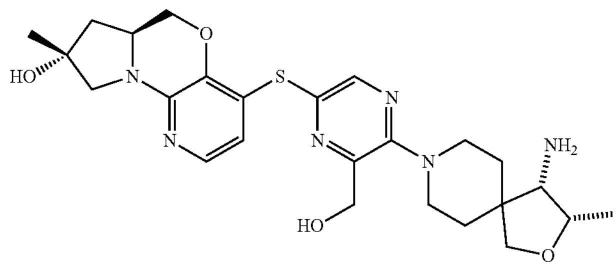 | |
| 20 | 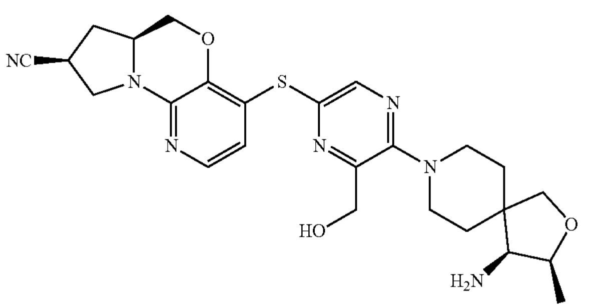 [SMILES: C[C@@H]1OCC2(CCN(c3ncc(Sc4ccnc5c4OC[C@@H]4C[C@H](C#N)CN54)nc3CO)CC2)[C@@H]1N] | 11 |
| 21 | 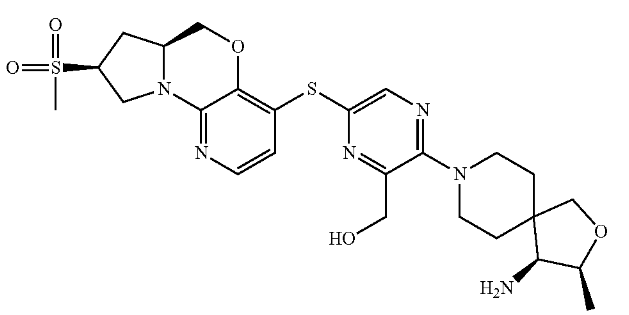 [SMILES: C[C@@H]1OCC2(CCN(c3ncc(Sc4ccnc5c4OC[C@@H]4C[C@H](S(C)(=O)=O)CN54)nc3CO)CC2)[C@@H]1N] | 13 |
| 22 | 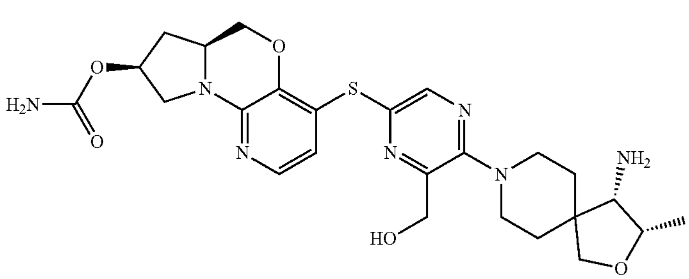 [SMILES: C[C@@H]1OCC2(CCN(c3ncc(Sc4ccnc5c4OC[C@@H]4C[C@H](OC(N)=O)CN54)nc3CO)CC2)[C@@H]1N] | 6 |

TABLE 4-continued

| Compound # from Table 1 | Structure | Shp2 IC$_{50}$(nM) |
|---|---|---|
| 23 | 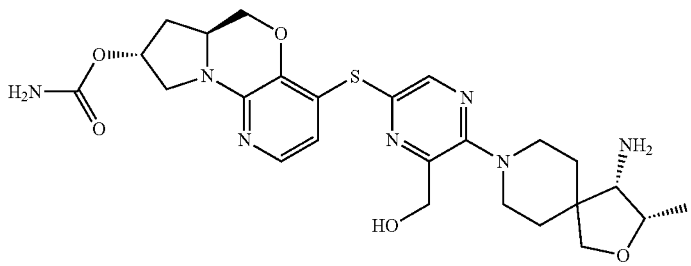 [SMILES: C[C@@H]1OCC2(CCN(c3ncc(Sc4ccnc5c4OC[C@@H]4C[C@@H](OC(N)=O)CN54)nc3CO)CC2)[C@@H]1N] | 8 |
| 24 | 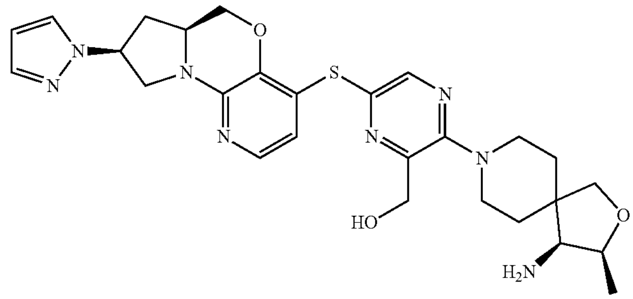 [SMILES: C[C@@H]1OCC2(CCN(c3ncc(Sc4ccnc5c4OC[C@@H]4C[C@H](n6cccn6)CN54)nc3CO)CC2)[C@@H]1N] | 10 |
| 25 | 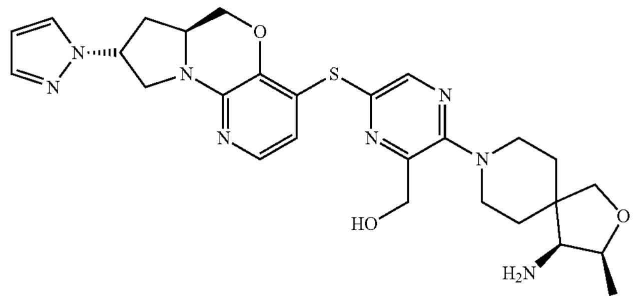 | 11 |
| 26 and 27 | | one of 26 and 27 is 10 and the other is 8 |

TABLE 4-continued

| Compound # from Table 1 | Structure | Shp2 IC$_{50}$(nM) |
|---|---|---|
| 28 | 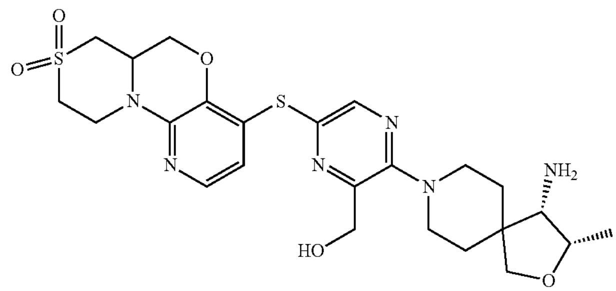 [SMILES: C[C@@H]1OCC2(CCN(c3ncc(Sc4ccnc5c4OCC4CS(=O)(=O)CCN54)nc3CO)CC2)[C@@H]1N] | 13 |
| 29 | 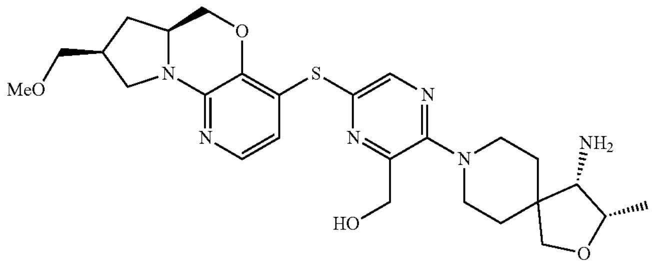 [SMILES: COC[C@H]1C[C@H]2COc3c(Sc4cnc(N5CCC6(CC5)CO[C@@H](C)[C@H]6N)c(CO)n4)ccnc3N2C1] | 3.6 |
| 30 | 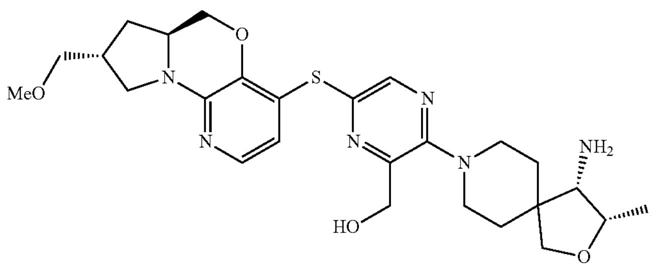 [SMILES: COC[C@@H]1C[C@H]2COc3c(Sc4cnc(N5CCC6(CC5)CO[C@@H](C)[C@H]6N)c(CO)n4)ccnc3N2C1] | 3.8 |
| 31 | 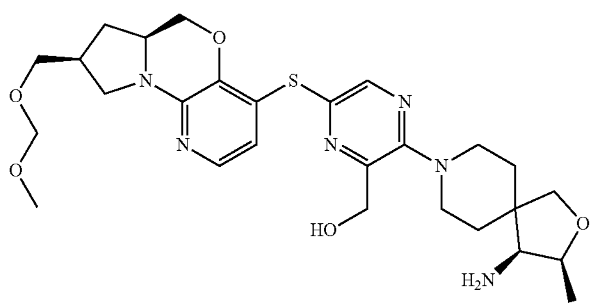 [SMILES: COCOC[C@H]1C[C@H]2COc3c(Sc4cnc(N5CCC6(CC5)CO[C@@H](C)[C@H]6N)c(CO)n4)ccnc3N2C1] | 4.2 |
| 32 | 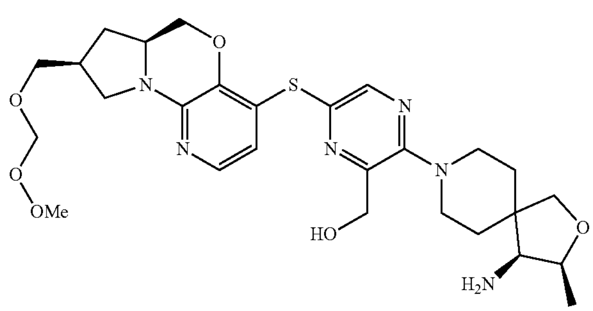 [SMILES: COOCOC[C@H]1C[C@H]2COc3c(Sc4cnc(N5CCC6(CC5)CO[C@@H](C)[C@H]6N)c(CO)n4)ccnc3N2C1] | 4 |

TABLE 4-continued

| Compound # from Table 1 | Structure | Shp2 IC$_{50}$(nM) |
|---|---|---|
| 33 | 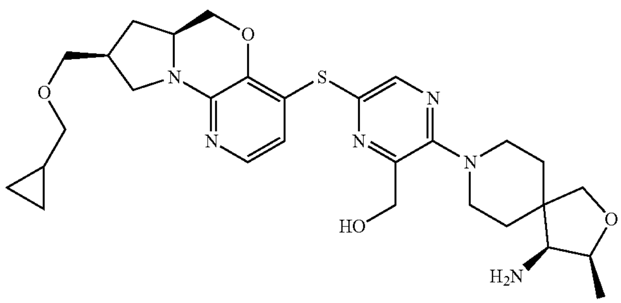 [SMILES: C[C@@H]1OCC2(CCN(c3ncc(Sc4ccnc5c4OC[C@@H]4C[C@H](COCC6CC6)CN54)nc3CO)CC2)[C@@H]1N] | 2.3 |
| 34 | 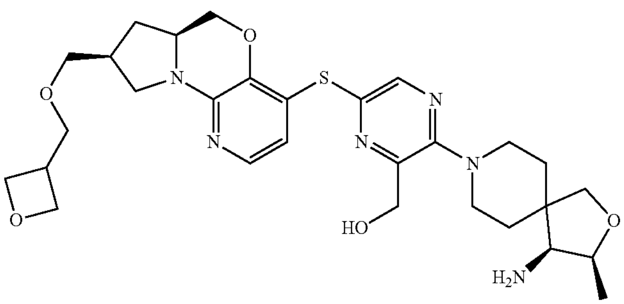 [SMILES: C[C@@H]1OCC2(CCN(c3ncc(Sc4ccnc5c4OC[C@@H]4C[C@H](COCC6COC6)CN54)nc3CO)CC2)[C@@H]1N] | 6.2 |
| 35 | 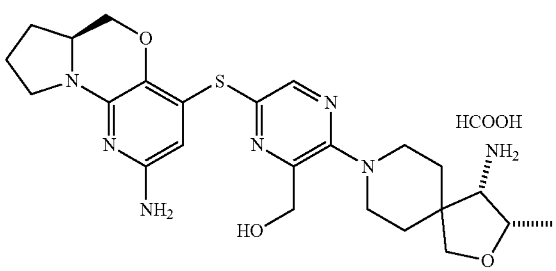 [SMILES: C[C@@H]1OCC2(CCN(c3ncc(Sc4cc(N)nc5c4OC[C@@H]4CCCN54)nc3CO)CC2)[C@@H]1N ; "HCOOH"] | 18 |
| 36 and 37 | | One of 36 and 37 is 2.7 and the other is 4.2 |

TABLE 4-continued

| Compound # from Table 1 | Structure | Shp2 IC$_{50}$(nM) |
|---|---|---|
| 38 | 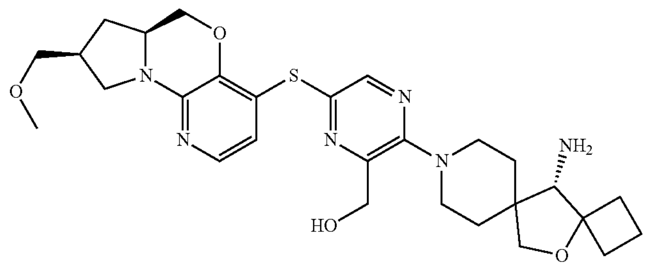 [SMILES: COC[C@H]1C[C@H]2COc3c(Sc4cnc(N5CCC6(CC5)COC5(CCC5)[C@H]6N)c(CO)n4)ccnc3N2C1] | 5.7 |
| 39 | 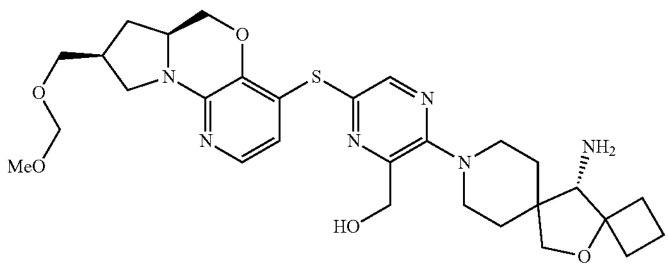 [SMILES: COCOC[C@H]1C[C@H]2COc3c(Sc4cnc(N5CCC6(CC5)COC5(CCC5)[C@H]6N)c(CO)n4)ccnc3N2C1] | 7.0 |
| 40 | 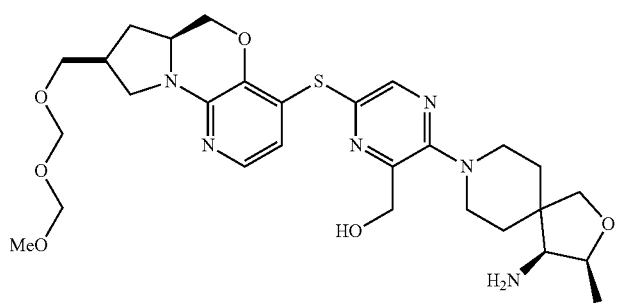 [SMILES: COCOCOC[C@H]1C[C@H]2COc3c(Sc4cnc(N5CCC6(CC5)CO[C@@H](C)[C@H]6N)c(CO)n4)ccnc3N2C1] | 5.9 |
| 41 | 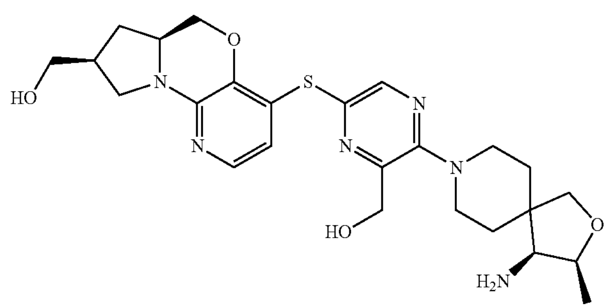 [SMILES: C[C@@H]1OCC2(CCN(c3ncc(Sc4ccnc5c4OC[C@@H]4C[C@H](CO)CN54)nc3CO)CC2)[C@@H]1N] | 5.0 |
| 42 | 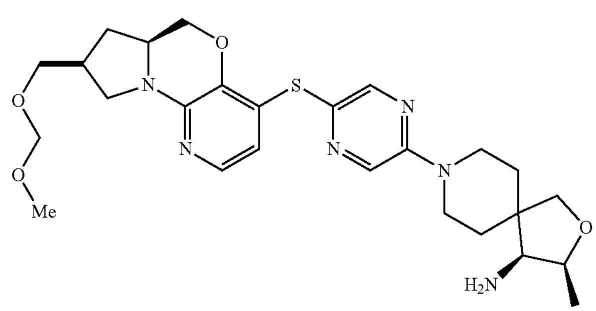 [SMILES: COCOC[C@H]1C[C@H]2COc3c(Sc4cnc(N5CCC6(CC5)CO[C@@H](C)[C@H]6N)cn4)ccnc3N2C1] | 5.9 |

TABLE 4-continued

| Compound # from Table 1 | Structure | Shp2 IC$_{50}$(nM) |
|---|---|---|
| 43 | 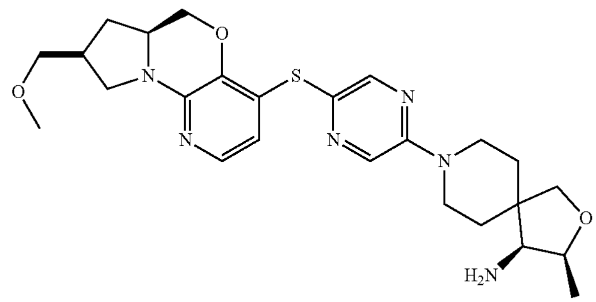 [SMILES: COC[C@H]1C[C@H]2COc3c(Sc4cnc(N5CCC6(CC5)CO[C@@H](C)[C@H]6N)cn4)ccnc3N2C1] | 4.5 |
| 44 | 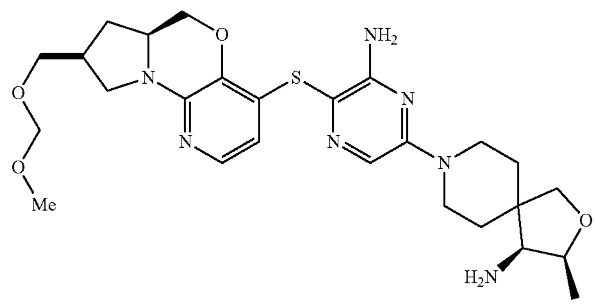 [SMILES: COCOC[C@H]1C[C@H]2COc3c(Sc4ncc(N5CCC6(CC5)CO[C@@H](C)[C@H]6N)nc4N)ccnc3N2C1] | 5.9 |
| 45 | 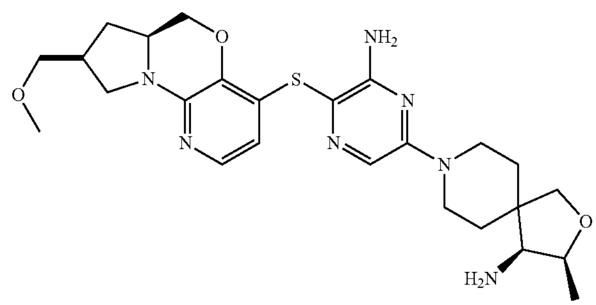 [SMILES: COC[C@H]1C[C@H]2COc3c(Sc4ncc(N5CCC6(CC5)CO[C@@H](C)[C@H]6N)nc4N)ccnc3N2C1] | 9.4 |
| 46 | 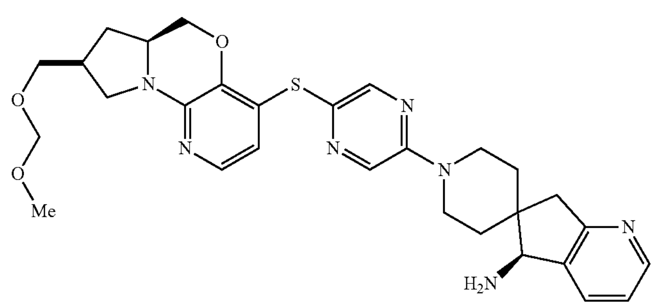 [SMILES: COCOC[C@H]1C[C@H]2COc3c(Sc4cnc(N5CCC6(CC5)Cc5ncccc5[C@H]6N)cn4)ccnc3N2C1] | 3.9 |
| 47 | 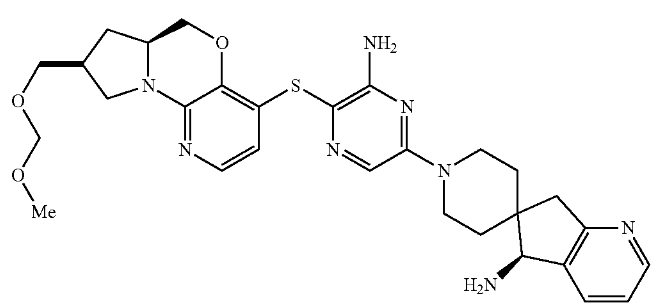 [SMILES: COCOC[C@H]1C[C@H]2COc3c(Sc4ncc(N5CCC6(CC5)Cc5ncccc5[C@H]6N)nc4N)ccnc3N2C1] | 8.4 |

TABLE 4-continued

| Compound # from Table 1 | Structure | Shp2 IC$_{50}$(nM) |
|---|---|---|
| 48 | 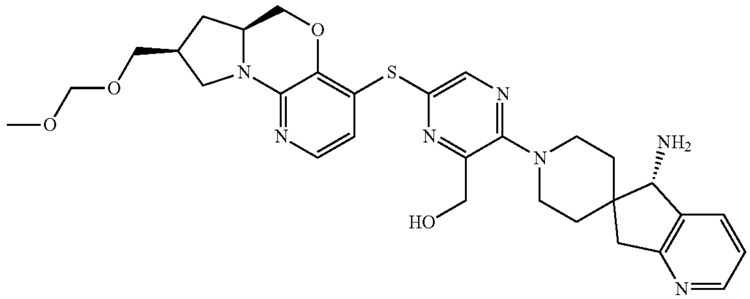 [SMILES: COCOC[C@H]1C[C@H]2COc3c(Sc4cnc(N5CCC6(CC5)Cc5ncccc5[C@H]6N)c(CO)n4)ccnc3N2C1] | 3.3 |
| 49 | 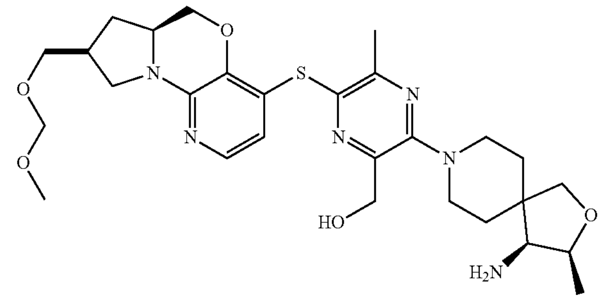 [SMILES: COCOC[C@H]1C[C@H]2COc3c(Sc4nc(CO)c(N5CCC6(CC5)CO[C@@H](C)[C@H]6N)nc4C)ccnc3N2C1] | 12 |
| 50 | 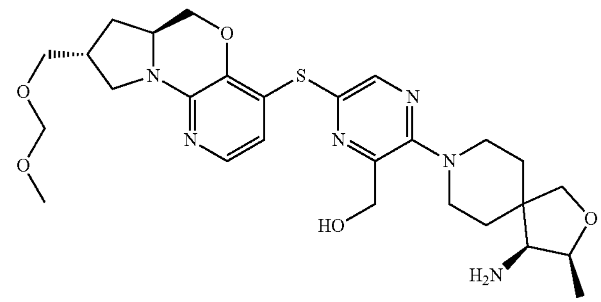 [SMILES: COCOC[C@@H]1C[C@H]2COc3c(Sc4cnc(N5CCC6(CC5)CO[C@@H](C)[C@H]6N)c(CO)n4)ccnc3N2C1] | 3.5 |
| 51 | 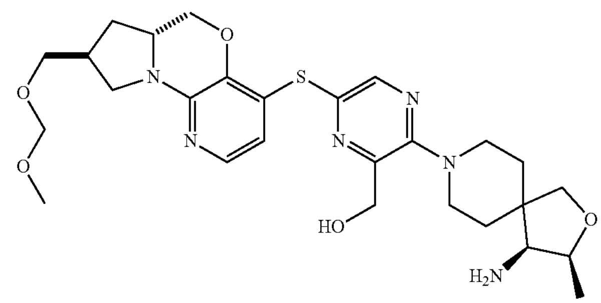 [SMILES: COCOC[C@H]1C[C@@H]2COc3c(Sc4cnc(N5CCC6(CC5)CO[C@@H](C)[C@H]6N)c(CO)n4)ccnc3N2C1] | 4.9 |
| 52 | | 3.7 | p-ERK Cellular Assay

Detroit562 cells were seeded in 96-well plate and cultured overnight (30,000 cells per well, 200 ul total volume). Following morning, cells were treated with compounds of the disclosure, with starting concentration at 10 uM and ½ log dilution down to 1M for 2 hours at 37° C. DMSO treatment serves as control. p-ERR was then measured using AphaLISA® SureFire® Ultra™ p-ERR 1/2 (Thr202/Tyr204) Assay Kit (PerkinElmer, ALSU-PERK-A500) following instruction. Briefly, medium was removed and add 50 ul 1× lysis buffer was added, followed by 10 minutes incubation on a plate shaker at room temperature. Then 10 ul of lysate was transferred to a white 384-well plate, and 5 ul Acceptor mix, and 5 ul Donor mix were added (both prepared according to manufacturer's instruction). The plate was wrapped with foil, shaken for 1-2 minutes on a plate reader and incubated for >2 hours. Signal was then measured on a CLARIOstar® plate reader. Percentage inhibition was calculated with DMSO treatment as 100% of signal, and $IC_{50}$ is calculated by Graphpad Prism 7.

FORMULATION EXAMPLES

The following are representative pharmaceutical formulations containing a compound of Formula (I).

Tablet Formulation

The following ingredients are mixed intimately and pressed into single scored tablets.

| Ingredient | Quantity per tablet (mg) |
| --- | --- |
| Compound of the disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per tablet (mg) |
| --- | --- |
| Compound of the disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL

Inhalation Composition

To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal spray solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 ul of spray for each application.

The invention claimed is:

1. A compound of Formula (A):

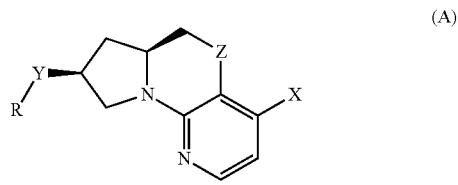

(A)

wherein X is halogen or thiol;
Y is null, $CH_2$, O, or C=O;
Z is $CH_2$ or O; and
R is selected from null, hydrogen, alkyl, alkoxy, hydroxyl, methoxyalkoxy, heterocyclylmethyloxy, and cycloalkylmethoxymethyl.
2. The compound of claim 1, wherein X is halogen.
3. The compound of claim 1, wherein X is iodine or bromine.
4. The compound of claim 1, where X is thiol.
5. The compound of claim 1, wherein Y is O.
6. The compound of claim 1, wherein Y is $CH_2$.
7. The compound of claim 1, where Z is O.
8. The compound of claim 1, where Z is $CH_2$.
9. The compound of claim 1, that is ((6aS,8S)-4-iodo-6a,7, tetrahydro-6H-pyrido[3,2-b]pyrrolo[1,2-d][1,4]oxazin-8-yl)methanol:

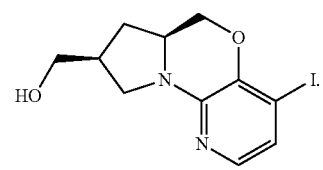 [SMILES: OC[C@H]1C[C@H]2COc3c(I)ccnc3N2C1]

10. The compound of claim 1, that is (6aS,8S)-4-iodo-6a,7,8,9-tetrahydro-6H-pyrido[3,2-b]pyrrolo[1,2-d][1,4]oxazin-8-ol:
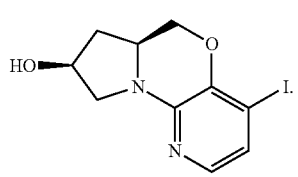

UNITED STATES PATENT AND TRADEMARK OFFICE
CERTIFICATE OF CORRECTION

| | | |
|---|---|---|
| PATENT NO. | : 11,518,772 B2 | |
| APPLICATION NO. | : 17/025790 | |
| DATED | : December 6, 2022 | |
| INVENTOR(S) | : Jiping Fu et al. | |

It is certified that error appears in the above-identified patent and that said Letters Patent is hereby corrected as shown below:

In the Claims

Column 214, Line 55 to 57 In Claim 9, replace:
"The compound of claim 1, that is ((6aS,8S)-4-iodo-6a,7, tetrahydro-6H-pyrido[3,2-b]pyrrolo[1,2-d][1,4]oxazin-8-yl)methanol"
With:
--The compound of claim 1, that is ((6aS,8S)-4-iodo-6a,7,8,9-tetrahydro-6H-pyrido[3,2-b]pyrrolo[1,2-d][1,4]oxazin-8-yl)methanol--

Signed and Sealed this
Thirty-first Day of January, 2023

Katherine Kelly Vidal
*Director of the United States Patent and Trademark Office*